US011118224B2

(12) United States Patent
Doudna et al.

(10) Patent No.: US 11,118,224 B2
(45) Date of Patent: *Sep. 14, 2021

(54) TYPE V CRISPR/CAS EFFECTOR PROTEINS FOR CLEAVING SSDNAS AND DETECTING TARGET DNAS

(71) Applicant: The Regents of the University of California, Oakland, CA (US)

(72) Inventors: Jennifer A. Doudna, Berkeley, CA (US); Janice S. Chen, Berkeley, CA (US); Lucas Benjamin Harrington, Berkeley, CA (US); Enbo Ma, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/896,731

(22) Filed: Jun. 9, 2020

(65) Prior Publication Data

US 2020/0299768 A1    Sep. 24, 2020

Related U.S. Application Data

(63) Continuation of application No. 16/262,257, filed on Jan. 30, 2019, which is a continuation of application No. 15/897,089, filed on Feb. 14, 2018, now Pat. No. 10,253,365.

(60) Provisional application No. 62/626,593, filed on Feb. 5, 2018, provisional application No. 62/590,106, filed on Nov. 22, 2017.

(51) Int. Cl.
| *C12Q 1/6876* | (2018.01) |
| *C12N 15/11* | (2006.01) |
| *C12N 9/22* | (2006.01) |
| *C12Q 1/6823* | (2018.01) |

(52) U.S. Cl.
CPC ............ *C12Q 1/6876* (2013.01); *C12N 9/22* (2013.01); *C12N 15/11* (2013.01); *C12Q 1/6823* (2013.01); *C12N 2310/20* (2017.05)

(58) Field of Classification Search
CPC .................................................. C12N 2310/20
See application file for complete search history.

(56) References Cited

U.S. PATENT DOCUMENTS

| 9,790,490 B2 * | 10/2017 | Zhang ................... C12N 15/111 |
| 10,253,365 B1 * | 4/2019 | Doudna ............... C12Q 1/6823 |
| 2016/0208243 A1 | 7/2016 | Zhang et al. |
| 2017/0211142 A1 | 7/2017 | Smargon et al. |
| 2018/0298445 A1 * | 10/2018 | Abudayyeh .......... C12Q 1/6804 |

FOREIGN PATENT DOCUMENTS

| CN | 107488710 A | 12/2017 |
| WO | WO 2016/205711 A1 | 12/2016 |
| WO | WO 2016/205749 A1 | 12/2016 |
| WO | WO 2016/205764 | 12/2016 |
| WO | WO 2017/147345 | 8/2017 |
| WO | WO 2017/184768 A1 | 10/2017 |
| WO | WO 2017/184786 A1 | 10/2017 |
| WO | WO 2017/189308 A1 | 11/2017 |

OTHER PUBLICATIONS

Koonin et al. (2017) Diversity, classification and evolution of CRISPR-Cas systems. Current Opinion in Microbiology, 37:67-78 (Year: 2017).*
Livak et al. (1995) Oligonucleotides with Fluorescent Dyes at Opposite Ends Provide a Quenched Probe System Useful for Detecting PCR Product and Nucleic Acid Hybridization. PCR Methods and Applications, 4:357-362 (Year: 1995).*
Burnstein, et al.; "New CRISPR-Cas systems from uncultivated microbes"; Nature; vol. 542, No. 7640, pp. 237-241 (Feb. 9, 2017).
Bustin; "Quantification of mRNA using real-time reverse transcription PCR (RT-PCR): trends and problems"; Journal of Molecular Endocrinology; vol. 29, pp. 23-29 (2002).
Chen, et al.; "CRISPR-Cas12a target binding unleashes indiscriminate single-stranded DNase activity"; Science; vol. 360, No. 6387, pp. 436-439 (Apr. 27, 2018).
Koonin, et al. "Diversity, classification and evolution of CRISPR-Cas systems"; Current Opinion in Microbiology; vol. 37, pp. 67-78 (2017).
Livak, et al.; "Oligonucleotides with Fluorescent Dyes at Opposite Ends Provide a Quenched Probe System Useful for Detecting PCR Product and Nucleic Acid Hybridization"; PCR Methods and Applications; vol. 4, pp. 357-362 (1995).
Shmakov, et al.; "Diversity and evolution of class 2 CRISPR-Cas systems"; Nature Reviews Microbiology; vol. 15, pp. 169-182 (Mar. 2017).

(Continued)

*Primary Examiner* — Neil P Hammell
(74) *Attorney, Agent, or Firm* — Bozicevic, Field & Francis LLP; Paula A. Borden

(57) ABSTRACT

Provided are compositions and methods for detecting a target DNA (double stranded or single stranded) in a sample. In some embodiments, a subject method includes: (a) contacting the sample with: (i) a type V CRISPR/Cas effector protein (e.g., a Cas12 protein such as Cas12a, Cas12b, Cas12c, Cas12d, Cas12e); (ii) a guide RNA (comprising a region that binds to the type V CRISPR/Cas effector protein, and a guide sequence that hybridizes with the target DNA); and (iii) a detector DNA that is single stranded (i.e., a "single stranded detector DNA") and does not hybridize with the guide sequence of the guide RNA; and (b) measuring a detectable signal produced by cleavage (by the type V CRISPR/Cas effector protein) of the single stranded detector DNA. Also provided are compositions and methods for cleaving single stranded DNAs (e.g., non-target ssDNAs), e.g., inside of a cell.

27 Claims, 56 Drawing Sheets

Specification includes a Sequence Listing.

(56) References Cited

OTHER PUBLICATIONS

Swarts, et al.; "Structural Basis for Guide RNA Processing and Seed-Dependent DNA Targeting by CRISPR-Cas12a"; Molecular Cell; vol. 66, pp. 221-233 (Apr. 20, 2017).
Zetsche, et al.; "Cpf1 Is a Single RNA-Guided Endonuclease of a Class 2 CRISPR-Cas System"; Cell; vol. 163, pp. 759-771 (Oct. 22, 2015).
East-Seletsky, et al.; "Two distinct RNase activites of CRISPR-C2c2 enable guide-RNA processing and RNA detection"; Nature; vol. 538, pp. 270-273 (Oct. 13, 2016).
Gootenberg, et al.; "Nucleic acid detection with CRISPR-Cas13a/C2c2"; Science; vol. 356, pp. 438-442 (Apr. 28, 2017).
Li, et al.; "CRISPR-Cas12a has bothcis- andtrans-cleavage activities on single-stranded DNA"; Cell Research; vol. 28, No. 4, pp. 491-493 (Mar. 12, 2018).

\* cited by examiner

FIG. 1A

Lachnospiraceae bacterium ND2006 (LbCas12a)
MSKLEKFTNCYSLSKTLRFKAIPVGKTQENIDNKRLLVEDEKRAEDYKGVKKLLDRYYLSFINDVLHSIKLKNLN
NYISLFRKKTRTEKENKELENLEINLRKEIAKAFKGNEGYKSLFKKDIIETILPEFLDDKDEIALVNSFNGFTTAFTG
FFDNRENMFSEEAKSTSIAFRCINENLTRYISNMDIFEKVDAIFDKHEVQEIKEKILNSDYDVEDFFEGEFFNFVL
TQEGIDVYNAIIGGFVTESGEKIKGLNEYINLYNQKTKQKLPKFKPLYKQVLSDRESLSFYGEGYTSDEEVLEVFR
NTLNKNSEIFSSIKKLEKLFKNFDEYSSAGIFVKNGPAISTISKDIFGEWNVIRDKWNAEYDDIHLKKKAVVTEKY
EDDRRKSFKKIGSFSLEQLQEYADADLSVVEKLKEIIQKVDEIYKVYGSSEKLFDADFVLEKSLKKNDAVVAIMK
DLLDSVKSFENYIKAFFGEGKETNRDESFYGDFVLAYDILLKVDHIYDAIRNYVTQKPYSKDKFKLYFQNPQFM
GGWDKDKETDYRATILRYGSKYYLAIMDKKYAKCLQKIDKDDVNGNYEKINYKLLPGPNKMLPKVFFSKKW
MAYYNPSEDIQKIYKNGTFKKGDMFNLNDCHKLIDFFKDSISRYPKWSNAYDFNFSETEKYKDIAGFYREVEE
QGYKVSFESASKKEVDKLVEEGKLYMFQIYNKDFSDKSHGTPNLHTMYFKLLFDENNHGQIRLSGGAELFMR
RASLKKEELVVHPANSPIANKNPDNPKKTTTLSYDVYKDKRFSEDQYELHIPIAINKCPKNIFKINTEVRVLLKHD
DNPYVIGIDRGERNLLYIVVVDGKGNIVEQYSLNEIINNFNGIRIKTDYHSLLDKKEKERFEARQNWTSIENIKEL
KAGYISQVVHKICELVEKYDAVIALEDLNSGFKNSRVKVEKQVYQKFEKMLIDKLNYMVDKKSNPCATGGALK
GYQITNKFESFKSMSTQNGFIFYIPAWLTSKIDPSTGFVNLLKTKYTSIADSKKFISSFDRIMYVPEEDLFEFALDY
KNFSRTDADYIKKWKLYSYGNRIRIFRNPKKNNVFDWEEVCLTSAYKELFNKYGINYQQGDIRALLCEQSDKA
FYSSFMALMSLMQMRNSITGRTDVDFLISPVKNSDGIFYDSRNYEAQENAILPKNADANGAYNIARKVLWA
IGQFKKAEDEKLDKVKIAISNKEWLEYAQTSVKH (SEQ ID NO: 1)

Acidaminococcus sp. BV3L6 (AsCas12a)
MTQFEGFTNLYQVSKTLRFELIPQGKTLKHIQEQGFIEEDKARNDHYKELKPIIDRIYKTYADQCLQLVQLDWE
NLSAAIDSYRKEKTEETRNALIEEQATYRNAIHDYFIGRTDNLTDAINKRHAEIYKGLFKAELFNGKVLKQLGTV
TTTEHENALLRSFDKFTTYFSGFYENRKNVFSAEDISTAIPHRIVQDNFPKFKENCHIFTRLITAVPSLREHFENV
KKAIGIFVSTSIEEVFSFPFYNQLLTQTQIDLYNQLLGGISREAGTEKIKGLNEVLNLAIQKNDETAHIIASLPHRFI
PLFKQILSDRNTLSFILEEFKSDEEVIQSFCKYKTLLRNENVLETAEALFNELNSIDLTHIFISHKKLETISSALCDH
WDTLRNALYERRISELTGKITKSAKEKVQRSLKHEDINLQEIISAAGKELSEAFKQKTSEILSHAHAALDQPLPTT
LKKQEEKEILKSQLDSLLGLYHLLDWFAVDESNEVDPEFSARLTGIKLMEPSLSFYNKARNYATKKPYSVEKFK
LNFQMPTLASGWDVNKEKNNGAILFVKNGLYYLGIMPKQKGRYKALSFEPTEKTSEGFDKMYYDYFPDAAK
MIPKCSTQLKAVTAHFQTHTTPILLSNNFIEPLEITKEIYDLNNPEKEPKKFQTAYAKKTGDQKGYREALCKWID
FTRDFLSKYTKTTSIDLSSLRPSSQYKDLGEYYAELNPLLYHISFQRIAEKEIMDAVETGKLYLFQIYNKDFAKGH
HGKPNLHTLYWTGLFSPENLAKTSIKLNGQAELFYRPKSRMKRMAHRLGEKMLNKKLKDQKTPIPDTLYQEL
YDYVNHRLSHDLSDEARALLPNVITKEVSHEIIKDRRFTSDKFFFHVPITLNYQAANSPSKFNQRVNAYLKEHPE
TPIIGIDRGERNLIYITVIDSTGKILEQRSLNTIQQFDYQKKLDNREKERVAARQAWSVVGTIKDLKQGYLSQVI
HEIVDLMIHYQAVVVLENLNFGFKSKRTGIAEKAVYQQFEKMLIDKLNCLVLKDYPAEKVGGVLNPYQLTDQF
TSFAKMGTQSGFLFYVPAPYTSKIDPLTGFVDPFVWKTIKNHESRKHFLEGFDFLHYDVKTGDFILHFKMNRN
LSFQRGLPGFMPAWDIVFEKNETQFDAKGTPFIAGKRIVPVIENHRFTGRYRDLYPANELIALLEEKGIVFRDG
SNILPKLLENDDSHAIDTMVALIRSVLQMRNSNAATGEDYINSPVRDLNGVCFDSRFQNPEWPMDADANG
AYHIALKGQLLLNHLKESKDLKLQNGISNQDWLAYIQELRN (SEQ ID NO: 2)

FIG. 1B

Francisella novicida U112 (FnCas12a)
MSIYQEFVNKYSLSKTLRFELIPQGKTLENIKARGLILDDEKRAKDYKKAKQIIDKYHQFFIEEILSSVCISEDLLQN
YSDVYFKLKKSDDDNLQKDFKSAKDTIKKQISEYIKDSEKFKNLFNQNLIDAKKGQESDLILWLKQSKDNGIELF
KANSDITDIDEALEIIKSFKGWTTYFKGFHENRKNVYSSNDIPTSIIYRIVDDNLPKFLENKAKYESLKDKAPEAIN
YEQIKKDLAEELTFDIDYKTSEVNQRVFSLDEVFEIANFNNYLNQSGITKFNTIIGGKFVNGENTKRKGINEYINL
YSQQINDKTLKKYKMSVLFKQILSDTESKSFVIDKLEDDSDVVTTMQSFYEQIAAFKTVEEKSIKETLSLLFDDLK
AQKLDLSKIYFKNDKSLTDLSQQVFDDYSVIGTAVLEYITQQIAPKNLDNPSKKEQELIAKKTEKAKYLSLETIKLA
LEEFNKHRDIDKQCRFEEILANFAAIPMIFDEIAQNKDNLAQISIKYQNQGKKDLLQASAEDDVKAIKDLLDQT
NNLLHKLKIFHISQSEDKANILDKDEHFYLVFEECYFELANIVPLYNKIRNYITQKPYSDEKFKLNFENSTLANGW
DKNKEPDNTAILFIKDDKYYLGVMNKKNNKIFDDKAIKENKGEGYKKIVYKLLPGANKMLPKVFFSAKSIKFYN
PSEDILRIRNHSTHTKNGSPQKGYEKFEFNIEDCRKFIDFYKQSISKHPEWKDFGFRFSDTQRYNSIDEFYREVE
NQGYKLTFENISESYIDSVVNQGKLYLFQIYNKDFSAYSKGRPNLHTLYWKALFDERNLQDVVYKLNGEAELFY
RKQSIPKKITHPAKEAIANKNKDNPKKESVFEYDLIKDKRFTEDKFFFHCPITINFKSSGANKFNDEINLLLKEKA
NDVHILSIDRGERHLAYYTLVDGKGNIIKQDTFNIIGNDRMKTNYHDKLAAIEKDRDSARKDWKKINNIKEMK
EGYLSQVVHEIAKLVIEYNAIVVFEDLNFGFKRGRFKVEKQVYQKLEKMLIEKLNYLVFKDNEFDKTGGVLRAY
QLTAPFETFKKMGKQTGIIYYVPAGFTSKICPVTGFVNQLYPKYESVSKSQEFFSKFDKICYNLDKGYFEFSFDY
KNFGDKAAKGKWTIASFGSRLINFRNSDKNHNWDTREVYPTKELEKLLKDYSIEYGHGECIKAAICGESDKKFF
AKLTSVLNTILQMRNSKTGTELDYLISPVADVNGNFFDSRQAPKNMPQDADANGAYHIGLKGLMLLGRIKN
NQEGKKLNLVIKNEEYFEFVQNRNN (SEQ ID NO: 3)

Porphyromonas macacae (PmCas12a)
MKTQHFFEDFTSLYSLSKTIRFELKPIGKTLENIKKNGLIRRDEQRLDDYEKLKKVIDEYHEDFIANILSSFSFSEEIL
QSYIQNLSESEARAKIEKTMRDTLAKAFSEDERYKSIFKKELVKKDIPVWCPAYKSLCKKFDNFTTSLVPFHENR
KNLYTSNEITASIPYRIVHVNLPKFIQNIEALCELQKKMGADLYLEMMENLRNVWPSFVKTPDDLCNLKTYNH
LMVQSSISEYNRFVGGYSTEDGTKHQGINEWINIYRQRNKEMRLPGLVFLHKQILAKVDSSSFISDTLENDDQ
VFCVLRQFRKLFWNTVSSKEDDAASLKDLFCGLSGYDPEAIYVSDAHLATISKNIFDRWNYISDAIRRKTEVLM
PRKKESVERYAEKISKQIKKRQSYSLAELDDLLAHYSEESLPAGFSLLSYFTSLGGQKYLVSDGEVILYEEGSNIW
DEVLIAFRDLQVILDKDFTEKKLGKDEEAVSVIKKALDSALRLRKFFDLLSGTGAEIRRDSSFYALYTDRMDKLKG
LLKMYDKVRNYLTKKPYSIEKFKLHFDNPSLLSGWDKNKELNNLSVIFRQNGYYYLGIMTPKGKNLFKTLPKLG
AEEMFYEKMEYKQIAEPMLMLPKVFFPKKTKPAFAPDQSVVDIYNKKTFKTGQKGFNKKDLYRLIDFYKEALT
VHEWKLFNFSFSPTEQYRNIGEFFDEVREQAYKVSMVNVPASYIDEAVENGKLYLFQIYNKDFSPYSKGIPNL
HTLYWKALFSEQNQSRVYKLCGGGELFYRKASLHMQDTTVHPKGISIHKKNLNKKGETSLFNYDLVKDKRFTE
DKFFFHVPISINYKNKKITNVNQMVRDYIAQNDDLQIIGIDRGERNLLYISRIDTRGNLLEQFSLNVIESDKGDL
RTDYQKILGDREQERLRRRQEWKSIESIKDLKDGYMSQVVHKICNMVVEHKAIVVLENLNLSFMKGRKKVEK
SVYEKFERMLVDKLNYLVVDKKNLSNEPGGLYAAYQLTNPLFSFEELHRYPQSGILFFVDPWNTSLTDPSTGF
VNLLGRINYTNVGDARKFFDRFNAIRYDGKGNILFDLDLSRFDVRVETQRKLWTLTTFGSRIAKSKKSGKWM
VERIENLSLCFLELFEQFNIGYRVEKDLKKAILSQDRKEFYVRLIYLFNLMMQIRNSDGEEDYILSPALNEKNLQF
DSRLIEAKDLPVDADANGAYNVARKGLMVVQRIKRGDHESIHRIGRAQWLRYVQEGIVE (SEQ ID NO: 4)

FIG. 1C

Moraxella bovoculi 237 (MbCas12a)
MLFQDFTHLYPLSKTVRFELKPIDRTLEHIHAKNFLSQDETMADMHQKVKVILDDYHRDFIADMMGEVKLTK
LAEFYDVYLKFRKNPKDDELQKQLKDLQAVLRKEIVKPIGNGGKYKAGYDRLFGAKLFKDGKELGDLAKFVIA
QEGESSPKLAHLAHFEKFSTYFTGFHDNRKNMYSDEDKHTAIAYRLIHENLPRFIDNLQILTTIKQKHSALYDQI
INELTASGLDVSLASHLDGYHKLLTQEGITAYNTLLGGISGEAGSPKIQGINELINSHHNQHCHKSERIAKLRPL
HKQILSDGMSVSFLPSKFADDSEMCQAVNEFYRHYADVFAKVQSLFDGFDDHQKDGIYVEHKNLNELSKQA
FGDFALLGRVLDGYYVDVVNPEFNERFAKAKTDNAKAKLTKEKDKFIKGVHSLASLEQAIEHYTARHDDESVQ
AGKLGQYFKHGLAGVDNPIQKIHNNHSTIKGFLERERPAGERALPKIKSGKNPEMTQLRQLKELLDNALNVA
HFAKLLTTKTTLDNQDGNFYGEFGVLYDELAKIPTLYNKVRDYLSQKPFSTEKYKLNFGNPTLLNGWDLNKEK
DNFGVILQKDGCYYLALLDKAHKKVFDNAPNTGKSIYQKMIYKYLEVRKQFPKVFFSKEAIAINYHPSKELVEIK
DKGRQRSDDERLKLYRFILECLKIHPKYDKKFEGAIGDIQLFKKDKKGREVPISEKDLFDKINGIFSSKPKLEMED
FFIGEFKRYNPSQDLVDQYNIYKKIDSNDNRKKENFYNNHPKFKKDLVRYYYESMCKHEEWEESFEFSKKLQDI
GCYVDVNELFTEIETRRLNYKISFCNINADYIDELVEQGQLYLFQIYNKDFSPKAHGKPNLHTLYFKALFSEDNL
ADPIYKLNGEAQIFYRKASLDMNETTIHRAGEVLENKNPDNPKKRQFVYDIIKDKRYTQDKFMLHVPITMNF
GVQGMTIKEFNKKVNQSIQQYDEVNVIGIDRGERHLLYLTVINSKGEILEQCSLNDITTASANGTQMTTPYHKI
LDKREIERLNARVGWGEIETIKELKSGYLSHVVHQISQLMLKYNAIVVLEDLNFGFKRGRFKVEKQIYQNFENA
LIKKLNHLVLKDKADDEIGSYKNALQLTNNFTDLKSIGKQTGFLFYVPAWNTSKIDPETGFVDLLKPRYENIAQS
QAFFGKFDKICYNADKDYFEFHIDYAKFTDKAKNSRQIWTICSHGDKRYVYDKTANQNKGAAKGINVNDELK
SLFARHHINEKQPNLVMDICQNNDKEFHKSLMYLLKTLLALRYSNASSDEDFILSPVANDEGVFFNSALADDT
QPQNADANGAYHIALKGLWLLNELKNSDDLNKVKLAIDNQTWLNFAQNR (SEQ ID NO: 5)

Moraxella bovoculi AAX08_00205 (Mb2Cas12a)
MGIHGVPAALFQDFTHLYPLSKTVRFELKPIGRTLEHIHAKNFLSQDETMADMYQKVKVILDDYHRDFIADM
MGEVKLTKLAEFYDVYLKFRKNPKDDGLQKQLKDLQAVLRKESVKPIGSGGKYKTGYDRLFGAKLFKDGKELG
DLAKFVIAQEGESSPKLAHLAHFEKFSTYFTGFHDNRKNMYSDEDKHTAIAYRLIHENLPRFIDNLQILTTIKQK
HSALYDQIINELTASGLDVSLASHLDGYHKLLTQEGITAYNRIIGEVNGYTNKHNQICHKSERIAKLRPLHKQILS
DGMGVSFLPSKFADDSEMCQAVNEFYRHYTDVFAKVQSLFDGFDDHQKDGIYVEHKNLNELSKQAFGDFA
LLGRVLDGYYVDVVNPEFNERFAKAKTDNAKAKLTKEKDKFIKGVHSLASLEQAIEHHTARHDDESVQAGKL
GQYFKHGLAGVDNPIQKIHNNHSTIKGFLERERPAGERALPKIKSGKNPEMTQLRQLKELLDNALNVAHFAKL
LTTKTTLDNQDGNFYGEFGVLYDELAKIPTLYNKVRDYLSQKPFSTEKYKLNFGNPTLLNGWDLNKEKDNFGV
ILQKDGCYYLALLDKAHKKVFDNAPNTGKNVYQKMVYKLLPGPNKMLPKVFFAKSNLDYYNPSAELLDKYAK
GTHKKGDNFNLKDCHALIDFFKAGINKHPEWQHFGFKFSPTSSYRDLSDFYREVEPQGYQVKFVDINADYIDE
LVEQGKLYLFQIYNKDFSPKAHGKPNLHTLYFKALFSEDNLADPIYKLNGEAQIFYRKASLDMNETTIHRAGEV
LENKNPDNPKKRQFVYDIIKDKRYTQDKFMLHVPITMNFGVQGMTIKEFNKKVNQSIQQYDEVNVIGIDRGE
RHLLYLTVINSKGEILEQRSLNDITTASANGTQVTTPYHKILDKREIERLNARVGWGEIETIKELKSGYLSHVVHQ
INQLMLKYNAIVVLEDLNFGFKRGRFKVEKQIYQNFENALIKKLNHLVLKDKADDEIGSYKNALQLTNNFTDLK
SIGKQTGFLFYVPAWNTSKIDPETGFVDLLKPRYENIAQSQAFFGKFDKICYNTDKGYFEFHIDYAKFTDKAKN
SRQKWAICSHGDKRYVYDKTANQNKGAAKGINVNDELKSLFARYHINDKQPNLVMDICQNNDKEFHKSLM
CLLKTLLALRYSNASSDEDFILSPVANDEGVFFNSALADDTQPQNADANGAYHIALKGLWLLNELKNSDDLNK
VKLAIDNQTWLNFAQNR (SEQ ID NO: 6)

FIG. 1D

Moraxella bovoculi AAX11_00205 (Mb3Cas12a)
MGIHGVPAALFQDFTHLYPLSKTVRFELKPIGKTLEHIHAKNFLNQDETMADMYQKVKAILDDYHRDFIADM
MGEVKLTKLAEFYDVYLKFRKNPKDDGLQKQLKDLQAVLRKEIVKPIGNGGKYKAGYDRLFGAKLFKDGKELG
DLAKFVIAQEGESSPKLAHLAHFEKFSTYFTGFHDNRKNMYSDEDKHTAIAYRLIHENLPRFIDNLQILATIKQK
HSALYDQIINELTASGLDVSLASHLDGYHKLLTQEGITAYNTLLGGISGEAGSRKIQGINELINSHHNQHCHKSE
RIAKLRPLHKQILSDGMGVSFLPSKFADDSEVCQAVNEFYRHYADVFAKVQSLFDGFDDYQKDGIYVEYKNL
NELSKQAFGDFALLGRVLDGYYVDVVNPEFNERFAKAKTDNAKAKLTKEKDKFIKGVHSLASLEQAIEHYTAR
HDDESVQAGKLGQYFKHGLAGVDNPIQKIHNNHSTIKGFLERERPAGERALPKIKSDKSPEIRQLKELLDNALN
VAHFAKLLTTKTTLHNQDGNFYGEFGALYDELAKIATLYNKVRDYLSQKPFSTEKYKLNFGNPTLLNGWDLNK
EKDNFGVILQKDGCYYLALLDKAHKKVFDNAPNTGKSVYQKMIYKLLPGPNKMLPKVFFAKSNLDYYNPSAE
LLDKYAQGTHKKGDNFNLKDCHALIDFFKAGINKHPEWQHFGFKFSPTSSYQDLSDFYREVEPQGYQVKFVD
INADYINELVEQGQLYLFQIYNKDFSPKAHGKPNLHTLYFKALFSEDNLVNPIYKLNGEAEIFYRKASLDMNETT
IHRAGEVLENKNPDNPKKRQFVYDIIKDKRYTQDKFMLHVPITMNFGVQGMTIKEFNKKVNQSIQQYDEVN
VIGIDRGERHLLYLTVINSKGEILEQRSLNDITTASANGTQMTTPYHKILDKREIERLNARVGWGEIETIKELKSG
YLSHVVHQISQLMLKYNAIVVLEDLNFGFKRGRFKVEKQIYQNFENALIKKLNHLVLKDKADDEIGSYKNALQL
TNNFTDLKSIGKQTGFLFYVPAWNTSKIDPETGFVDLLKPRYENIAQSQAFFGKFDKICYNADRGYFEFHIDYA
KFNDKAKNSRQIWKICSHGDKRYVYDKTANQNKGATIGVNVNDELKSLFTRYHINDKQPNLVMDICQNNDK
EFHKSLMYLLKTLLALRYSNASSDEDFILSPVANDEGVFFNSALADDTQPQNADANGAYHIALKGLWLLNELK
NSDDLNKVKLAIDNQTWLNFAQNR (SEQ ID NO: 7)

Thiomicrospira sp. XS5 (TsCas12a)
MGIHGVPAATKTFDSEFFNLYSLQKTVRFELKPVGETASFVEDFKNEGLKRVVSEDERRAVDYQKVKEIIDDYH
RDFIEESLNYFPEQVSKDALEQAFHLYQKLKAAKVEEREKALKEWEALQKKLREKVVKCFSDSNKARFSRIDKK
ELIKEDLINWLVAQNREDDIPTVETFNNFTTYFTGFHENRKNIYSKDDHATAISFRLIHENLPKFFDNVISFNKLK
EGFPELKFDKVKEDLEVDYDLKHAFEIEYFVNFVTQAGIDQYNYLLGGKTLEDGTKKQGMNEQINLFKQQQT
RDKARQIPKLIPLFKQILSERTESQSFIPKQFESDQELFDSLQKLHNNCQDKFTVLQQAILGLAEADLKKVFIKTS
DLNALSNTIFGNYSVFSDALNLYKESLKTKKAQEAFEKLPAHSIHDLIQYLEQFNSSLDAEKQQSTDTVLNYFIKT
DELYSRFIKSTSEAFTQVQPLFELEALSSKRRPPESEDEGAKGQEGFEQIKRIKAYLDTLMEAVHFAKPLYLVKG
RKMIEGLDKDQSFYEAFEMAYQELESLIIPIYNKARSYLSRKPFADKFKINFDNNTLLSGWDANKETANASILF
KKDGLYYLGIMPKGKTFLFDYFVSSEDSEKLKQRRQKTAEEALAQDGESYFEKIRYKLLPGASKMLPKVFFSNK
NIGFYNPSDDILRIRNTASHTKNGTPQKGHSKVEFNLNDCHKMIDFFKSSIQKHPEWGSFGFTFSDTSDFED
MSAFYREVENQGYVISFDKIKETYIQSQVEQGNLYLFQIYNKDFSPYSKGKPNLHTLYWKALFEEANLNNVVA
KLNGEAEIFFRRHSIKASDKVVHPANQAIDNKNPHTEKTQSTFEYDLVKDKRYTQDKFFFHVPISLNFKAQGVS
KFNDKVNGFLKGNPDVNIIGIDRGERHLLYFTVVNQKGEILVQESLNTLMSDKGHVNDYQQKLDKKEQERDA
ARKSWTTVENIKELKEGYLSHVVHKLAHLIIKYNAIVCLEDLNFGFKRGRFKVEKQVYQKFEKALIDKLNYLVFK
EKELGEVGHYLTAYQLTAPFESFKKLGKQSGILFYVPADYTSKIDPTTGFVNFLDLRYQSVEKAKQLLSDFNAIR
FNSVQNYFEFEIDYKKLTPKRKVGTQSKWVICTYGDVRYQNRRNQKGHWETEEVNVTEKLKALFASDSKTTT
VIDYANDDNLIDVILEQDKASFFKELLWLLKLTMTLRHSKIKSEDDFILSPVKNEQGEFYDSRKAGEVWPKDAD
ANGAYHIALKGLWNLQQINQWEKGKTLNLAIKNQDWFSFIQEKPYQE (SEQ ID NO: 8)

FIG. 1E

Butyrivibrio sp. NC3005 (BsCas12a)
MGIHGVPAAYYQNLTKKYPVSKTIRNELIPIGKTLENIRKNNILESDVKRKQDYEHVKGIMDEYHKQLINEALD
NYMLPSLNQAAEIYLKKHVDVEDREEFKKTQDLLRREVTGRLKEHENYTKIGKKDILDLLEKLPSISEEDYNALE
SFRNFYTYFTSYNKVRENLYSDEEKSSTVAYRLINENLPKFLDNIKSYAFVKAAGVLADCIEEEEQDALFMVETF
NMTLTQEGIDMYNYQIGKVNSAINLYNQKNHKVEEFKKIPKMKVLYKQILSDREEVFIGEFKDDETLLSSIGAY
GNVLMTYLKSEKINIFFDALRESEGKNVYVKNDLSKTTMSNIVFGSWSAFDELLNQEYDLANENKKKDDKYFE
KRQKELKKNKSYTLEQMSNLSKEDISPIENYIERISEDIEKICIYNGEFEKIVVNEHDSSRKLSKNIKAVKVIKDYLD
SIKELEHDIKLINGSGQELEKNLVVYVGQEEALEQLRPVDSLYNLTRNYLTKKPFSTEKVKLNFNKSTLLNGWDK
NKETDNLGILFFKDGKYYLGIMNTTANKAFVNPPAAKTENVFKKVDYKLLPGSNKMLPKVFFAKSNIGYYNPS
TELYSNYKKGTHKKGPSFSIDDCHNLIDFFKESIKKHEDWSKFGFEFSDTADYRDISEFYREVEKQGYKLTFTDID
ESYINDLIEKNELYLFQIYNKDFSEYSKGKLNLHTLYFMMLFDQRNLDNVVYKLNGEAEVFYRPASIAENELVIH
KAGEGIKNKNPNRAKVKETSTFSYDIVKDKRYSKYKFTLHIPITMNFGVDEVRRFNDVINNALRTDDVNVIGI
DRGERNLLYVVVINSEGKILEQISLNSIINKEYDIETNYHALLDEREDDRNKARKDWNTIENIKELKTGYLSQVV
NVVAKLVLKYNAIICLEDLNFGFKRGRQKVEKQVYQKFEKMLIEKLNYLVIDKSREQVSPEKMGGALNALQLT
SKFKSFAELGKQSGIIYYVPAYLTSKIDPTTGFVNLFYIKYENIEKAKQFFDGFDFIRFNKKDDMFEFSFDYKSFTQ
KACGIRSKWIVYTNGERIIKYPNPEKNNLFDEKVINVTDEIKGLFKQYRIPYENGEDIKEIIISKAEADFYKRLFRLL
HQTLQMRNSTSDGTRDYIISPVKNDRGEFFCSEFSEGTMPKDADANGAYNIARKGLWVLEQIRQKDEGEKV
NLSMTNAEWLKYAQLHLL (SEQ ID NO: 9)

AacCas12b
MAVKSIKVKLRLDDMPEIRAGLWKLHKEVNAGVRYYTEWLSLLRQENLYRRSPNGDGEQECDKTAEECKAE
LLERLRARQVENGHRGPAGSDDELLQLARQLYELLVPQAIGAKGDAQQIARKFLSPLADKDAVGGLGIAKAG
NKPRWVRMREAGEPGWEEEKEKAETRKSADRTADVLRALADFGLKPLMRVYTDSEMSSVEWKPLRKGQA
VRTWDRDMFQQAIERMMSWESWNQRVGQEYAKLVEQKNRFEQKNFVGQEHLVHLNQLQQDMKEAS
PGLESKEQTAHYVTGRALRGSDKVFEKWGKLAPDAPFDLYDAEIKNVQRRNTRRFGSHDLFAKLAEPEYQAL
WREDASFLTRYAVYNSILRKLNHAKMFATFTLPDATAHPIWTRFDKLGGNLHQYTFLFNEFGERRHAIRFHKL
LKVENGVAREVDDVTVPISMSEQLDNLLPRDPNEPIALYFRDYGAEQHFTGEFGGAKIQCRRDQLAHMHRR
RGARDVYLNVSVRVQSQSEARGERRPPYAAVFRLVGDNHRAFVHFDKLSDYLAEHPDDGKLGSEGLLSGLR
VMSVDLGLRTSASISVFRVARKDELKPNSKGRVPFFFPIKGNDNLVAVHERSQLLKLPGETESKDLRAIREERQ
RTLRQLRTQLAYLRLLVRCGSEDVGRRERSWAKLIEQPVDAANHMTPDWREAFENELQKLKSLHGICSDKE
WMDAVYESVRRVWRHMGKQVRDWRKDVRSGERPKIRGYAKDVVGGNSIEQIEYLERQYKFLKSWSFFGK
VSGQVIRAEKGSRFAITLREHIDHAKEDRLKKLADRIIMEALGYVYALDERGKGKWVAKYPPCQLILLEELSEYQ
FNNDRPPSENNQLMQWSHRGVFQELINQAQVHDLLVGTMYAAFSSRFDARTGAPGIRCRRVPARCTQEH
NPEPFPWWLNKFVVEHTLDACPLRADDLIPTGEGEIFVSPFSAEEGDFHQIHADLNAAQNLQQRLWSDFDIS
QIRLRCDWGEVDGELVLIPRLTGKRTADSYSNKVFYTNTGVTYYERERGKKRRKVFAQEKLSEEEAELLVEADE
AREKSVVLMRDPSGIINRGNWTRQKEFWSMVNQRIEGYLVKQIRSRVPLQDSACENTGDI
(SEQ ID NO: 10)

FIG. 2 crRNA repeat sequences

LbCas12a crRNA:
5' AAUUUCUACUAAGUGUAGAU [spacer] 3' (SEQ ID NO: 11)

AsCas12a crRNA:
5' AAUUUCUACUCUUGUAGAU [spacer] 3' (SEQ ID NO: 12)

FnCas12a crRNA:
5' AAUUUCUACUGUUGUAGAU [spacer] 3' (SEQ ID NO: 13)

PmCas12a crRNA:
5' AAUUUCUACUAUUGUAGAU [spacer] 3' (SEQ ID NO: 14)

MbCas12a/Mb2Cas12a/Mb3Cas12a crRNA:
5' AAUUUCUACUGUUUGUAGAU [spacer] 3' (SEQ ID NO: 15)

TsCas12a crRNA
5' AAUUUCUACUGUUGUAGAU [spacer] 3' (SEQ ID NO: 16)

BsCas12a crRNA
5' AAUUUCUACUAUUGUAGAU [spacer] 3' (SEQ ID NO: 17)

AacCas12b single guide RNA (sgRNA)
5' GUCUAGAGGACAGAAUUUUUCAACGGGUGUGCCAAUGGCCACUUUCCAGGUGGCAAAGCCCGUUGAGCUUCUCAAAUCUGAGAAGUGGCAC [spacer] 3' (SEQ ID NO: 19)

PAMs

LbCas12a PAM: 5'-TTTN-3'

AsCas12a PAM: 5'-TTTN-3'

FnCas12a PAM: 5'-TTN-3'

PmCas12a PAM: 5'-TTN-3'

MbCas12a/Mb2Cas12a/Mb3Cas12a PAM: 5'-TTN-3'

TsCas12a PAM: 5'-TTN-3'

BsCas12a PAM: 5'-TTN-3'

AacCas12b PAM: 5'-TTN-3'

FIG. 5B

| | | |
|---|---|---|
| For pairing with Cpf1new_PAM1a_NTS | | GCTTGTGGCCGTTTACGTCGCCGTCCAGCTCGACCAGGATGGGCACCACCCCGGC (SEQ ID NO:41) |
| LbCpf1_aT0x5 | | TAAACGGCCACAAGC (SEQ ID NO:177) |
| LbCpf1_aT1x5 | PAM1a_TS | CGACGTAAACGGCCACAAGC (SEQ ID NO:65) |
| LbCpf1_aT2x5 | PAM1a_TS | GACGGCGACGTAAACGGCCACAAGC (SEQ ID NO:66) |
| LbCpf1_aT3x5 | PAM1a_TS | AGCTGGACGGCGACGTAAACGGCCACAAGC (SEQ ID NO:67) |
| LbCpf1_aT4x5 | PAM1a_TS | GGTCGAGCTGGACGGCGACGTAAACGGCCACAAGC (SEQ ID NO:68) |
| LbCpf1_aT5x5 | PAM1a_TS | ATCCTGGTCGAGCTGGACGGCGACGTAAACGGCCACAAGC (SEQ ID NO:69) |
| For pairing with Cpf1new_PAM1a_TS | | GCCGGGGTGGTGCCCATCCTGGTCGAGCTGGACGGCGACGTAAACGGCCACAAGC (SEQ ID NO:42) |
| LbCpf1_aNT0x5 | | GCTTGTGGCCGTTTA (SEQ ID NO:178) |
| LbCpf1_aNT1x5 | PAM1a_NTS | GCTTGTGGCCGTTTACGTCG (SEQ ID NO:70) |
| LbCpf1_aNT2x5 | PAM1a_NTS | GCTTGTGGCCGTTTACGTCGCCGTC (SEQ ID NO:71) |
| LbCpf1_aNT3x5 | PAM1a_NTS | GCTTGTGGCCGTTTACGTCGCCGTCCAGCT (SEQ ID NO:72) |
| LbCpf1_aNT4x5 | PAM1a_NTS | GCTTGTGGCCGTTTACGTCGCCGTCCAGCTCGACC (SEQ ID NO:73) |
| LbCpf1_aNT5x5 | PAM1a_NTS | GCTTGTGGCCGTTTACGTCGCCGTCCAGCTCGACCAGGAT (SEQ ID NO:74) |

FIG. 7
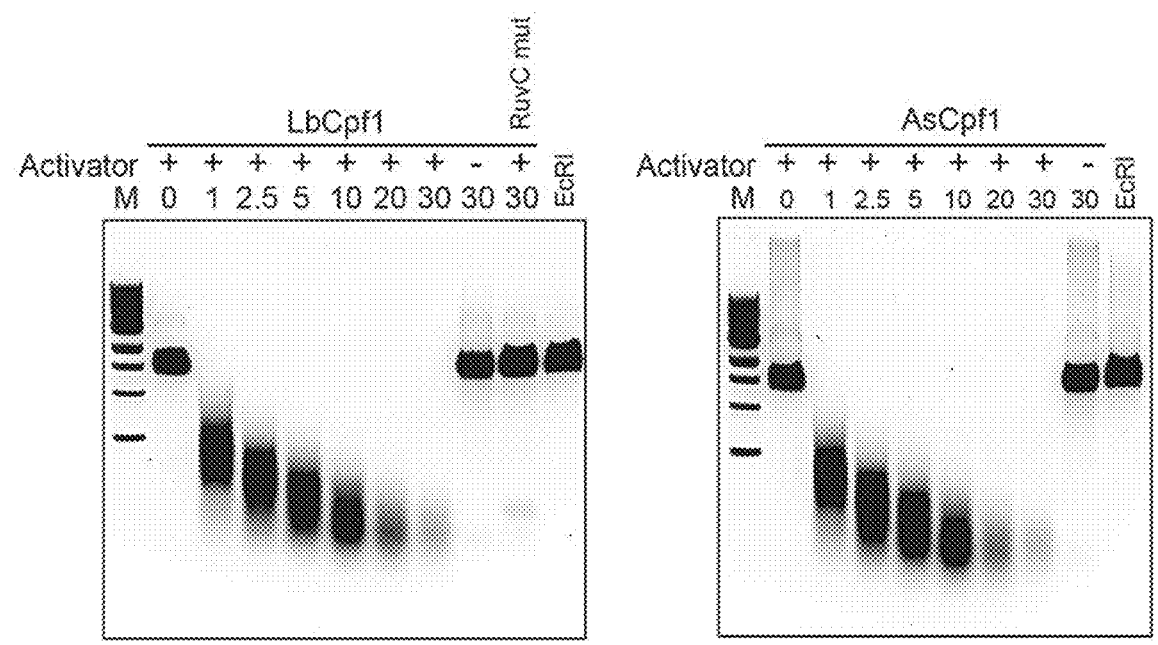
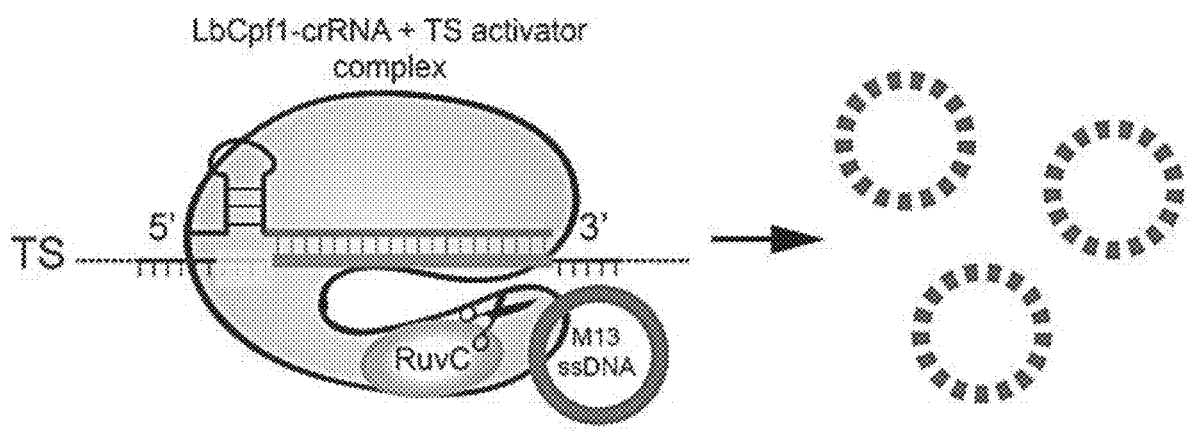

FIG. 9A
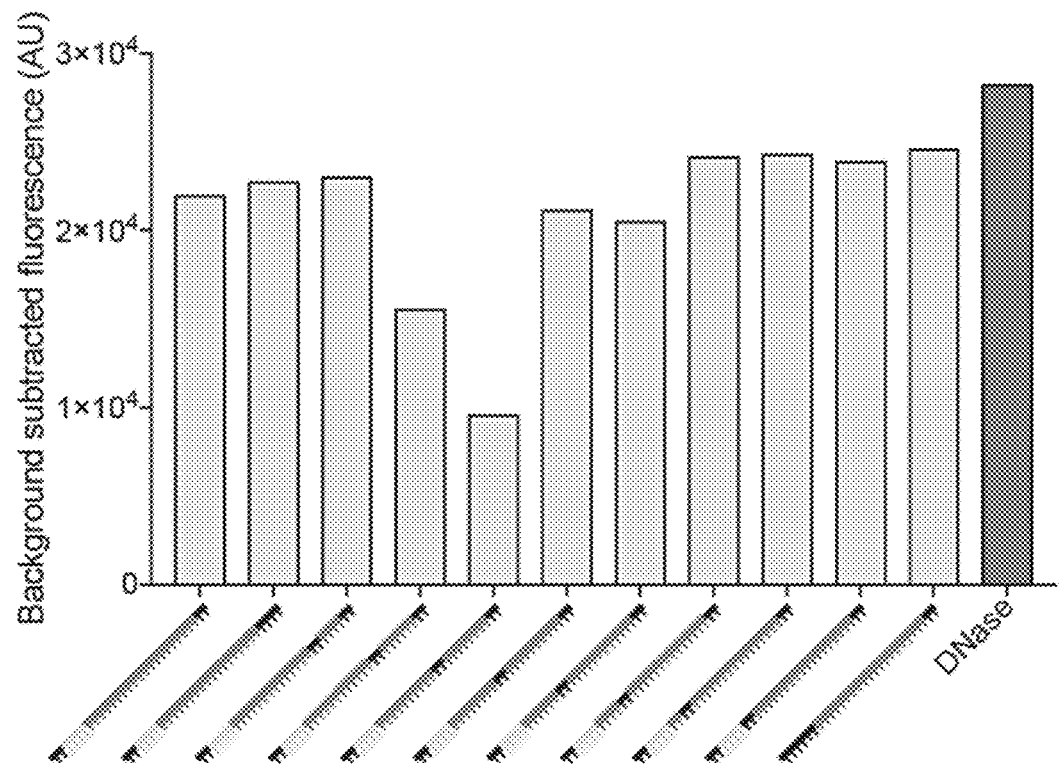
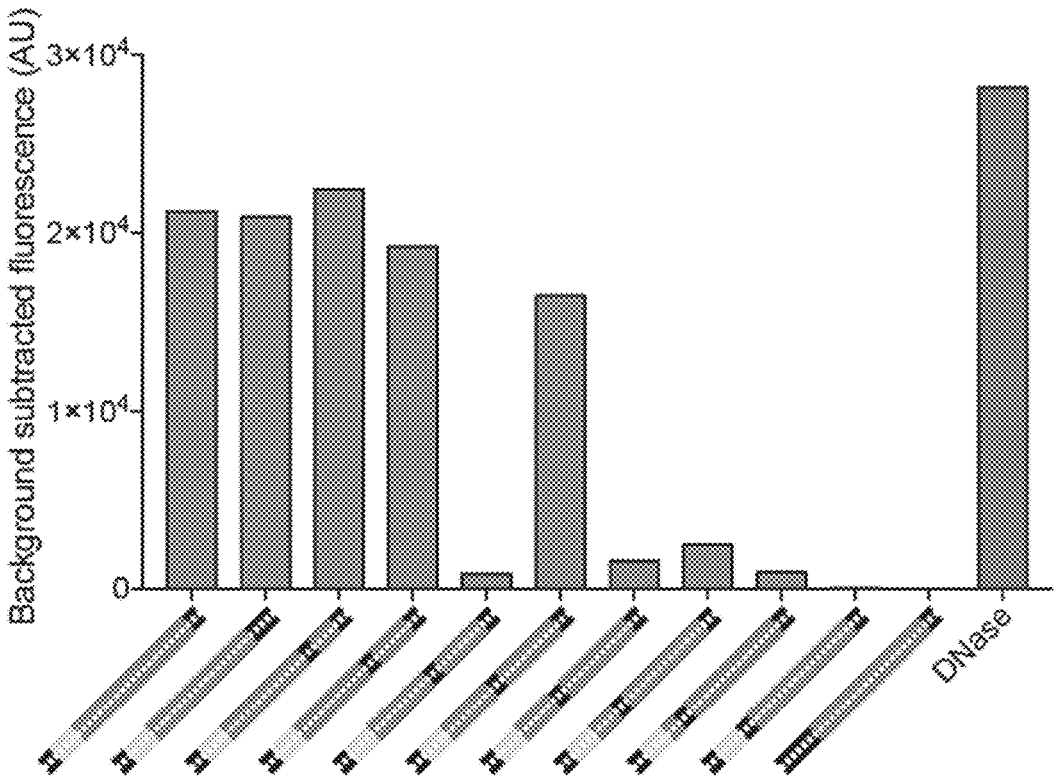

Clinically relevant DNA viruses:

- Double-stranded DNA:
  - Papovavirus (HPV)
  - Hepadnavirus (HBV)
  - Herpesvirus (HSV)
  - Adenovirus
  - Poxvirus (smallpox)

- Single-stranded DNA:
  - Parvovirus (AAV)

63% nucleotide sequence identity (SEQ ID NO:163)
HPV16  6245 ACTGGCTTTGGTGCTATGGACTTTACTACATTACAGGCTAACAAAAGTGA 6294
            ||||| | |||||| |||||||||||| |||||| || | || ||| ||||
HPV18  6219 ACTGGATATGGTGCCATGGACTTTAGTACATTGCAAGATACTAAATGTGA 6268
(SEQ ID NO:164)

FIG. 11B
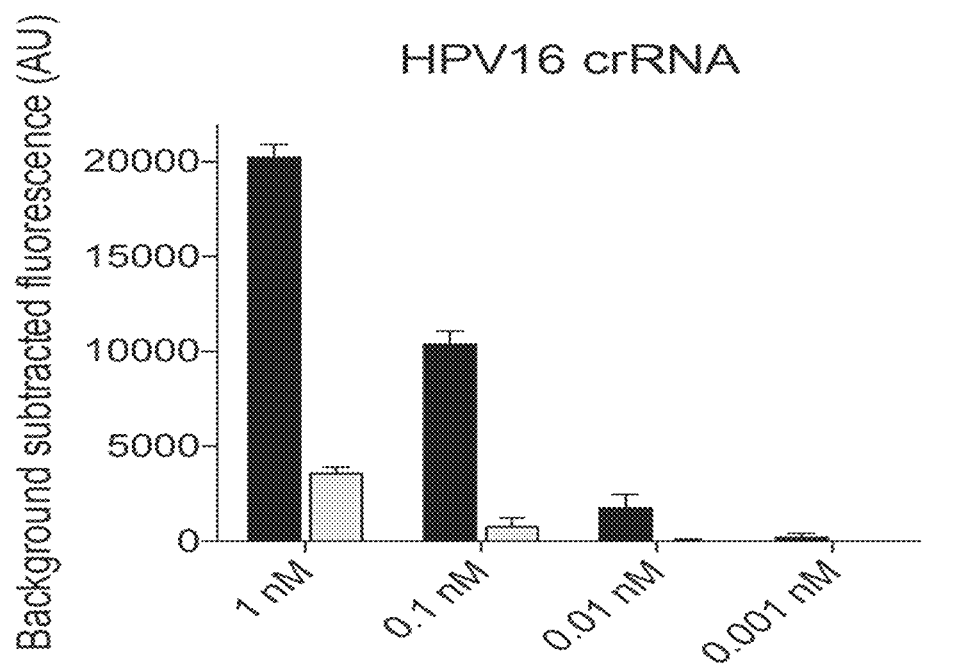
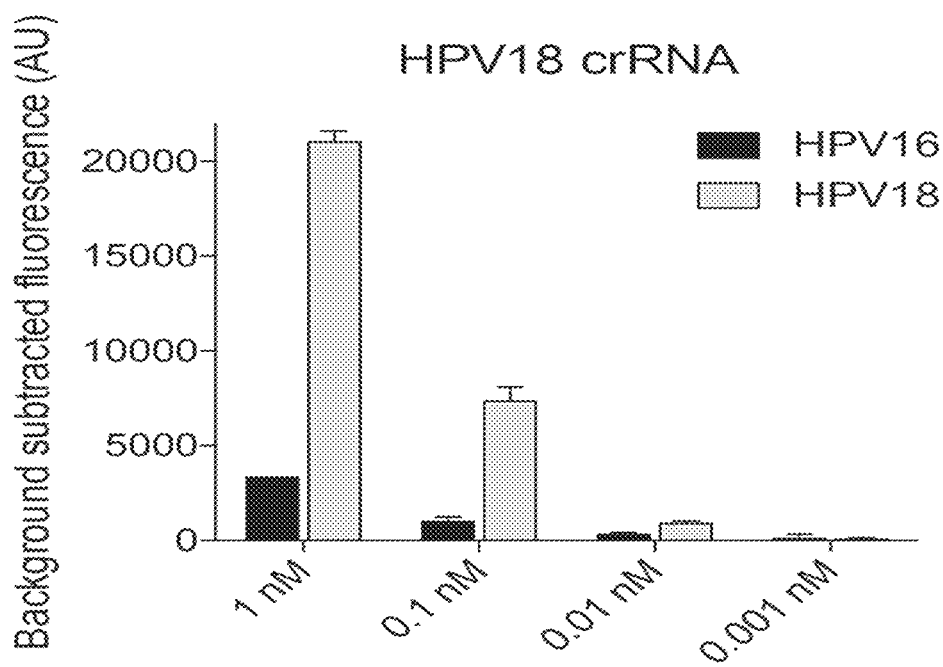

FIG. 13A
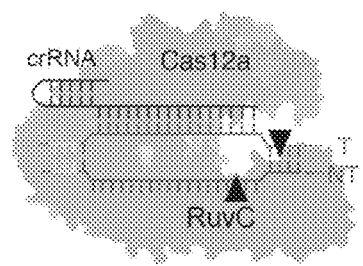
FIG. 13B
FIG. 13C
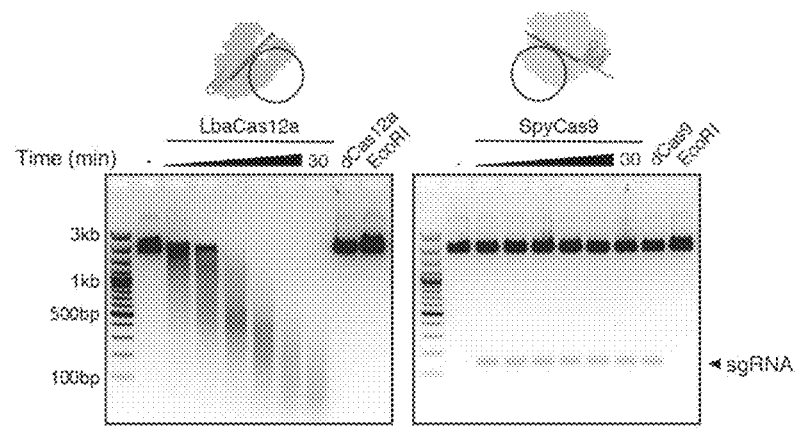
FIG 14A
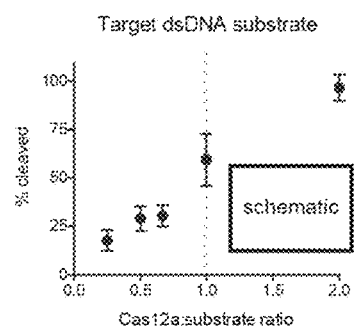
FIG. 14B
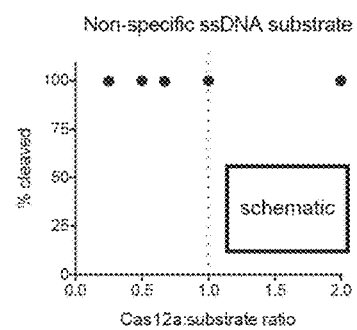
FIG. 14C
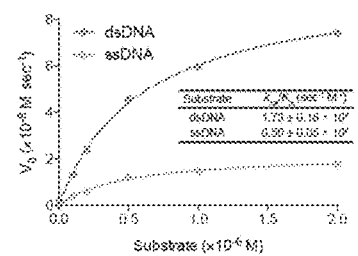

FIG. 15A  FIG. 15B  FIG. 15C
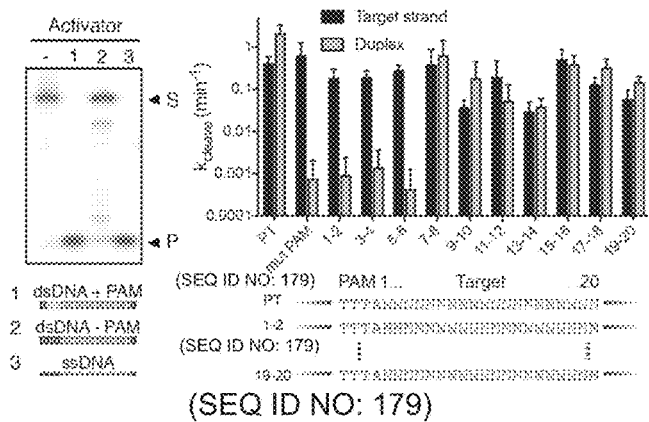
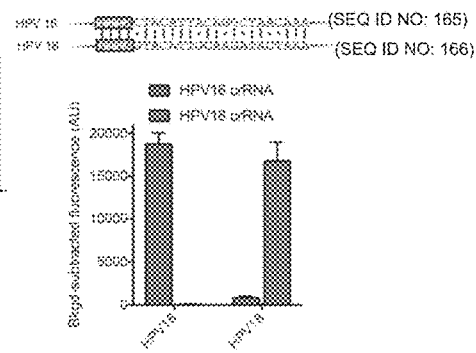
FIG. 16A
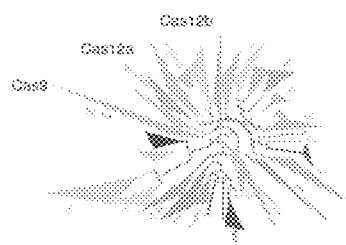
FIG. 16B
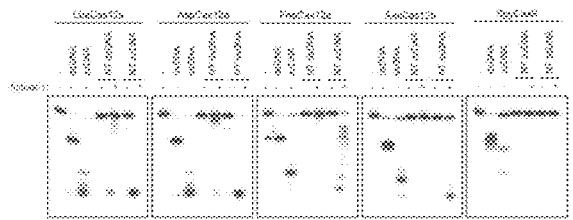
FIG. 16C
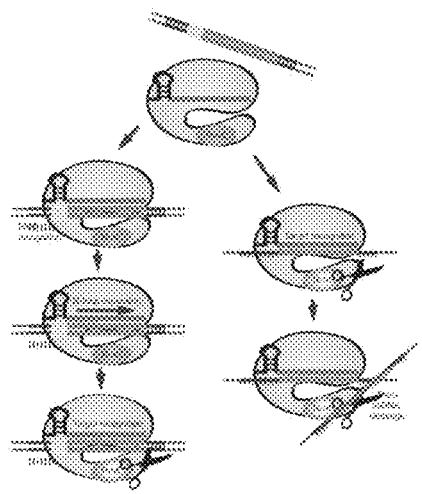

FIG. 27A
FIG. 27B
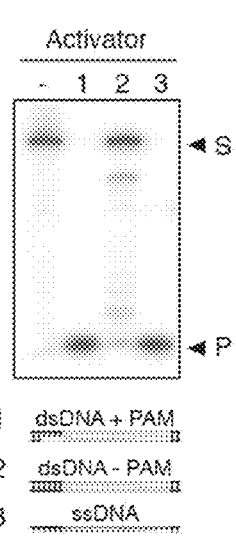
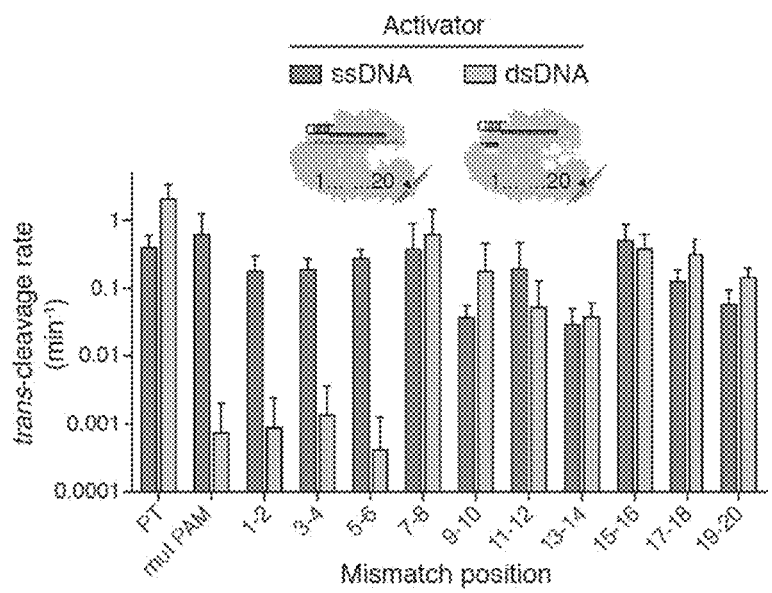
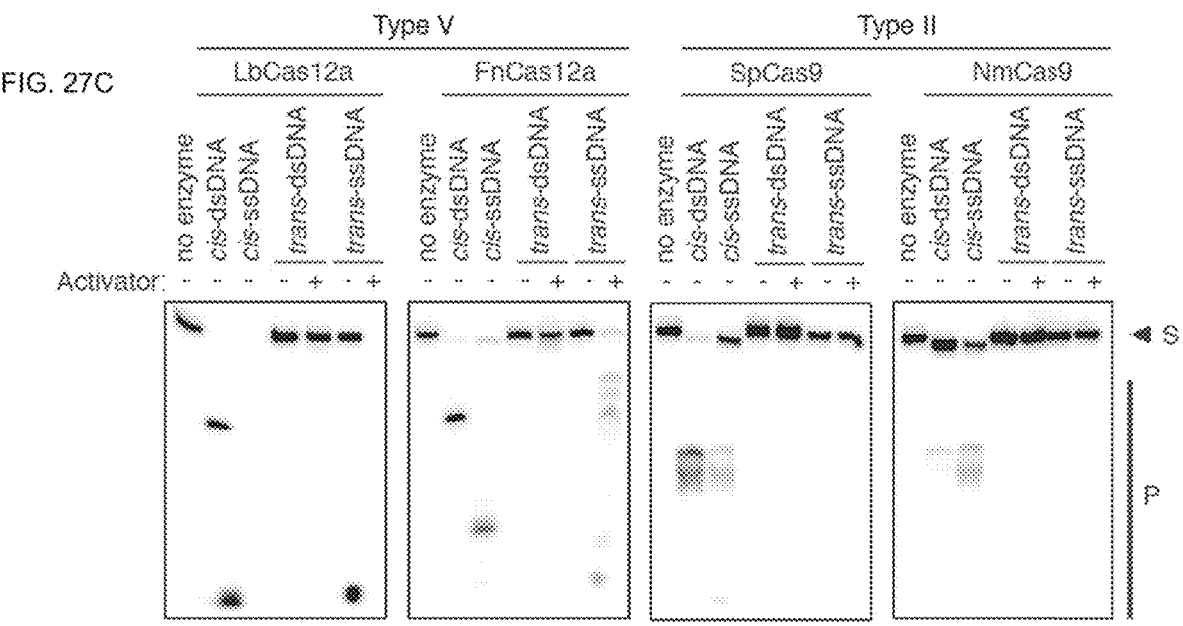
FIG. 27C (SEQ ID NO: 173) HPV16
(SEQ ID NO: 174) HPV18

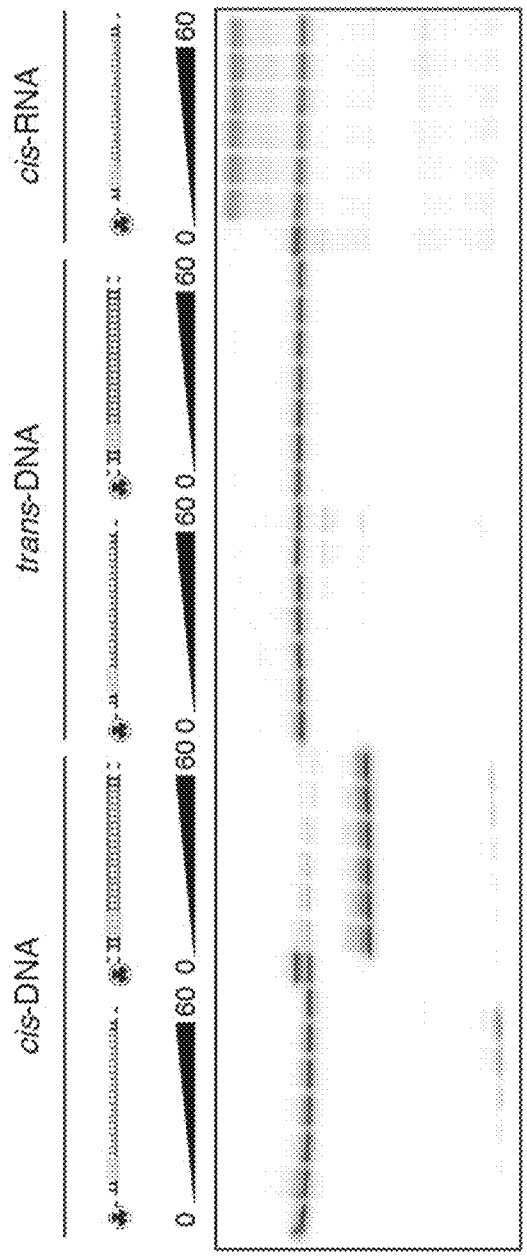
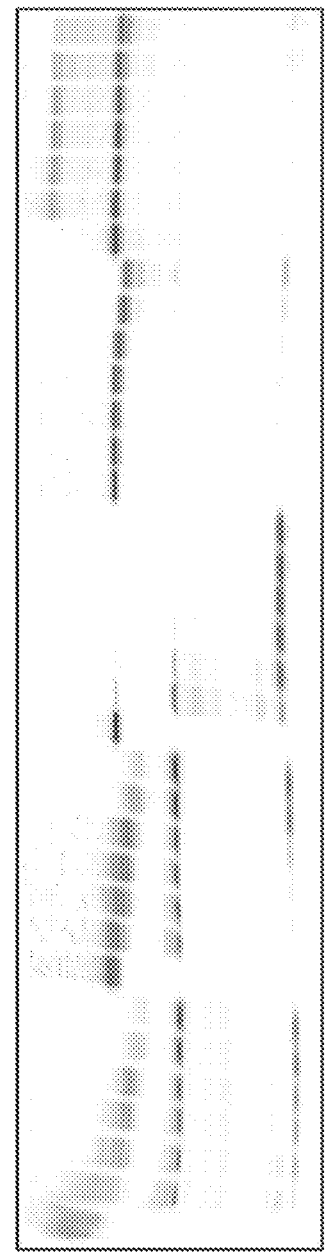
FIG. 34A
FIG. 34B LbCas12a-crRNA complex
FIG. 34C LbCas12a-crRNA + TS activator complex
LbCas12a-crRNA + excess TS activator complex FIG. 36A
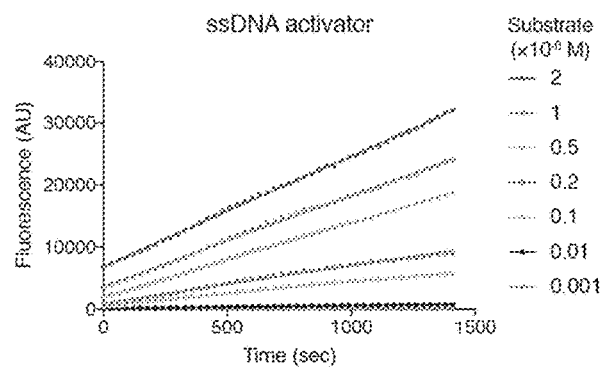
FIG. 36B
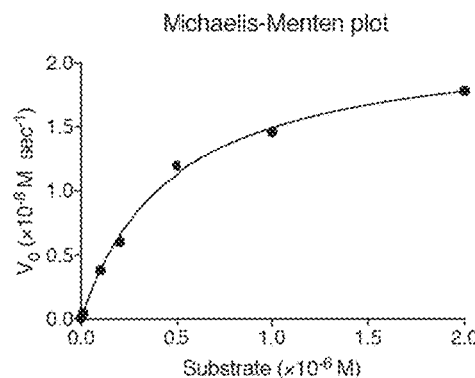
FIG. 36C
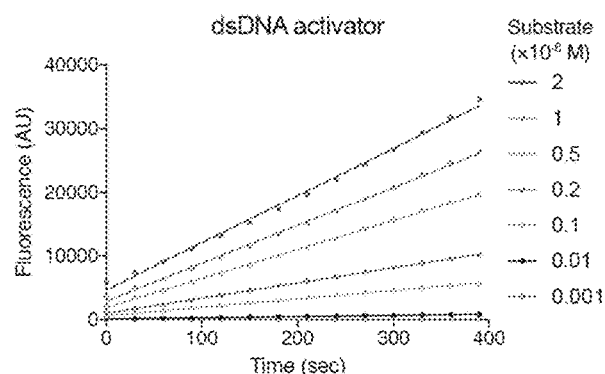
FIG. 36D
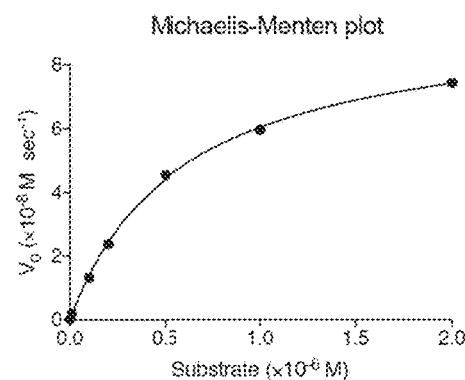
FIG. 36E
| Activator | $k_{cat}$ (sec$^{-1}$) | $K_m$ (M$^{-1}$) | $k_{cat}/K_m$ (sec$^{-1}$ M$^{-1}$) |
|---|---|---|---|
| ssDNA | $2.50 \pm 0.30 \times 10^2$ | $4.94 \pm 0.16 \times 10^{-7}$ | $5.10 \pm 0.47 \times 10^8$ |
| dsDNA | $1.25 \pm 0.27 \times 10^3$ | $7.25 \pm 1.74 \times 10^{-7}$ | $1.73 \pm 0.18 \times 10^9$ |

FIG. 39A
HPV 16 ..........TTTACTACATTACAGGCTAACAAA.......... (SEQ ID NO: 173)
HPV 18 ..........TTTAGTACATTGCAAGATACTAAA.......... (SEQ ID NO: 174)
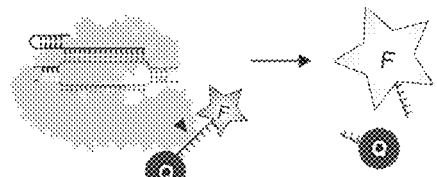
FIG. 39B
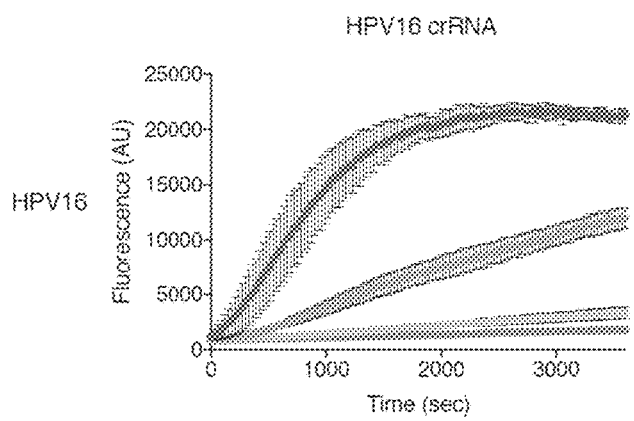
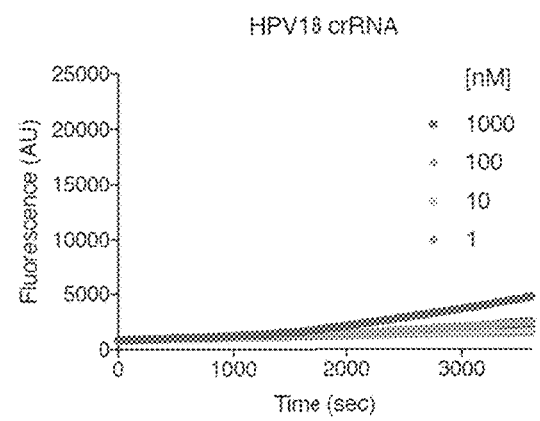
FIG. 39D
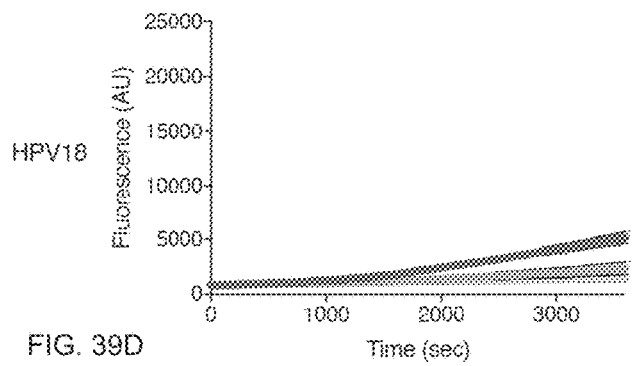
FIG. 39E
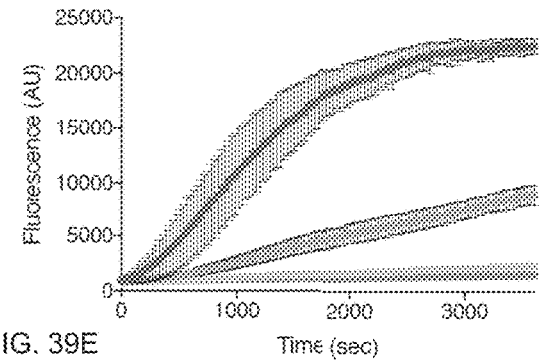
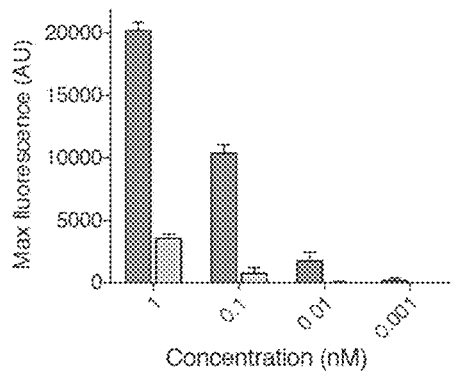
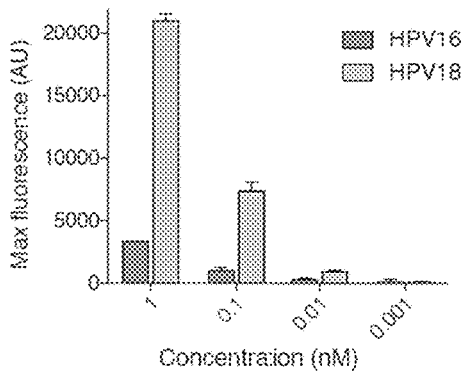

| # | 16 | 18 | HPV types |
|---|---|---|---|
| 1 | 2 | 0 | 16 |
| 2 | 0 | 0 | - |
| 3 | 0 | 0 | 32/42 |
| 4 | 0 | 1 | 18 |
| 5 | 2 | 0 | 16 90/106 |
| 6 | 0 | 0 | 35 |
| 7 | 1 | 2 | 16 18 |
| 8 | 0 | 0 | 31 35 |
| 9 | 0 | 0 | - |
| 10 | 0 | 4 | 6/11 18 26/69 58 70 84 Mix1 |
| 11 | 4 | 0 | 6/11 16 31 33 51 59 82+ 84 90/106 102/89 Mix1 |
| 12 | 0 | 0 | 56 Mix1 |
| 13 | 0 | 0 | - |
| 14 | 3 | 3 | 16 18 53 56 |
| 15 | 0 | 0 | - |
| 16 | 0 | 2 | 6/11 18 30 51 53 70 |
| 17 | 4 | 4 | 16 18 39 53 56 68 |
| 18 | 0 | 0 | - |
| 19 | 0 | 0 | 31 Mix1 |
| 20 | 4 | 0 | 16 33 83 102/89 |
| 21 | 0 | 0 | 6/11 |
| 22 | 0 | 4 | 18 33 58 |
| 23 | 0 | 0 | - |
| 24 | 0 | 1 | 6/11 18 |
| 25 | 3 | 0 | 6/11 16 39 52 62 |

FIG. 43A
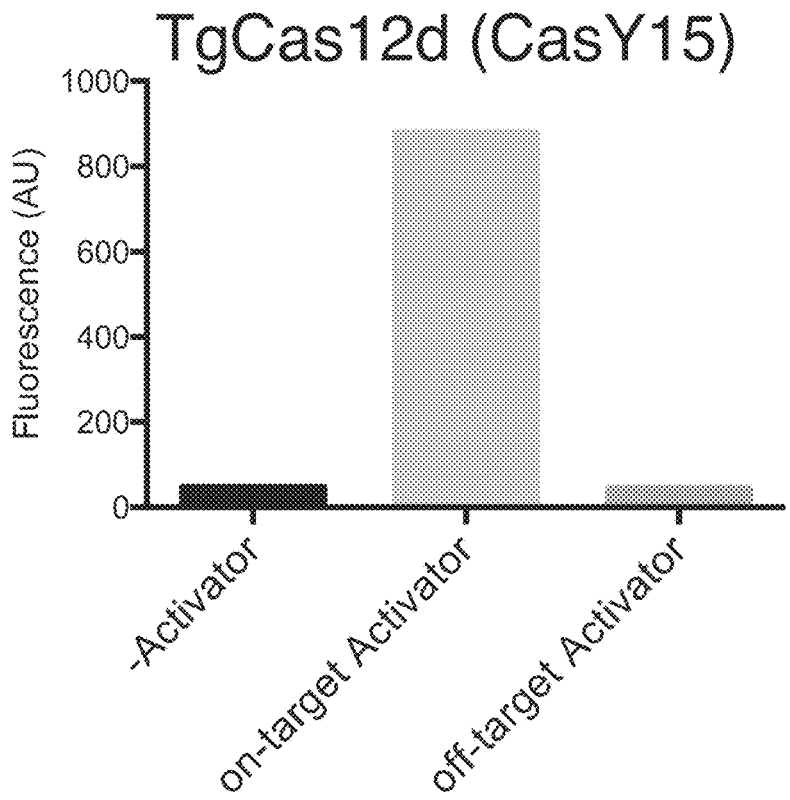
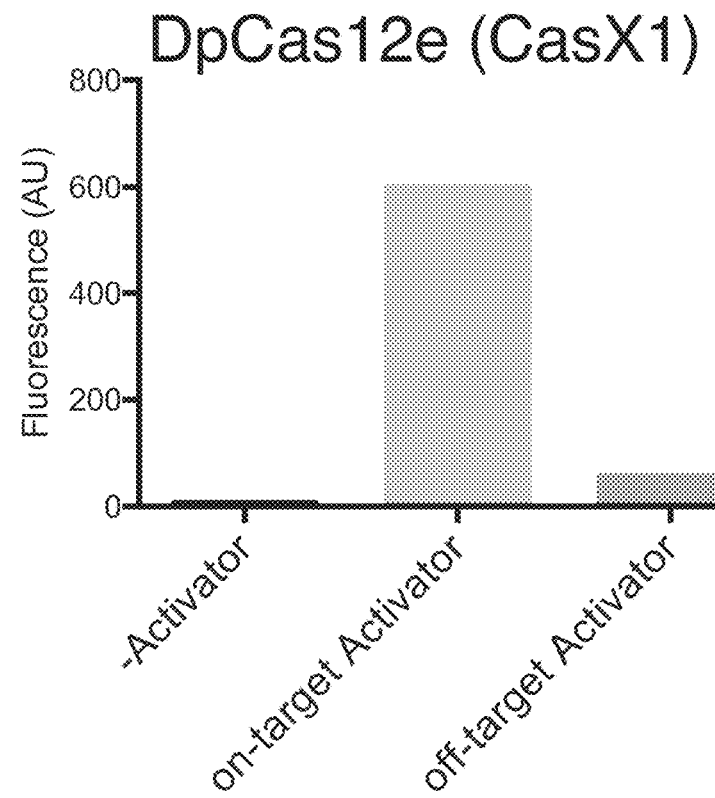

TYPE V CRISPR/CAS EFFECTOR PROTEINS FOR CLEAVING SSDNAS AND DETECTING TARGET DNAS

CROSS-REFERENCE

This application is a continuation of U.S. patent application Ser. No. 16/262,257, filed Jan. 30, 2019, which is a continuation of U.S. patent application Ser. No. 15/897,089, filed Feb. 24, 2018, now U.S. Pat. No. 10,253,365, which claims the benefit of U.S. Provisional Patent Application No. 62/590,106, filed Nov. 22, 2017, and U.S. Provisional Patent Application No. 62/626,593, filed Feb. 5, 2018, which applications are incorporated herein by reference in their entirety.

STATEMENT REGARDING FEDERALLY SPONSORED RESEARCH

This invention was made with government support under Grant No. 1244557 awarded by the National Science Foundation. The government has certain rights in the invention.

INTRODUCTION

Bacterial adaptive immune systems employ CRISPRs (clustered regularly interspaced short palindromic repeats) and CRISPR-associated (Cas) proteins for RNA-guided nucleic acid cleavage. The CRISPR-Cas systems thereby confer adaptive immunity in bacteria and archaea via RNA-guided nucleic acid interference. To provide anti-viral immunity, processed CRISPR array transcripts (crRNAs) assemble with Cas protein-containing surveillance complexes that recognize nucleic acids bearing sequence complementarity to the virus derived segment of the crRNAs, known as the spacer.

Class 2 CRISPR-Cas systems are streamlined versions in which a single Cas protein (an effector protein, e.g., a type V Cas effector protein such as Cpf1) bound to RNA is responsible for binding to and cleavage of a targeted sequence. The programmable nature of these minimal systems has facilitated their use as a versatile technology that continues to revolutionize the field of genome manipulation.

SUMMARY

Class 2 CRISPR-Cas systems (e.g., type V CRISPR/Cas systems such as Cas12 family systems) are characterized by effector modules that include a single effector protein. For example, in a type V CRISPR/Cas system, the effector protein—a CRISPR/Cas endonuclease (e.g., a Cas12a protein)—interacts with (binds to) a corresponding guide RNA (e.g., a Cas12a guide RNA) to form a ribonucleoprotein (RNP) complex that is targeted to a particular site in a target nucleic acid via base pairing between the guide RNA and a target sequence within the target nucleic acid molecule.

The present disclosure provides compositions and methods that take advantage of the discovery that type V CRISPR/Cas proteins (e.g., Cas 12 proteins such as Cpf1 (Cas12a) and C2c1 (Cas12b)) can promiscuously cleave non-targeted single stranded DNA (ssDNA) once activated by detection of a target DNA. Once a type V CRISPR/Cas effector protein (e.g., a Cas12 protein such as Cas12a, Cas12b, Cas12c, Cas12d, Cas12e) is activated by a guide RNA, which occurs when a sample includes a target DNA to which the guide RNA hybridizes (i.e., the sample includes the targeted DNA), the protein becomes a nuclease that promiscuously cleaves ssDNAs (i.e., non-target ssDNAs, i.e., ssDNAs to which the guide sequence of the guide RNA does not hybridize). Thus, when the targeted DNA (double or single stranded) is present in the sample (e.g., in some cases above a threshold amount), the result is cleavage of ssDNAs in the sample, which can be detected using any convenient detection method (e.g., using a labeled single stranded detector DNA).

Provided are compositions and methods for detecting a target DNA (double stranded or single stranded) in a sample. In some cases, a subject method includes: (a) contacting the sample with: (i) a type V CRISPR/Cas effector protein (e.g., a Cas12 protein such as Cas12a, Cas12b, Cas12c, Cas12d, Cas12e); (ii) a guide RNA (comprising a region that binds to the type V CRISPR/Cas effector protein, and a guide sequence that hybridizes with the target DNA); and (iii) a detector DNA that is single stranded (i.e., a "single stranded detector DNA") and does not hybridize with the guide sequence of the guide RNA; and (b) measuring a detectable signal produced by cleavage (by the type V CRISPR/Cas effector protein) of the single stranded detector DNA. In some cases, the single stranded detector DNA includes a fluorescence-emitting dye pair (e.g., a fluorescence-emitting dye pair is a fluorescence resonance energy transfer (FRET) pair, a quencher/fluor pair). In some cases, the target DNA is a viral DNA (e.g., papovavirus, hepadnavirus, herpesvirus, adenovirus, poxvirus, parvovirus, and the like).

Also provided are compositions and methods for cleaving single stranded DNAs (ssDNAs). In some cases, such methods include contacting a population of nucleic acids, wherein said population comprises a target DNA and a plurality of non-target ssDNAs, with: (i) a type V CRISPR/Cas effector protein (e.g., a Cas12 protein such as Cas12a, Cas12b, Cas12c, Cas12d, Cas12e); and (ii) a guide RNA (comprising a region that binds to the type V CRISPR/Cas effector protein, and a guide sequence that hybridizes with the target DNA), where the type V CRISPR/Cas effector protein cleaves non-target ssDNAs of said plurality. In some cases, the contacting is inside of a cell such as a eukaryotic cell, a plant cell, a mammalian cell, etc. (e.g., in vitro, ex vivo, in vivo).

Also provided are compositions (e.g., kits) for practicing the subject methods.

BRIEF DESCRIPTION OF THE DRAWINGS

FIGS. 1A-1E provide amino acid sequences of various Type V CRISPR/Cas effector proteins (depicted are Cas12a and Cas12b sequences).

FIG. 2 provides example guide RNA sequences (e.g., crRNA repeat sequences and an example single guide RNA sequence) and example PAM sequences.

FIGS. 4A-4B present data related to non-specific DNase activity by Cas12a.

FIGS. 5A-5B present data related to non-target strand cleavage.

FIG. 7 presents data related to rapid "shredding" of M13 phage ssDNA.

FIGS. 9A-9B present data related to mismatches at the PAM-proximal end.

FIGS. 11A-11B present data related to distinguishing viral serotypes using a subject method of detection.

FIG. 12 presents a schematic model for DNA cleavage by CRISPR-Cas12a.

FIGS. 13A-13C present data showing that Cas12a target recognition activates non-specific single stranded DNA cleavage. FIG. 13A. Cartoon of the Cas12a-crRNA complex targeting a dsDNA substrate with cleavage sites depicting the 5' overhang staggered cut. FIG. 13B. Timecourse of purified LbaCas12a targeting the circular, single-stranded M13 DNA phage in vitro reveals a robust shredding pattern. FIG. 13C. Timecourse of purified SpyCas9 targeting M13 ssDNA phage.

FIGS. 14A-14C present data showing that Cas12a trans-cleavage activity requires a complementary activator. FIG. 14A. Radiolabeled target dsDNA or FIG. 14B.) non-specific ssDNA incubated with molar ratios of LbaCas12a-crRNA as indicated. Each point represents quantified % cleavage after 30-minutes at 37 C, when the reaction was at completion. FIG. 14C. Michaelis-Menten kinetics of LbCas12a trans-cleavage using a dsDNA or ssDNA activator.

FIGS. 15A-15C present data showing that specificity of trans-cleavage activation involves PAM recognition and DNA unwinding. FIG. 15A. Trans-cleavage products on a denaturing PAGE gel with the indicated activators. FIG. 15B. Observed trans-cleavage rates using a ssDNA or dsDNA activator with indicated mismatches. FIG. 15C. LbaCas12a can distinguish two closely related dsDNA HPV sequences.

FIGS. 16A-16C present data showing that non-specific ssDNA cleavage activity is conserved across Type V CRISPR systems. FIG. 16A. Phylogenetic tree highlighting indicated type V effector proteins. FIG. 16B. Cleavage gels depicting activator-dependent trans-cleavage across type V effector proteins, but not the type II effector SpyCas9. FIG. 16C. Model for PAM-dependent and PAM-independent activation of cis and trans-cleavage.

FIGS. 27A-27C present data showing specificity and conservation of trans-cleavage activation.

FIG. 29 presents a schematic model for PAM-dependent and PAM-independent activation of cis and trans-cleavage by Cas12a.

FIGS. 34A-34C present data showing that LbCas12a trans-cleavage degrades complementary and non-specific ssDNA, but not ssRNA.

FIGS. 36A-36E present data showing Michaelis-Menten analysis that reveals robust trans-cleavage activity with a ssDNA and dsDNA activator.

FIGS. 39A-39E present data showing that Cas12a can distinguish two closely related HPV sequences.

FIGS. 43A-43B present data showing identification of target nucleic acid by DETECTR using Cas12d and Cas12e proteins.

DEFINITIONS

Figure 3A:
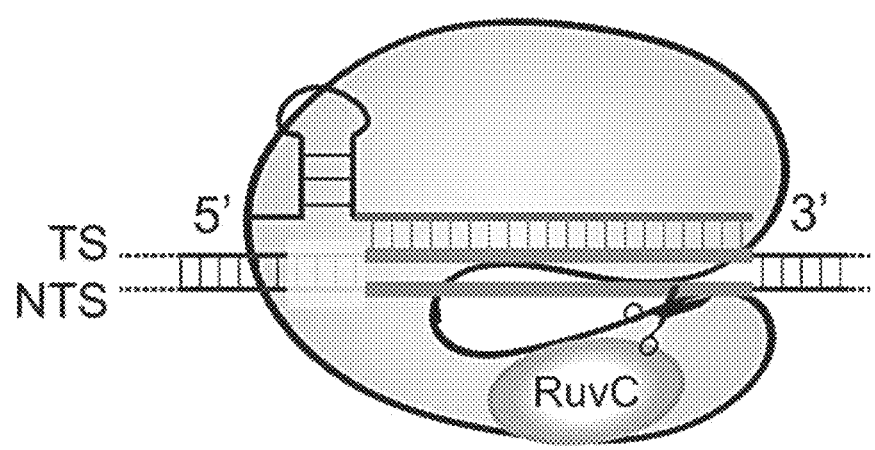
FIGS. 3A-3B present data related to non-complementary strand cleavage.

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

The term "oligonucleotide" refers to a polynucleotide of between 4 and 100 nucleotides of single- or double-stranded nucleic acid (e.g., DNA, RNA, or a modified nucleic acid).

However, for the purposes of this disclosure, there is no upper limit to the length of an oligonucleotide. Oligonucleotides are also known as "oligomers" or "oligos" and can be isolated from genes, transcribed (in vitro and/or in vivo), or chemically synthesized. The terms "polynucleotide" and "nucleic acid" should be understood to include, as applicable to the embodiments being described, single-stranded (such as sense or antisense) and double-stranded polynucleotides.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine/adenosine) (A) pairing with thymidine/thymidine (T), A pairing with uracil/uridine (U), and guanine/guanosine) (G) pairing with cytosine/cytidine (C). In addition, for hybridization between two RNA molecules (e.g., dsRNA), and for hybridization of a DNA molecule with an RNA molecule (e.g., when a DNA target nucleic acid base pairs with a guide RNA, etc.): G can also base pair with U. For example, G/U base-pairing is partially responsible for the degeneracy (i.e., redundancy) of the genetic code in the context of tRNA anti-codon base-pairing with codons in mRNA. Thus, in the context of this disclosure, a G (e.g., of a protein-binding segment (e.g., dsRNA duplex) of a guide RNA molecule; of a target nucleic acid (e.g., target DNA) base pairing with a guide RNA) is considered complementary to both a U and to C. For example, when a G/U base-pair can be made at a given nucleotide position of a protein-binding segment (e.g., dsRNA duplex) of a guide RNA molecule, the position is not considered to be non-complementary, but is instead considered to be complementary.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more).

It is understood that the sequence of a polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure, a 'bulge', and the like). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. The remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a guide RNA and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

By "binding domain" it is meant a protein domain that is able to bind non-covalently to another molecule. A binding domain can bind to, for example, an RNA molecule (an RNA-binding domain) and/or a protein molecule (a protein-binding domain) In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, Phyre2, etc.), available over the world wide web at sites including ncbi(dot)nlm(dot)nili(dot)gov/BLAST, ebi(dot)ac(dot)uk/Tools/msa/tcoffee/, ebi(dot)ac(dot)uk/Tools/msa/muscle/, mafft(dot)cbrc(dot)jp/alignment/software/, sbg(dot)bio(dot)ic(dot)ac(dot)uk/~phyre2/. See, e.g., Altschul et al. (1990), J. Mol. Bioi. 215:403-10.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., protein coding) and/or regulate translation of an encoded polypeptide.

As used herein, a "promoter sequence" is a DNA regulatory region capable of binding RNA polymerase and initiating transcription of a downstream (3' direction) coding or non-coding sequence. Eukaryotic promoters will often, but not always, contain "TATA" boxes and "CAT" boxes. Various promoters, including inducible promoters, may be used to drive the various nucleic acids (e.g., vectors) of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a type V CRISPR/Cas effector protein" includes a plurality of such type V CRISPR/Cas effector proteins and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As noted above, the inventors have discovered that that type V CRISPR/Cas proteins, e.g., Cas12 proteins such as Cpf1 (Cas12a) and C2c1 (Cas12b) can promiscuously cleave non-targeted single stranded DNA (ssDNA) once activated by detection of a target DNA (double or single stranded). Once a type V CRISPR/Cas effector protein (e.g., a Cas12 protein such as Cas12a, Cas12b, Cas12c, Cas12d, Cas12e) is activated by a guide RNA, which occurs when the guide RNA hybridizes to a target sequence of a target DNA (i.e., the sample includes the targeted DNA), the protein becomes a nuclease that promiscuously cleaves ssDNAs (i.e., the nuclease cleaves non-target ssDNAs, i.e., ssDNAs to which the guide sequence of the guide RNA does not hybridize). Thus, when the target DNA is present in the sample (e.g., in some cases above a threshold amount), the result is cleavage of ssDNAs in the sample, which can be detected using any convenient detection method (e.g., using a labeled single stranded detector DNA).

Provided are compositions and methods for detecting a target DNA (double stranded or single stranded) in a sample. In some cases, a detector DNA is used that is single stranded (ssDNA) and does not hybridize with the guide sequence of the guide RNA (i.e., the detector ssDNA is a non-target ssDNA). Such methods can include (a) contacting the sample with: (i) a type V CRISPR/Cas effector protein (e.g., a Cas12 protein); (ii) a guide RNA comprising: a region that binds to the type V CRISPR/Cas effector protein, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the type V CRISPR/Cas effector protein, thereby detecting the target DNA. As noted above, once a subject Type V CRISPR/Cas effector protein (e.g., a Cas12 protein such as Cas12a, Cas12b, Cas12c, Cas12d, Cas12e) is activated by a guide RNA, which occurs when the sample includes a target DNA to which the guide RNA hybridizes (i.e., the sample includes the targeted target DNA), the Type V CRISPR/Cas effector protein (e.g., a Cas12 protein such as Cas12a, Cas12b, Cas12c, Cas12d, Cas12e) is activated and functions as an endoribonuclease that non-specifically cleaves ssDNAs (including non-target ssDNAs) present in the sample. Thus, when the targeted target DNA is present in the sample (e.g., in some cases above a threshold amount), the result is cleavage of ssDNA (including non-target ssDNA) in the sample, which can be detected using any convenient detection method (e.g., using a labeled detector ssDNA).

Also provided are compositions and methods for cleaving single stranded DNAs (ssDNAs) (e.g., non-target ssDNAs). Such methods can include contacting a population of nucleic acids, wherein said population comprises a target DNA and a plurality of non-target ssDNAs, with: (i) a type V CRISPR/Cas effector protein; and (ii) a guide RNA comprising: a region that binds to the type V CRISPR/Cas effector protein, and a guide sequence that hybridizes with the target DNA, wherein the type V CRISPR/Cas effector protein cleaves non-target ssDNAs of said plurality. Such a method can be used, e.g., to cleave foreign ssDNAs (e.g., viral DNAs) in a cell.

The contacting step of a subject method can be carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

The guide RNA can be provided as RNA or as a nucleic acid encoding the guide RNA (e.g., a DNA such as a recombinant expression vector). The Type V CRISPR/Cas effector protein (e.g., a Cas12 protein such as Cas12a, Cas12b, Cas12c, Cas12d, Cas12e) can be provided as a protein or as a nucleic acid encoding the protein (e.g., an mRNA, a DNA such as a recombinant expression vector). In some cases, two or more (e.g., 3 or more, 4 or more, 5 or more, or 6 or more) guide RNAs can be provided by (e.g., using a precursor guide RNA array, which can be cleaved by the Type V CRISPR/Cas effector protein into individual ("mature") guide RNAs).

In some cases (e.g., when contacting with a guide RNA and a Type V CRISPR/Cas effector protein (e.g., a Cas12 protein such as Cas12a, Cas12b, Cas12c, Cas12d, Cas12e)), the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, in some cases the sample is contacted for 40 minutes or less prior to the measuring step. In some cases the sample is contacted for 20 minutes or less prior to the measuring step. In some cases the sample is contacted for 10 minutes or less prior to the measuring step. In some cases the sample is contacted for 5 minutes or less prior to the measuring step. In some cases the sample is contacted for 1 minute or less prior to the measuring step. In some cases the sample is contacted for from 50 seconds to 60 seconds prior to the measuring step. In some cases the sample is contacted for from 40 seconds to 50 seconds prior to the measuring step. In some cases the sample is contacted for from 30 seconds to 40 seconds prior to the measuring step. In some cases the sample is contacted for from 20 seconds to 30 seconds prior to the measuring step. In some cases the sample is contacted for from 10 seconds to 20 seconds prior to the measuring step.

A method of the present disclosure for detecting a target DNA (single-stranded or double-stranded) in a sample can detect a target DNA with a high degree of sensitivity. In some cases, a method of the present disclosure can be used to detect a target DNA present in a sample comprising a plurality of DNAs (including the target DNA and a plurality of non-target DNAs), where the target DNA is present at one or more copies per $10^7$ non-target DNAs (e.g., one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs). In some cases, a method of the present disclosure can be used to detect a target DNA present in a sample comprising a plurality of DNAs (including the target DNA and a plurality of non-target DNAs), where the target DNA is present at one or more copies per $10^{18}$ non-target DNAs (e.g., one or more copies per $10^{15}$ non-target DNAs, one or more copies per $10^{12}$ non-target DNAs, one or more copies per $10^9$ non-target DNAs, one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs).

In some cases, a method of the present disclosure can detect a target DNA present in a sample, where the target DNA is present at from one copy per $10^7$ non-target DNAs to one copy per 10 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^{18}$ non-target DNAs to one copy per 10 non-target DNAs (e.g., from 1 copy per $10^{18}$ non-target DNAs to 1 copy per $10^2$ non-target DNAs, from 1 copy per $10^{15}$ non-target DNAs to 1 copy per $10^2$ non-target DNAs, from 1 copy per $10^{12}$ non-target DNAs to 1 copy per $10^2$ non-target DNAs, from 1 copy per $10^9$ non-target DNAs to 1 copy per $10^2$ non-target DNAs, from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^7$ non-target DNAs to one copy per 100 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 100 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 100 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, the threshold of detection, for a subject method of detecting a target DNA in a sample, is 10 nM or less. The term "threshold of detection" is used herein to describe the minimal amount of target DNA that must be present in a sample in order for detection to occur. Thus, as an illustrative example, when a threshold of detection is 10 nM, then a signal can be detected when a target DNA is present in the sample at a concentration of 10 nM or more. In some cases, a method of the present disclosure has a threshold of detection of 5 nM or less. In some cases, a method of the present disclosure has a threshold of detection of 1 nM or less. In some cases, a method of the present disclosure has a threshold of detection of 0.5 nM or less. In some cases, a method of the present disclosure has a threshold of detection of 0.1 nM or less. In some cases, a method of the present disclosure has a threshold of detection of 0.05 nM or less. In some cases, a method of the present disclosure has a threshold of detection of 0.01 nM or less. In some cases, a method of the present disclosure has a threshold of detection of 0.005 nM or less. In some cases, a method of the present disclosure has a threshold of detection of 0.001 nM or less. In some cases, a method of the present disclosure has a threshold of detection of 0.0005 nM or less. In some cases, a method of the present disclosure has a threshold of detection of 0.0001 nM or less. In some cases, a method of the present disclosure has a threshold of detection of 0.00005 nM or less. In some cases, a method of the present disclosure has a threshold of detection of 0.00001 nM or less. In some cases, a method of the present disclosure has a threshold of detection of 10 pM or less. In some cases, a method of the present disclosure has a threshold of detection of 1 pM or less. In some cases, a method of the present disclosure has a threshold of detection of 500 fM or less. In some cases, a method of the present disclosure has a threshold of detection of 250 fM or less. In some cases, a method of the present disclosure has a threshold of detection of 100 fM or less. In some cases, a method of the present disclosure has a threshold of detection of 50 fM or less. In some cases, a method of the present disclosure has a threshold of detection of 500 aM (attomolar) or less. In some cases, a method of the present disclosure has a threshold of detection of 250 aM or less. In some cases, a method of the present disclosure has a threshold of detection of 100 aM or less. In some cases, a method of the present disclosure has a threshold of detection of 50 aM or less. In some cases, a method of the present disclosure has a threshold of detection of 10 aM or less. In some cases, a method of the present disclosure has a threshold of detection of 1 aM or less.

In some cases, the threshold of detection (for detecting the target DNA in a subject method), is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 800 fM to 100 pM. In some cases, a method of the present disclosure has a threshold of detection in a range of from 1 pM to 10 pM. In some cases, a method of the present disclosure has a threshold of detection in a range of from 10 fM to 500 fM, e.g., from 10 fM to 50 fM, from 50 fM to 100 fM, from 100 fM to 250 fM, or from 250 fM to 500 fM.

In some cases, the minimum concentration at which a target DNA can be detected in a sample is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 800 fM to 100 pM. In some cases, the minimum concentration at which a target DNA can be detected in a sample is in a range of from 1 pM to 10 pM.

In some cases, the threshold of detection (for detecting the target DNA in a subject method), is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 1 aM to 800 aM. In some cases, a method of the present disclosure has a threshold of detection in a range of from 50 aM to 1 pM. In some cases, a method of the present disclosure has a threshold of detection in a range of from 50 aM to 500 fM.

In some cases, the minimum concentration at which a target DNA can be detected in a sample is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 1 aM to 500 pM.

In some cases, the minimum concentration at which a target DNA can be detected in a sample is in a range of from 100 aM to 500 pM.

In some cases, a subject composition or method exhibits an attomolar (aM) sensitivity of detection. In some cases, a subject composition or method exhibits a femtomolar (fM) sensitivity of detection. In some cases, a subject composition or method exhibits a picomolar (pM) sensitivity of detection. In some cases, a subject composition or method exhibits a nanomolar (nM) sensitivity of detection.

Target DNA

A target DNA can be single stranded (ssDNA) or double stranded (dsDNA). When the target DNA is single stranded, there is no preference or requirement for a PAM sequence in the target DNA. However, when the target DNA is dsDNA, a PAM is usually present adjacent to the target sequence of the target DNA (e.g., see discussion of the PAM elsewhere herein). The source of the target DNA can be the same as the source of the sample, e.g., as described below.

The source of the target DNA can be any source. In some cases the target DNA is a viral DNA (e.g., a genomic DNA of a DNA virus). As such, subject method can be for detecting the presence of a viral DNA amongst a population of nucleic acids (e.g., in a sample). A subject method can also be used for the cleavage of non-target ssDNAs in the present of a target DNA. For example, if a method takes place in a cell, a subject method can be used to promiscuously cleave non-target ssDNAs in the cell (ssDNAs that do not hybridize with the guide sequence of the guide RNA) when a particular target DNA is present in the cell (e.g., when the cell is infected with a virus and viral target DNA is detected).

Examples of possible target DNAs include, but are not limited to, viral DNAs such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, *Pityriasis Rosea*, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. In some cases, the target DNA is parasite DNA. In some cases, the target DNA is bacterial DNA, e.g., DNA of a pathogenic bacterium.

Samples

A subject sample includes nucleic acid (e.g., a plurality of nucleic acids). The term "plurality" is used herein to mean two or more. Thus, in some cases a sample includes two or more (e.g., 3 or more, 5 or more, 10 or more, 20 or more, 50 or more, 100 or more, 500 or more, 1,000 or more, or 5,000 or more) nucleic acids (e.g., DNAs). A subject method can be used as a very sensitive way to detect a target DNA present in a sample (e.g., in a complex mixture of nucleic acids such as DNAs). In some cases the sample includes 5 or more DNAs (e.g., 10 or more, 20 or more, 50 or more, 100 or more, 500 or more, 1,000 or more, or 5,000 or more DNAs) that differ from one another in sequence. In some cases, the sample includes 10 or more, 20 or more, 50 or more, 100 or more, 500 or more, $10^3$ or more, $5 \times 10^3$ or more, $10^4$ or more, $5 \times 10^4$ or more, $10^5$ or more, $5 \times 10^5$ or more, $10^6$ or more $5 \times 10^6$ or more, or $10^7$ or more, DNAs. In some cases, the sample comprises from 10 to 20, from 20 to 50, from 50 to 100, from 100 to 500, from 500 to $10^3$, from $10^3$ to $5 \times 10^3$, from $5 \times 10^3$ to $10^4$, from $10^4$ to $5 \times 10^4$, from $5 \times 10^4$ to $10^5$, from $10^5$ to $5 \times 10^5$, from $5 \times 10^5$ to $10^6$, from $10^6$ to $5 \times 10^6$, or from $5 \times 10^6$ to $10^7$, or more than $10^7$, DNAs. In some cases, the sample comprises from 5 to $10^7$ DNAs (e.g., that differ from one another in sequence)(e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to $10^5$, from 20 to 50,000, or from 20 to 30,000 DNAs). In some cases the sample includes 20 or more DNAs that differ from one another in sequence. In some cases, the sample includes DNAs from a cell lysate (e.g., a eukaryotic cell lysate, a mammalian cell lysate, a human cell lysate, a prokaryotic cell lysate, a plant cell lysate, and the like). For example, in some cases the sample includes DNA from a cell such as a eukaryotic cell, e.g., a mammalian cell such as a human cell.

The term "sample" is used herein to mean any sample that includes DNA (e.g., in order to determine whether a target DNA is present among a population of DNAs). The sample can be derived from any source, e.g., the sample can be a synthetic combination of purified DNAs; the sample can be a cell lysate, an DNA-enriched cell lysate, or DNAs isolated and/or purified from a cell lysate. The sample can be from a patient (e.g., for the purpose of diagnosis). The sample can be from permeabilized cells. The sample can be from crosslinked cells. The sample can be in tissue sections. The sample can be from tissues prepared by crosslinking followed by delipidation and adjustment to make a uniform refractive index. Examples of tissue preparation by crosslinking followed by delipidation and adjustment to make a uniform refractive index have been described in, for example, Shah et al., Development (2016) 143, 2862-2867 doi:10.1242/dev.138560.

A "sample" can include a target DNA and a plurality of non-target DNAs. In some cases, the target DNA is present in the sample at one copy per 10 non-target DNAs, one copy per 20 non-target DNAs, one copy per 25 non-target DNAs, one copy per 50 non-target DNAs, one copy per 100 non-target DNAs, one copy per 500 non-target DNAs, one copy per $10^3$ non-target DNAs, one copy per $5 \times 10^3$ non-target DNAs, one copy per $10^4$ non-target DNAs, one copy per $5 \times 10^4$ non-target DNAs, one copy per $10^5$ non-target DNAs, one copy per $5 \times 10^5$ non-target DNAs, one copy per $10^6$ non-target DNAs, or less than one copy per $10^6$ non-target DNAs. In some cases, the target DNA is present in the sample at from one copy per 10 non-target DNAs to 1 copy per 20 non-target DNAs, from 1 copy per 20 non-target DNAs to 1 copy per 50 non-target DNAs, from 1 copy per 50 non-target DNAs to 1 copy per 100 non-target DNAs, from 1 copy per 100 non-target DNAs to 1 copy per 500 non-target DNAs, from 1 copy per 500 non-target DNAs to 1 copy per $10^3$ non-target DNAs, from 1 copy per $10^3$ non-target DNAs to 1 copy per $5 \times 10^3$ non-target DNAs, from 1 copy per $5 \times 10^3$ non-target DNAs to 1 copy per $10^4$ non-target DNAs, from 1 copy per $10^4$ non-target DNAs to 1 copy per $10^5$ non-target DNAs, from 1 copy per $10^5$ non-target DNAs to 1 copy per $10^6$ non-target DNAs, or from 1 copy per $10^6$ non-target DNAs to 1 copy per $10^7$ non-target DNAs.

Suitable samples include but are not limited to saliva, blood, serum, plasma, urine, aspirate, and biopsy samples. Thus, the term "sample" with respect to a patient encompasses blood and other liquid samples of biological origin, solid tissue samples such as a biopsy specimen or tissue cultures or cells derived therefrom and the progeny thereof.

The definition also includes samples that have been manipulated in any way after their procurement, such as by treatment with reagents; washed; or enrichment for certain cell populations, such as cancer cells. The definition also includes sample that have been enriched for particular types of molecules, e.g., DNAs. The term "sample" encompasses biological samples such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising DNAs that is obtained from such cells (e.g., a cell lysate or other cell extract comprising DNAs).

A sample can comprise, or can be obtained from, any of a variety of cells, tissues, organs, or acellular fluids. Suitable sample sources include eukaryotic cells, bacterial cells, and archaeal cells. Suitable sample sources include single-celled organisms and multi-cellular organisms. Suitable sample sources include single-cell eukaryotic organisms; a plant or a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell, tissue, or organ; a cell, tissue, or organ from an invertebrate animal (e.g. fruit fly, cnidarian, echinoderm, nematode, an insect, an arachnid, etc.); a cell, tissue, fluid, or organ from a vertebrate animal (e.g., fish, amphibian, reptile, bird, mammal); a cell, tissue, fluid, or organ from a mammal (e.g., a human; a non-human primate; an ungulate; a feline; a bovine; an ovine; a caprine; etc.). Suitable sample sources include nematodes, protozoans, and the like. Suitable sample sources include parasites such as helminths, malarial parasites, etc.

Suitable sample sources include a cell, tissue, or organism of any of the six kingdoms, e.g., Bacteria (e.g., Eubacteria); Archaebacteria; Protista; Fungi; Plantae; and Animalia. Suitable sample sources include plant-like members of the kingdom Protista, including, but not limited to, algae (e.g., green algae, red algae, glaucophytes, cyanobacteria); fungus-like members of Protista, e.g., slime molds, water molds, etc; animal-like members of Protista, e.g., *flagellates* (e.g., *Euglena*), amoeboids (e.g., amoeba), sporozoans (e.g, Apicomplexa, Myxozoa, Microsporidia), and ciliates (e.g., Paramecium). Suitable sample sources include members of the kingdom Fungi, including, but not limited to, members of any of the phyla: Basidiomycota (club fungi; e.g., members of *Agaricus, Amanita, Boletus, Cantherellus*, etc.); Ascomycota (sac fungi, including, e.g., *Saccharomyces*); Mycophycophyta (lichens); Zygomycota (conjugation fungi); and Deuteromycota. Suitable sample sources include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sample sources include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, hill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Ayes (birds); and Mammalian (mammals) Suitable plants include any monocotyledon and any dicotyledon.

Suitable sources of a sample include cells, fluid, tissue, or organ taken from an organism; from a particular cell or group of cells isolated from an organism; etc. For example, where the organism is a plant, suitable sources include xylem, the phloem, the cambium layer, leaves, roots, etc. Where the organism is an animal, suitable sources include particular tissues (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some cases, the source of the sample is a (or is suspected of being a diseased cell, fluid, tissue, or organ. In some cases, the source of the sample is a normal (non-diseased) cell, fluid, tissue, or organ. In some cases, the source of the sample is a (or is suspected of being a pathogen-infected cell, tissue, or organ. For example, the source of a sample can be an individual who may or may not be infected—and the sample could be any biological sample (e.g., blood, saliva, biopsy, plasma, serum, bronchoalveolar lavage, sputum, a fecal sample, cerebrospinal fluid, a fine needle aspirate, a swab sample (e.g., a buccal swab, a cervical swab, a nasal swab), interstitial fluid, synovial fluid, nasal discharge, tears, buffy coat, a mucous membrane sample, an epithelial cell sample (e.g., epithelial cell scraping), etc.) collected from the individual. In some cases, the sample is a cell-free liquid sample. In some cases, the sample is a liquid sample that can comprise cells. Pathogens include viruses, fungi, helminths, protozoa, malarial parasites, *Plasmodium* parasites, *Toxoplasma* parasites, *Schistosoma* parasites, and the like. "Helminths" include roundworms, heartworms, and phytophagous nematodes (Nematoda), flukes (Tematoda), Acanthocephala, and tapeworms (Cestoda). Protozoan infections include infections from *Giardia* spp., *Trichomonas* spp., African trypanosomiasis, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum, Plasmodium vivax, Trypanosoma cruzi* and *Toxoplasma gondii*. Fungal pathogens include, but are not limited to:

*Cryptococcus neoformans, Histoplasma capsulatum, Coccidioides immitis, Blastomyces dermatitidis, Chlamydia trachomatis,* and *Candida albicans.* Pathogenic viruses include, e.g., immunodeficiency virus (e.g., HIV); influenza virus; dengue; West Nile virus; herpes virus; yellow fever virus; Hepatitis Virus C; Hepatitis Virus A; Hepatitis Virus B; papillomavirus; and the like. Pathogenic viruses can include DNA viruses such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, *Pityriasis Rosea,* kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. Pathogens can include, e.g., DNAviruses [e.g.: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, *Pityriasis Rosea,* kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like], *Mycobacterium tuberculosis, Streptococcus agalactiae,* methicillin-resistant *Staphylococcus aureus, Legionella pneumophila, Streptococcus pyogenes, Escherichia coli, Neisseria gonorrhoeae, Neisseria meningitidis,* Pneumococcus, *Cryptococcus neoformans, Histoplasma capsulatum, Hemophilus influenzae* B, *Treponema pallidum,* Lyme disease spirochetes, *Pseudomonas aeruginosa, Mycobacterium leprae, Brucella abortus,* rabies virus, influenza virus, cytomegalovirus, herpes simplex virus I, herpes simplex virus II, human serum parvolike virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae.*

Measuring a Detectable Signal

In some cases, a subject method includes a step of measuring (e.g., measuring a detectable signal produced by Type V CRISPR/Cas effector protein (e.g., a Cas12 protein such as Cas12a, Cas12b, Cas12c, Cas12d, Cas12e)-mediated ssDNA cleavage). Because a Type V CRISPR/Cas effector protein (e.g., a Cas12 protein such as Cas12a, Cas12b, Cas12c, Cas12d, Cas12e) cleaves non-targeted ssDNA once activated, which occurs when a guide RNA hybridizes with a target DNA in the presence of a Type V CRISPR/Cas effector protein (e.g., a Cas12 protein such as Cas12a, Cas12b, Cas12c, Cas12d, Cas12e), a detectable signal can be any signal that is produced when ssDNA is cleaved. For example, in some cases the step of measuring can include one or more of: gold nanoparticle based detection (e.g., see Xu et al., Angew Chem Int Ed Engl. 2007; 46(19):3468-70; and Xia et al., Proc Natl Acad Sci USA. 2010 Jun. 15; 107(24):10837-41), fluorescence polarization, colloid phase transition/dispersion (e.g., Baksh et al., Nature. 2004 Jan. 8; 427(6970):139-41), electrochemical detection, semiconductor-based sensing (e.g., Rothberg et al., Nature. 2011 Jul. 20; 475(7356):348-52; e.g., one could use a phosphatase to generate a pH change after ssDNA cleavage reactions, by opening 2'-3' cyclic phosphates, and by releasing inorganic phosphate into solution), and detection of a labeled detector ssDNA (see elsewhere herein for more details). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

Figure 46:
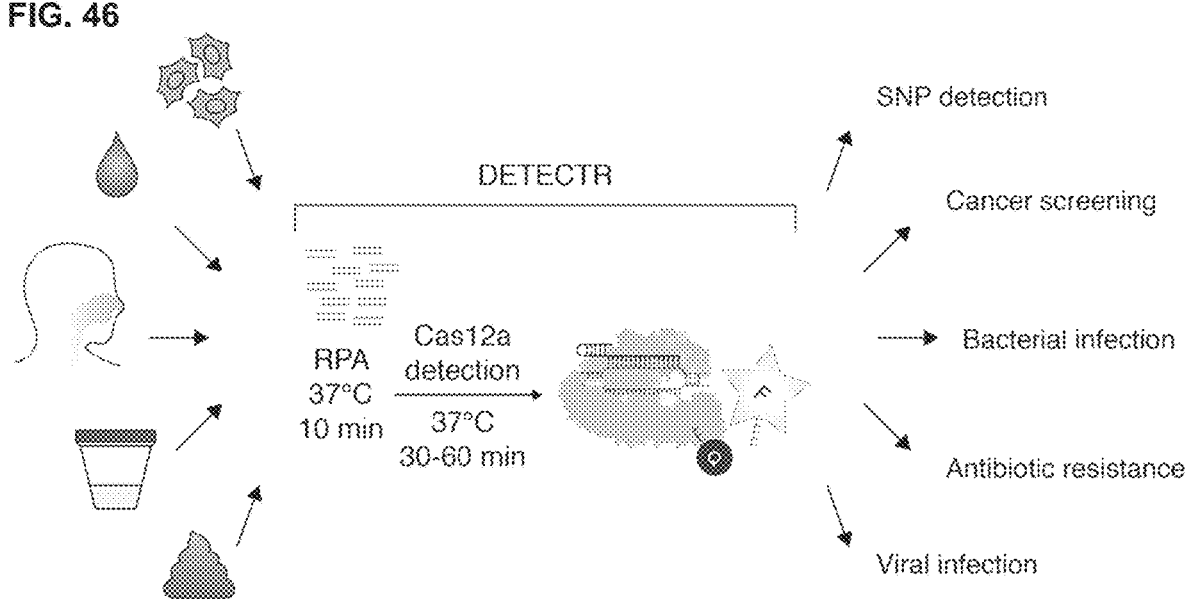
FIG. 46 presents a schematic illustrating DETECTR as a platform for rapid, point-of-care diagnostics.

The measuring can in some cases be quantitative, e.g., in the sense that the amount of signal detected can be used to determine the amount of target DNA present in the sample. The measuring can in some cases be qualitative, e.g., in the sense that the presence or absence of detectable signal can indicate the presence or absence of targeted DNA (e.g., virus, SNP, etc.). In some cases, a detectable signal will not be present (e.g., above a given threshold level) unless the targeted DNA(s) (e.g., virus, SNP, etc.) is present above a particular threshold concentration. In some cases, the threshold of detection can be titrated by modifying the amount of Type V CRISPR/Cas effector protein (e.g., a Cas12 protein such as Cas12a, Cas12b, Cas12c, Cas12d, Cas12e), guide RNA, sample volume, and/or detector ssDNA (if one is used). As such, for example, as would be understood by one of ordinary skill in the art, a number of controls can be used if desired in order to set up one or more reactions, each set up to detect a different threshold level of target DNA, and thus such a series of reactions could be used to determine the amount of target DNA present in a sample (e.g., one could use such a series of reactions to determine that a target DNA is present in the sample 'at a concentration of at least X'). Non-limiting examples of applications of/uses for the compositions and methods of the disclosure include those depicted in FIG. 46. The figure depicts embodiments in which nucleic acids of the sample are amplified (denoted as "RPA" in FIG. 46 prior to contact with a Cas12 protein, but the same applications/uses (e.g., SNP detection, cancer screening, detection of bacterial infection, detection of antibiotic resistance, detection of viral infection, and the like) can apply to embodiments in which no amplification step is included. The compositions and methods of this disclosure can be used to detect any DNA target. For example, any virus that integrates nucleic acid material into the genome can be detected because a subject sample can include cellular genomic DNA—and the guide RNA can be designed to detect integrated nucleotide sequence.

In some cases, a method of the present disclosure can be used to determine the amount of a target DNA in a sample (e.g., a sample comprising the target DNA and a plurality of non-target DNAs). Determining the amount of a target DNA in a sample can comprise comparing the amount of detectable signal generated from a test sample to the amount of detectable signal generated from a reference sample. Determining the amount of a target DNA in a sample can comprise: measuring the detectable signal to generate a test measurement; measuring a detectable signal produced by a reference sample to generate a reference measurement; and comparing the test measurement to the reference measurement to determine an amount of target DNA present in the sample.

For example, in some cases, a method of the present disclosure for determining the amount of a target DNA in a sample comprises: a) contacting the sample (e.g., a sample comprising the target DNA and a plurality of non-target DNAs) with: (i) a guide RNA that hybridizes with the target DNA, (ii) a Type V CRISPR/Cas effector protein (e.g., a Cas12 protein such as Cas12a, Cas12b, Cas12c, Cas12d, Cas12e) that cleaves RNAs present in the sample, and (iii) a detector ssDNA; b) measuring a detectable signal produced by Type V CRISPR/Cas effector protein (e.g., a Cas12 protein such as Cas12a, Cas12b, Cas12c, Cas12d, Cas12e)-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

As another example, in some cases, a method of the present disclosure for determining the amount of a target DNA in a sample comprises: a) contacting the sample (e.g., a sample comprising the target DNA and a plurality of non-target DNAs) with: i) a precursor guide RNA array comprising two or more guide RNAs each of which has a different guide sequence; (ii) a Type V CRISPR/Cas effector protein (e.g., a Cas12 protein such as Cas12a, Cas12b, Cas12c, Cas12d, Cas12e) that cleaves the precursor guide RNA array into individual guide RNAs, and also cleaves RNAs of the sample; and (iii) a detector ssDNA; b) measuring a detectable signal produced by Type V CRISPR/Cas effector protein (e.g., a Cas12 protein such as Cas12a, Cas12b, Cas12c, Cas12d, Cas12e)-mediated ssDNA cleavage (e.g., cleavage of the detector ssDNA), generating a test measurement; c) measuring a detectable signal produced by each of two or more reference samples to generate two or more reference measurements; and d) comparing the test measurement to the reference measurements to determine an amount of target DNA present in the sample.

Amplification of Nucleic Acids in the Sample

In some embodiments, sensitivity of a subject composition and/or method (e.g., for detecting the presence of a target DNA, such as viral DNA or a SNP, in cellular genomic DNA) can be increased by coupling detection with nucleic acid amplification. In some cases, the nucleic acids in a sample are amplified prior to contact with a type V CRISPR/Cas effector protein (e.g., a Cas12 protein) that cleaved ssDNA (e.g., amplification of nucleic acids in the sample can begin prior to contact with a type V CRISPR/Cas effector protein). In some cases, the nucleic acids in a sample are amplified simultaneous with contact with a type V CRISPR/Cas effector protein (e.g., a Cas12 protein). For example, in some cases a subject method includes amplifying nucleic acids of a sample (e.g., by contacting the sample with amplification components) prior to contacting the amplified sample with a type V CRISPR/Cas effector protein (e.g., a Cas12 protein). In some cases a subject method includes contacting a sample with amplification components at the same time (simultaneous with) that the sample is contacted with a type V CRISPR/Cas effector protein (e.g., a Cas12 protein). If all components are added simultaneously (amplification components and detection components such as a type V CRISPR/Cas effector protein, e.g., a Cas12 protein, a guide RNA, and a detector DNA), it is possible that the trans-cleavage activity of the type V CRISPR/Cas effector protein (e.g., a Cas12 protein), will begin to degrade the nucleic acids of the sample at the same time the nucleic acids are undergoing amplification. However, even if this is the case, amplifying and detecting simultaneously can still increase sensitivity compared to performing the method without amplification.

In some cases specific sequences (e.g., sequences of a virus, sequences that include a SNP of interest) are amplified from the sample, e.g., using primers. As such, a sequence to which the guide RNA will hybridize can be amplified in order to increase sensitivity of a subject detection method—this could achieve biased amplification of a desired sequence in order to increase the number of copies of the sequence of interest present in the sample relative to other sequences present in the sample. As one illustrative example, if a subject method is being used to determine whether a given sample includes a particular virus (or a particular SNP), a desired region of viral sequence (or non-viral genomic sequence) can be amplified, and the region amplified will include the sequence that would hybridize to the guide RNA if the viral sequence (or SNP) were in fact present in the sample.

As noted, in some cases the nucleic acids are amplified (e.g., by contact with amplification components) prior to contacting the amplified nucleic acids with a type V CRISPR/Cas effector protein (e.g., a Cas12 protein). In some cases, amplification occurs for 10 seconds or more, (e.g., 30 seconds or more, 45 seconds or more, 1 minute or more, 2 minutes or more, 3 minutes or more, 4 minutes or more, 5 minutes or more, 7.5 minutes or more, 10 minutes or more, etc.) prior to contact with an active type V CRISPR/Cas effector protein (e.g., a Cas12 protein). In some cases, amplification occurs for 2 minutes or more (e.g., 3 minutes or more, 4 minutes or more, 5 minutes or more, 7.5 minutes or more, 10 minutes or more, etc.) prior to contact with an active type V CRISPR/Cas effector protein (e.g., a Cas12 protein). In some cases, amplification occurs for a period of time in a range of from 10 seconds to 60 minutes (e.g., 10 seconds to 40 minutes, 10 seconds to 30 minutes, 10 seconds to 20 minutes, 10 seconds to 15 minutes, 10 seconds to 10 minutes, 10 seconds to 5 minutes, 30 seconds to 40 minutes, 30 seconds to 30 minutes, 30 seconds to 20 minutes, 30 seconds to 15 minutes, 30 seconds to 10 minutes, 30 seconds to 5 minutes, 1 minute to 40 minutes, 1 minute to 30 minutes, 1 minute to 20 minutes, 1 minute to 15 minutes, 1 minute to 10 minutes, 1 minute to 5 minutes, 2 minutes to 40 minutes, 2 minutes to 30 minutes, 2 minutes to 20 minutes, 2 minutes to 15 minutes, 2 minutes to 10 minutes, 2 minutes to 5 minutes, 5 minutes to 40 minutes, 5 minutes to 30 minutes, 5 minutes to 20 minutes, 5 minutes to 15 minutes, or 5 minutes to 10 minutes). In some cases, amplification occurs for a period of time in a range of from 5 minutes to 15 minutes. In some cases, amplification occurs for a period of time in a range of from 7 minutes to 12 minutes.

In some cases, a sample is contacted with amplification components at the same time as contact with a type V CRISPR/Cas effector protein (e.g., a Cas12 protein). In some such cases, the type V CRISPR/Cas effector protein in inactive at the time of contact and is activated once nucleic acids in the sample have been amplified.

Various amplification methods and components will be known to one of ordinary skill in the art and any convenient method can be used (see, e.g., Zanoli and Spoto, Biosensors (Basel). 2013 March; 3(1): 18-43; Gill and Ghaemi, Nucleosides, Nucleotides, and Nucleic Acids, 2008, 27: 224-243; Craw and Balachandrana, Lab Chip, 2012, 12, 2469-2486; which are herein incorporated by reference in their entirety). Nucleic acid amplification can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP), co-amplification at lower denaturation temperature-PCR (COLD-PCR), allele-specific PCR, intersequence-specific PCR (ISS-PCR), whole genome amplification (WGA), inverse PCR, and thermal asymmetric interlaced PCR (TAIL-PCR).

In some cases the amplification is isothermal amplification. The term "isothermal amplification" indicates a method of nucleic acid (e.g., DNA) amplification (e.g., using enzymatic chain reaction) that can use a single temperature incubation thereby obviating the need for a thermal cycler. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. By combining with a reverse transcription step, these amplification methods can be used to isothermally amplify RNA.

Examples of isothermal amplification methods include but are not limited to: loop-mediated isothermal Amplification (LAMP), helicase-dependent Amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR) and isothermal multiple displacement amplification (IMDA).

In some cases, the amplification is recombinase polymerase amplification (RPA) (see, e.g., U.S. Pat. Nos. 8,030,000; 8,426,134; 8,945,845; 9,309,502; and 9,663,820, which are hereby incorporated by reference in their entirety). Recombinase polymerase amplification (RPA) uses two opposing primers (much like PCR) and employs three enzymes—a recombinase, a single-stranded DNA-binding protein (SSB) and a strand-displacing polymerase. The recombinase pairs oligonucleotide primers with homologous sequence in duplex DNA, SSB binds to displaced strands of DNA to prevent the primers from being displaced, and the strand displacing polymerase begins DNA synthesis where the primer has bound to the target DNA. Adding a reverse transcriptase enzyme to an RPA reaction can facilitate detection RNA as well as DNA, without the need for a separate step to produce cDNA. One example of components for an RPA reaction is as follows (see, e.g., U.S. Pat. Nos. 8,030,000; 8,426,134; 8,945,845; 9,309,502; 9,663,820): 50 mM Tris pH 8.4, 80 mM Potassium acetate, 10 mM Magnesium acetate, 2 mM DTT, 5% PEG compound (Carbowax-20M), 3 mM ATP, 30 mM Phosphocreatine, 100 ng/µl creatine kinase, 420 ng/µl gp32, 140 ng/µl UvsX, 35 ng/µl UvsY, 2000M dNTPs, 300 nM each oligonucleotide, 35 ng/µl Bsu polymerase, and a nucleic acid-containing sample).

In a transcription mediated amplification (TMA), an RNA polymerase is used to make RNA from a promoter engineered in the primer region, and then a reverse transcriptase synthesizes cDNA from the primer. A third enzyme, e.g., Rnase H can then be used to degrade the RNA target from cDNA without the heat-denatured step. This amplification technique is similar to Self-Sustained Sequence Replication (3SR) and Nucleic Acid Sequence Based Amplification (NASBA), but varies in the enzymes employed. For another example, helicase-dependent amplification (HDA) utilizes a thermostable helicase (Tte-UvrD) rather than heat to unwind dsDNA to create single-strands that are then available for hybridization and extension of primers by polymerase. For yet another example, a loop mediated amplification (LAMP) employs a thermostable polymerase with strand displacement capabilities and a set of four or more specific designed primers. Each primer is designed to have hairpin ends that, once displaced, snap into a hairpin to facilitate self-priming and further polymerase extension. In a LAMP reaction, though the reaction proceeds under isothermal conditions, an initial heat denaturation step is required for double-stranded targets. In addition, amplification yields a ladder pattern of various length products. For yet another example, a strand displacement amplification (SDA) combines the ability of a restriction endonuclease to nick the unmodified strand of its target DNA and an exonuclease-deficient DNA polymerase to extend the 3' end at the nick and displace the downstream DNA strand.

Detector DNA

In some cases, a subject method includes contacting a sample (e.g., a sample comprising a target DNA and a plurality of non-target ssDNAs) with: i) a Type V CRISPR/Cas effector protein (e.g., a Cas12 protein such as Cas12a, Cas12b, Cas12c, Cas12d, Cas12e); ii) a guide RNA (or precursor guide RNA array); and iii) a detector DNA that is single stranded and does not hybridize with the guide sequence of the guide RNA. For example, in some cases, a subject method includes contacting a sample with a labeled single stranded detector DNA (detector ssDNA) that includes a fluorescence-emitting dye pair; the Type V CRISPR/Cas effector protein (e.g., a Cas12 protein such as Cas12a, Cas12b, Cas12c, Cas12d, Cas12e) cleaves the labeled detector ssDNA after it is activated (by binding to the guide RNA in the context of the guide RNA hybridizing to a target DNA); and the detectable signal that is measured is produced by the fluorescence-emitting dye pair. For example, in some cases, a subject method includes contacting a sample with a labeled detector ssDNA comprising a fluorescence resonance energy transfer (FRET) pair or a quencher/fluor pair, or both. In some cases, a subject method includes contacting a sample with a labeled detector ssDNA comprising a FRET pair. In some cases, a subject method includes contacting a sample with a labeled detector ssDNA comprising a fluor/quencher pair.

Fluorescence-emitting dye pairs comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair," both of which terms are discussed in more detail below. The term "fluorescence-emitting dye pair" is used interchangeably with the phrase "a FRET pair and/or a quencher/fluor pair."

In some cases (e.g., when the detector ssDNA includes a FRET pair) the labeled detector ssDNA produces an amount of detectable signal prior to being cleaved, and the amount of detectable signal that is measured is reduced when the labeled detector ssDNA is cleaved. In some cases, the labeled detector ssDNA produces a first detectable signal prior to being cleaved (e.g., from a FRET pair) and a second detectable signal when the labeled detector ssDNA is cleaved (e.g., from a quencher/fluor pair). As such, in some cases, the labeled detector ssDNA comprises a FRET pair and a quencher/fluor pair.

In some cases, the labeled detector ssDNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Förster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in some cases, a subject labeled detector ssDNA includes two signal partners (a signal pair), when one signal partner is a FRET donor moiety and the other signal partner is a FRET acceptor moiety. A subject labeled detector ssDNA that includes such a FRET pair (a FRET donor moiety and a FRET acceptor moiety) will thus exhibit a detectable signal (a FRET signal) when the signal partners are in close proximity (e.g., while on the same RNA molecule), but the signal will be reduced (or absent) when the partners are separated (e.g., after cleavage of the RNA molecule by a Type V CRISPR/Cas effector protein (e.g., a Cas12 protein such as Cas12a, Cas12b, Cas12c, Cas12d, Cas12e)).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to those presented in Table 1. See also: Bajar et al. Sensors (Basel). 2016 Sep. 14; 16(9); and Abraham et al. PLoS One. 2015 Aug. 3; 10(8):e0134436.

TABLE 1

Examples of FRET pairs (donor and acceptor FRET moieties)

| Donor | Acceptor |
|---|---|
| Tryptophan | Dansyl |
| IAEDANS (1) | DDPM (2) |
| BFP | DsRFP |
| Dansyl | Fluorescein isothiocyanate (FITC) |
| Dansyl | Octadecylrhodamine |
| Cyan fluorescent protein (CFP) | Green fluorescent protein (GFP) |
| CF (3) | Texas Red |
| Fluorescein | Tetramethylrhodamine |
| Cy3 | Cy5 |
| GFP | Yellow fluorescent protein (YFP) |
| BODIPY FL (4) | BODIPY FL (4) |
| Rhodamine 110 | Cy3 |
| Rhodamine 6G | Malachite Green |
| FITC | Eosin Thiosemicarbazide |
| B-Phycoerythrin | Cy5 |
| Cy5 | Cy5.5 |

(1) 5-(2-iodoacetylaminoethyl)aminonaphthalene-1-sulfonic acid
(2) N-(4-dimethylamino-3,5-dinitrophenyl)maleimide
(3) carboxyfluorescein succinimidyl ester
(4) 4,4-difluoro-4-bora-3a,4a-diaza-s-indacene In some cases, a detectable signal is produced when the labeled detector ssDNA is cleaved (e.g., in some cases, the labeled detector ssDNA comprises a quencher/fluor pair). One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the labeled detector ssDNA is cleaved. For example, in some cases, the signal exhibited by one signal partner (a signal moiety) is quenched by the other signal partner (a quencher signal moiety), e.g., when both are present on the same ssDNA molecule prior to cleavage by a Type V CRISPR/Cas effector protein (e.g., a Cas12 protein such as Cas12a, Cas12b, Cas12c, Cas12d, Cas12e). Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector ssDNA by a Type V CRISPR/Cas effector protein (e.g., a Cas12 protein such as Cas12a, Cas12b, Cas12c, Cas12d, Cas12e)), but the signal will be quenched when the partners are in close proximity (e.g., prior to cleavage of the detector ssDNA by a Type V CRISPR/Cas effector protein (e.g., a Cas12 protein such as Cas12a, Cas12b, Cas12c, Cas12d, Cas12e)).

A quencher moiety can quench a signal from the signal moiety (e.g., prior to cleave of the detector ssDNA by a Type V CRISPR/Cas effector protein (e.g., a Cas12 protein such as Cas12a, Cas12b, Cas12c, Cas12d, Cas12e)) to various degrees. In some cases, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in some cases, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In some cases, no signal (e.g., above background) is detected in the presence of the quencher moiety.

In some cases, the signal detected in the absence of the quencher moiety (when the signal partners are separated) is at least 1.2 fold greater (e.g., at least 1.3 fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In some cases, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

In some cases, cleavage of a labeled detector ssDNA can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in some cases, cleavage of a subject labeled detector ssDNA can be detected by a color-shift. Such a shift can be expressed as a loss of an amount of signal of one color (wavelength), a gain in the amount of another color, a change in the ration of one color to another, and the like.

Type V CRISPR/Cas Effector Proteins

Type V CRISPR/Cas effector proteins are a subtype of Class 2 CRISPR/Cas effector proteins. For examples of type V CRISPR/Cas systems and their effector proteins (e.g., Cas12 family proteins such as Cas12a), see, e.g., Shmakov et al., Nat Rev Microbiol. 2017 March; 15(3):169-182: "Diversity and evolution of class 2 CRISPR-Cas systems." Examples include, but are not limited to: Cas12 family (Cas12a, Cas12b, Cas12c), C2c4, C2c8, C2c5, C2c10, and C2c9; as well as CasX (Cas12e) and CasY (Cas12d). Also see, e.g., Koonin et al., Curr Opin Microbiol. 2017 June; 37:67-78: "Diversity, classification and evolution of CRISPR-Cas systems."

As such in some cases, a subject type V CRISPR/Cas effector protein is a Cas12 protein (e.g., Cas12a, Cas12b, Cas12c). In some cases, a subject type V CRISPR/Cas effector protein is a Cas12 protein such as Cas12a, Cas12b, Cas12c, Cas12d, Cas12e, Cas12d, or Cas12e. In some cases, a subject type V CRISPR/Cas effector protein is a Cas12a protein. In some cases, a subject type V CRISPR/Cas effector protein is a Cas12b protein. In some cases, a subject type V CRISPR/Cas effector protein is a Cas12c protein. In some cases, a subject type V CRISPR/Cas effector protein is a Cas12d protein. In some cases, a subject type V CRISPR/Cas effector protein is a Cas12e protein. In some cases, a subject type V CRISPR/Cas effector protein is protein selected from: Cas12 (e.g., Cas12a, Cas12b, Cas12c, Cas12d, Cas12e), C2c4, C2c8, C2c5, C2c10, and C2c9. In some cases, a subject type V CRISPR/Cas effector protein is a protein selected from: C2c4, C2c8, C2c5, C2c10, and C2c9. In some cases, a subject type V CRISPR/Cas effector protein is protein selected from: C2c4, C2c8, and C2c5. In some cases, a subject type V CRISPR/Cas effector protein is protein selected from: C2c10 and C2c9.

In some cases, the subject type V CRISPR/Cas effector protein is a naturally-occurring protein (e.g., naturally occurs in prokaryotic cells). In other cases, the Type V CRISPR/Cas effector protein is not a naturally-occurring polypeptide (e.g., the effector protein is a variant protein, a chimeric protein, includes a fusion partner, and the like). Examples of naturally occurring Type V CRISPR/Cas effector proteins include, but are not limited to, those depicted in FIGS. 1A-1E. Any Type V CRISPR/Cas effector protein can be suitable for the compositions (e.g., nucleic acids, kits, etc.) and methods of the present disclosure (e.g., as long as the Type V CRISPR/Cas effector protein forms a complex with a guide RNA and exhibits ssDNA cleavage activity of non-target ssDNAs once it is activated (by hybridization of and associated guide RNA to its target DNA).

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12 protein (e.g., Cas12a, Cas12b, Cas12c) (e.g., a Cas12 protein depicted in FIGS. 1A-1E). For example, in some cases a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12 protein (e.g., Cas12a, Cas12b, Cas12c) (e.g., a Cas12 protein depicted in FIGS. 1A-1E). In some cases a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12 protein (e.g., Cas12a, Cas12b, Cas12c) (e.g., a Cas12 protein depicted in FIGS. 1A-1E). In some cases a type V CRISPR/Cas effector protein comprises an amino acid sequence having 90% or more sequence identity (e.g., 95% or more, 97% or more, 98% or more, 99% or more, or 100% sequence identity) with a Cas12 protein (e.g., Cas12a, Cas12b, Cas12c) (e.g., a Cas12 protein depicted in FIGS. 1A-1E). In some cases a type V CRISPR/Cas effector protein comprises a Cas12 amino acid sequence (e.g., Cas12a, Cas12b, Cas12c) depicted in FIGS. 1A-1E.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12a protein (e.g., a Cas12a protein depicted in FIGS. 1A-1E). For example, in some cases a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12a protein (e.g., a Cas12a protein depicted in FIGS. 1A-1E). In some cases a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12a protein (e.g., a Cas12a protein depicted in FIGS. 1A-1E). In some cases a type V CRISPR/Cas effector protein comprises an amino acid sequence having 90% or more sequence identity (e.g., 95% or more, 97% or more, 98% or more, 99% or more, or 100% sequence identity) with a Cas12a protein (e.g., a Cas12a protein depicted in FIGS. 1A-1E). In some cases a type V CRISPR/Cas effector protein comprises a Cas12a amino acid sequence depicted in FIGS. 1A-1E.

In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Lachnospiraceae bacterium ND2006 Cas12a protein amino acid sequence depicted in FIGS. 1A-1E. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Acidaminococcus* spBV3L6 Cas12a protein amino acid sequence depicted in FIGS. 1A-1E. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Francisella novicida* U112 Cas12a protein amino acid sequence depicted in FIGS. 1A-1E. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Porphyromonas macacae* Cas12a protein amino acid sequence depicted in FIGS. 1A-1E. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Moraxella bovoculi* 237 Cas12a protein amino acid sequence depicted in FIGS. 1A-1E. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Moraxella bovoculi* AAX08_00205 Cas12a protein amino acid sequence depicted in FIGS. 1A-1E. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Moraxella bovoculi* AAX11_00205 Cas12a protein amino acid sequence depicted in FIGS. 1A-1E. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Thiomicrospira* sp. XS5 Cas12a protein amino acid sequence depicted in FIGS. 1A-1E. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the *Butyrivibrio* sp. NC3005 Cas12a protein amino acid sequence depicted in FIGS. 1A-1E. In some cases, a suitable type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the AACCas12b amino acid sequence depicted in FIGS. 1A-1E.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12b protein (e.g., a Cas12b protein depicted in FIGS. 1A-1E). For example, in some cases a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12b protein (e.g., a Cas12b protein depicted in FIGS. 1A-1E). In some cases a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12b protein (e.g., a Cas12b protein depicted in FIGS. 1A-1E). In some cases a type V CRISPR/Cas effector protein comprises an amino acid sequence having 90% or more sequence identity (e.g., 95% or more, 97% or more, 98% or more, 99% or more, or 100% sequence identity) with a Cas12b protein (e.g., a Cas12b protein depicted in FIGS. 1A-1E). In some cases a type V CRISPR/Cas effector protein comprises a Cas12b amino acid sequence depicted in FIGS. 1A-1E.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12, C2c4, C2c8, C2c5, C2c10, or C2c9 protein. For example, in some cases a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12, C2c4, C2c8, C2c5, C2c10, or C2c9 protein. In some cases a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12, C2c4, C2c8, C2c5, C2c10, or C2c9 protein. In some cases a type V CRISPR/Cas effector protein comprises an amino acid sequence having 90% or more sequence identity (e.g., 95% or more, 97% or more, 98% or more, 99% or more, or 100% sequence identity) with a Cas12, C2c4, C2c8, C2c5, C2c10, or C2c9 protein. In some cases a type V CRISPR/Cas effector protein comprises a Cas12, C2c4, C2c8, C2c5, C2c10, or C2c9 amino acid sequence.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12, C2c4, C2c8, or C2c5protein. For example, in some cases a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12, C2c4, C2c8, or C2c5protein. In some cases a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12, C2c4, C2c8, or C2c5 protein. In some cases a type V CRISPR/Cas effector protein comprises an amino acid sequence having 90% or more sequence identity (e.g., 95% or more, 97% or more, 98% or more, 99% or more, or 100% sequence identity) with a Cas12, C2c4, C2c8, or C2c5 protein. In some cases a type V CRISPR/Cas effector protein comprises a Cas12, C2c4, C2c8, or C2c5 amino acid sequence.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a C2c4, C2c8, or C2c5 protein. For example, in some cases a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a C2c4, C2c8, or C2c5 protein. In some cases a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a C2c4, C2c8, or C2c5 protein. In some cases a type V CRISPR/Cas effector protein comprises an amino acid sequence having 90% or more sequence identity (e.g., 95% or more, 97% or more, 98% or more, 99% or more, or 100% sequence identity) with a C2c4, C2c8, or C2c5 protein. In some cases a type V CRISPR/Cas effector protein comprises a C2c4, C2c8, or C2c5 amino acid sequence.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a Cas12, C2c10, or C2c9 protein. For example, in some cases a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a Cas12, C2c10, or C2c9 protein. In some cases a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12, C2c10, or C2c9 protein. In some cases a type V CRISPR/Cas effector protein comprises an amino acid sequence having 90% or more sequence identity (e.g., 95% or more, 97% or more, 98% or more, 99% or more, or 100% sequence identity) with a Cas12, C2c10, or C2c9 protein. In some cases a type V CRISPR/Cas effector protein comprises a Cas12, C2c10, or C2c9 amino acid sequence.

In some cases, a type V CRISPR/Cas effector protein comprises an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with a C2c10 or C2c9 protein. For example, in some cases a type V CRISPR/Cas effector protein comprises an amino acid sequence having 50% or more sequence identity (e.g., 60% or more, 70% or more, 80% or more, 85% or more, 90% or more, 95% or more, 97% or more, 98% or more, 99% or more, or 100% sequence identity) with a C2c10 or C2c9 protein. In some cases a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a C2c10 or C2c9 protein. In some cases a type V CRISPR/Cas effector protein comprises an amino acid sequence having 90% or more sequence identity (e.g., 95% or more, 97% or more, 98% or more, 99% or more, or 100% sequence identity) with a C2c10 or C2c9 protein. In some cases a type V CRISPR/Cas effector protein comprises a C2c10 or C2c9 amino acid sequence.

In some cases, a subject type V CRISPR/Cas effector protein (e.g., a Cas12 protein such as Cas12a, Cas12b, Cas12c, Cas12d, Cas12e) is fused to (conjugated to) a heterologous polypeptide. In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some cases, a type V CRISPR/Cas effector protein (e.g., a Cas12 protein) does not include a NLS so that the protein is not targeted to the nucleus (which can be advantageous, e.g., when it desirable to cleave non-target ssDNAs in the cytosol). In some cases, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like).

In some cases a type V CRISPR/Cas effector protein (e.g., a Cas12 protein such as Cas12a, Cas12b, Cas12c, Cas12d, Cas12e) includes (is fused to) a nuclear localization signal (NLS) (e.g., in some cases 2 or more, 3 or more, 4 or more, or 5 or more NLSs). Thus, in some cases, a type V CRISPR/Cas effector protein includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a type V CRISPR/Cas effector protein (e.g., a Cas12 protein such as Cas12a, Cas12b, Cas12c, Cas12d, Cas12e) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a type V CRISPR/Cas effector protein includes (is fused to) between 2 and 5 NLSs (e.g., 2-4, or 2-3 NLSs). Non-limiting examples of NLSs include an NLS sequence derived from: the NLS of the SV40 virus large T-antigen, having the amino acid sequence PKKKRKV (SEQ ID NO: 136); the NLS from nucleoplasmin (e.g., the nucleoplasmin bipartite NLS with the sequence KRPAATKKAGQAKKKK (SEQ ID NO: 137)); the c-myc NLS having the amino acid sequence PAAKRVKLD (SEQ ID NO: 138) or RQRRNELKRSP (SEQ ID NO: 139); the hRNPA1 M9 NLS having the sequence NQSSNFGPMKGGNFGGRSSGPYGGGGQYFAKPRNQGGY (SEQ ID NO: 140); the sequence RMRIZFKNKGKDTAELRRRRVEVSVELRKAKKDEQILKRRNV (SEQ ID NO: 141) of the IBB domain from importin-alpha; the sequences VSRKRPRP (SEQ ID NO: 142) and PPKKARED (SEQ ID NO: 143) of the myoma T protein; the sequence PQPKKKPL (SEQ ID NO: 144) of human p53; the sequence SALIKKKKKMAP (SEQ ID NO: 145) of mouse c-abl IV; the sequences DRLRR (SEQ ID NO: 146) and PKQKKRK (SEQ ID NO: 147) of the influenza virus NS1; the sequence RKLKKKIKKL (SEQ ID NO: 148) of the Hepatitis virus delta antigen; the sequence REKKKFLKRR (SEQ ID NO: 149) of the mouse Mx1 protein; the sequence KRKGDEVDGVDEVAKKKSKK (SEQ ID NO: 150) of the human poly(ADP-ribose) polymerase; and the sequence RKCLQAGMNLEARKTKK (SEQ ID NO: 151) of the steroid hormone receptors (human) glucocorticoid. In general, NLS (or multiple NLSs) are of sufficient strength to drive accumulation of the protein in a detectable amount in the nucleus of a eukaryotic cell. Detection of accumulation in the nucleus may be performed by any suitable technique.

Protospacer Adjacent Motif (PAM)

A Type V CRISPR/Cas effector protein binds to target DNA at a target sequence defined by the region of complementarity between the DNA-targeting RNA and the target DNA. As is the case for many CRISPR/Cas endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some cases, the PAM for a Type V CRISPR/Cas effector protein is immediately 5' of the target sequence (e.g., of the non-complementary strand of the target DNA— the complementary strand hybridizes to the guide sequence of the guide RNA while the non-complementary strand does not directly hybridize with the guide RNA and is the reverse complement of the non-complementary strand). In some cases (e.g., when Cas12a or Cas12b as described herein is used), the PAM sequence is 5'-TTN-3'. In some cases, the PAM sequence is 5'-TTTN-3.' (e.g., see FIG. 2).

In some cases, different Type V CRISPR/Cas effector proteins (i.e., Type V CRISPR/Cas effector proteins from various species) may be advantageous to use in the various provided methods in order to capitalize on a desired feature (e.g., specific enzymatic characteristics of different Type V CRISPR/Cas effector proteins). Type V CRISPR/Cas effector proteins from different species may require different PAM sequences in the target DNA. Thus, for a particular Type V CRISPR/Cas effector protein of choice, the PAM sequence requirement may be different than the 5'-TTN-3' or 5'-TTTN-3' sequence described above. Various methods (including in silico and/or wet lab methods) for identification of the appropriate PAM sequence are known in the art and are routine, and any convenient method can be used.

Guide RNA

A nucleic acid molecule (e.g., a natural crRNA) that binds to a type V CRISPR/Cas effector protein (e.g., a Cas12 protein such as Cas12a, Cas12b, Cas12c, Cas12d, Cas12e), forming a ribonucleoprotein complex (RNP), and targets the complex to a specific target sequence within a target DNA is referred to herein as a "guide RNA." It is to be understood that in some cases, a hybrid DNA/RNA can be made such that a guide RNA includes DNA bases in addition to RNA bases—but the term "guide RNA" is still used herein to encompass such hybrid molecules. A subject guide RNA includes a guide sequence (also referred to as a "spacer") (that hybridizes to target sequence of a target DNA) and a constant region (e.g., a region that is adjacent to the guide sequence and binds to the type V CRISPR/Cas effector protein). A "constant region" can also be referred to herein as a "protein-binding segment." In some cases, e.g., for Cas12a, the constant region is 5' of the guide sequence.

Guide Sequence

The guide sequence has complementarity with (hybridizes to) a target sequence of the target DNA. In some cases, the guide sequence is 15-28 nucleotides (nt) in length (e.g., 15-26, 15-24, 15-22, 15-20, 15-18, 16-28, 16-26, 16-24, 16-22, 16-20, 16-18, 17-26, 17-24, 17-22, 17-20, 17-18, 18-26, 18-24, or 18-22 nt in length). In some cases, the guide sequence is 18-24 nucleotides (nt) in length. In some cases, the guide sequence is at least 15 nt long (e.g., at least 16, 18, 20, or 22 nt long). In some cases, the guide sequence is at least 17 nt long. In some cases, the guide sequence is at least 18 nt long. In some cases, the guide sequence is at least 20 nt long.

In some cases, the guide sequence has 80% or more (e.g., 85% or more, 90% or more, 95% or more, or 100% complementarity) with the target sequence of the target DNA. In some cases, the guide sequence is 100% complementary to the target sequence of the target DNA. In some cases, the target DNA includes at least 15 nucleotides (nt) of complementarity with the guide sequence of the guide RNA.

Constant Region

Examples of constant regions for guide RNAs that can be used with a type V CRISPR/Cas effector protein (e.g., a Cas12 protein such as Cas12a, Cas12b, Cas12c, Cas12d, Cas12e) are presented in FIG. 2.

In some cases, a subject guide RNA includes a nucleotide sequence having 70% or more identity (e.g., 80% or more, 85% or more, 90% or more, 95% or more, 98% or more, 99% or more, or 100% identity) with any one of the crRNA repeat sequences set forth in FIG. 2. In some cases, a subject guide RNA includes a nucleotide sequence having 90% or more identity (e.g., 95% or more, 98% or more, 99% or more, or 100% identity) with any one of the crRNA repeat sequences set forth in FIG. 2. In some cases, a subject guide RNA includes a crRNA nucleotide sequence set forth in FIG. 2.

In some cases, the guide RNA includes a double stranded RNA duplex (dsRNA duplex).

In some cases, a guide RNA includes a dsRNA duplex with a length of from 2 to 12 bp (e.g., from 2 to 10 bp, 2 to 8 bp, 2 to 6 bp, 2 to 5 bp, 2 to 4 bp, 3 to 12 bp, 3 to 10 bp, 3 to 8 bp, 3 to 6 bp, 3 to 5 bp, 3 to 4 bp, 4 to 12 bp, 4 to 10 bp, 4 to 8 bp, 4 to 6 bp, or 4 to 5 bp). In some cases, a guide RNA includes a dsRNA duplex that is 2 or more bp in length (e.g., 3 or more, 4 or more, 5 or more, 6 or more, or 7 or more bp in length). In some cases, a guide RNA includes a dsRNA duplex that is longer than the dsRNA duplex of a corresponding wild type guide RNA. In some cases, a guide RNA includes a dsRNA duplex that is shorter than the dsRNA duplex of a corresponding wild type guide RNA.

In some cases, the constant region of a guide RNA is 15 or more nucleotides (nt) in length (e.g., 18 or more, 20 or more, 21 or more, 22 or more, 23 or more, 24 or more, 25 or more, 26 or more, 27 or more, 28 or more, 29 or more, 30 or more, 31 or more nt, 32 or more, 33 or more, 34 or more, or 35 or more nt in length). In some cases, the constant region of a guide RNA is 18 or more nt in length.

In some cases, the constant region of a guide RNA has a length in a range of from 12 to 100 nt (e.g., from 12 to 90, 12 to 80, 12 to 70, 12 to 60, 12 to 50, 12 to 40, 15 to 100, 15 to 90, 15 to 80, 15 to 70, 15 to 60, 15 to 50, 15 to 40, 20 to 100, 20 to 90, 20 to 80, 20 to 70, 20 to 60, 20 to 50, 20 to 40, 25 to 100, 25 to 90, 25 to 80, 25 to 70, 25 to 60, 25 to 50, 25 to 40, 28 to 100, 28 to 90, 28 to 80, 28 to 70, 28 to 60, 28 to 50, 28 to 40, 29 to 100, 29 to 90, 29 to 80, 29 to 70, 29 to 60, 29 to 50, or 29 to 40 nt). In some cases, the constant region of a guide RNA has a length in a range of from 28 to 100 nt. In some cases, the region of a guide RNA that is 5' of the guide sequence has a length in a range of from 28 to 40 nt.

In some cases, the constant region of a guide RNA is truncated relative to (shorter than) the corresponding region of a corresponding wild type guide RNA. In some cases, the constant region of a guide RNA is extended relative to (longer than) the corresponding region of a corresponding wild type guide RNA. In some cases, a subject guide RNA is 30 or more nucleotides (nt) in length (e.g., 34 or more, 40 or more, 45 or more, 50 or more, 55 or more, 60 or more, 65 or more, 70 or more, or 80 or more nt in length). In some cases, the guide RNA is 35 or more nt in length.

Precursor Guide RNA Array

A Type V CRISPR/Cas effector protein (e.g., a Cas12 protein such as Cas12a, Cas12b, Cas12c, Cas12d, Cas12e) can cleave a precursor guide RNA into a mature guide RNA, e.g., by endoribonucleolytic cleavage of the precursor. A Type V CRISPR/Cas effector protein (e.g., a Cas12 protein such as Cas12a, Cas12b, Cas12c, Cas12d, Cas12e) can cleave a precursor guide RNA array (that includes more than one guide RNA arrayed in tandem) into two or more individual guide RNAs. Thus, in some cases a precursor guide RNA array comprises two or more (e.g., 3 or more, 4 or more, 5 or more, 2, 3, 4, or 5) guide RNAs (e.g., arrayed in tandem as precursor molecules). In other words, in some cases, two or more guide RNAs can be present on an array (a precursor guide RNA array). A Type V CRISPR/Cas effector protein (e.g., a Cas12 protein such as Cas12a, Cas12b, Cas12c, Cas12d, Cas12e) can cleave the precursor guide RNA array into individual guide RNAs In some cases a subject guide RNA array includes 2 or more guide RNAs (e.g., 3 or more, 4 or more, 5 or more, 6 or more, or 7 or more, guide RNAs). The guide RNAs of a given array can target (i.e., can include guide sequences that hybridize to) different target sites of the same target DNA (e.g., which can increase sensitivity of detection) and/or can target different target DNA molecules (e.g., single nucleotide polymorphisms (SNPs), different strains of a particular virus, etc.), and such could be used for example to detect multiple strains of a virus. In some cases, each guide RNA of a precursor guide RNA array has a different guide sequence. In some cases, two or more guide RNAs of a precursor guide RNA array have the same guide sequence.

In some cases, the precursor guide RNA array comprises two or more guide RNAs that target different target sites within the same target DNA molecule. For example, such a scenario can in some cases increase sensitivity of detection by activating Type V CRISPR/Cas effector protein (e.g., a Cas12 protein such as Cas12a, Cas12b, Cas12c, Cas12d, Cas12e) when either one hybridizes to the target DNA molecule. As such, in some cases as subject composition (e.g., kit) or method includes two or more guide RNAs (in the context of a precursor guide RNA array, or not in the context of a precursor guide RNA array, e.g., the guide RNAs can be mature guide RNAs).

In some cases, the precursor guide RNA array comprises two or more guide RNAs that target different target DNA molecules. For example, such a scenario can result in a positive signal when any one of a family of potential target DNAs is present. Such an array could be used for targeting a family of transcripts, e.g., based on variation such as single nucleotide polymorphisms (SNPs) (e.g., for diagnostic purposes). Such could also be useful for detecting whether any one of a number of different strains of virus is present. Such could also be useful for detecting whether any one of a number of different species, strains, isolates, or variants of a bacterium is present (e.g., different species, strains, isolates, or variants of *Mycobacterium*, different species, strains, isolates, or variants of *Neisseria*, different species, strains, isolates, or variants of *Staphylococcus aureus*; different species, strains, isolates, or variants of *E. coli*; etc.). As such, in some cases as subject composition (e.g., kit) or method includes two or more guide RNAs (in the context of a precursor guide RNA array, or not in the context of a precursor guide RNA array, e.g., the guide RNAs can be mature guide RNAs).

Nucleic Acid Modifications

In some cases, a labeled detector ssDNA (and/or a guide RNA) comprises one or more modifications, e.g., a base modification, a backbone modification, a sugar modification, etc., to provide the nucleic acid with a new or enhanced feature (e.g., improved stability). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable modifications include modified nucleic acid backbones and non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a labeled detector ssDNA (and/or a guide RNA) comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some cases, a labeled detector ssDNA (and/or a guide RNA) comprises a 6-membered morpholino ring in place of a ribose ring. In some cases, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A labeled detector ssDNA (and/or a guide RNA) can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH$_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A labeled detector ssDNA (and/or a guide RNA) can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

Other suitable sugar substituent groups include methoxy (—O—CH$_3$), aminopropoxy (—OCH$_2$CH$_2$CH$_2$NH$_2$), allyl (—CH$_2$—CH=CH$_2$), —O-allyl CH$_2$—CH=CH$_2$) and fluoro (F). 2'-sugar substituent groups may be in the arabino (up) position or ribo (down) position. A suitable 2'-arabino modification is 2'-F Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A labeled detector ssDNA (and/or a guide RNA) may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Introducing Components into a Target Cell

A guide RNA (or a nucleic acid comprising a nucleotide sequence encoding same) and/or a type V CRISPR/Cas effector protein can be introduced into a host cell by any of a variety of well-known methods. As a non-limiting example, a guide RNA and/or type V CRISPR/Cas effector protein can be combined with a lipid. As another non-limiting example, a guide RNA and/or type V CRISPR/Cas effector protein can be combined with a particle, or formulated into a particle.

Methods of introducing a nucleic acid and/or protein into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al. Adv Drug Deliv Rev. 2012 Sep. 13. pii: 50169-409X(12)00283-9. doi: 10.1016/j.addr.2012.09.023), and the like.

A guide RNA can be introduced, e.g., as a DNA molecule encoding the guide RNA, or can be provided directly as an RNA molecule (or a hybrid molecule when applicable). In some cases, a type V CRISPR/Cas effector protein is provided as a nucleic acid (e.g., an mRNA, a DNA, a plasmid, an expression vector, a viral vector, etc.) that encodes the protein. In some cases, the type V CRISPR/Cas effector protein is provided directly as a protein (e.g., without an associated guide RNA or with an associate guide RNA, i.e., as a ribonucleoprotein complex—RNP). Like a guide RNA, a type V CRISPR/Cas effector protein can be introduced into a cell (provided to the cell) by any convenient method; such methods are known to those of ordinary skill in the art. As an illustrative example, a type V CRISPR/Cas effector protein can be injected directly into a cell (e.g., with or without a guide RNA or nucleic acid encoding a guide RNA). As another example, a preformed complex of a type V CRISPR/Cas effector protein and a guide RNA (an RNP) can be introduced into a cell (e.g., eukaryotic cell) (e.g., via injection, via nucleofection; via a protein transduction domain (PTD) conjugated to one or more components, e.g., conjugated to the type V CRISPR/Cas effector protein, conjugated to a guide RNA; etc.).

In some cases, a nucleic acid (e.g., a guide RNA; a nucleic acid comprising a nucleotide sequence encoding a type V CRISPR/Cas effector protein; etc.) and/or a polypeptide (e.g., a type V CRISPR/Cas effector protein) is delivered to a cell (e.g., a target host cell) in a particle, or associated with a particle. The terms "particle" and "nanoparticle" can be used interchangeably, as appropriate.

This can be achieved, e.g., using particles or lipid envelopes, e.g., a ribonucleoprotein (RNP) complex can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5).

A type V CRISPR/Cas effector protein (or an mRNA comprising a nucleotide sequence encoding the protein) and/or guide RNA (or a nucleic acid such as one or more expression vectors encoding the guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent publication 20110293703) are also useful in the administration of polynucleotides, and can be used. In one aspect, aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used, sugar-based particles may be used, for example GalNAc, as described with reference to WO2014118272 (incorporated herein by reference) and Nair, J K et al., 2014, Journal of the American Chemical Society 136 (49), 16958-16961). In some cases, lipid nanoparticles (LNPs) are used. Spherical Nucleic Acid (SNA™) constructs and other nanoparticles (particularly gold nanoparticles) can be used to a target cell. See, e.g., Cutler et al., J. Am. Chem. Soc. 2011 133:9254-9257, Hao et al., Small 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192. Semi-solid and soft nanoparticles are also suitable for delivery. An exosome can be used for delivery. Exosomes are endogenous nano-vesicles that transport RNAs and proteins, and which can deliver RNA to the brain and other target organs. Supercharged proteins can be used for delivery to a cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can facilitate the functional delivery of these macromolecules into mammalian cells both in vitro and in vivo. Cell Penetrating Peptides (CPPs) can be used for delivery. CPPs typically have an amino acid composition that either contains a high relative abundance of positively charged amino acids such as lysine or arginine or has sequences that contain an alternating pattern of polar/charged amino acids and non-polar, hydrophobic amino acids.

Target Cells of Interest

Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuña, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

Because the guide RNA provides specificity by hybridizing to target nucleic acid, a mitotic and/or post-mitotic cell of interest in the disclosed methods may include a cell of any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell of an invertebrate animal (e.g. fruit fly, cnidarian, echinoderm, nematode, etc.), a cell of a vertebrate animal (e.g., fish, amphibian, reptile, bird, mammal), a cell of a mammal, a cell of a rodent, a cell of a human, etc.).

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Kits

The present disclosure provides a kit for detecting a target DNA, e.g., in a sample comprising a plurality of DNAs. In some cases, the kit comprises: (a) a labeled detector ssDNA (e.g., a labeled detector ssDNA comprising a fluorescence-emitting dye pair, i.e., a FRET pair and/or a quencher/fluor pair); and (b) one or more of: (i) a guide RNA, and/or a nucleic acid encoding said guide RNA; (ii) a precursor guide RNA array comprising two or more guide RNAs (e.g., each of which has a different guide sequence), and/or a nucleic acid encoding the precursor guide RNA array; and (iii) a Type V CRISPR/Cas effector protein (e.g., a Cas12 protein such as Cas12a, Cas12b, Cas12c, Cas12d, Cas12e), and/or a nucleic acid encoding said Type V CRISPR/Cas effector protein. In some cases a nucleic acid encoding a precursor guide RNA array includes sequence insertion sites for the insertion of guide sequences by a user.

In some cases, a subject kit comprises: (a) a labeled detector ssDNA comprising a fluorescence-emitting dye pair, i.e., a FRET pair and/or a quencher/fluor pair; and (b) one or more of: (i) a guide RNA, and/or a nucleic acid encoding said guide RNA; (ii); a precursor guide RNA array comprising two or more guide RNAs (e.g., each of which has a different guide sequence), and/or a nucleic acid encoding the precursor guide RNA array; and (iii) a Type V CRISPR/Cas effector protein (e.g., a Cas12 protein such as Cas12a, Cas12b, Cas12c, Cas12d, Cas12e), and/or a nucleic acid encoding said Type V CRISPR/Cas effector protein.

Positive Controls

A kit of the present disclosure (e.g., one that comprises a labeled detector ssDNA and a type V CRISPR/Cas effector protein) can also include a positive control target DNA. In some cases, the kit also includes a positive control guide RNA that comprises a nucleotide sequence that hybridizes to the control target DNA. In some cases, the positive control target DNA is provided in various amounts, in separate containers. In some cases, the positive control target DNA is provided in various known concentrations, in separate containers, along with control non-target DNAs.

Nucleic Acids

While the RNAs of the disclosure (e.g., guide RNAs and precursor guide RNA arrays) can be synthesized using any convenient method (e.g., chemical synthesis, in vitro using an RNA polymerase enzyme, e.g., T7 polymerase, T3 polymerase, SP6 polymerase, etc.), nucleic acids encoding guide RNAs and/or precursor guide RNA arrays are also envisioned. Additionally, while Type V CRISPR/Cas effector proteins (e.g., a Cas12 protein such as Cas12a, Cas12b, Cas12c, Cas12d, Cas12e) of the disclosure can be provided (e.g., as part of a kit) in protein form, nucleic acids (such as mRNA and/or DNA) encoding the Type V CRISPR/Cas effector protein (e.g., a Cas12 protein such as Cas12a, Cas12b, Cas12c, Cas12d, Cas12e)(s) can also be provided.

For example, in some cases, a kit of the present disclosure comprises a nucleic acid (e.g., a DNA, e.g., a recombinant expression vector) that comprises a nucleotide sequence encoding a guide RNA. In some cases, the nucleotide sequence encodes a guide RNA without a guide sequence. For example, in some cases, the nucleic acid comprises a nucleotide sequence encoding a constant region of a guide RNA (a guide RNA without a guide sequence), and comprises an insertion site for a nucleic acid encoding a guide sequence. In some cases, a kit of the present disclosure comprises a nucleic acid (e.g., an mRNA, a DNA, e.g., a recombinant expression vector) that comprises a nucleotide sequence encoding a Type V CRISPR/Cas effector protein (e.g., a Cas12 protein such as Cas12a, Cas12b, Cas12c, Cas12d, Cas12e).

In some cases, a kit of the present disclosure comprises a nucleic acid (e.g., a DNA, e.g., a recombinant expression vector) that comprises a nucleotide sequence encoding a precursor guide RNA array (e.g., in some cases where each guide RNA of the array has a different guide sequence). In some cases, one or more of the encoded guide RNAs of the array does not have a guide sequence, e.g., the nucleic acid can include insertion site(s) for the guide sequence(s) of one or more of the guide RNAs of the array. In some cases, a subject guide RNA can include a handle from a precursor crRNA but does not necessarily have to include multiple guide sequences.

In some cases, the guide RNA-encoding nucleotide sequence (and/or the precursor guide RNA array-encoding nucleotide sequence) is operably linked to a promoter, e.g., a promoter that is functional in a prokaryotic cell, a promoter that is functional in a eukaryotic cell, a promoter that is functional in a mammalian cell, a promoter that is functional in a human cell, and the like. In some cases, a nucleotide sequence encoding a Type V CRISPR/Cas effector protein (e.g., a Cas12 protein such as Cas12a, Cas12b, Cas12c, Cas12d, Cas12e) is operably linked to a promoter, e.g., a promoter that is functional in a prokaryotic cell, a promoter that is functional in a eukaryotic cell, a promoter that is functional in a mammalian cell, a promoter that is functional in a human cell, a cell type-specific promoter, a regulatable promoter, a tissue-specific promoter, and the like.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-45 (SET A) and 1-54 (SET B) are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Set A

1. A method of detecting a target DNA in a sample, the method comprising:
    (a) contacting the sample with:
        (i) a type V CRISPR/Cas effector protein;
        (ii) a guide RNA comprising: a region that binds to the type V CRISPR/Cas effector protein, and a guide sequence that hybridizes with the target DNA; and
        (iii) a detector DNA that is single stranded and does not hybridize with the guide sequence of the guide RNA; and
    (b) measuring a detectable signal produced by cleavage of the single stranded detector DNA by the type V CRISPR/Cas effector protein, thereby detecting the target DNA.

2. The method of 1, comprising contacting the sample with a precursor guide RNA array, wherein the type V CRISPR/Cas effector protein cleaves the precursor guide RNA array to produce said guide RNA and at least one additional guide RNA.

3. The method of 1 or 2, wherein the target DNA is single stranded.

4. The method of 1 or 2, wherein the target DNA is double stranded.

5. The method of any one of 1-4, wherein the target DNA is viral DNA.

6. The method of any one of 1-4, wherein the target DNA is papovavirus, hepdnavirus, herpesvirus, adenovirus, poxvirus, or parvovirus DNA.

7. The method of any one of 1-4, wherein the type V CRISPR/Cas effector protein is a Cas12 protein.

8. The method of any one of 1-6, wherein the type V CRISPR/Cas effector protein is a Cas12a (Cpf1) or Cas12b (C2c1) protein.

9. The method according to any one of 1-8, wherein the sample comprises DNA molecules from a cell lysate.

10. The method according to any one of 1-9, wherein the sample comprises cells.

11. The method according to any one of 1-10, wherein said contacting is carried out inside of a cell in vitro, ex vivo, or in vivo.

12. The method according to 11, wherein the cell is a eukaryotic cell.

13. The method according to any one of 1-12, wherein the target DNA can be detected at a concentration as low as 200 fM.

14. The method according to any one of 1-13, comprising determining an amount of the target DNA present in the sample.

15. The method according to 14, wherein said determining comprises:
    measuring the detectable signal to generate a test measurement;
    measuring a detectable signal produced by a reference sample or cell to generate a reference measurement; and
    comparing the test measurement to the reference measurement to determine an amount of target DNA present in the sample.

16. The method according to any one of 1-15, wherein measuring a detectable signal comprises one or more of: gold nanoparticle based detection, fluorescence polarization, colloid phase transition/dispersion, electrochemical detection, and semiconductor-based sensing.

17. The method according to any one of 1-16, wherein the single stranded detector DNA comprises a fluorescence-emitting dye pair.

18. The method according to 17, wherein the fluorescence-emitting dye pair produces an amount of detectable signal prior to cleavage of the single stranded detector DNA, and the amount of detectable signal is reduced after cleavage of the single stranded detector DNA.

19. The method according to 17, wherein the single stranded detector DNA produces a first detectable signal prior to being cleaved and a second detectable signal after cleavage of the single stranded detector DNA.

20. The method according to any one of 17-19, wherein the fluorescence-emitting dye pair is a fluorescence resonance energy transfer (FRET) pair.

21. The method according to 17, wherein an amount of detectable signal increases after cleavage of the single stranded detector DNA.

22. The method according to 17 or 21, wherein the fluorescence-emitting dye pair is a quencher/fluor pair.

23. The method according to any one of 17-22, wherein the single stranded detector DNA comprises two or more fluorescence-emitting dye pairs.

24. The method according to 23, wherein said two or more fluorescence-emitting dye pairs include a fluorescence resonance energy transfer (FRET) pair and a quencher/fluor pair.

25. The method according to any one of 1-24, wherein the single stranded detector DNA comprises a modified nucleobase, a modified sugar moiety, and/or a modified nucleic acid linkage.

26. A kit for detecting a target DNA in a sample, the kit comprising:
(a) a guide RNA, or a nucleic acid encoding the guide RNA, or a precursor guide RNA array comprising the guide RNA, or a nucleic acid encoding the precursor guide RNA array; wherein the guide RNA comprises: a region that binds to a type V CRISPR/Cas effector protein, and a guide sequence that is complementary to a target DNA; and
(b) a labeled detector DNA that is single stranded and does not hybridize with the guide sequence of the guide RNA.

27. The kit of 26, further comprising a type V CRISPR/Cas effector protein.

28. The kit of 27, wherein the type V CRISPR/Cas effector protein is a Cas12 protein.

29. The kit of 27, wherein the type V CRISPR/Cas effector protein is a Cas12a (Cpf1) or Cas12b (C2c1) protein.

30. The kit of any one of 26-29, wherein the single stranded detector DNA comprises a fluorescence-emitting dye pair.

31. The kit of 30, wherein the fluorescence-emitting dye pair is a FRET pair.

32. The kit of 30, wherein the fluorescence-emitting dye pair is a quencher/fluor pair.

33. The kit of any one of 30-32, wherein the single stranded detector DNA comprises two or more fluorescence-emitting dye pairs.

34. The kit of 33, wherein said two or more fluorescence-emitting dye pairs include a first fluorescence-emitting dye pair that produces a first detectable signal and a second fluorescence-emitting dye pair that produces a second detectable signal.

35. A method of cleaving single stranded DNAs (ssDNAs), the method comprising:
contacting a population of nucleic acids, wherein said population comprises a target DNA and a plurality of non-target ssDNAs, with:
(i) a type V CRISPR/Cas effector protein; and
(ii) a guide RNA comprising: a region that binds to the type V CRISPR/Cas effector protein, and a guide sequence that hybridizes with the target DNA,
wherein the type V CRISPR/Cas effector protein cleaves non-target ssDNAs of said plurality.

36. The method of 35, comprising contacting the sample with a precursor guide RNA array, wherein the type V CRISPR/Cas effector protein cleaves the precursor guide RNA array to produce said guide RNA and at least one additional guide RNA.

37. The method of 35 or 36, wherein said contacting is inside of a cell in vitro, ex vivo, or in vivo.

38. The method of 37, wherein the cell is a eukaryotic cell.

39. The method of 38, wherein the eukaryotic cell is a plant cell.

40. The method of any one of 37-39, wherein the non-target ssDNAs are foreign to the cell.

41. The method of 40, wherein the non-target ssDNAs are viral DNAs.

42. The method of any one of 35-41, wherein the target DNA is single stranded.

43. The method of any one of 35-41, wherein the target DNA is double stranded.

44. The method of any one of 35-43, wherein the target DNA is viral DNA.

45. The method of any one of 35-43, wherein the target DNA is papovavirus, hepdnavirus, herpesvirus, adenovirus, poxvirus, or parvovirus DNA.

Set B

1. A method of detecting a target DNA in a sample, the method comprising:
(a) contacting the sample with:
(i) a type V CRISPR/Cas effector protein;
(ii) a guide RNA comprising: a region that binds to the type V CRISPR/Cas effector protein, and a guide sequence that hybridizes with the target DNA; and
(iii) a detector DNA that is single stranded and does not hybridize with the guide sequence of the guide RNA; and
(b) measuring a detectable signal produced by cleavage of the single stranded detector DNA by the type V CRISPR/Cas effector protein, thereby detecting the target DNA.

2. The method of 1, comprising contacting the sample with a precursor guide RNA array, wherein the type V CRISPR/Cas effector protein cleaves the precursor guide RNA array to produce said guide RNA and at least one additional guide RNA.

3. The method of 1 or 2, wherein the target DNA is single stranded.

4. The method of 1 or 2, wherein the target DNA is double stranded.

5. The method of any one of 1-4, wherein the target DNA is viral DNA.

6. The method of any one of 1-4, wherein the target DNA is papovavirus, hepdnavirus, herpesvirus, adenovirus, poxvirus, or parvovirus DNA.

7. The method of any one of 1-4, wherein the type V CRISPR/Cas effector protein is a Cas12 protein.

8. The method of any one of 1-6, wherein the type V CRISPR/Cas effector protein is a Cas12a (Cpf1) or Cas12b (C2c1) protein.

9. The method of any one of 1-6, wherein the type V CRISPR/Cas effector protein is a Cas12d (CasY) or Cas12e (CasX) protein.

10. The method according to any one of 1-9, wherein the sample comprises DNA molecules from a cell lysate.

11. The method according to any one of 1-10, wherein the sample comprises cells.

12. The method according to any one of 1-11, wherein said contacting is carried out inside of a cell in vitro, ex vivo, or in vivo.

13. The method according to 12, wherein the cell is a eukaryotic cell.

14. The method according to any one of 1-13, wherein the target DNA can be detected at a concentration as low as 200 fM.

15. The method according to any one of 1-14, comprising determining an amount of the target DNA present in the sample.

16. The method according to 15, wherein said determining comprises:
    measuring the detectable signal to generate a test measurement;
    measuring a detectable signal produced by a reference sample or cell to generate a reference measurement; and
    comparing the test measurement to the reference measurement to determine an amount of target DNA present in the sample.

17. The method according to any one of 1-16, wherein measuring a detectable signal comprises one or more of: gold nanoparticle based detection, fluorescence polarization, colloid phase transition/dispersion, electrochemical detection, and semiconductor-based sensing.

18. The method according to any one of 1-17, wherein the single stranded detector DNA comprises a fluorescence-emitting dye pair.

19. The method according to 18, wherein the fluorescence-emitting dye pair produces an amount of detectable signal prior to cleavage of the single stranded detector DNA, and the amount of detectable signal is reduced after cleavage of the single stranded detector DNA.

20. The method according to 18, wherein the single stranded detector DNA produces a first detectable signal prior to being cleaved and a second detectable signal after cleavage of the single stranded detector DNA.

21. The method according to any one of 18-20, wherein the fluorescence-emitting dye pair is a fluorescence resonance energy transfer (FRET) pair.

22. The method according to 18, wherein an amount of detectable signal increases after cleavage of the single stranded detector DNA.

23. The method according to 18 or 22, wherein the fluorescence-emitting dye pair is a quencher/fluor pair.

24. The method according to any one of 18-23, wherein the single stranded detector DNA comprises two or more fluorescence-emitting dye pairs.

25. The method according to 24, wherein said two or more fluorescence-emitting dye pairs include a fluorescence resonance energy transfer (FRET) pair and a quencher/fluor pair.

26. The method according to any one of 1-25, wherein the single stranded detector DNA comprises a modified nucleobase, a modified sugar moiety, and/or a modified nucleic acid linkage.

27. The method according to any one of 1-26, wherein the method comprises amplifying nucleic acids in the sample.

28. The method according to 27, wherein said amplifying comprises isothermal amplification.

29. The method according to 28, wherein the isothermal amplification comprises recombinase polymerase amplification (RPA).

30. The method according to any one of 27-29, wherein said amplifying begins prior to the contacting of step (a).

31. The method according to any one of 27-29, wherein said amplifying begins together with the contacting of step (a).

32. A kit for detecting a target DNA in a sample, the kit comprising:
    (a) a guide RNA, or a nucleic acid encoding the guide RNA, or a precursor guide RNA array comprising the guide RNA, or a nucleic acid encoding the precursor guide RNA array; wherein the guide RNA comprises: a region that binds to a type V CRISPR/Cas effector protein, and a guide sequence that is complementary to a target DNA; and
    (b) a labeled detector DNA that is single stranded and does not hybridize with the guide sequence of the guide RNA.

33. The kit of 32, further comprising a type V CRISPR/Cas effector protein.

34. The kit of 33, wherein the type V CRISPR/Cas effector protein is a Cas12 protein.

35. The kit of 33, wherein the type V CRISPR/Cas effector protein is a Cas12a (Cpf1) or Cas12b (C2c1) protein.

36. The kit of 33, wherein the type V CRISPR/Cas effector protein is a Cas12d (CasY) or Cas12e (CasX) protein.

37. The kit of any one of 32-36, wherein the single stranded detector DNA comprises a fluorescence-emitting dye pair.

38. The kit of 37, wherein the fluorescence-emitting dye pair is a FRET pair.

39. The kit of 37, wherein the fluorescence-emitting dye pair is a quencher/fluor pair.

40. The kit of any one of 37-39, wherein the single stranded detector DNA comprises two or more fluorescence-emitting dye pairs.

41. The kit of 40, wherein said two or more fluorescence-emitting dye pairs include a first fluorescence-emitting dye pair that produces a first detectable signal and a second fluorescence-emitting dye pair that produces a second detectable signal.

42. The kit of any one of 32-41, further comprising nucleic acid amplification components.

43. The kit of 42, wherein the nucleic acid amplification components are components for recombinase polymerase amplification (RPA).

44. A method of cleaving single stranded DNAs (ssDNAs), the method comprising:
    contacting a population of nucleic acids, wherein said population comprises a target DNA and a plurality of non-target ssDNAs, with:
    (i) a type V CRISPR/Cas effector protein; and
    (ii) a guide RNA comprising: a region that binds to the type V CRISPR/Cas effector protein, and a guide sequence that hybridizes with the target DNA,
    wherein the type V CRISPR/Cas effector protein cleaves non-target ssDNAs of said plurality.

45. The method of 44, comprising contacting the sample with a precursor guide RNA array, wherein the type V CRISPR/Cas effector protein cleaves the precursor guide RNA array to produce said guide RNA and at least one additional guide RNA.

46. The method of 44 or 45, wherein said contacting is inside of a cell in vitro, ex vivo, or in vivo.

47. The method of 46, wherein the cell is a eukaryotic cell.

48. The method of 47, wherein the eukaryotic cell is a plant cell.

49. The method of any one of 46-48, wherein the non-target ssDNAs are foreign to the cell.
50. The method of 49, wherein the non-target ssDNAs are viral DNAs.
51. The method of any one of 44-50, wherein the target DNA is single stranded.
52. The method of any one of 44-50, wherein the target DNA is double stranded.
53. The method of any one of 44-52, wherein the target DNA is viral DNA.
54. The method of any one of 44-52, wherein the target DNA is papovavirus, hepdnavirus, herpesvirus, adenovirus, poxvirus, or parvovirus DNA.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Figure 3B:
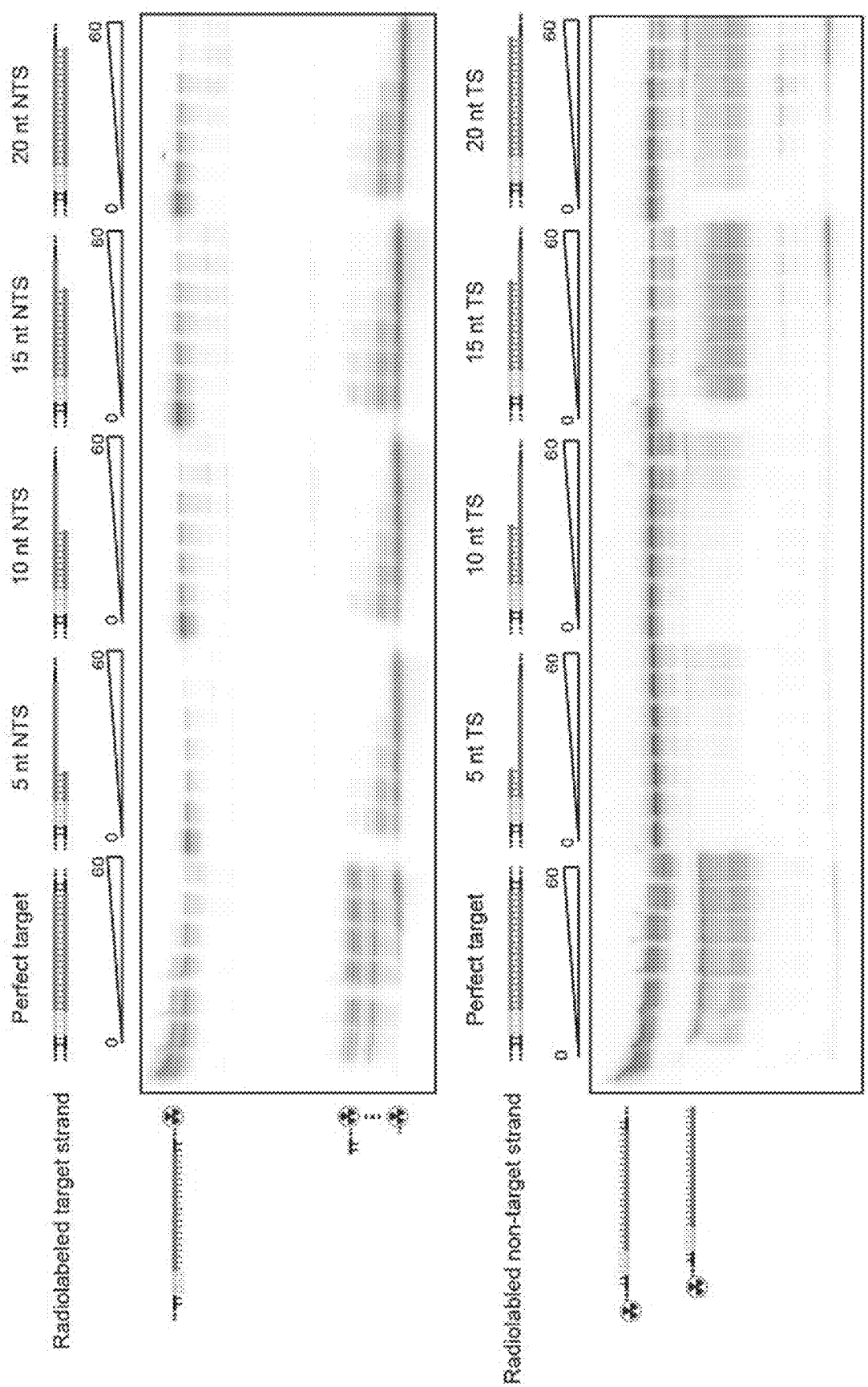

FIGS. 3A-3B. Non-complementary strand cleavage is dictated by complementary strand recognition. The length of the non-target strand (NTS) (top gel) or target strand (TS) (bottom gel) was altered to determine the substrate requirements for Cas12 cleavage. LbCas12a-crRNA complexes are in large excess over radiolabeled substrates, and cleavage products are resolved by denaturing polyacrylamide gel electrophoresis (PAGE). The TS was trimmed to single nucleotides regardless of the length of the NTS, whereas the NTS was cleaved only when at least 15 nt of complementary TS is present.

Figure 4A:
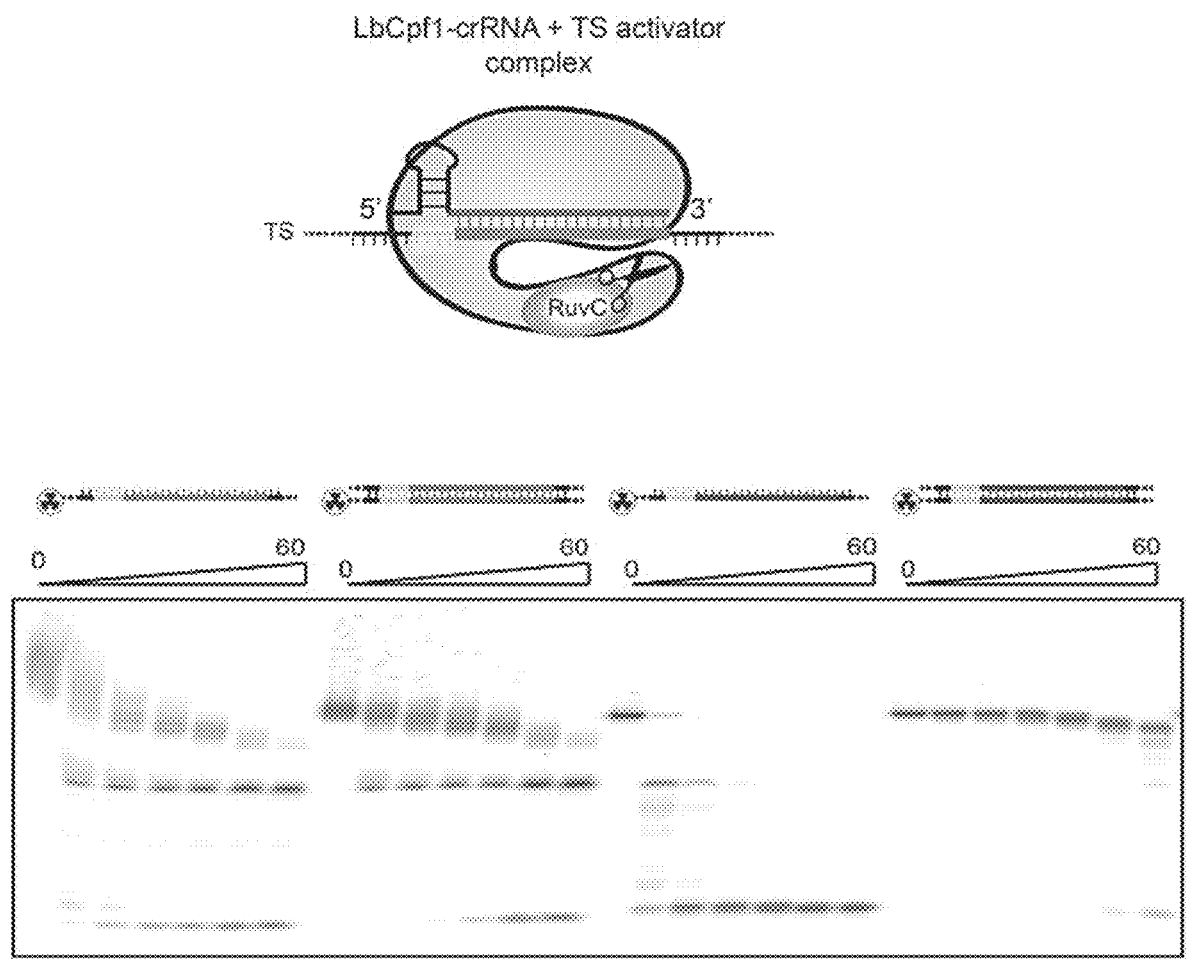
Figure 4B:
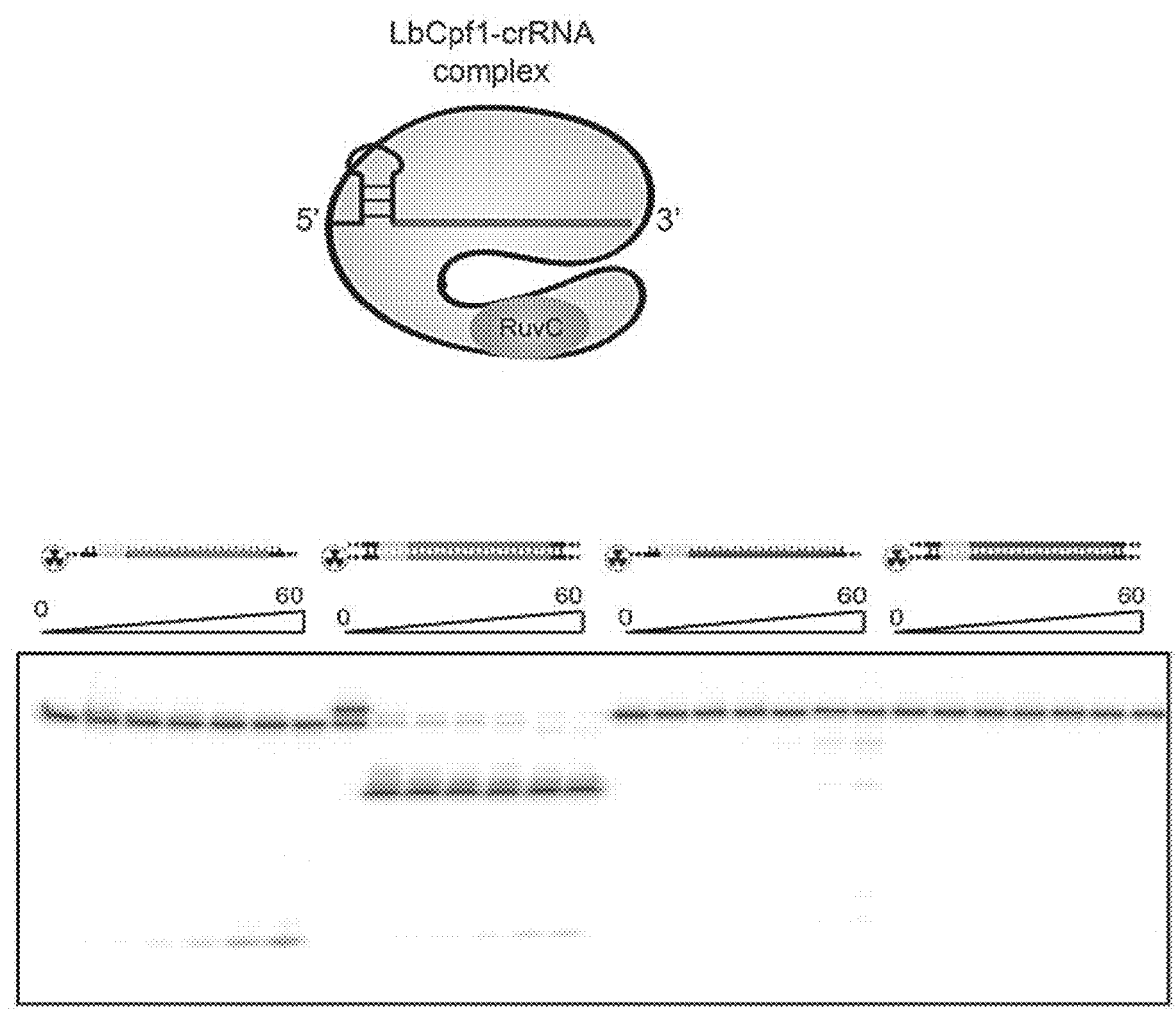

FIGS. 4A-4B. Complementary strand binding unleashes non-specific DNase activity by Cas12a. It was tested whether a non-complementary, random ssDNA is prone to degradation upon Cas12a activation by a complementary target strand. LbCas12a-crRNA complexes are in large excess over radiolabeled substrates, and cleavage products are resolved by denaturing PAGE. The random ssDNA radiolabeled target (blue) was degraded only when LbCas12a was pre-complexed with an "activator" complementary target strand. The random dsDNA radiolabeled target (blue) was protected from cleavage.

Figure 5A:
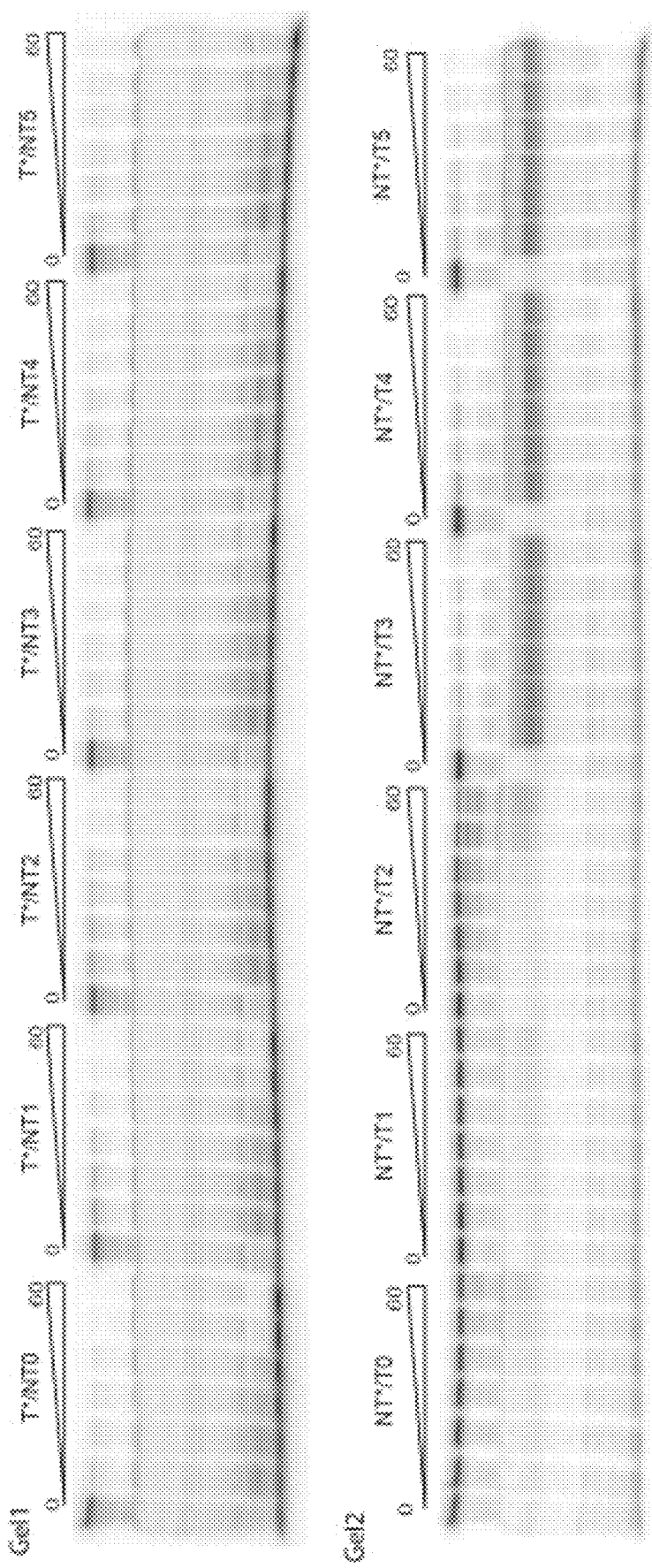

FIGS. 5A-5B. The non-target strand was cleaved only in the presence of a target strand with at least 15 nt of complementarity. LbCpf1 cleaved target strand DNA regardless of the length of the non-target strand. LbCpf1 cleaved non-target strand DNA only when the target strand had at least 15 nt of complementarity.

Figure 6:
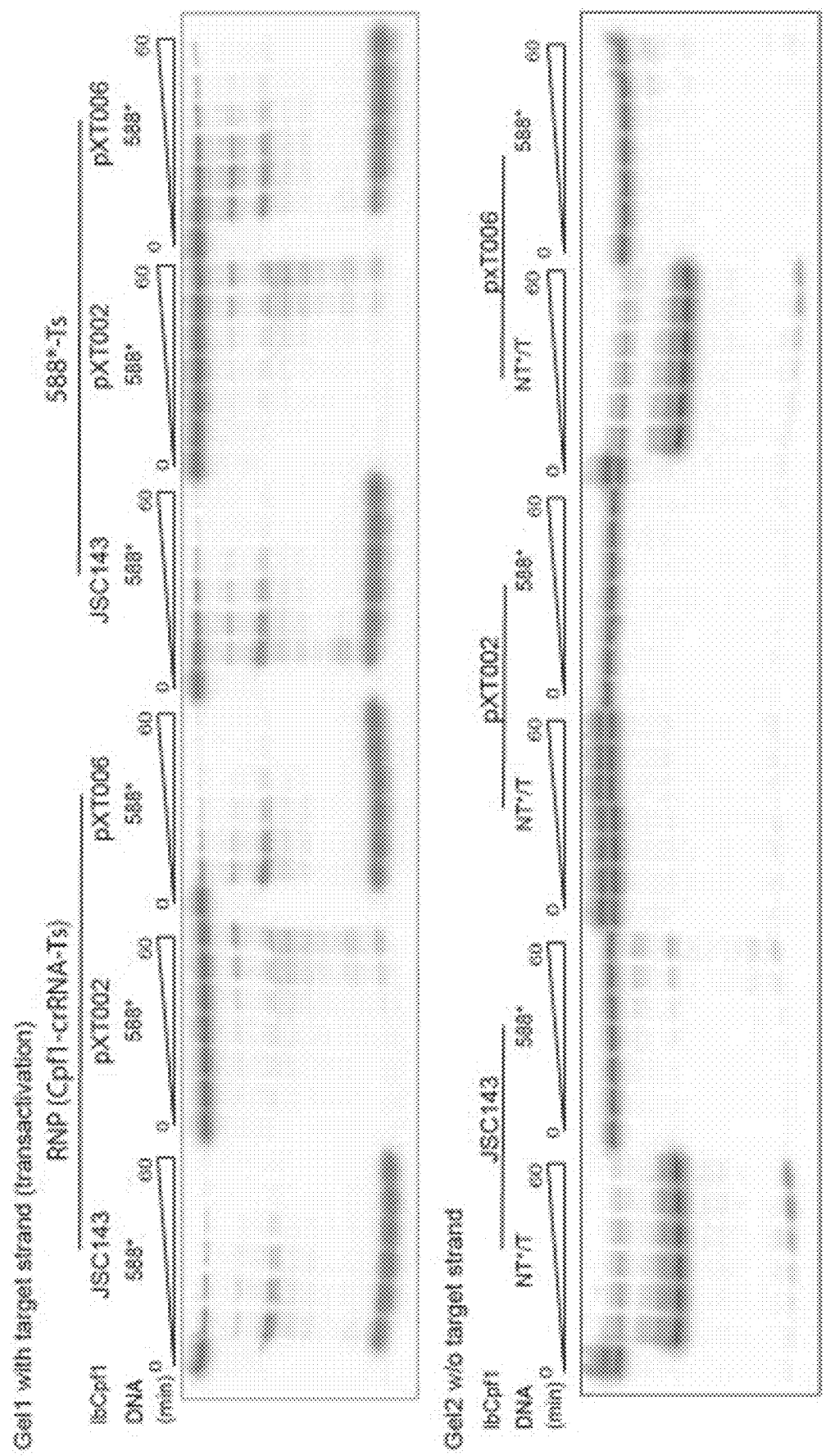
FIG. 6 presents data related to showing that the RuvC nuclease is responsible for trans-cleavage of ssDNA.

FIG. 6. The RuvC nuclease is responsible for trans-cleavage of ssDNA. In the presence of the activator target strand, non-specific trans-cleavage was not observed with a catalytically-inactive RuvC nuclease (pXT002). Trans-cleavage was still observed with a RNA-processing dead mutant (pXT006).

FIG. 7. Targeting by two homologs of Cas12a results in rapid "shredding" of M13 phage ssDNA. It was tested whether free 5' or 3' ends were required for trans-cleavage by using M13 phage circular ssDNA as a trans substrate. LbCas12a-crRNA and AsCas12a-crRNA was pre-complexed with a ssDNA activator (with no sequence complementarity to M13 phage) and incubated with M13 ssDNA at 37 C; products were resolved on a 1.5% agarose gel and visualized with SyberGold. Rapid shredding was observed at the earliest time point (1 min), and was both activator- and RuvC-dependent. The same trend with AsCas12a was observed suggesting that this activity is likely conserved across Cas12a homologs.

Figure 8:
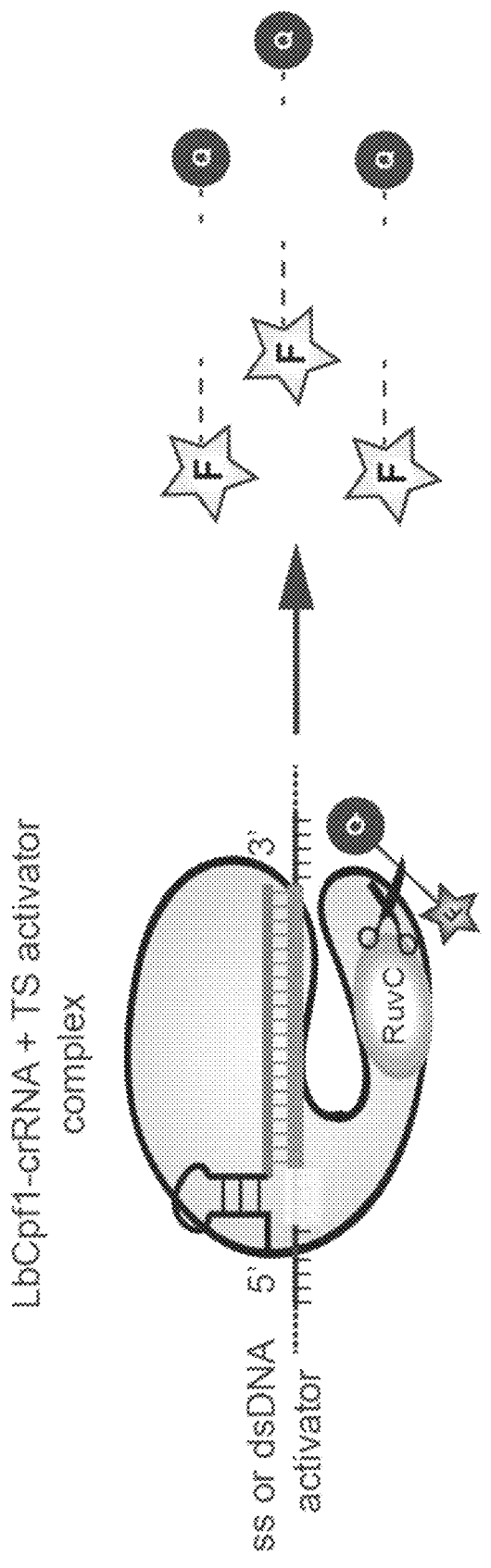
FIG. 8 presents data related to detection using an FQ-based assay.

FIG. 8. Trans-cleavage by Cas12a can be detected using an FQ-based assay. To improve the throughput of measuring trans-cleavage, an FQ-based assay using a DNase Alert substrate (IDT) was adapted as a probe for trans-activation. A fluorescence signal was released upon cleavage of the substrate, which contained a DNA linker and neighboring quencher.

Figure 9B:
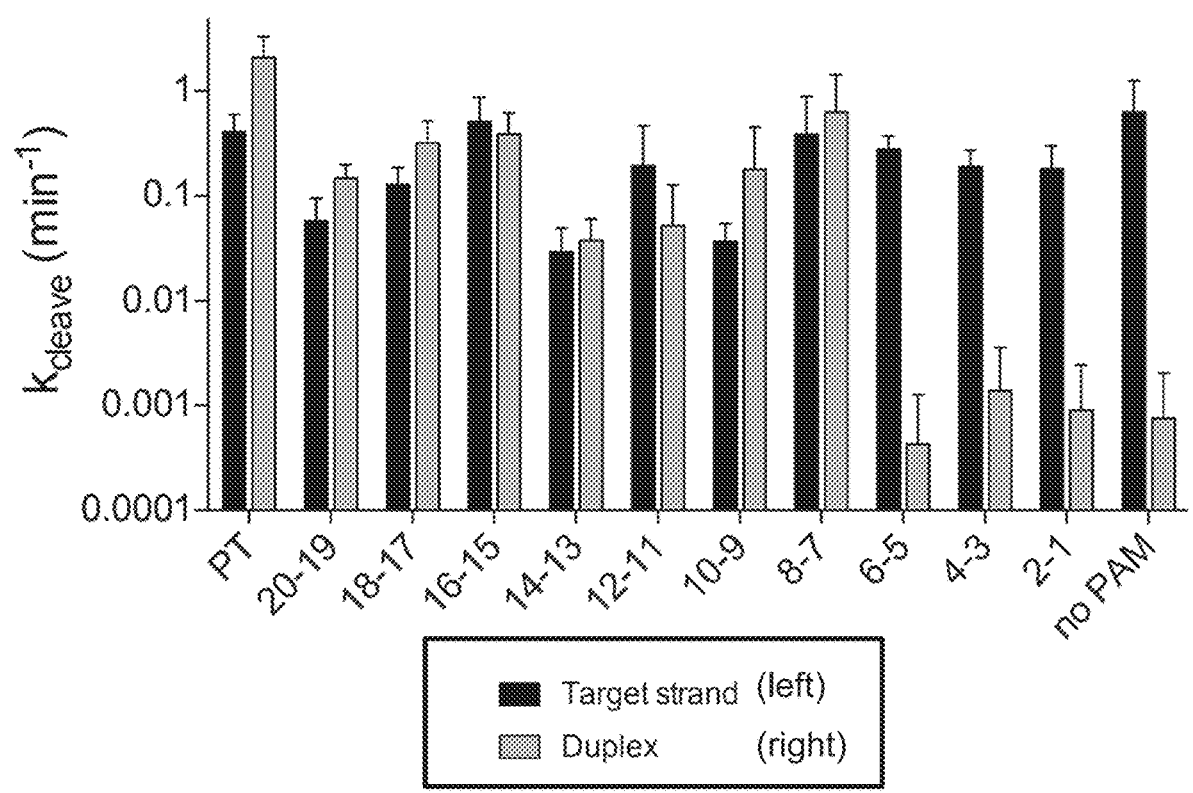

FIGS. 9A-9B. Trans-activation is sensitive to mismatches at the PAM-proximal end with duplexed substrates, but not with single-stranded substrates. Using the FQ-based assay, the mismatch tolerance for activating trans-cleavage was tested. LbCas12a-crRNA was pre-complexed with either ssDNA or dsDNA containing 2 bp mismatches from the PAM-distal to PAM-proximal end, or a mutated PAM. The top panel shows background-subtracted max fluorescence after 1 h incubation at 37 C for ssDNA (left) or dsDNA (right). The bottom panel shows observed cleavage rates after 1 h incubation at 37 C. Mismatches appeared highly tolerated in the case of ssDNA substrates, but PAM-proximal mismatches were poorly tolerated in the case of dsDNA substrates likely due to inadequate RNA strand invasion. Notably, trans-cleavage was PAM-independent when Cas12a is activated by ssDNA.

Figure 10:
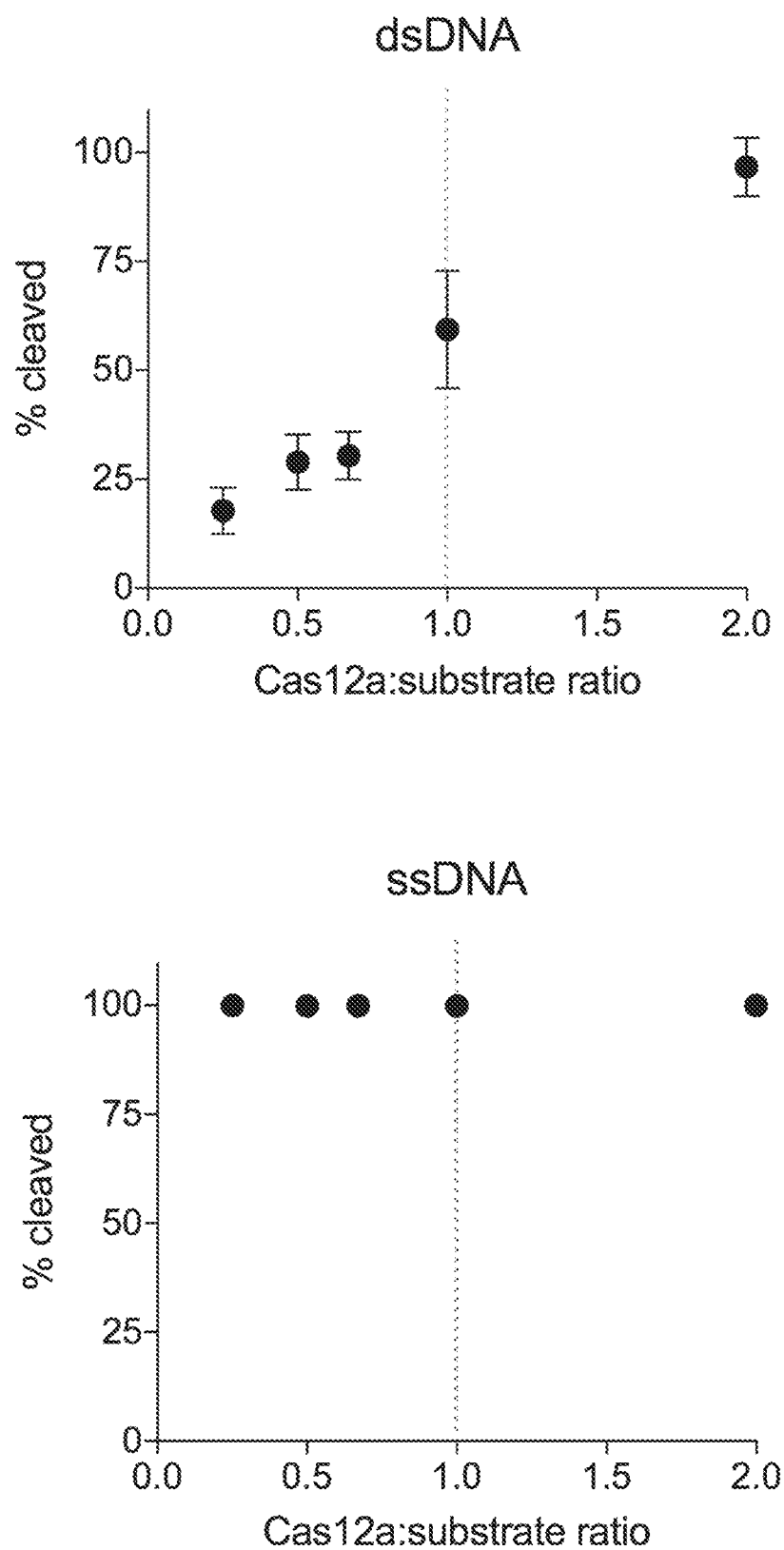
FIG. 10 presents data related to turnover kinetics.

FIG. 10. dsDNA target (cis) cleavage follows single-turnover kinetics, whereas ssDNA (trans) cleavage is multiple-turnover. Turnover kinetics were assayed for cis and trans cleavage by incubating radiolabeled dsDNA (left) or random ssDNA (right) with respective LbCas12a-crRNA ratios. Each point represents quantified % cleavage after a 30 minute incubation with LbCas12a at 37 C (via denaturing PAGE). For the ssDNA kinetics, LbCas12a-crRNA was pre-complexed with ssDNA activator before addition of radiolabeled random ssDNA. The data show that cis cleavage by LbCas12a is single-turnover, whereas trans cleavage is multiple turnover.

Figure 11A:
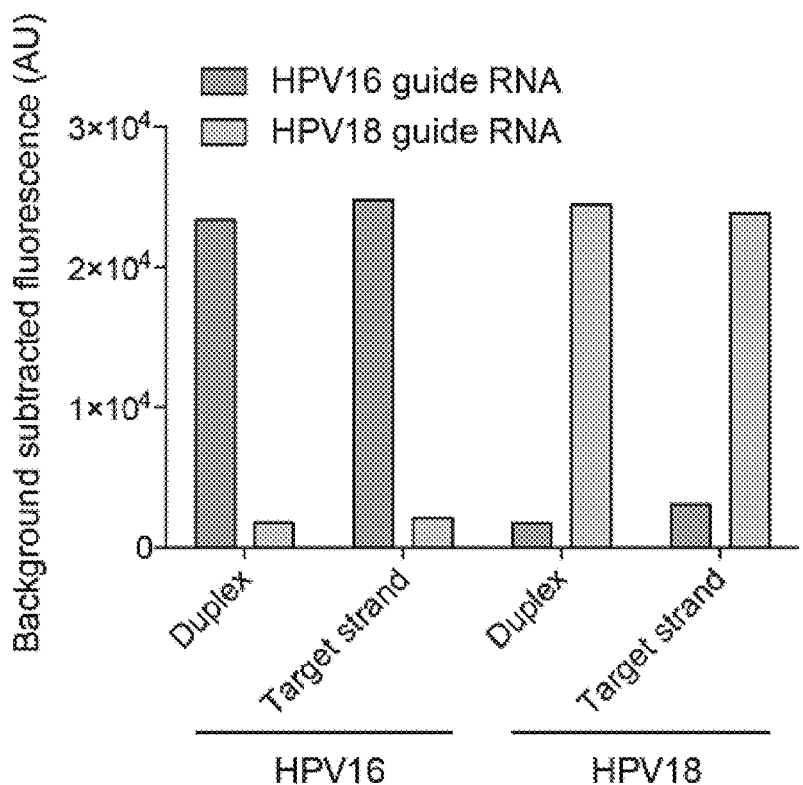

FIGS. 11A-11B. Trans-ssDNA cleavage by Cas12a can be harnessed as a simple diagnostic to distinguish viral serotypes such as HPV and other clinically relevant DNA viruses. Cas12a can detect targets as low as picomolar concentrations. To demonstrate that LbCas12a trans-activity can be harnessed as a simple diagnostic, the FQ-based assay using DNase Alert substrate was used to test whether one could distinguish two closely-related HPV sequences (HPV16 and HPV18) that are considered high-risk strains for cervical cancer. LbCas12 is pre-incubated with a crRNA targeting a HPV16 and HPV18 sequence adjacent to a TTTA PAM; the two sequences differ by 6 nucleotides. 500 bp fragments of HPV16 and HPV18 were cloned into a plasmid backbone (~6 kb total) as a proxy for the full HPV genome (~8 kb), and incubated with LbCas12a-crRNA for 30 min (top) or 1 h (bottom) at 37 C. HPV serotypes were easily distinguished and the method could detect down to ~10 pM of target. This method could in principle be extended to detect any DNA virus, and examples of clinically-relevant DNA viruses are listed herein.

Figure 12:
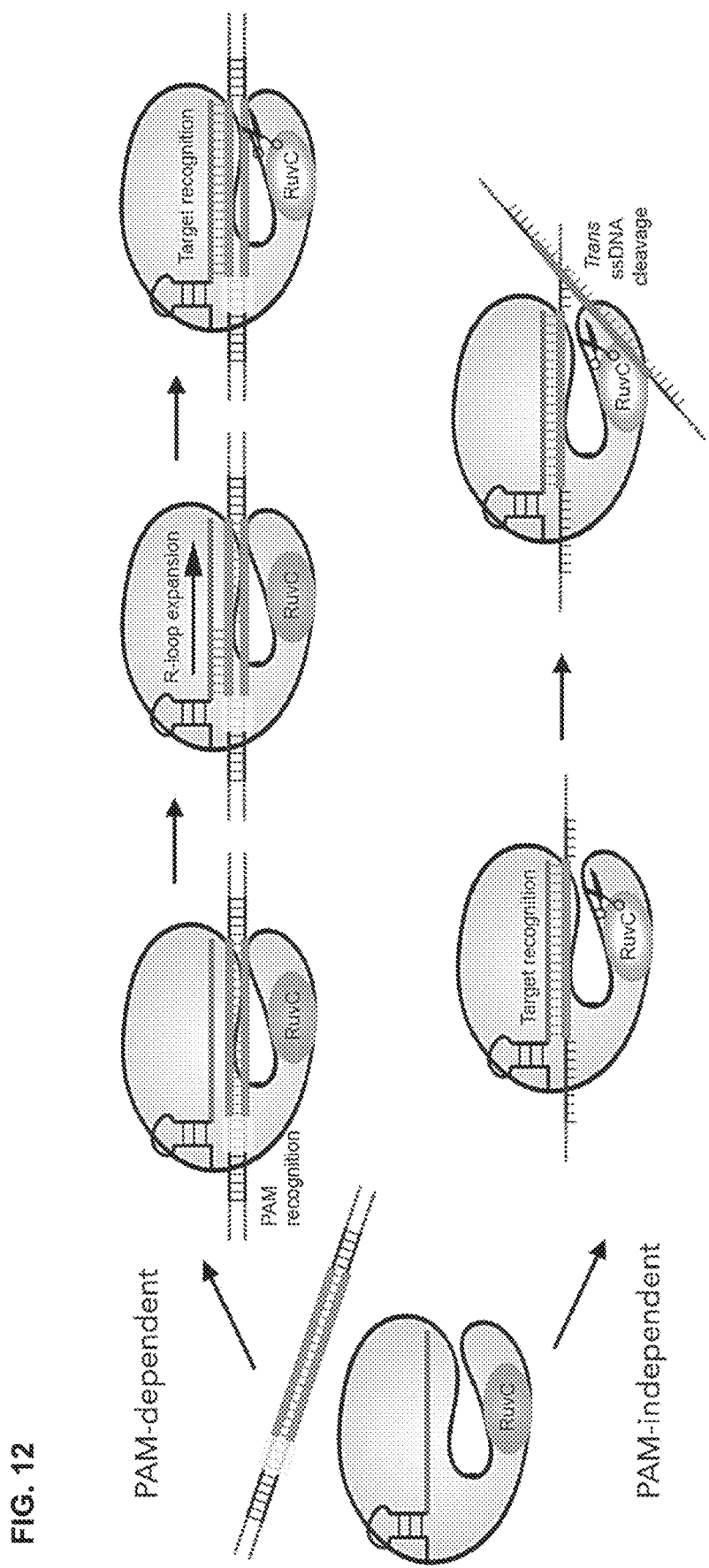

FIG. 12. A unifying model for DNA cleavage by CRISPR-Cas12a Cas12a-crRNA complex binds to a substrate in PAM-dependent (dsDNA) or PAM-independent (ssDNA) manner. When the dsDNA PAM is recognized, the duplex is interrogated by RNA strand invasion and recognition of the complementary target strand activates the RuvC nuclease to cleave both the unwound TS and NTS. Binding of the complementary ssDNA also triggers the RuvC nuclease to degrade any ssDNAs.

Example 2

CRISPR-Cas12a (Cpf1) belongs to a family of RNA-guided DNA targeting enzymes that bind and cut DNA as components of bacterial adaptive immune systems. Like CRISPR-Cas9, Cas12a and related enzymes are also powerful genome editing tools based on their ability to induce genetic changes in cells at sites of double-stranded DNA cuts. In the course of investigating the DNA substrate selectivity of Cas12a, the inventors were surprised to find that RNA-guided DNA binding unleashes robust, non-specific single-stranded DNA (ssDNA) cleavage activity sufficient to completely degrade both linear and circular ssDNA molecules. This activity, catalyzed by the same active site responsible for site-specific dsDNA cutting, shredded ssDNA irrespective of sequence requirements and with rapid multiple-turnover cleavage kinetics. Activation of ssDNA cutting required faithful recognition of a DNA target sequence matching the guide sequence of the guide RNA with specificity sufficient to distinguish between closely related viral serotypes. The data provided herein show that Cas12a-catalyzed ssDNA degradation, not observed for CRISPR-Cas9 enzymes, is a fundamental property of other Cas12-family proteins, revealing a fascinating and surprising parallel with the RNA-triggered general RNase activity of the type VI CRISPR-Cas13 enzymes.

Results

CRISPR-Cas adaptive immunity in bacteria and archaea uses RNA-guided nucleases to identify and cut foreign nucleic acids. The CRISPR-Cas9 family of enzymes has been widely deployed for gene editing applications in eukaryotes based on the precision of double-stranded DNA (dsDNA) cleavage induced by two catalytic domains, RuvC and HNH, at sequences complementary to a guide RNA sequence. A second family of enzymes harnessed for gene editing, CRISPR-Cas12a (formerly known as Cpf1), uses a single catalytic domain (RuvC) for guide RNA-directed dsDNA cleavage (FIG. 13A). Distinct from Cas9, Cas12a enzymes also process individual guide RNAs from a longer precursor transcript and generate dsDNA breaks with staggered 5' and 3' ends, features that have attracted interest in Cas12a for gene editing applications. Despite its adoption as a genome-editing tool, the substrate specificity and DNA cleavage mechanism of Cas12a are yet to be fully elucidated.

While the DNA substrate requirements for Cas12a activation were being investigated, Lachnospiraceae bacterium ND2006 Cas12a (LbaCas12a) was tested for guide RNA-directed single-stranded DNA (ssDNA) cleavage, a capability of various CRISPR-Cas9 orthologs. Purified LbaCas12a or SpyCas9 proteins were assembled with guide RNAs that have base pairing complementarity to circular, single-stranded M13 DNA phage. Although SpyCas9 catalyzed site-specific M13 cleavage, generating linear phage molecules as expected, LbaCas12a surprisingly induced rapid and complete degradation of M13 by a cleavage mechanism that could not be explained by sequence-specific DNA cutting (FIG. 13B). This robust ssDNA degradation was not observed in experiments using an LbaCas12a protein containing inactivating mutations in the RuvC catalytic domain. These results suggested that LbaCas12a possesses a unique ssDNA shredding activity that requires the same active site used for RNA-directed dsDNA cutting.

Figure 17:
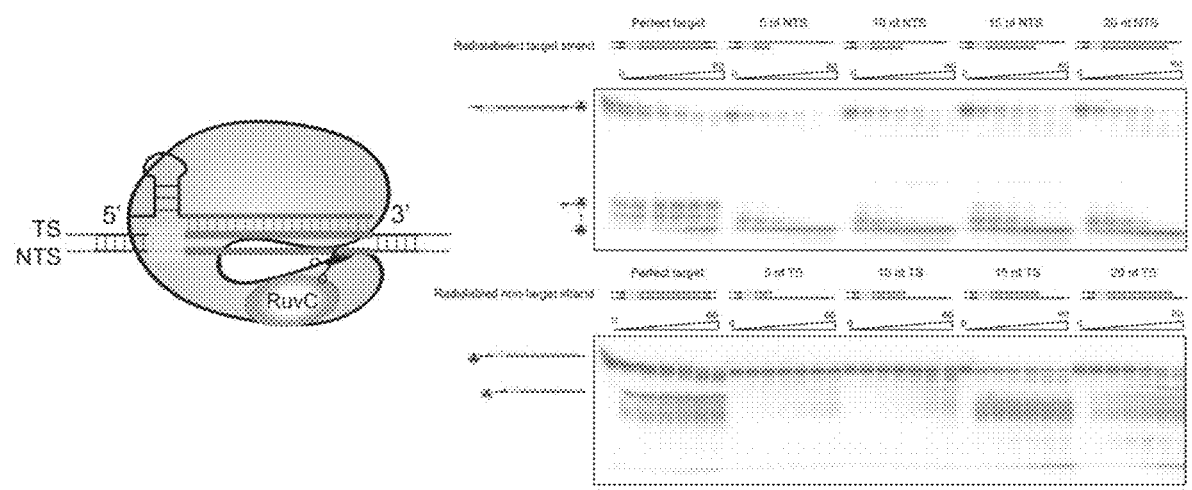
FIG. 17 presents data showing that target strand recognition is a pre-requisite for single-stranded DNA cleavage.
Figure 18:
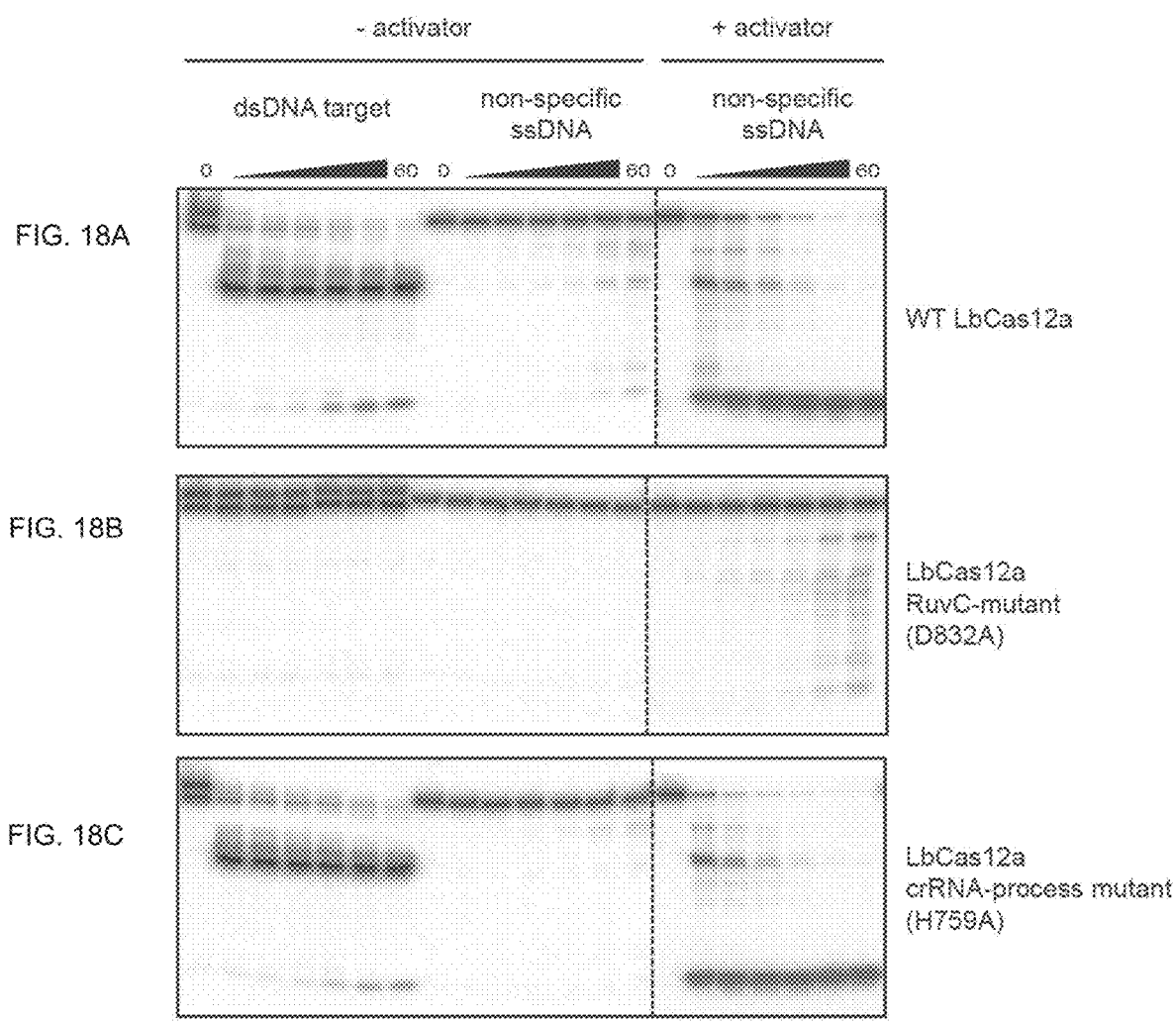
FIGS. 18A-18C present data showing that the RuvC nuclease is responsible for non-specific DNase activity.
Figure 19:
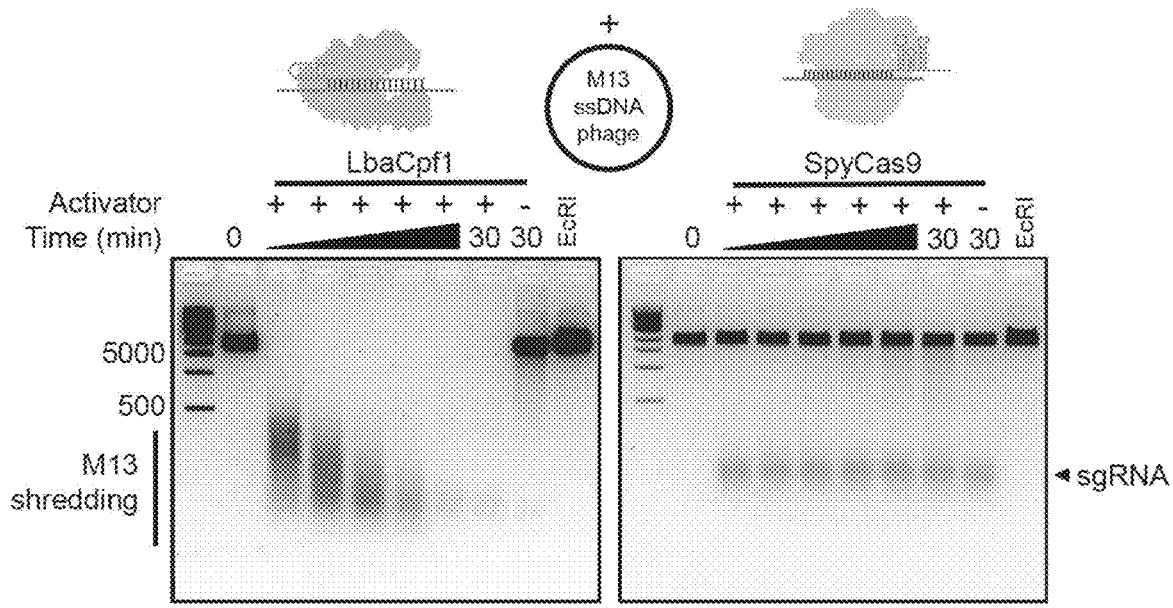
FIG. 19 presents data showing that the circular, single-stranded M13 DNA phage is degraded in trans by a pre-activated LbaCas12a complex.
Figure 20A:
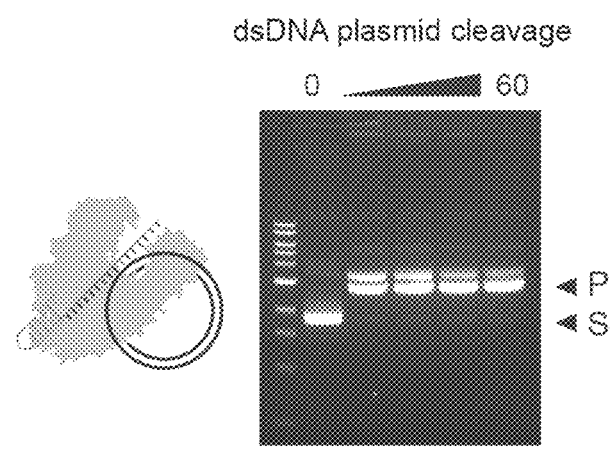
FIGS. 20A-20B present data showing that LbaCas12a is activated by a dsDNA plasmid for trans-cleavage.
Figure 20B:
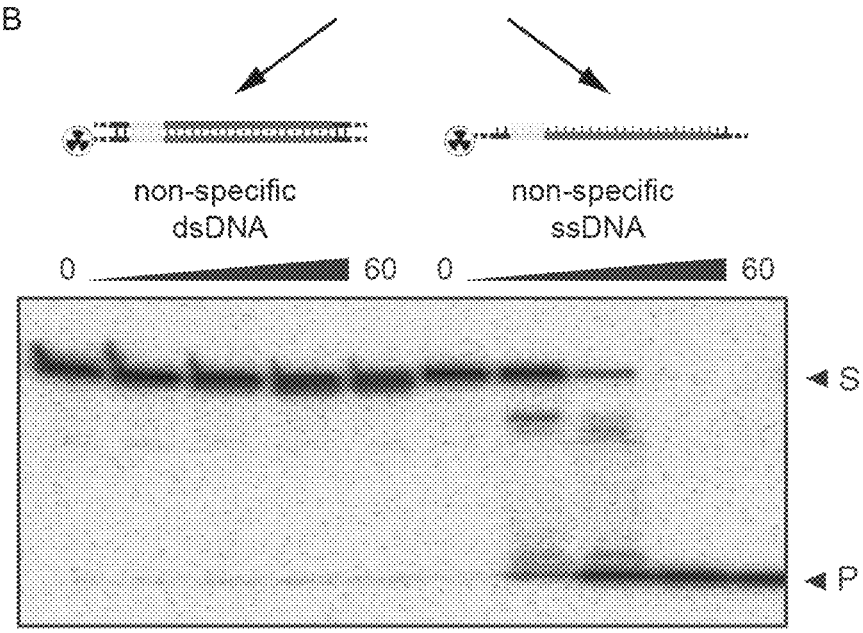
Figure 21:
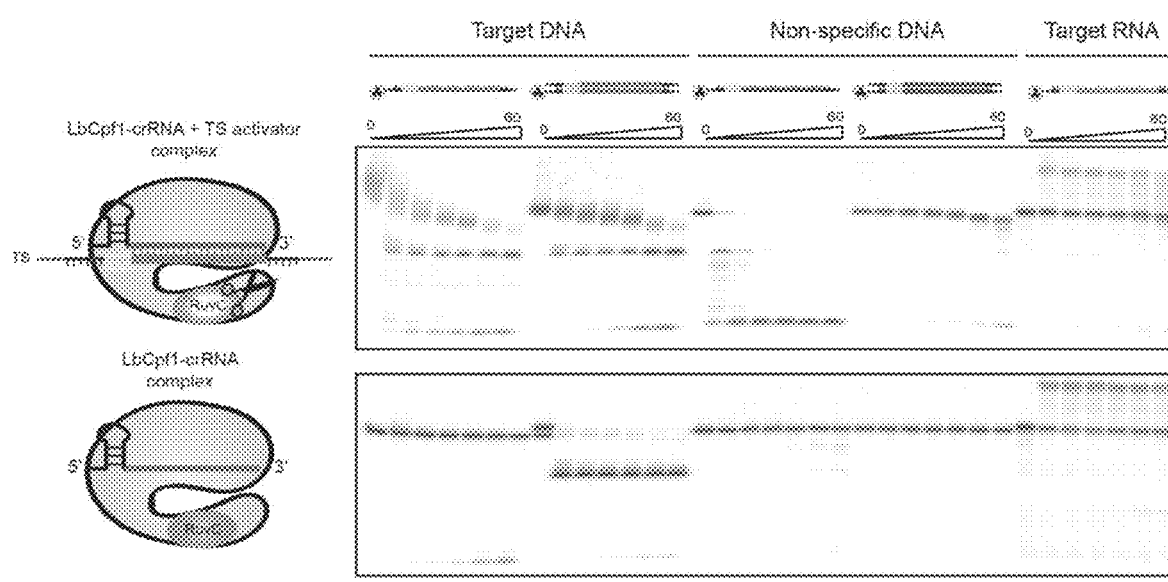
FIG. 21 presents data showing that LbaCas12a trans-cleavage degrades complementary and non-specific ssDNA, but not ssRNA.

The non-target strand (NTS) was cleaved only when the target strand (TS) contained at least 15 nt of complementarity with the guide RNA (FIG. 17). These results suggested that TS recognition is a prerequisite for ssDNA cutting, raising the possibility that LbaCas12a possesses non-specific ssDNase activity. To test the idea that a TS-activated LbaCas12a could cut any ssDNA, LbaCas12a was pre-complexed with a crRNA and complementary ssDNA or dsDNA activator, and introduced an unrelated radiolabeled ssDNA, dsDNA or ssRNA in trans. Remarkably, both ssDNA and dsDNA activators triggered LbaCas12a to completely degrade the ssDNA trans-substrate to its 5'end label in a RuvC-dependent manner (FIGS. 18A-18C, FIG. 19, FIGS. 20A-20B), whereas the dsDNA and ssRNA trans-substrates remained protected from the activated complex (FIG. 21). Together, these findings revealed that Cas12a DNA binding unleashes robust, non-specific ssDNase trans-activity by the RuvC nuclease.

Figure 22:
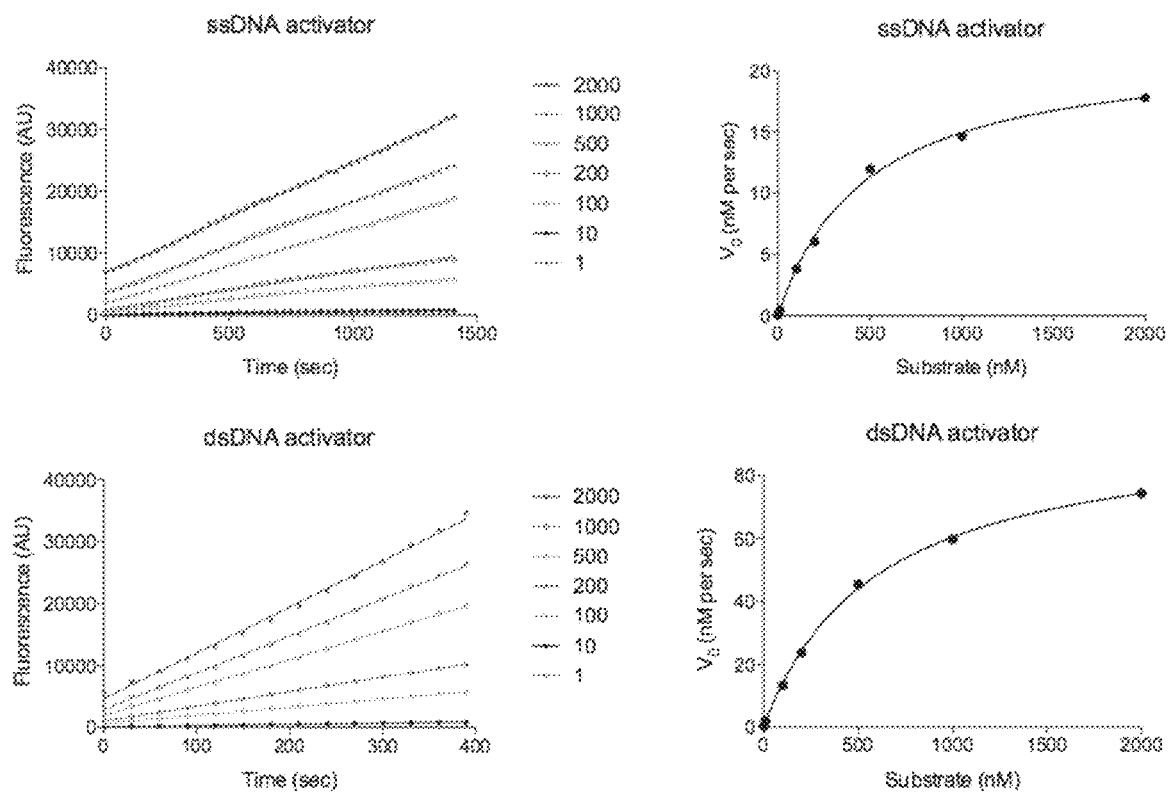
FIG. 22 presents data showing that Michaelis-Menten kinetics reveals robust trans-cleavage activity with a ssDNA and dsDNA activator.

The rapid degradation of a trans substrate suggested that the kinetics of non-specific ssDNA trans-cleavage may be fundamentally different from cis-cleavage, in which LbaCas12a targets a complementary dsDNA substrate. To investigate how a single RuvC nuclease cuts by two different mechanisms, substrate turnover was observed by titrating molar ratios of either LbaCas12a-crRNA or LbaCas12a-crRNA-ssDNA activator complexes against a dsDNA target (cis) or non-specific ssDNA (trans) substrate, respectively. The fraction of cleaved target dsDNA was proportional to the molar ratio of LbaCas12a-crRNA to DNA, demonstrating that cis-cleavage is single-turnover (FIG. 14A). In contrast, the fraction of cleaved non-specific ssDNA was saturated at sub-equimolar ratios, revealing that trans-cleavage follows multiple turnover kinetics (FIG. 14B). To further examine the Michaelis-Menten kinetics of trans-cleavage, a real-time, fluorophore quencher (FQ)-labeled DNA reporter assay was adapted to measure non-specific DNase activity under conditions where LbaCas12a-crRNA is stably bound to a ssDNA or dsDNA activator. LbaCas12a pre-complexed with a ssDNA activator revealed a highly robust activity that yielded a catalytic efficiency ($k_{cat}/K_m$) of $5.1 \times 10^8$ $s^{-1}$ $M^{-1}$. When pre-complexed with a dsDNA activator, the catalytic efficiency was nearly an order of magnitude faster and approached the rate of diffusion with a $k_{cat}/K_m$ measurement of $1.7 \times 10^9$ $s^{-1}$ $M^{-1}$ (FIG. 14C, FIG. 22). These differences in catalytic efficiencies suggest a potential role for the NTS of the dsDNA activator to stabilize the Cas12a complex in an optimal conformation for cutting a trans-ssDNA substrate.

Figure 23:
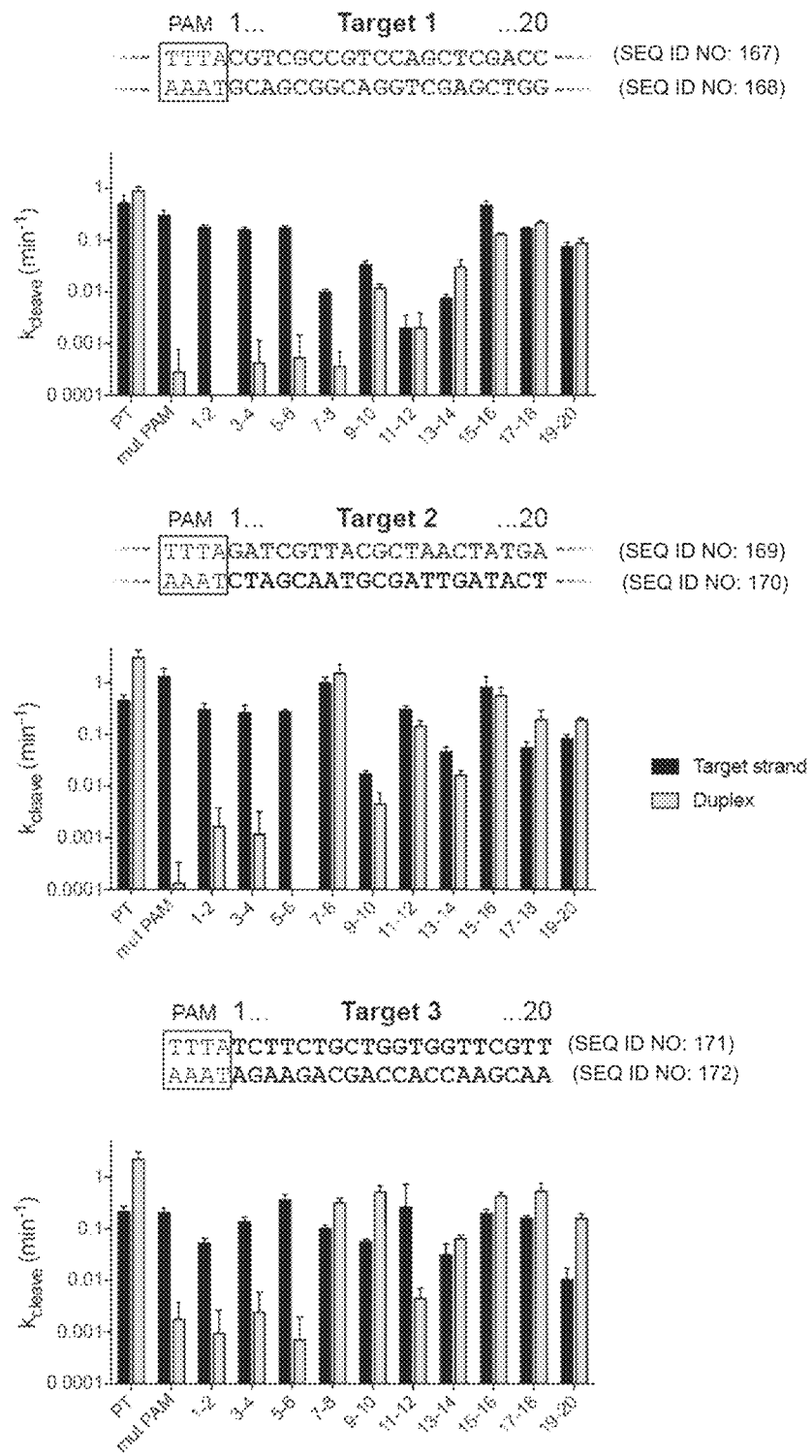
FIG. 23 presents data showing that the PAM sequence and PAM-proximal mismatches in a dsDNA activator provide specificity for trans-activation.

The substrate specificity of a ssDNA versus dsDNA activator for trans-cleavage was next considered. First, experiments were performed to confirm that PAM recognition is critical for activation by a complementary dsDNA but not for a matching ssDNA, consistent with the requirements for target binding (FIG. 15A). To test whether mismatches along the activator sequence could impact the rate of trans-cleavage, two base-pair (bp) mismatches were introduced across the target sequence in either a ssDNA or dsDNA activator. Using the FQ-based assay, LbaCas12a was pre-loaded with the crRNA and activator before addition of the ssDNA reporter, and the real-time increase in fluorescence signal was measured as a proxy for the observed trans-cleavage rate. Whereas mismatches across the ssDNA activator sequence were generally well tolerated, mismatches in the PAM or "seed region" of the dsDNA activator were poorly tolerated (FIG. 15B, FIG. 23). These trends using a dsDNA activator suggest that PAM recognition and unidirectional DNA unwinding provide additional regulation for trans-cleavage. However, extensive base complementary between the crRNA and target strand is the only requirement for activating trans-cleavage.

Figure 24:
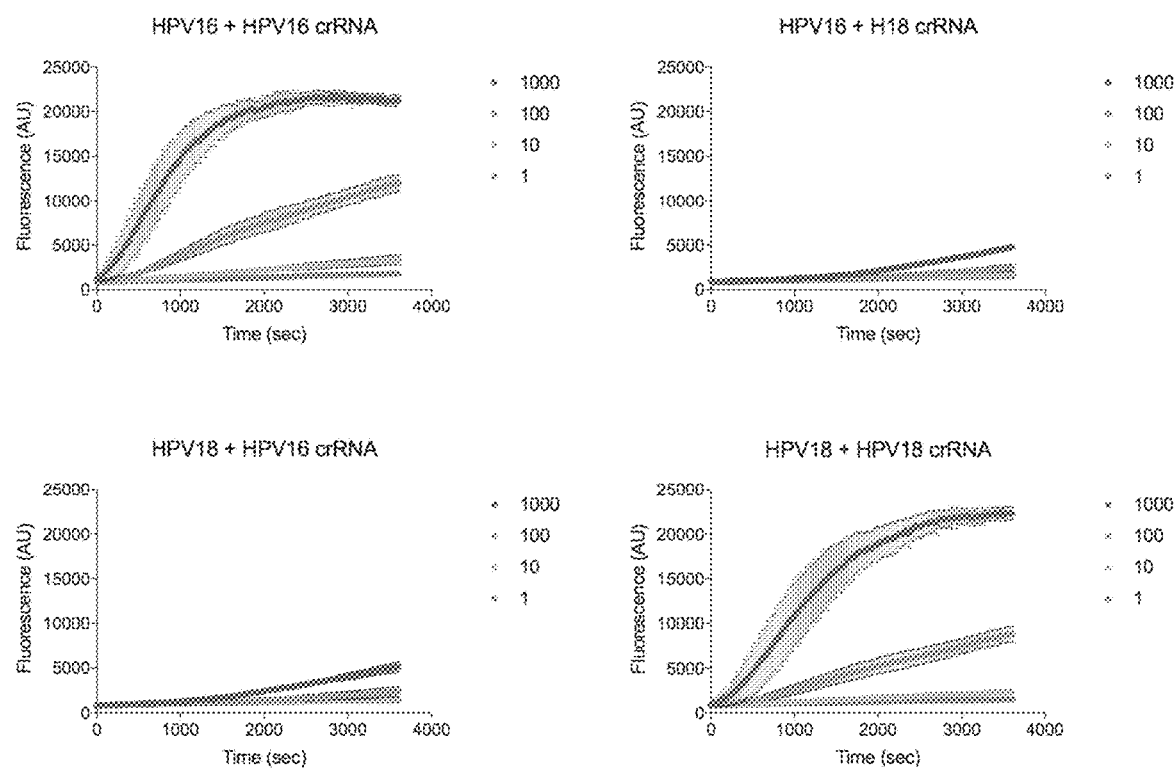
FIG. 24 presents data showing an HPV detection assay timecourse detected using a subject method of detection (e.g., labeled detector ssDNA).

Because LbaCas12a demonstrated higher specificity using dsDNA activators for trans-cleavage, the FQ-based assay was used to test whether LbaCas12a could be readily programmed to distinguish between two closely-related dsDNA viruses. As a proof-of-principle, the Human papillomavirus (HPV) serotypes 16 (HPV16) and 18 (HPV18) were selected, which account for approximately 70% of all cases of cervical cancer following persistent HPV infection. LbaCas12a was first pre-complexed with a crRNA targeting an HPV16 or HPV18 sequence adjacent to a TTTA PAM that differ by only 6 nucleotides (FIG. 15C). As a proxy for the full HPV genome (~8 kb), 500 bp fragments of HPV16 and HPV18 were cloned into a ~5 kb plasmid, and incubated the HPV-containing plasmid with LbaCas12a-crRNA. Robust activation of trans-cleavage was observed only when LbaCas12a was in the presence of at least ~10 pM of its cognate HPV target (FIG. 15D, FIG. 24), suggesting that the native specificity of dsDNA recognition and trans-cleavage activation by LbaCas12a could in principle be extended to detect any dsDNA virus.

It was then tested whether this trans-cleavage activity might be conserved among the Cas12a family, and even more broadly across evolutionarily distinct type V effector proteins. Two lines of evidence hinted at this possibility: first, target-bound crystal structures of Cas12b (previously known as C2c1) suggested that its RuvC catalytic pocket accommodates both the TS and the NTS for cleavage, similar to the cis-cleavage mechanism proposed for Cas12a. Second, despite low sequence and structural similarity between these subtypes, a unifying structural feature among all Cas12 proteins is the RuvC nuclease domain near the C-terminal end of the polypeptide. Therefore, two additional Cas12a orthologs from *Acidaminococcus* sp. (AspCas12a) and *Francisella novicida* (FnoCas12a) were selected, as well as a Cas12b protein from *Alicyclobacillus acidoterrestris* (AacCas12b) to test for cis- and trans-cleavage (FIG. 16A). Despite varying efficiencies, all of the homologs evaluated demonstrated non-specific ssDNase activity when pre-complexed with a complementary ssDNA activator (FIG. 16B), suggesting that trans-cleavage is a fundamental property of Cas12-family proteins. These experiments further underscore the functional convergence of trans-cleavage between the DNA-targeting type V and RNA-targeting type VI effector proteins.

The data herein suggest a new mechanism for target interference by the Cas12 protein family and a new model is proposed herein in which the Cas12-guide RNA complex binds to a DNA substrate in a PAM-dependent (dsDNA) or PAM-independent (ssDNA) manner (FIG. 16C). Following PAM recognition for a dsDNA substrate, RNA strand invasion and target recognition activates the RuvC nuclease to cleave the unwound TS and trim back the NTS, thereby generating the staggered dsDNA break and robustly activating ssDNA trans-cleavage. Binding of a complementary ssDNA bypasses PAM recognition and RNA strand invasion, but is sufficient to trigger the RuvC nuclease to degrade any ssDNAs.

Example 3: CRISPR-Cas12a Target Binding Unleashes Indiscriminate Single-Stranded DNase Activity The data presented here show that RNA-guided DNA binding unleashes robust, indiscriminate single-stranded DNA (ssDNA) cleavage activity in Cas12 proteins (e.g., Cas12a) sufficient to completely degrade both linear and circular ssDNA molecules. The data show that target-activated non-specific ssDNase activity, catalyzed by the same active site responsible for site-specific dsDNA cutting, is a fundamental property of type V CRISPR-Cas12 enzymes. Activation of ssDNA cutting requires faithful recognition of a DNA target sequence matching the guide sequence of the guide RNA with specificity capable of distinguishing closely related DNA sequences. Target-dependent Cas12 ssDNase activation was combined with isothermal amplification to create a method termed DNA Endonuclease Targeted CRISPR Trans Reporter (DETECTR), which achieved attomolar sensitivity for nucleic acid detection. DETECTR is demonstrated here to facilitate rapid and specific detection of DNA (e.g., HPV) in human patient samples, thereby providing a simple platform for nucleic acid-based, point-of-care diagnostics.

Figure 25A:
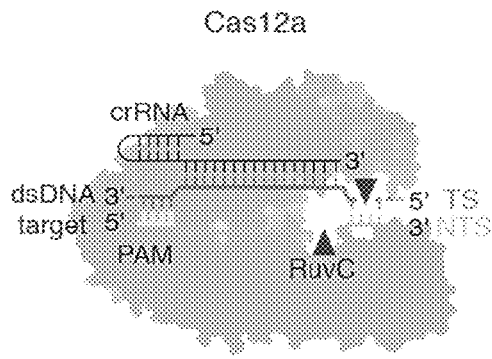
FIGS. 25A-25C present data showing that Cas12a target recognition activates non-specific single stranded DNA cleavage.

CRISPR-Cas adaptive immunity in bacteria and archaea uses RNA-guided nucleases to target and degrade foreign nucleic acids. The CRISPR-Cas9 family of proteins has been widely deployed for gene editing applications based on the precision of double-stranded DNA (dsDNA) cleavage induced by two catalytic domains, RuvC and HNH, at sequences complementary to a guide RNA sequence. A second family of enzymes, CRISPR-Cas12a (Cpf1), uses a single RuvC catalytic domain for guide RNA-directed dsDNA cleavage (FIG. 25A). Distinct from Cas9, Cas12a enzymes recognize a T-rich protospacer adjacent motif (PAM), catalyze their own guide RNA (crRNA) maturation and generate a PAM-distal dsDNA break with staggered 5' and 3' ends, features that have attracted interest for gene editing applications.

Figure 25B:
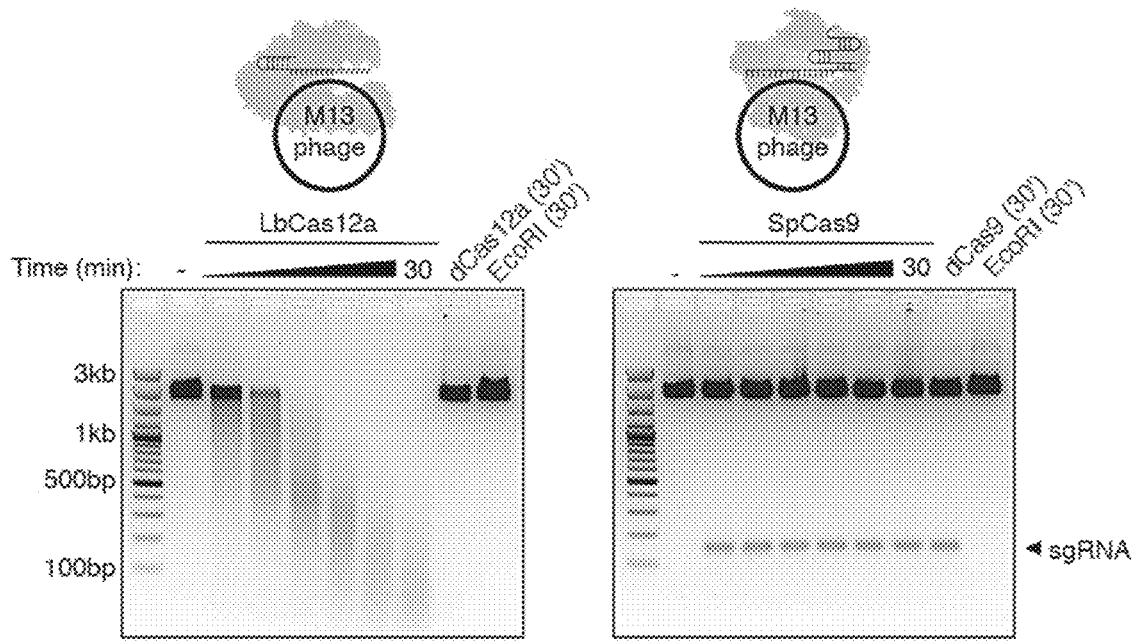
Figure 25C:
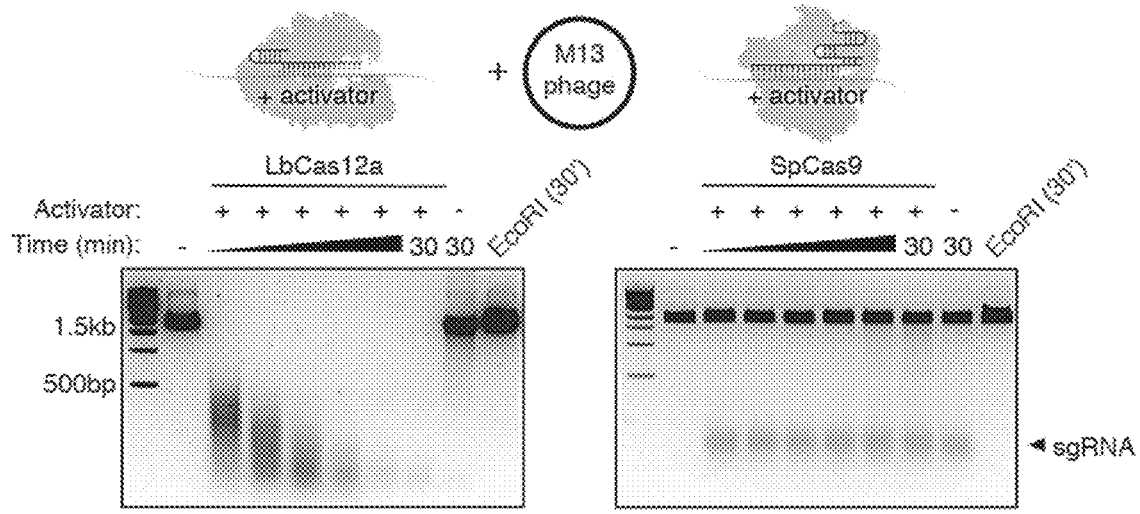

While investigating substrate requirements for Cas12a activation, Lachnospiraceae bacterium ND2006 Cas12a (LbCas12a) was tested for guide RNA-directed single-stranded DNA (ssDNA) cleavage, a capability of diverse CRISPR-Cas9 orthologs. Purified LbCas12a or *Streptococcus pyogenes* Cas9 (SpCas9) proteins (FIG. 30) were assembled with guide RNA sequences targeting a circular, single-stranded M13 DNA phage. In contrast to SpCas9, it was surprising to find that LbCas12a induced rapid and complete degradation of M13 by a cleavage mechanism that could not be explained by sequence-specific DNA cutting (FIG. 25B). This ssDNA shredding activity, not observed using an LbCas12a protein containing an inactivating mutation in the RuvC catalytic domain (D832A), raised the possibility that a target-bound LbCas12a could degrade any ssDNA, regardless of complementarity to the guide RNA. To test this idea, LbCas12a or SpCas9 was assembled with a different guide RNA and its complementary ssDNA that has no sequence homology to M13 phage genome sequence, and single-stranded M13 DNA was added to the reaction. Remarkably, LbCas12a catalyzed M13 degradation only in the presence of this complementary ssDNA "activator", an activity not observed for SpCas9 (FIG. 25C). These findings revealed that binding of the LbCas12a-crRNA complex to a guide-complementary ssDNA unleashed robust, non-specific ssDNA trans-cleavage activity.

FIGS. 25A-25C. Cas12a target recognition activated non-specific single-stranded DNA cleavage. FIG. 25A. Cas12a-crRNA complex binds a dsDNA substrate and generates a 5' overhang staggered cut using a single RuvC nuclease. FIGS. 25B-25C. Representative M13 ssDNA cleavage timecourses with purified LbCas12a (left) and SpCas9 (right) complexed with a FIG. 25B guide RNA complementary to M13 phage or FIG. 25C a guide RNA and complementary ssDNA activator with no sequence homology to M13 phage.

Figure 30:
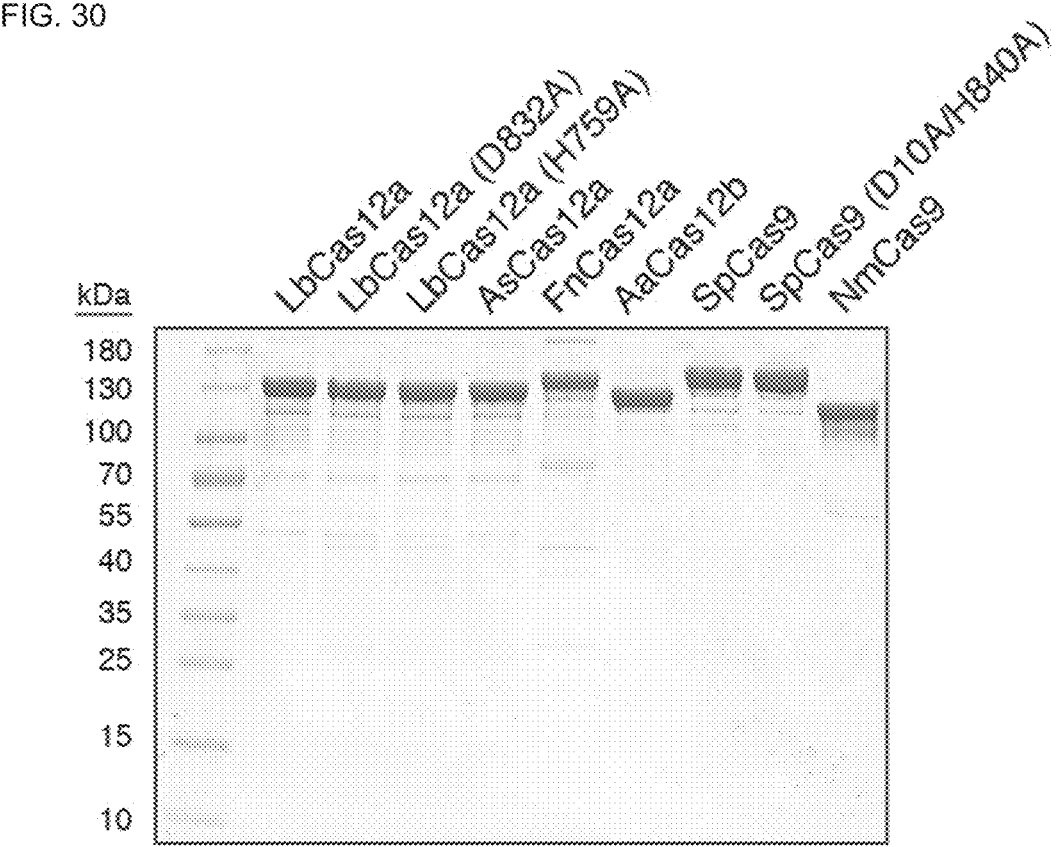
FIG. 30 presents data showing purification of Cas12 and Cas9 proteins.

FIG. 30. Purification of Cas12 and Cas9 proteins. SDS-PAGE gel of all purified Cas12 and Cas9 proteins used in this study.

Figure 31A:
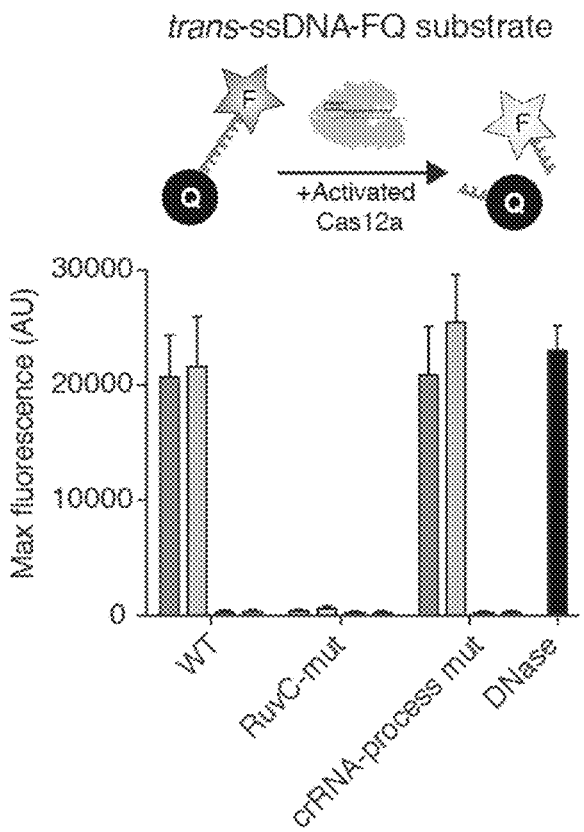
FIGS. 31A-31B present data showing that LbCas12a is a DNA-activated general DNase.
Figure 31B:
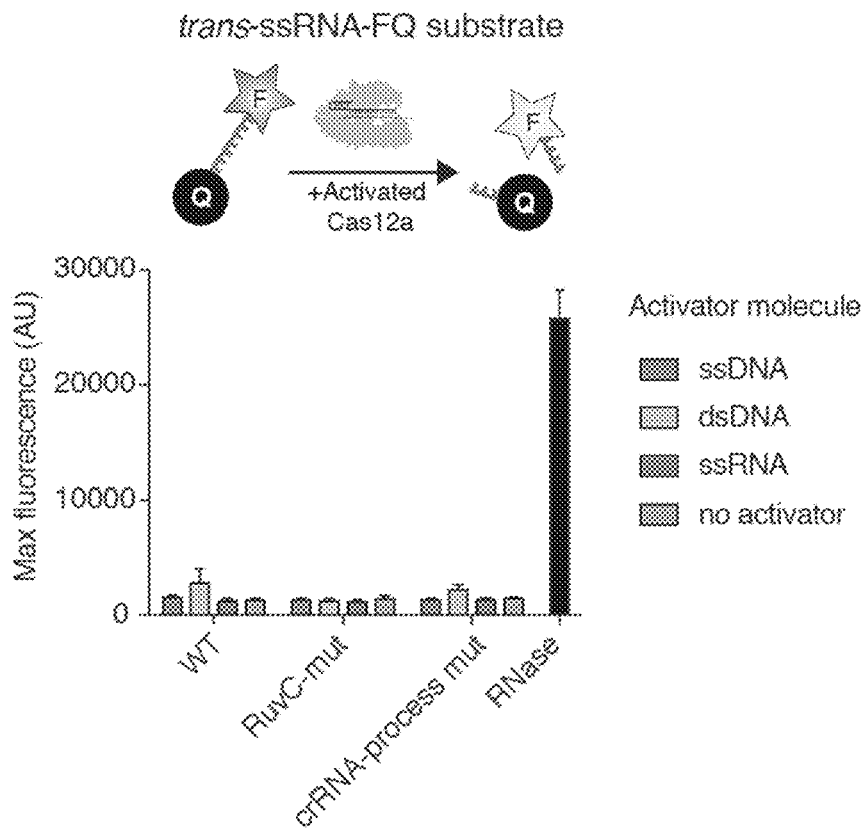

The requirements for LbCas12a-catalyzed trans-cleavage activity was next investigated. Using a fluorophore quencher (FQ)-labeled reporter assay, LbCas12a was assembled with its crRNA and either a complementary ssDNA, dsDNA or single-stranded RNA (ssRNA), and an unrelated ssDNA- or ssRNA-FQ reporter was introduced in trans (FIGS. 31A-31B). Both the crRNA-complementary ssDNA or dsDNA (the activator) triggered LbCas12a to cleave the ssDNA-FQ reporter substrate (FIG. 31A). However, ssRNA was neither capable of activating trans-cleavage nor susceptible to degradation by LbCas12a (FIG. 31B) confirming that LbCas12a harbors a DNA-activated general DNase activity.

FIGS. 31A-31B. LbCas12a is a DNA-activated general DNase. Quantification of maximum fluorescence signal generated after incubating LbCas12a-crRNA-activator with a custom FIG. 31A trans-ssDNA-FQ or FIG. 31B trans-ssRNA-FQ reporter for 1 h at 37° C., with DNase I or RNase A controls where indicated. Error bars represent the mean±s.d., where n=3 replicates.

Figure 26A:
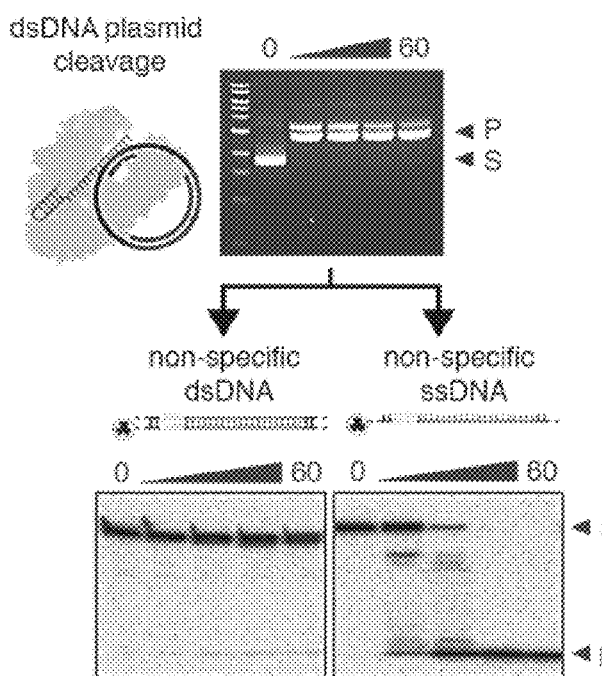
FIGS. 26A-26D present data related to kinetics of Cas12a ssDNA trans-cleavage.
Figures 35A, 35B:
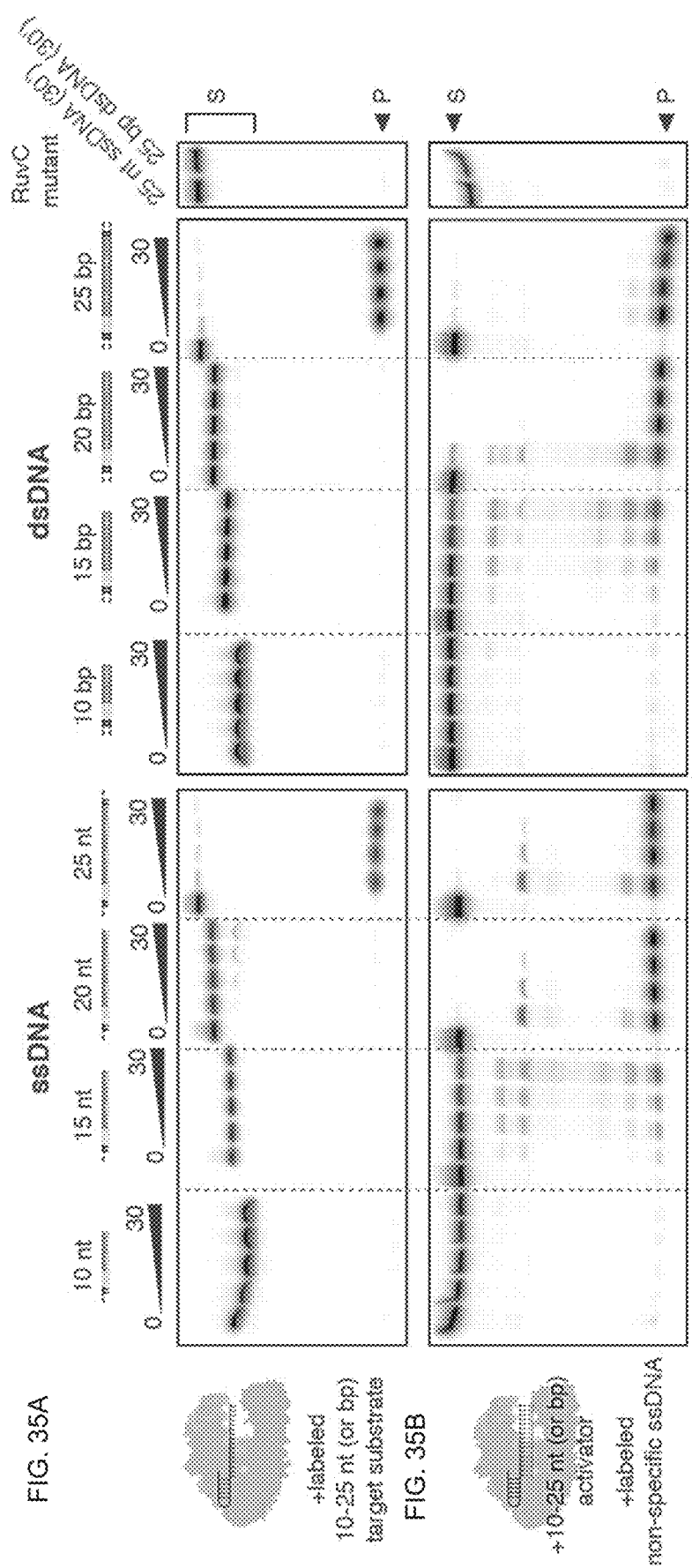
FIGS. 35A-35B present data showing that target strand cleavage by Cas12a is not required for triggering non-specific ssDNase activity.

To determine how LbCas12a-catalyzed ssDNA cleavage activity relates to site-specific dsDNA cutting, the length requirements of both the target strand (TS) and non-target strand (NTS) for LbCas12a activation was tested using radiolabeled oligonucleotides. Although TS cutting occurred irrespective of the NTS length (FIG. 32A), NTS cleavage occurred only when the TS contained at least 15 nucleotides (nt) of complementarity with the crRNA (FIG. 32B). This showed that TS recognition is a prerequisite for NTS cutting. To test whether LbCas12a remains active for non-specific ssDNA cleavage after sequence-specific binding and cleavage of a dsDNA substrate, a dsDNA plasmid was first cut with an LbCas12a-crRNA complex, and then an unrelated dsDNA or ssDNA was added to the reaction (FIG. 26A). Whereas the non-specific dsDNA substrate remained intact, the ssDNA was rapidly degraded in a RuvC-domain dependent manner (FIG. 26A; FIGS. 33A-33C; FIGS. 34A-34C). Using truncated activators that are too short to be cleaved, it was next determined that only target DNA binding is required to activate trans-ssDNA cleavage (FIGS. 35A-35B). Together, these results show that RNA-guided DNA binding activates LbCas12a for both site-specific dsDNA cutting and non-specific ssDNA trans-cleavage.

Figure 26B:
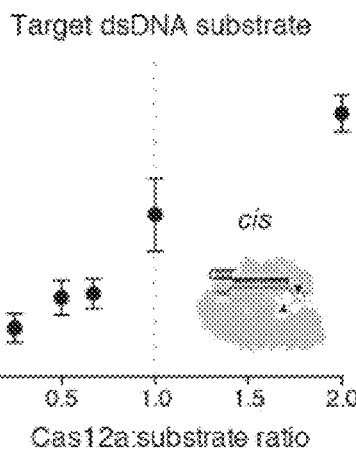
Figure 26C:
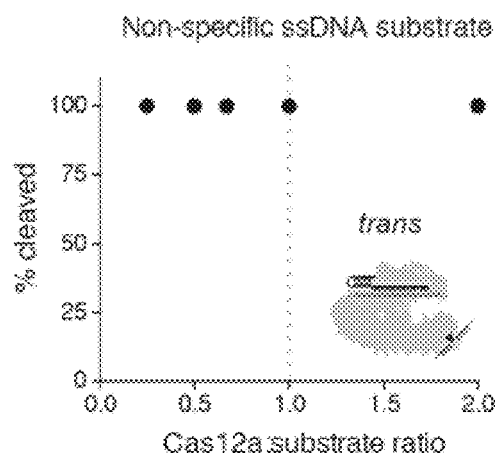
Figure 26D:
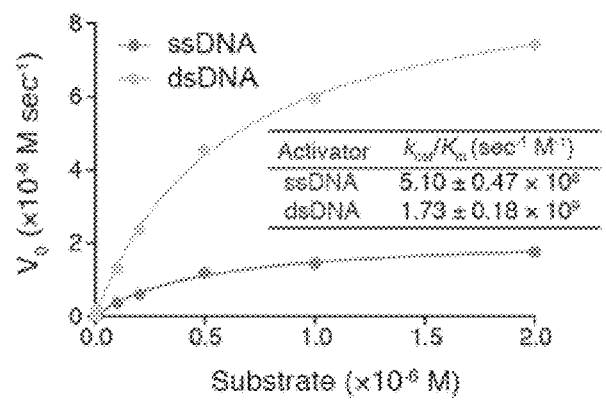

FIGS. 26A-26D. Kinetics of Cas12a ssDNA trans-cleavage. FIG. 26A Sequence-specific plasmid DNA cleavage reactions by LbCas12a-crRNA (top) were introduced to a separate radiolabeled dsDNA or ssDNA substrate of unrelated sequence (bottom); timecourses represent minutes. FIG. 26B Target dsDNA or FIG. 26C non-specific ssDNA incubated with molar ratios of LbCas12a-crRNA as indicated. Each point represents the mean quantified percent cleavage after 30 minutes at 37° C., at which time the reaction was at completion. Error bars represent the mean±s.d., where n=3 replicates. FIG. 26D Representative Michaelis-Menten plot for LbCas12a-catalyzed ssDNA trans-cleavage using a dsDNA or ssDNA activator. Measured $k_{cat}/K_m$ values report mean±s.d., where n=3 replicates.

Figure 32A:
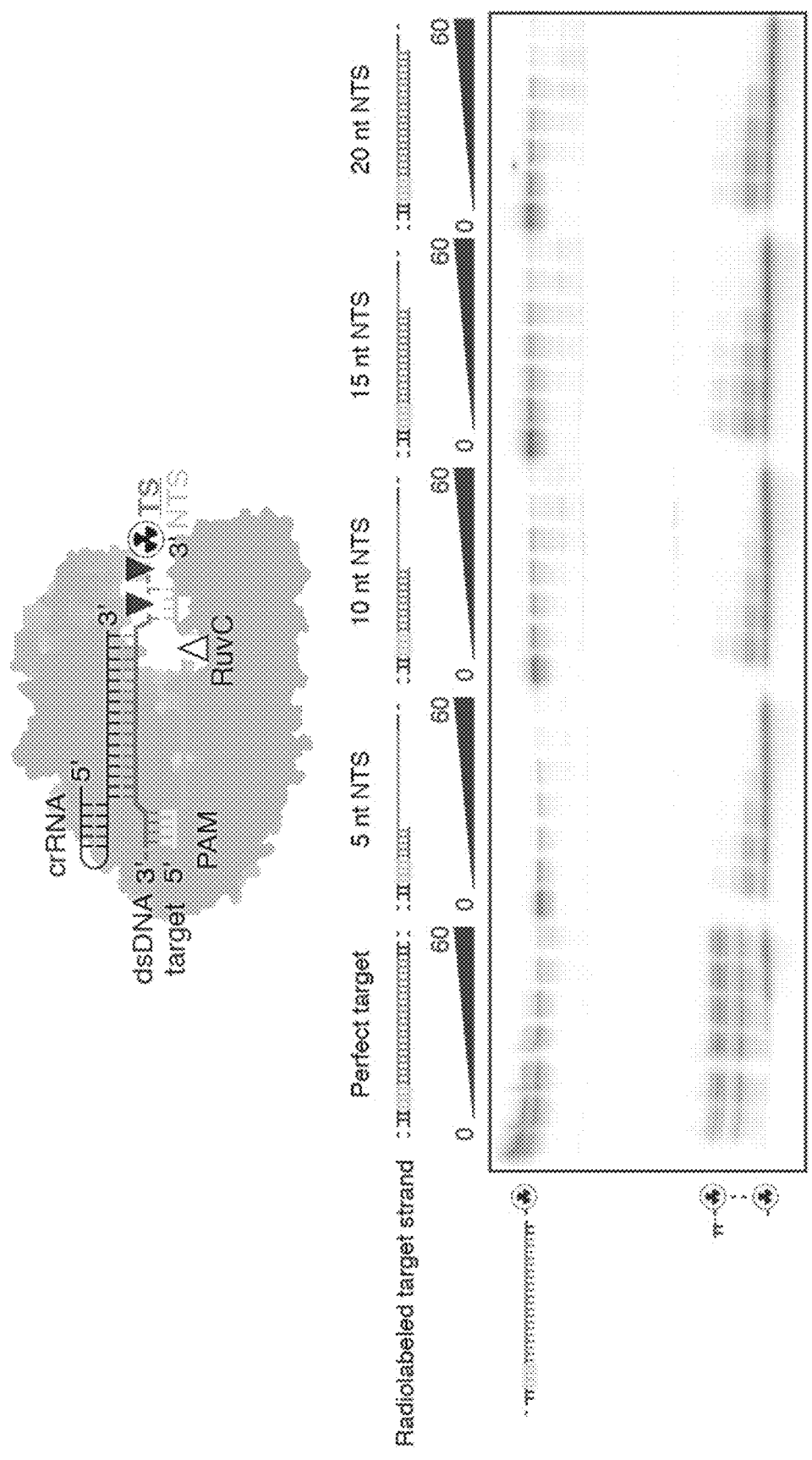
FIGS. 32A-32B present data showing that target strand recognition is a pre-requisite for single-stranded DNA cleavage
Figure 32B:
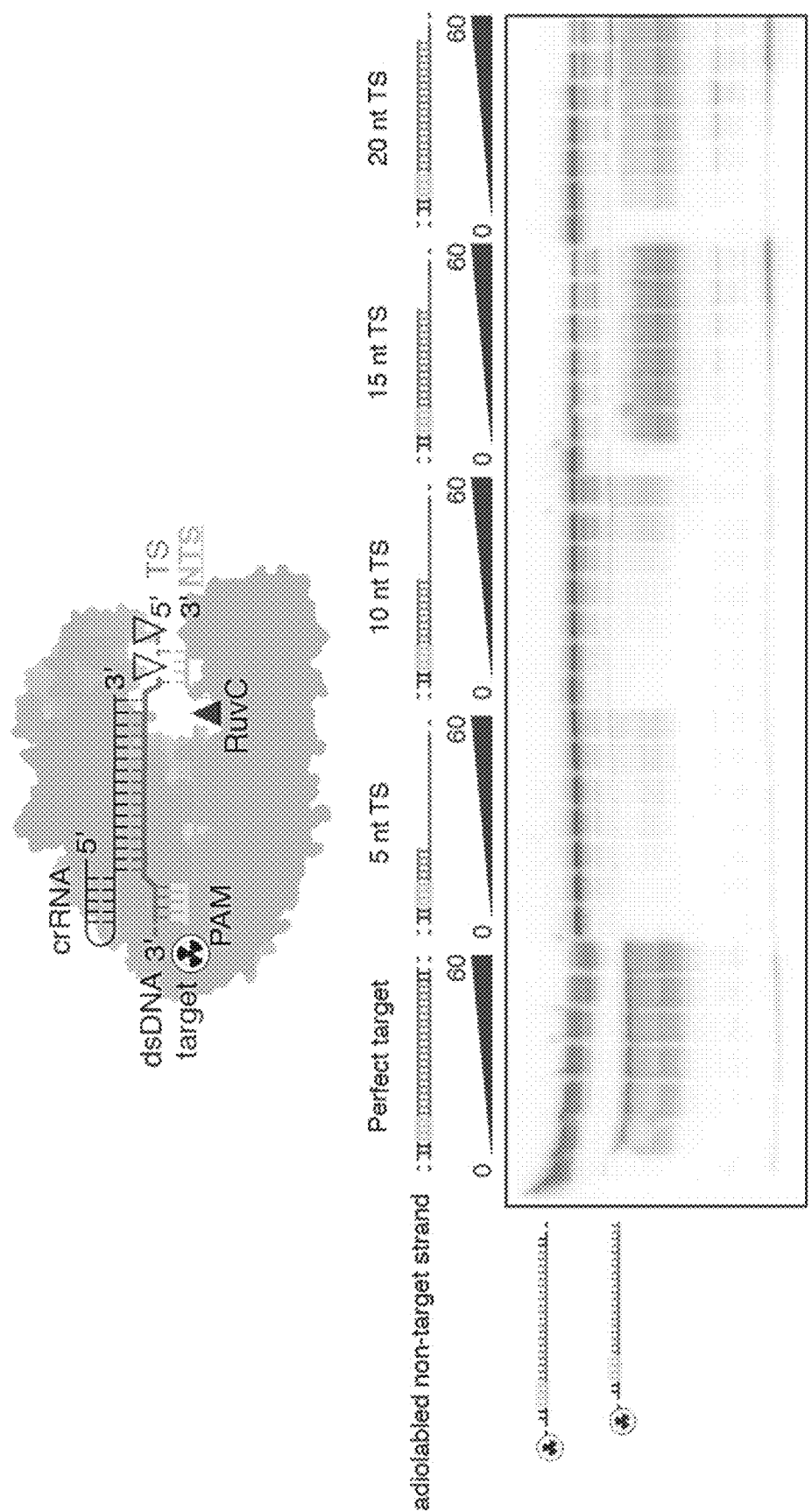
Figures 33A, 33B, 33C:
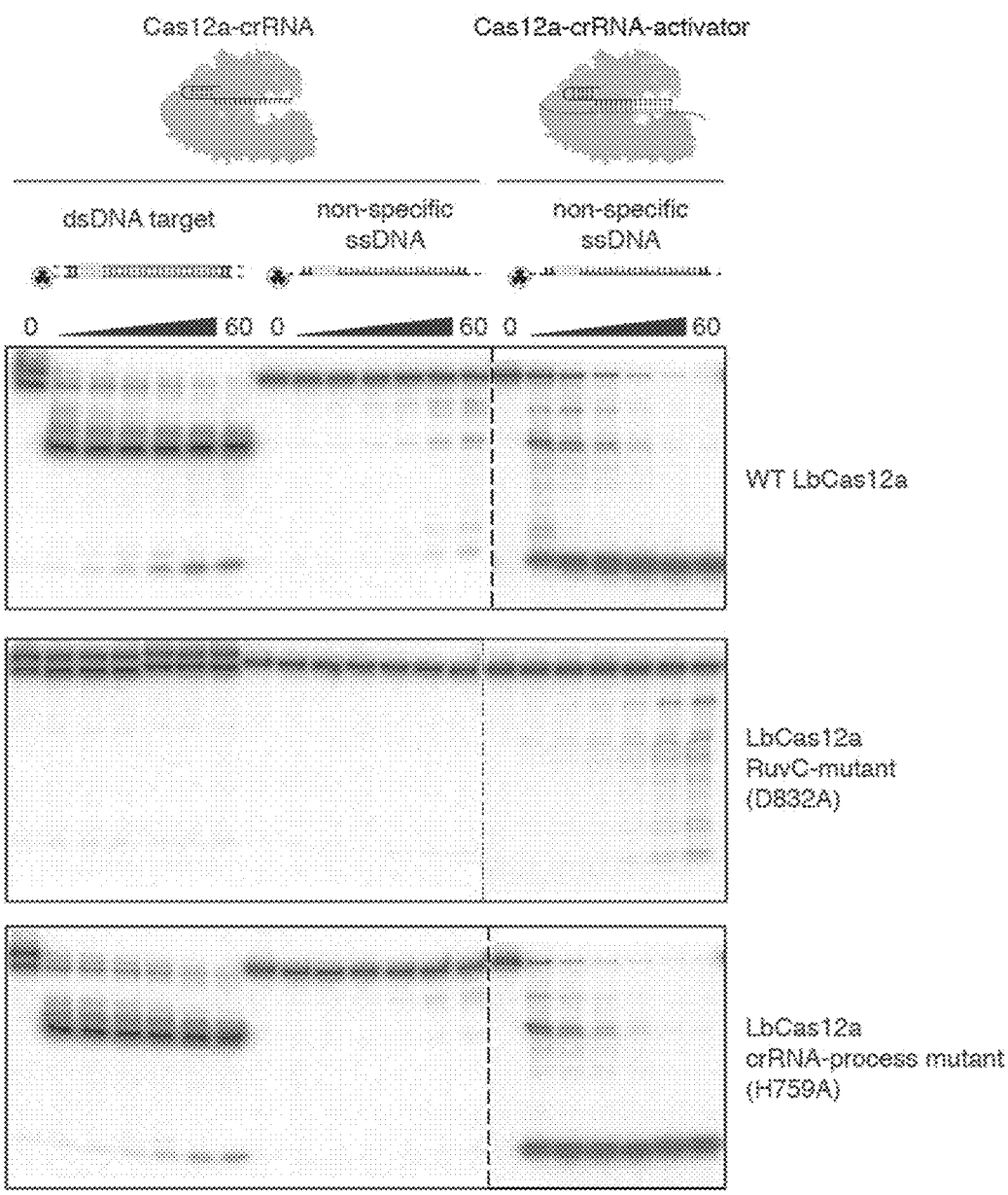
FIGS. 33A-33C present data showing that the RuvC nuclease domain is responsible for activator-dependent, non-specific DNase activity.

FIGS. 32A-32B. Target strand recognition is a pre-requisite for single-stranded DNA cleavage. Cleavage timecourse assays using LbCas12a with FIG. 32A truncated non-target strand (NTS) annealed to a radiolabeled target strand (TS), FIG. 32B truncated TS annealed to a radiolabeled NTS. Timecourses represent minutes and cleavage products resolved by denaturing PAGE. Schematic on right depicts cleavage of the radiolabeled TS FIG. 32A or NTS FIG. 32B, which generates a Cas12a-mediated staggered cut.

FIGS. 33A-33C. The RuvC nuclease domain is responsible for activator-dependent, non-specific DNase activity. Cleavage timecourse gel with radiolabeled non-target strand of a complementary dsDNA and non-specific ssDNA substrate using FIG. 33A WT LbCas12a, FIG. 33B RuvC catalytic mutant (D832A) and FIG. 33C crRNA-processing mutant (H759A), with or without a ssDNA activator. Timecourses represent minutes and cleavage products were resolved by denaturing PAGE.

FIGS. 34A-34C. LbCas12a trans-cleavage degrades complementary and non-specific ssDNA, but not ssRNA. Cleavage timecourse gels of LbCas12a-crRNA complexes using FIG. 34A no activator, FIG. 34B ssDNA activator in 1.2-fold molar excess, or FIG. 34C ssDNA activator in 100-fold molar excess. Radiolabeled substrates are indicated, where cis indicates a complementary target and trans indicates a non-complementary sequence. For cis substrates, the non-target strand was radiolabeled. Timecourses represent minutes and cleavage products were resolved by denaturing PAGE.

FIGS. 35A-35B. Target strand cleavage by Cas12a is not required for triggering non-specific ssDNase activity. Cleavage timecourse assays using LbCas12a with FIG. 35A radiolabeled target strand with either a ssDNA (10-25 nt) or dsDNA (10-25 bp) substrate, or FIG. 35B radiolabeled non-specific ssDNA substrate in the presence of either a ssDNA (10-25 nt) or dsDNA (10-25 bp) activator. Timecourses represent minutes and cleavage products were resolved by denaturing PAGE.

The rapid degradation of a trans substrate suggested that the kinetics of LbCas12a-catalyzed site-specific dsDNA (cis-) cleavage and non-specific ssDNA (trans-) cleavage are fundamentally different. Stoichiometric titration experiments showed that cis-cleavage is single-turnover (FIG. 26B), whereas trans-cleavage is multiple-turnover (FIG. 26C). Although the Cas12a-crRNA complex remains bound to the dsDNA target following cis-cleavage, the complex releases its PAM-distal cleavage products from the RuvC active site, enabling ssDNA substrate access and turnover. Using the FQ assay, it was found that LbCas12a-crRNA bound to a ssDNA activator molecule catalyzed trans-ssDNA cleavage at a rate of ~250 per second and a catalytic efficiency ($k_{cat}/K_m$) of $5.1 \times 10^8$ s$^{-1}$ M$^{-1}$. When bound to a dsDNA activator, LbCas12a-crRNA catalyzed ~1250 turnovers per second with a catalytic efficiency approaching the rate of diffusion with a $k_{cat}/K_m$ of $1.7 \times 10^9$ s$^{-1}$ M$^{-1}$ (FIG. 26D; FIGS. 36A-36E). These differences suggested that the NTS of the dsDNA activator helps stabilize the Cas12a complex in an optimal conformation for trans-ssDNA cutting.

FIGS. 36A-36E. Michaelis-Menten analysis revealed robust trans-cleavage activity with a ssDNA and dsDNA activator. Representative plots of initial velocity versus time for a FIG. 36A ssDNA or FIG. 36C dsDNA activator, using 0.1 nM effective LbCas12a-crRNA-activator complex and increasing DNaseAlert substrate concentrations at 37° C. Michaelis-Menten fits for the corresponding FIG. 36B ssDNA or FIG. 36D dsDNA activator. FIG. 36E Calculated $k_{cat}$, $K_m$ and $k_{cat}/K_m$ values report the mean±s.d., where n=3 replicates.

The specificity of trans-cleavage activation was next tested using either a ssDNA or dsDNA activator. The PAM sequence required for dsDNA binding by CRISPR-Cas12a was found to be critical for catalytic activation by a crRNA-complementary dsDNA, but not for a crRNA-complementary ssDNA (FIG. 27A). Two base-pair (bp) mismatches introduced along the crRNA-complementary sequence of either a ssDNA or dsDNA activator molecule slowed the trans-cleavage rate of a ssDNA-FQ reporter by up to ~100 fold, depending on the mismatch position. For only the dsDNA activator, alterations to the PAM sequence or mismatches between the crRNA and PAM-adjacent "seed region" also had large inhibitory effects on trans-ssDNA cleavage activity (FIG. 27B; FIG. 37A), similar to the mismatch tolerance pattern observed in Cas12a off-target studies. Together, these data are consistent with PAM-mediated dsDNA target binding and the role of base pairing between the crRNA and the target strand to activate trans-ssDNA cutting.

FIGS. 27A-27C. Specificity and conservation of trans-cleavage activation. FIG. 27A LbCas12a-crRNA in the absence or presence of indicated activator, incubated with a radiolabeled non-specific ssDNA substrate (S) for 30 min at 37° C.; products (P) resolved by denaturing PAGE. FIG. 27B Observed trans-cleavage rates for LbCas12a using a ssDNA or dsDNA activator with indicated mismatches; rates represent the average of three different targets measured in triplicate, and error bars represent mean±s.d., where n=9 (three replicates for three independent targets). FIG. 27C Radiolabeled cis (complementary) or trans (non-complementary) substrates were incubated with Cas12a-crRNA or Cas9-sgRNA in the presence or absence of a ssDNA activator for 30 min at 37° C.; a cis-dsDNA substrate was used in the "no enzyme" lanes. Substrate (S) and nucleotide products (P) were resolved by denaturing PAGE.

Figure 37:
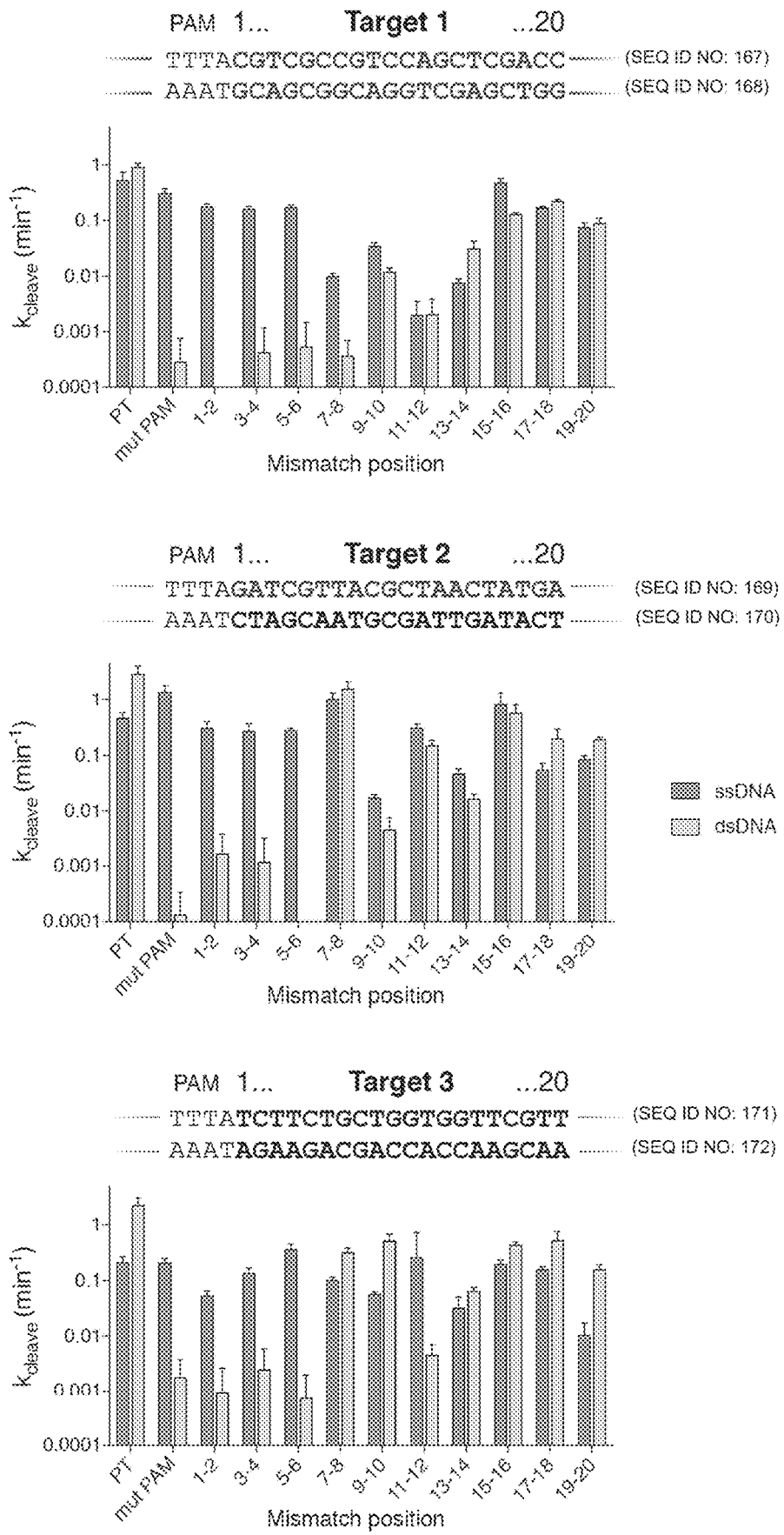
FIG. 37 presents data showing that PAM sequence and PAM-proximal mismatches in a dsDNA activator provide specificity for trans-activation.

FIG. 37. The PAM sequence and PAM-proximal mismatches in a dsDNA activator provided specificity for trans-activation. Quantification of trans-cleavage kinetics using mismatched substrates for three distinct target sequences; error bars represent the mean±s.d., where n=3 replicates.

Figure 38:
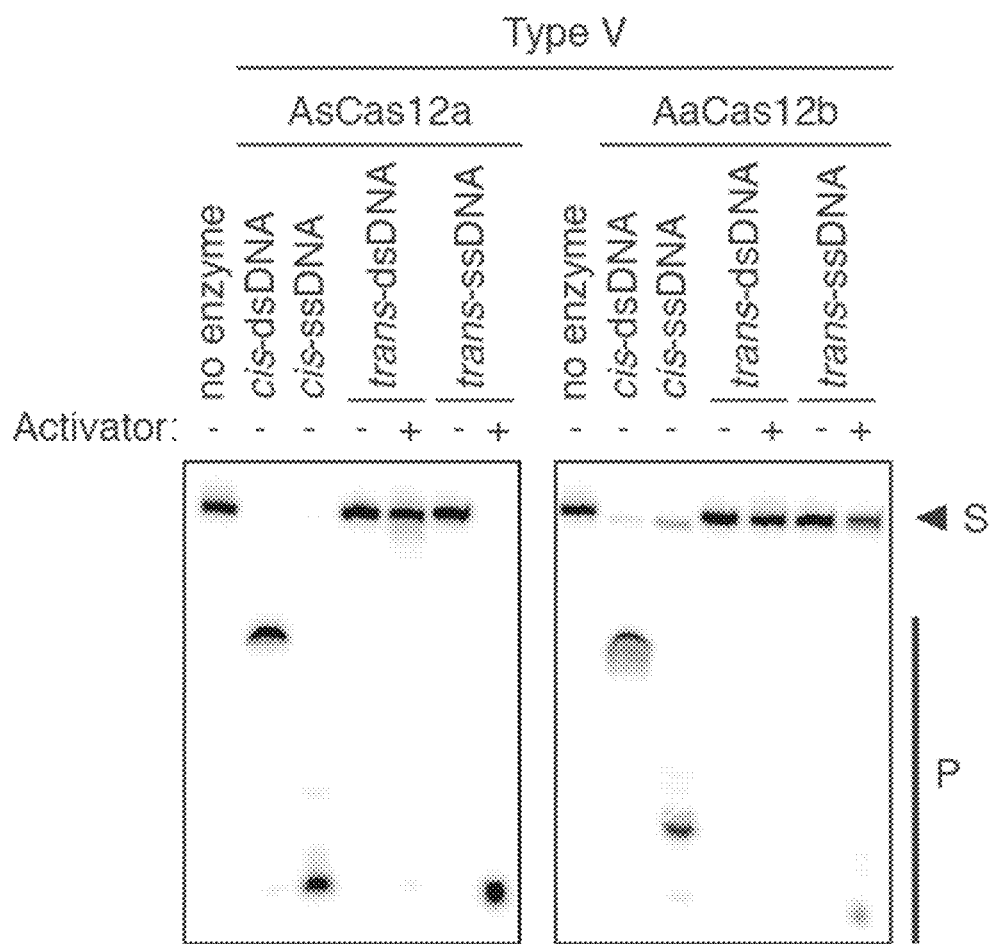
FIG. 38 presents data showing that activator-dependent, non-specific ssDNA cleavage activity is conserved across type V CRISPR interference proteins.

The data suggested that this trans-ssDNA cutting activity might be a property shared by other Cas12a enzymes, and perhaps more evolutionarily distinct type V CRISPR effector proteins, considering that all type V effectors contain a single RuvC nuclease domain Consistent with this possibility, purified Cas12a orthologs from *Acidaminococcus* sp. (AsCas12a) and *Francisella novicida* (FnCas12a), as well as a Cas12b protein from *Alicyclobacillus acidoterrestris* (AaCas12b), all catalyzed non-specific ssDNase cleavage when assembled with crRNA and a complementary ssDNA activator (FIG. 27C; FIG. 38). In contrast, none of the type II CRISPR-Cas9 proteins tested showed evidence for trans-ssDNA cleavage (FIG. 27C; FIG. 38), suggesting that target-dependent activation of non-specific ssDNA cleavage is a fundamental feature of all type V CRISPR-Cas12 proteins. These results reveal the unexpected functional convergence of Cas12 enzymes with the type III CRISPR-Csm/Cmr and type VI CRISPR-Cas13 effectors, which also exhibit target-activated, non-specific ssDNase or ssRNase activity, respectively.

FIG. 38. Activator-dependent, non-specific ssDNA cleavage activity was found to be conserved across type V CRISPR interference proteins. Radiolabeled cis (complementary) or trans (non-complementary) substrates were incubated with Cas12-crRNA in the presence or absence of a ssDNA activator for 30 min at 37° C. (or 47.5° C. for AaCas12b). For cis-dsDNA, non-target strand is 5' end labeled, while the target strand (complementary to guide RNA) is 5' end labeled for cis-ssDNA; trans-ssDNA and dsDNA are non-specific DNAs. In "no enzyme" lanes, 5' end labeled trans-ssDNA is loaded. Substrate (S) and nucleotide products (P) are resolved by denaturing PAGE.

Figure 40A:
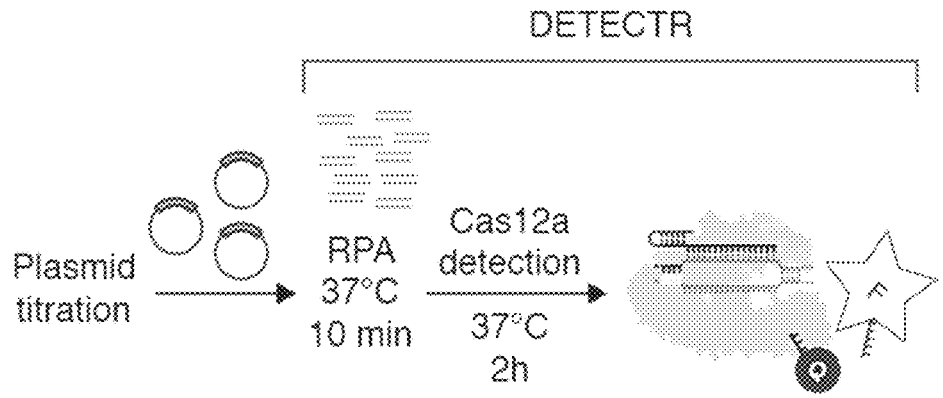
FIGS. 40A-40B present data showing that isothermal amplification coupled with Cas12a detection yields DETECTR, which can achieve attomolar sensitivity

It was next tested whether LbCas12a could be repurposed as a DNA detection platform for use in clinical specimens, based on its ability to induce a fluorescent readout in response to a specific dsDNA sequence. In particular, accurate and rapid identification of human papillomavirus (HPV) is critical for identification of those at risk of HPV-related pre-cancer and cancer, with types 16 (HPV16) and 18 (HPV18) accounting for the majority of precancerous lesions. To test if LbCas12a-catalyzed trans-ssDNA cleavage can distinguish between these two dsDNA viruses, a 20 nt target sequence located next to a TTTA PAM that varied by only six base pairs between the two HPV genotypes was selected (FIGS. 39A-39E). Plasmids containing a ~500 bp fragment of the HPV16 or HPV18 genome, including the target sequence, were incubated with the LbCas12a-crRNA complex targeting either the HPV16 or HPV18 fragment and a quenched-fluorescent ssDNA reporter. After one hour, LbCas12a produced a robust fluorescent signal only in the presence of the cognate HPV target, whose identity could be distinguished down to ~10 pM of plasmid (FIGS. 39A-39E). To enhance assay sensitivity, isothermal amplification by Recombinase Polymerase Amplification (RPA) was coupled with LbCas12a to develop a rapid one-pot detection method termed DNA Endonuclease Targeted CRISPR Trans Reporter (DETECTR) (FIG. 40A). When programmed to recognize its cognate plasmid, DETECTR was able to identify targets with attomolar sensitivity (FIG. 40B).

FIGS. 39A-39E. Cas12a distinguishes two closely related HPV sequences. FIG. 39A. Alignment of 20 nt targeting sequences within HPV16 and HPV18 genomes that differ by 6 nucleotides, with a schematic of Cas12a detection using a ssDNA-FQ reporter. Fluorescence timecourses with LbCas12a preassembled with a crRNA targeting FIG. 39B HPV16 or FIG. 39C HPV16 in the presence of a dsDNA plasmid containing an HPV16 (top row) or HPV18 (middle row) genomic fragment and DNaseAlert substrate, with fluorescence measurements taken every 30 seconds for 1 h at 37° C. FIG. 39D. Maximum fluorescence signal obtained from timecourses in FIG. 39B and FIG. 39C. Error bars represent mean±s.d., where n=3 replicates.

Figure 40B:
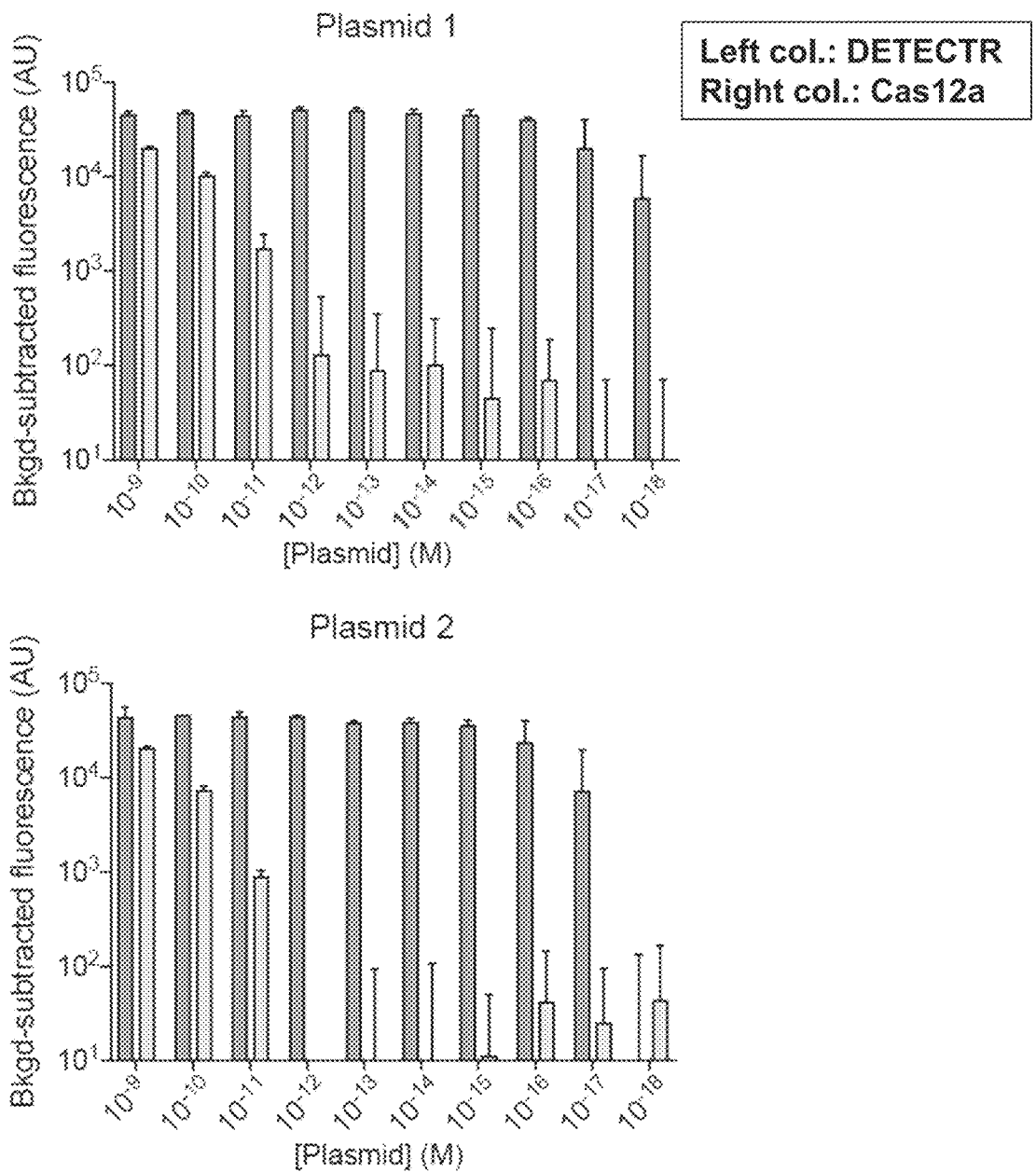

FIGS. 40A-40B. Isothermal amplification coupled with Cas12a detection yielded DETECTR, which achieved attomolar sensitivity. FIG. 40A Schematic of DETECTR, consisting of isothermal amplification by RPA and Cas12a detection using a ssDNA-FQ reporter. FIG. 40B Titration of two independent plasmids detected by DETECTR or Cas12a alone. Note that DETECTR achieve attomolar sensitivity. Error bars represent mean±s.d., where n=3 replicates.

Figure 28A:
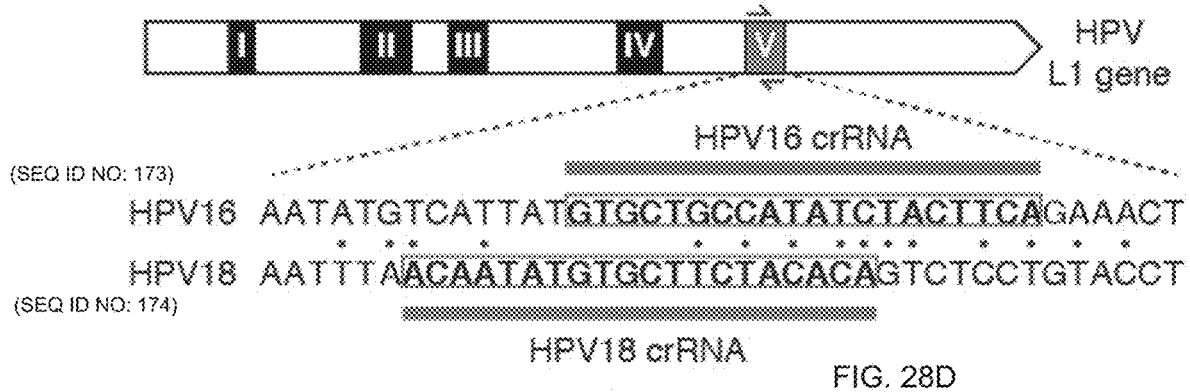
FIGS. 28A-28D present data showing rapid identification of HPV types 16 and 18 in human samples by DETECTR.

To assess whether HPV could be detected in more complex mixtures, DNA extracted from cultured human cells infected with HPV types 16 (SiHa), 18 (HeLa), or without HPV (BJAB) was added to LbCas12a complexed with a crRNA targeting the hypervariable loop V of the L1 gene within HPV16 or HPV18 (FIG. 28A).

Figure 28B:
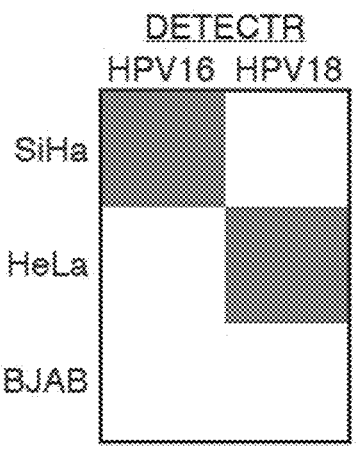
Figure 41A:
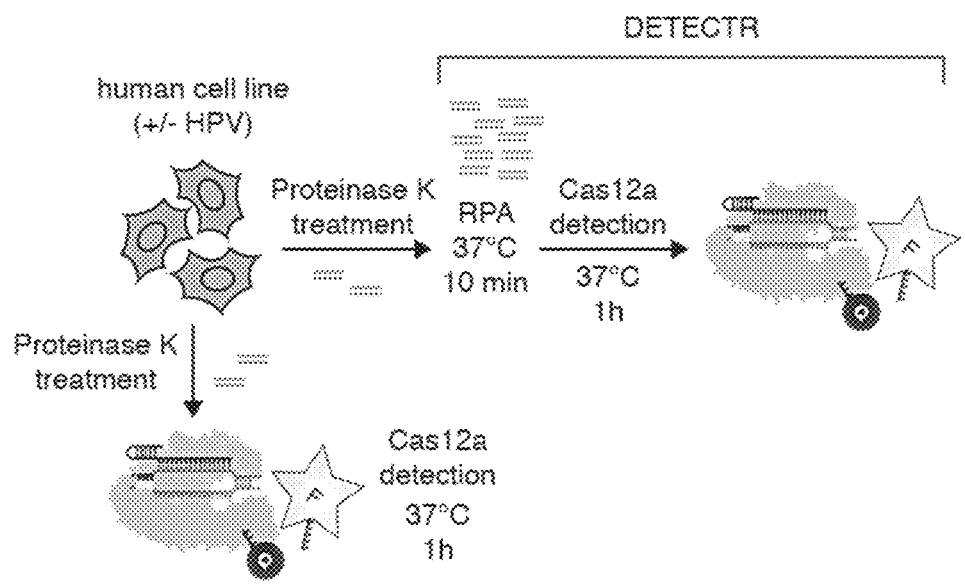
FIGS. 41A-41D present data showing identification of HPV types 16 and 18 in human cell lines and patient samples by DETECTR
Figure 41B:
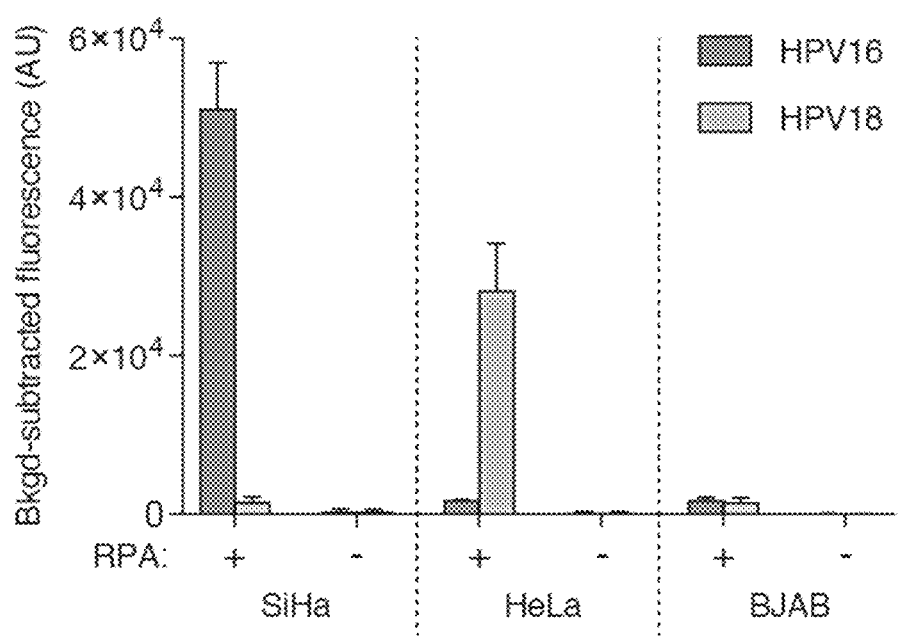
Figure 41C:
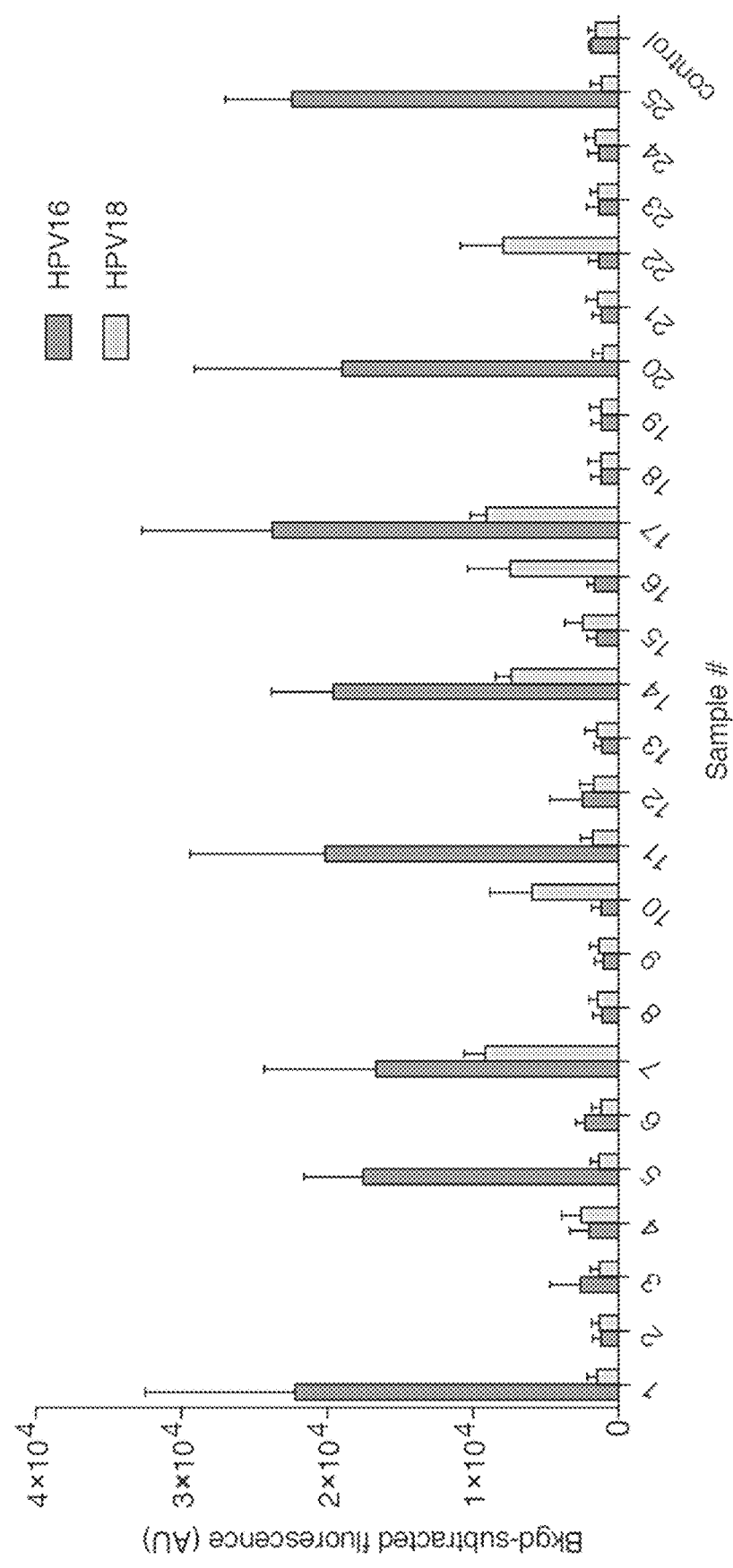
Figure 41D:
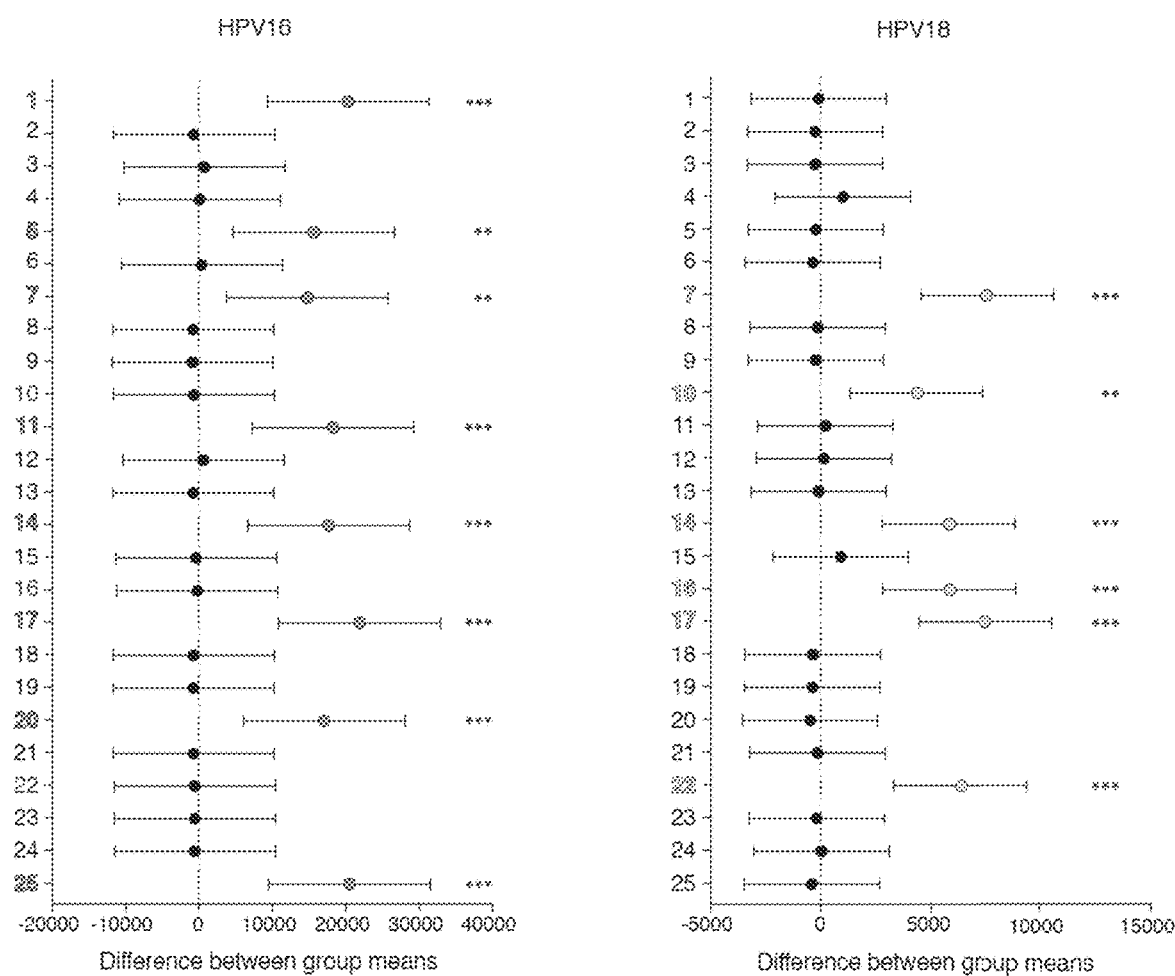
Figures 42A, 42B:
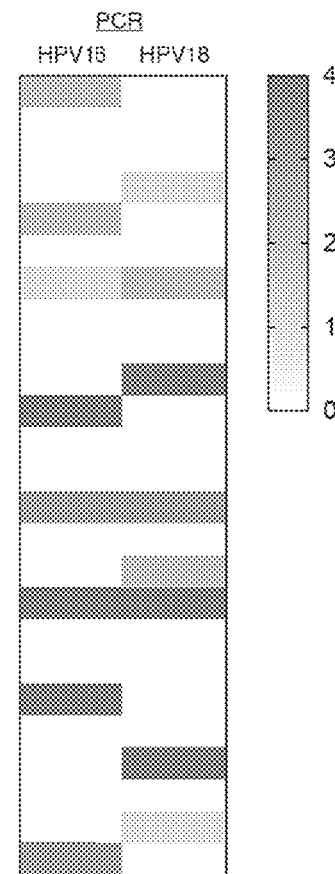
FIGS. 42A-42B present data showing PCR and hybrid capture validation and genotyping of HPV in human clinical samples.

Whereas LbCas12a-crRNA alone was not sensitive enough to detect HPV, DETECTR unambiguously identified HPV types 16 and 18 only in SiHa and HeLa cells, respectively (FIG. 28B; FIGS. 41A-41B). To investigate the utility of DETECTR on patient samples, crude DNA extractions from 25 human anal swabs previously analyzed by a PCR-based method for HPV infection were tested (FIGS. 42A-42B). Within one hour, DETECTR accurately identified the presence or absence of HPV16 (25/25 agreement) and HPV18 (23/25 agreement) in 25 patient samples containing a heterogeneous mixture of HPV types, with good correlation between the PCR-based intensity and DETECTR signal (FIGS. 28C-28D; FIGS. 41C-41D; FIGS. 42A-42B). Furthermore, the absence of fluorescence signal in specimens that were not infected with HPV types 16 or 18, but did contain other HPV types, was an indicator of good specificity by DETECTR. These results demonstrate a new platform for CRISPR-based diagnostics, and suggest that DETECTR could in principle be extended to rapidly detect any DNA sequence of interest with high sensitivity and specificity.

Figure 28C:
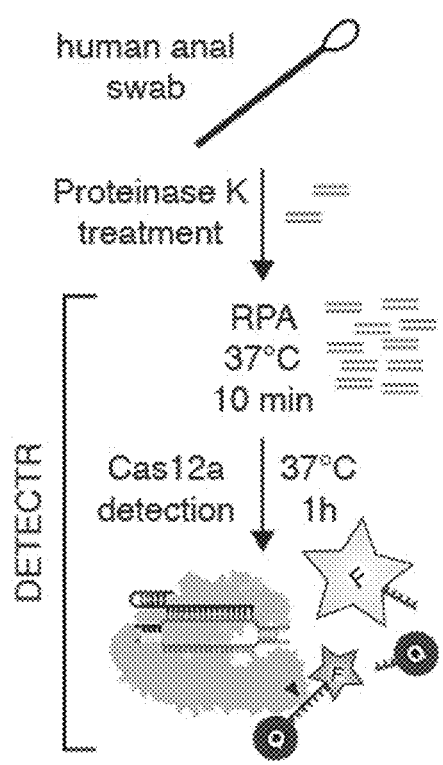
Figure 28D:
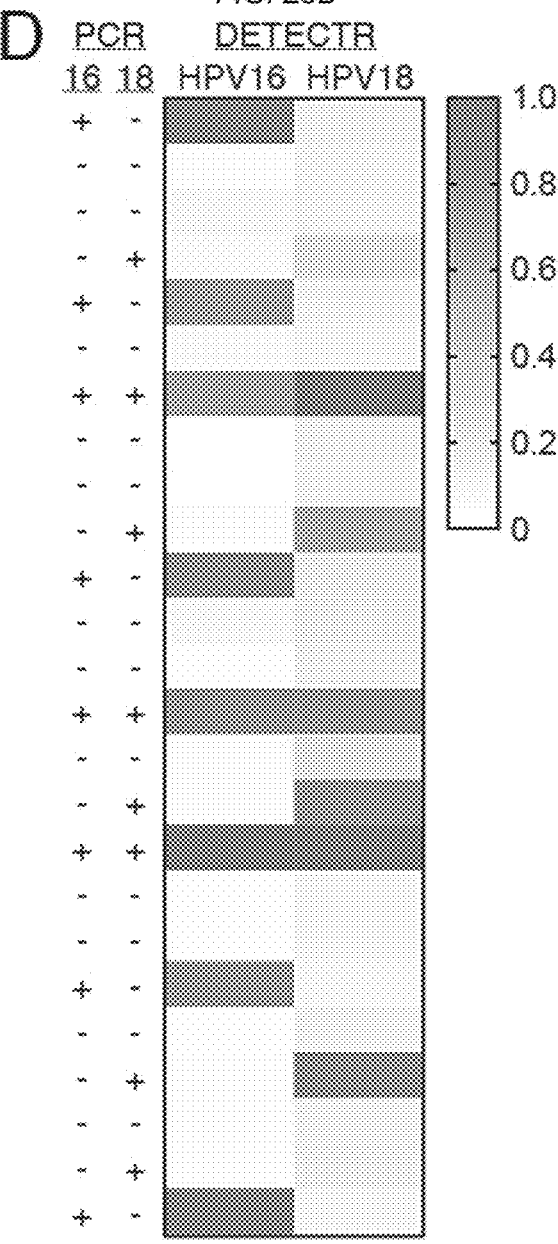

FIGS. 28A-28D. Rapid identification of HPV types 16 and 18 in human samples by DETECTR. FIG. 28A. Diagram of HPV16 and HPV18 sequences within the hypervariable loop V of the L1 gene targeted by Cas12a; highlighted bases indicate 5' PAM sequence. FIG. 28B. Heatmap represents normalized mean fluorescence values of HPV types 16 and 18 detected in human cell lines by DETECTR; normalized scale represented in FIG. 28D. FIG. 28C. Schematic outlining DNA extraction from human anal samples to HPV identification by DETECTR. FIG. 28D. Identification of HPV types 16 and 18 in 25 patient samples by PCR (left) and DETECTR (right); DETECTR heatmap represents normalized mean fluorescence values.

FIGS. 41A-41D. Identification of HPV types 16 and 18 in human cell lines and patient samples by DETECTR. FIG. 41A Schematic of HPV detection by DETECTR or Cas12a alone. FIG. 41B Detection of HPV types 16 or 18 in SiHa (integrated HPV16), HeLa (integrated HPV18) and BJAB (no HPV) human cell lines, with or without RPA amplification. FIG. 41C. Detection of HPV types 16 or 18 by DETECTR in 25 human anal clinical samples; BJAB cell line (no HPV) used as a control. Error bars represent mean±s.d., where n=3 replicates. FIG. 41D Plot of 95% confidence intervals of difference between control and sample groups, based on a one-way ANOVA with Dunnett's post test, where n=3 replicates. Highlighted sample numbers indicate positive detection of HPV16 (left) or HPV18 (right) in patient samples, where p≤0.01 and *p≤0.001.

FIGS. 42A-42B. PCR and hybrid capture validation and genotyping of HPV in human clinical samples. FIG. 42A Summary of PCR-based detection of HPV types 16 (column 2 and yellow circles) and 18 (column 3 and orange circles) and identification of other HPV types by PCR in 25 in patient samples (column 4) (2); subjective intensive values (0-4 scale) were assigned for each PCR-based validation (columns 2 and 3). FIG. 42B Heatmap depiction of PCR results.

Figure 29:
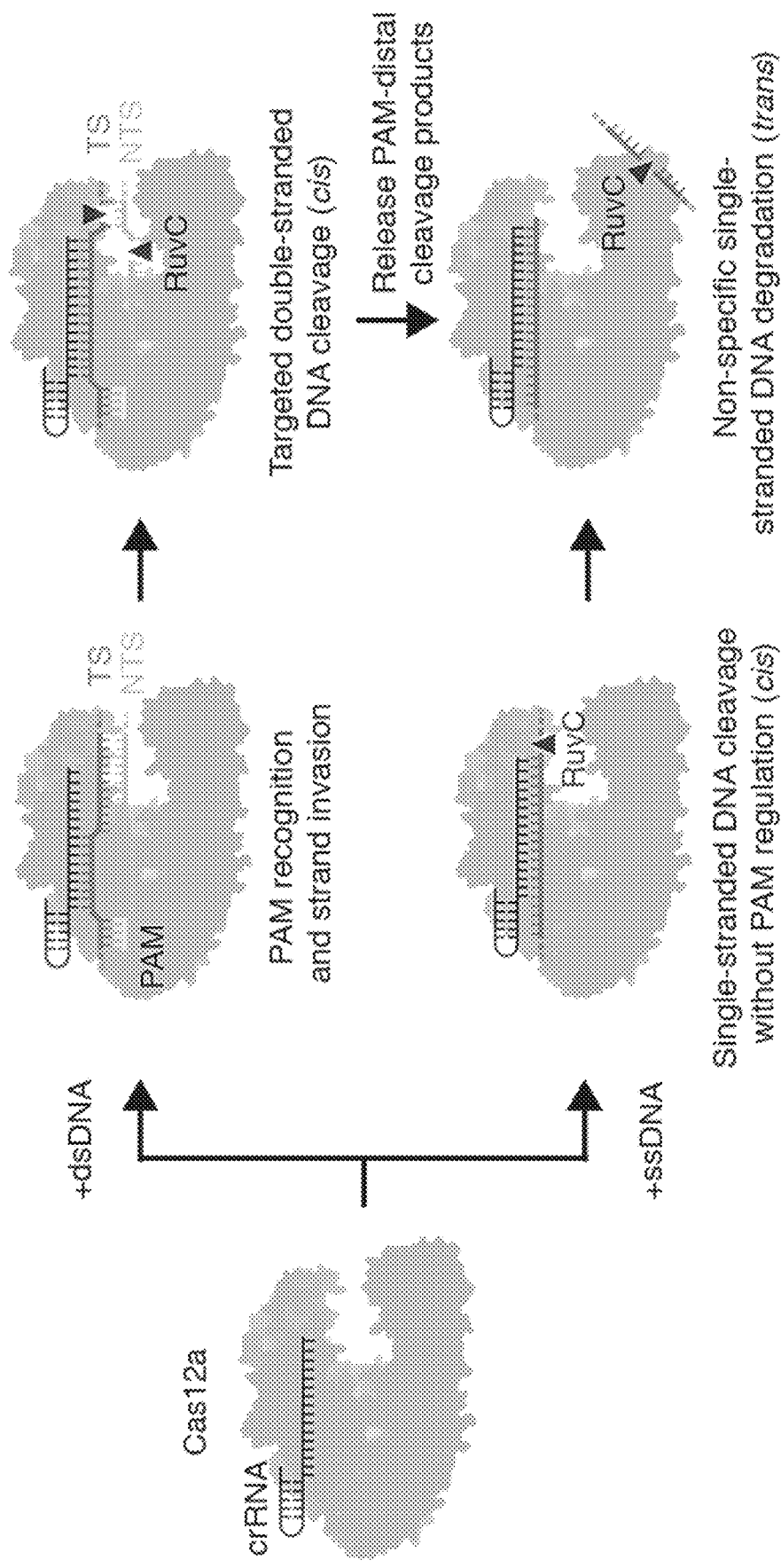

Together, these findings support a unifying mechanism of target interference that begins with the Cas12-guide RNA complex binding to a complementary DNA sequence in a PAM-dependent (dsDNA) or PAM-independent (ssDNA) manner (FIG. 29). Within a host bacterium, such enzyme activation could provide simultaneous protection from both dsDNA and ssDNA phages, and could also target ssDNA sequences that arise temporarily during phage replication or transcription. In a genome-editing context, target-activated ssDNA cutting by Cas12 may be a rare event, but it has the potential to cleave transiently exposed ssDNA at replication forks, R-loops and transcription bubbles, or ssDNA templates used for homology-directed repair. Finally, unleashing the ssDNase activity of Cas12 proteins offers a new strategy to improve the speed, sensitivity and specificity of nucleic acid detection for point-of-care diagnostic applications.

FIG. 29. Model for PAM-dependent and PAM-independent activation of cis and trans-cleavage by Cas12a. The Cas12a-crRNA complex binds to a complementary dsDNA in a PAM-dependent manner (top) or ssDNA in a PAM-independent manner (bottom), which is sufficient to unleash indiscriminate ssDNase activity by the RuvC nuclease. Cas12 proteins (e.g., Cas12a) can also release their PAM-distal cleavage products, which exposes the RuvC active site for multiple rounds of non-specific ssDNA degradation.

TABLE 2

Nucleic acids used in this study.

| Name | Sequence | SEQ ID NO. |
|---|---|---|
| RNA | | |
| LbCas12a crRNA-Target 1 | UAAUUUCUACUAAGUGUAGAUCGUC GCCGUCCAGCUCGACC | 20 |
| LbCas12a crRNA-pUC19 | UAAUUUCUACUAAGUGUAGAUCAAC GUCGUGACUGGGAAAACCCU | 21 |
| LbCas12a crRNA-M13 | UAAUUUCUACUAAGUGUAGAUAACG AACCACCAGCAGAAGA | 22 |
| LbCas12a crRNA-Target 2 | UAAUUUCUACUAAGUGUAGAUGAUC GUUACGCUAACUAUGA | 23 |
| LbCas12a crRNA-Target 3 | UAAUUUCUACUAAGUGUAGAUCCUG GGUGUUCCACAGCUGA | 24 |
| LbCas12a crRNA-Plasmid 1 | UAAUUUCUACUAAGUGUAGAUCUAC AUUACAGGCUAACAAA | 25 |
| LbCas12a crRNA-Plasmid 2 | UAAUUUCUACUAAGUGUAGAUGUAC AUUGCAAGAUACUAAA | 26 |

TABLE 2-continued

Nucleic acids used in this study.

| Name | Sequence | SEQ ID NO. |
|---|---|---|
| LbCas12a crRNA-HPV16-L1 | UAAUUUCUACUAAGUGUAGAUUGAAGUAGAUAUGGCAGCAC | 27 |
| LbCas12a crRNA-HPV18-L1 | UAAUUUCUACUAAGUGUAGAUACAAUAUGUGCUUCUACACA | 28 |
| AsCas12a crRNA-Target 2 | UAAUUUCUACUCUUGUAGAUGAUCGUUACGCUAACUAUGA | 29 |
| FnCas12a crRNA-Target 2 | UAAUUUCUACUGUUGUAGAUGAUCGUUACGCUAACUAUGA | 30 |
| AaCas12b crRNA-Target 2 | GUCUAGAGGACAGAAUUUUUCAACGGGUGUGCCAAUGGCCACUUUCCAGGUGGCAAAGCCCGUUGAGCUUCUCAAAUCUGAGAAGUGGCACGAUCGUUACGCUAACUAUGA | 31 |
| SpCas9 sgRNA-Target 1 | CGUCGCCGUCCAGCUCGACCGUUUUAGAGCUAUGCUGUUUUGGAAACAAAACAGCAUAGCAAGUUAAAAUAAGGCUAGUCCGUUAUCAACUUGAAAAAGUGGCACCGAGUCGGUGC | 32 |
| SpCas9 sgRNA-M13 | AACGAACCACCAGCAGAAGAGUUUUAGAGCUAUGCUGUUUUGGAAACAAAACAGCAUAGCAAGUUAAAAUAAGGCUAGUCCGUUAUCAACUUGAAAAAGUGGCACCGAGUCGGUGC | 33 |
| SpCas9 sgRNA-Target 2 | GAUCGUUACGCUAACUAUGAGUUUUAGAGCUAUGCUGUUUUGGAAACAAAACAGCAUAGCAAGUUAAAAUAAGGCUAGUCCGUUAUCAACUUGAAAAAGUGGCACCGAGUCGGUGC | 34 |
| NmCas9 sgRNA-Target 2 | GAUCGUUACGCUAACUAUGAGUUGUAGCUCCCUUUCUCAUUUCGCAGUGCGAAAGCACUGCGAAAUGAGAACCGUUGCUACAAUAAGGCCGUCUGAAAAGAUGUGCCGCAACGCUCUGCCCCUUAAAGCUUCUGC | 35 |
| CjCas9 sgRNA-Target 2 | GAUCGUUACGCUAACUAUGAGUUUUAGUCCCUUUUAAAUUUCUUUAUGGUAAAAUUAUAAUCUCAUAAGAAAUUUAAAAAGGGACUAAAAUAAAGAGUUUUGCGGGACUCUGCGGGGUUACAAUCCCCUAAAACCGCUU | 36 |
| Target 1 ssRNA | GCCGGGGUGGUGCCCAUCCUGGUCGAGCUGGACGGCGACGUAAACGGCCACAAGC | 37 |
| Target 2 ssRNA | UAGCAUUCCACAGACAGCCCUCAUAGUUAGCGUAACGAUCUAAAGUUUUGUCGUC | 38 |

DNA

| non-specific NTS | AGCTTGTCTGCCATGGACATGCAGACTATACTGTTATTGTTGTACAGACCGAATTCCC | 39 |
| non-specific TS | GGGAATTCGGTCTGTACAACAATAACAGTATAGTCTGCATGTCCATGGCAGACAAGCT | 40 |
| Target 1_NTS | GCTTGTGGCCGTTTACGTCGCCGTCCAGCTCGACCAGGATGGGCACCACCCCGGC | 41 |

TABLE 2-continued

Nucleic acids used in this study.

| Name | Sequence | SEQ ID NO. |
|---|---|---|
| Target 1_TS | GCCGGGGTGGTGCCCATCCTGGTCGA GCTGGACGGCGACGTAAACGGCCAC AAGC | 42 |
| Target 1_20-19_NTS | GCTTGTGGCCGTTTACGTCGCCGTCC AGCTCGAGGAGGATGGGCACCACCCC GGC | 43 |
| Target 1_20-19_TS | GCCGGGGTGGTGCCCATCCTCCTCGA GCTGGACGGCGACGTAAACGGCCAC AAGC | 44 |
| Target 1_18-17_NTS | GCTTGTGGCCGTTTACGTCGCCGTCC AGCTCCTCCAGGATGGGCACCACCCC GGC | 45 |
| Target 1_18-17_TS | GCCGGGGTGGTGCCCATCCTGGAGGA GCTGGACGGCGACGTAAACGGCCAC AAGC | 46 |
| Target 1_16-15_NTS | GCTTGTGGCCGTTTACGTCGCCGTCC AGCAGGACCAGGATGGGCACCACCCC GGC | 47 |
| Target 1_16-15_TS | GCCGGGGTGGTGCCCATCCTGGTCCT GCTGGACGGCGACGTAAACGGCCAC AAGC | 48 |
| Target 1_14-13_NTS | GCTTGTGGCCGTTTACGTCGCCGTCC ACGTCGACCAGGATGGGCACCACCCC GGC | 49 |
| Target 1_14-13_TS | GCCGGGGTGGTGCCCATCCTGGTCGA CGTGGACGGCGACGTAAACGGCCAC AAGC | 50 |
| Target 1_12-11_NTS | GCTTGTGGCCGTTTACGTCGCCGTCG TGCTCGACCAGGATGGGCACCACCCC GGC | 51 |
| Target 1_12-11_TS | GCCGGGGTGGTGCCCATCCTGGTCGA GCACGACGGCGACGTAAACGGCCAC AAGC | 52 |
| Target 1_10-9_NTS | GCTTGTGGCCGTTTACGTCGCCGAGC AGCTCGACCAGGATGGGCACCACCCC GGC | 53 |
| Target 1_10-9_TS | GCCGGGGTGGTGCCCATCCTGGTCGA GCTGCTCGGCGACGTAAACGGCCAC AAGC | 54 |
| Target 1_8-7_NTS | GCTTGTGGCCGTTTACGTCGCGCTCC AGCTCGACCAGGATGGGCACCACCCC GGC | 55 |
| Target 1_8-7_TS | GCCGGGGTGGTGCCCATCCTGGTCGA GCTGGAGCGCGACGTAAACGGCCAC AAGC | 56 |
| Target 1_6-5_NTS | GCTTGTGGCCGTTTACGTCCGCGTCC AGCTCGACCAGGATGGGCACCACCCC GGC | 57 |
| Target 1_6-5_TS | GCCGGGGTGGTGCCCATCCTGGTCGA GCTGGACGCGGACGTAAACGGCCAC AAGC | 58 |
| Target 1_4-3_NTS | GCTTGTGGCCGTTTACGAGGCCGTCC AGCTCGACCAGGATGGGCACCACCCC GGC | 59 |

TABLE 2-continued

Nucleic acids used in this study.

| Name | Sequence | SEQ ID NO. |
|---|---|---|
| Target 1_4-3_TS | GCCGGGGTGGTGCCCATCCTGGTCGA GCTGGACGGCCTCGTAAACGGCCAC AAGC | 60 |
| Target 1_2-1_NTS | GCTTGTGGCCGTTTAAGCTCGCCGTCC AGCTCGACCAGGATGGGCACCACCCC GGC | 61 |
| Target 1_2-1_TS | GCCGGGGTGGTGCCCATCCTGGTCGA GCTGGACGGCGAGCTAAACGGCCAC AAGC | 62 |
| Target 1_mut-PAM_NTS | GCTTGTGGCCGAGCACGTCGCCGTCC AGCTCGACCAGGATGGGCACCACCCC GGC | 63 |
| Target 1_mut-PAM_TS | GCCGGGGTGGTGCCCATCCTGGTCGA GCTGGACGGCGACGTGCTCGGCCACA AGC | 64 |
| Target 1_5nt_TS | CGACGTAAACGGCCACAAGC | 65 |
| Target 1_10nt_TS | GACGGCGACGTAAACGGCCACAAGC | 66 |
| Target 1_15nt_TS | AGCTGGACGGCGACGTAAACGGCCA CAAGC | 67 |
| Target 1_20nt_TS | GGTCGAGCTGGACGGCGACGTAAAC GGCCACAAGC | 68 |
| Target 1_25nt_TS | ATCCTGGTCGAGCTGGACGGCGACG TAAACGGCCACAAGC | 69 |
| Target 1_5nt_NTS | GCTTGTGGCCGTTTACGTCG | 70 |
| Target 1_10nt_NTS | GCTTGTGGCCGTTTACGTCGCCGTC | 71 |
| Target 1_15nt_NTS | GCTTGTGGCCGTTTACGTCGCCGTCC AGCT | 72 |
| Target 1_20nt_NTS | GCTTGTGGCCGTTTACGTCGCCGTCC AGCTCGACC | 73 |
| Target 1_25nt_NTS | GCTTGTGGCCGTTTACGTCGCCGTCC AGCTCGACCAGGAT | 74 |
| Target 2_NTS | GACGACAAAACTTTAGATCGTTACGC TAACTATGAGGGCTGTCTGTGGAATG CTA | 75 |
| Target 2_TS | TAGCATTCCACAGACAGCCCTCATAGT TAGCGTAACGATCTAAAGTTTTGTCG TC | 76 |
| Target 2_20-19_NTS | GACGACAAAACTTTAGATCGTTACGC TAACTATCTGGGCTGTCTGTGGAATGC TA | 77 |
| Target 2_20-19_TS | TAGCATTCCACAGACAGCCCAGATAG TTAGCGTAACGATCTAAAGTTTTGTC GTC | 78 |
| Target 2_18-17_NTS | GACGACAAAACTTTAGATCGTTACGC TAACTTAGAGGGCTGTCTGTGGAATG CTA | 79 |
| Target 2_18-17_TS | TAGCATTCCACAGACAGCCCTCTAAGT TAGCGTAACGATCTAAAGTTTTGTCG TC | 80 |
| Target 2_16-15_NTS | GACGACAAAACTTTAGATCGTTACGC TAAGAATGAGGGCTGTCTGTGGAATG CTA | 81 |

TABLE 2-continued

Nucleic acids used in this study.

| Name | Sequence | SEQ ID NO. |
|---|---|---|
| Target 2_16-15_TS | TAGCATTCCACAGACAGCCCTCATTCT TAGCGTAACGATC<u>TAAA</u>GTTTTGTCG TC | 82 |
| Target 2_14-13_NTS | GACGACAAAAC<u>TTTA</u>GATCGTTACGC TTTCTATGAGGGCTGTCTGTGGAATGC TA | 83 |
| Target 2_14-13_TS | TAGCATTCCACAGACAGCCCTCATAG AAAGCGTAACGATC<u>TAAA</u>GTTTTGTC GTC | 84 |
| Target 2_12-11_NTS | GACGACAAAAC<u>TTTA</u>GATCGTTACGG AAACTATGAGGGCTGTCTGTGGAATG CTA | 85 |
| Target 2_12-11_TS | TAGCATTCCACAGACAGCCCTCATAGT TTCCGTAACGATC<u>TAAA</u>GTTTTGTCGT C | 86 |
| Target 2_10-9_NTS | GACGACAAAAC<u>TTTA</u>GATCGTTAGCC TAACTATGAGGGCTGTCTGTGGAATG CTA | 87 |
| Target 2_10-9_TS | TAGCATTCCACAGACAGCCCTCATAGT TAGGCTAACGATC<u>TAAA</u>GTTTTGTCG TC | 88 |
| Target 2_8-7_NTS | GACGACAAAAC<u>TTTA</u>GATCGTATCGC TAACTATGAGGGCTGTCTGTGGAATG CTA | 89 |
| Target 2_8-7_TS | TAGCATTCCACAGACAGCCCTCATAGT TAGCGATACGATC<u>TAAA</u>GTTTTGTCG TC | 90 |
| Target 2_6-5_NTS | GACGACAAAAC<u>TTTA</u>GATCCATACGC TAACTATGAGGGCTGTCTGTGGAATG CTA | 91 |
| Target 2_6-5_TS | TAGCATTCCACAGACAGCCCTCATAGT TAGCGTATGGATC<u>TAAA</u>GTTTTGTCG TC | 92 |
| Target 2_4-3_NTS | GACGACAAAAC<u>TTTA</u>GAAGGTTACGC TAACTATGAGGGCTGTCTGTGGAATG CTA | 93 |
| Target 2_4-3_TS | TAGCATTCCACAGACAGCCCTCATAGT TAGCGTAACCTTC<u>TAAA</u>GTTTTGTCGT C | 94 |
| Target 2_2-1_NTS | GACGACAAAAC<u>TTTA</u>CTTCGTTACGC TAACTATGAGGGCTGTCTGTGGAATG CTA | 95 |
| Target 2_2-1_TS | TAGCATTCCACAGACAGCCCTCATAGT TAGCGTAACGAAG<u>TAAA</u>GTTTTGTCG TC | 96 |
| Target 2_mut-PAM_NTS | GACGACAAAAC<u>AGCA</u>GATCGTTACGC TAACTATGAGGGCTGTCTGTGGAATG CTA | 97 |
| Target 2_mut-PAM_TS | TAGCATTCCACAGACAGCCCTCATAGT TAGCGTAACGATC<u>TGCT</u>GTTTTGTCGT C | 98 |
| Target 2_NmCas9_NTS | GACGACAAAACTTTAGATCGTTACGC TAACTATGA<u>GGGCGAGT</u>TGTGGAATG CTA | 99 |
| Target 2_NmCas9_TS | TAGCATTCCACA<u>ACTCGCCC</u>TCATAGT TAGCGTAACGATCTAAAGTTTTGTCG TC | 100 |

TABLE 2-continued

Nucleic acids used in this study.

| Name | Sequence | SEQ ID NO. |
|---|---|---|
| Target 2_CjCas9_TS | GACGACAAAACTTTAGATCGTTACGC TAACTATGA<u>GGGCCAAA</u>TGTGGAATG CTA | 101 |
| Target 2_CjCas9_TS | TAGCATTCCACA<u>TTTGGCCC</u>TCATAGT TAGCGTAACGATCTAAAGTTTTGTCG TC | 102 |
| Target 3_NTS | AGTTGTGTTAG<u>TTTA</u>CCTGGGTGTTCC ACAGCTGATAGTGATTGCCTTGAATA AA | 103 |
| Target 3_TS | TTTATTCAAGGCAATCACTATCAGCTG TGGAACACCCAGG<u>TAAA</u>CTAACACAA CT | 104 |
| Target 3_20-19_NTS | AGTTGTGTTAG<u>TTTA</u>CCTGGGTGTTCC ACAGCTCTTAGTGATTGCCTTGAATAA A | 105 |
| Target 3_20-19_TS | TTTATTCAAGGCAATCACTAAGAGCTG TGGAACACCCAGG<u>TAAA</u>CTAACACAA CT | 106 |
| Target 3_18-17_NTS | AGTTGTGTTAG<u>TTTA</u>CCTGGGTGTTCC ACAGGAGATAGTGATTGCCTTGAATA AA | 107 |
| Target 3_18-17_TS | TTTATTCAAGGCAATCACTATCTCCTG TGGAACACCCAGG<u>TAAA</u>CTAACACAA CT | 108 |
| Target 3_16-15_NTS | AGTTGTGTTAG<u>TTTA</u>CCTGGGTGTTCC ACTCCTGATAGTGATTGCCTTGAATAA A | 109 |
| Target 3_16-15_TS | TTTATTCAAGGCAATCACTATCAGGAG TGGAACACCCAGG<u>TAAA</u>CTAACACAA CT | 110 |
| Target 3_14-13_NTS | AGTTGTGTTAG<u>TTTA</u>CCTGGGTGTTCC TGAGCTGATAGTGATTGCCTTGAATA AA | 111 |
| Target 3_14-13_TS | TTTATTCAAGGCAATCACTATCAGCTC AGGAACACCCAGG<u>TAAA</u>CTAACACAA CT | 112 |
| Target 3_12-11_NTS | AGTTGTGTTAG<u>TTTA</u>CCTGGGTGTTG ACAGCTGATAGTGATTGCCTTGAAT AAA | 113 |
| Target 3_12-11_TS | TTTATTCAAGGCAATCACTATCAGCTG TCCAACACCCAGG<u>TAAA</u>CTAACACAA CT | 114 |
| Target 3_10-9_NTS | AGTTGTGTTAG<u>TTTA</u>CCTGGGTGAAC CACAGCTGATAGTGATTGCCTTGAAT AAA | 115 |
| Target 3_10-9_TS | TTTATTCAAGGCAATCACTATCAGCTG TGGTTCACCCAGG<u>TAAA</u>CTAACACAA CT | 116 |
| Target 3_8-7_NTS | AGTTGTGTTAG<u>TTTA</u>CCTGGGACTTCC ACAGCTGATAGTGATTGCCTTGAATA AA | 117 |
| Target 3_8-7_TS | TTTATTCAAGGCAATCACTATCAGCTG TGGAAGTCCCAGG<u>TAAA</u>CTAACACAA CT | 118 |

TABLE 2-continued

Nucleic acids used in this study.

| Name | Sequence | SEQ ID NO. |
|---|---|---|
| Target 3_6-5_NTS | AGTTGTGTTAGTTTACCTGCCTGTTCCACAGCTGATAGTGATTGCCTTGAATAAA | 119 |
| Target 3_6-5_TS | TTTATTCAAGGCAATCACTATCAGCTGTGGAACAGGCAGGTAAACTAACACAACT | 120 |
| Target 3_4-3_NTS | AGTTGTGTTAGTTTACCACGGTGTTCCACAGCTGATAGTGATTGCCTTGAATAAA | 121 |
| Target 3_4-3_TS | TTTATTCAAGGCAATCACTATCAGCTGTGGAACACCGTGGTAAACTAACACAACT | 122 |
| Target 3_2-1_NTS | AGTTGTGTTAGTTTAGGTGGGTGTTCCACAGCTGATAGTGATTGCCTTGAATAAA | 123 |
| Target 3_2-1_TS | TTTATTCAAGGCAATCACTATCAGCTGTGGAACACCCACCTAAACTAACACAACT | 124 |
| Target 3_mut-PAM_NTS | AGTTGTGTTAGAGCACCTGGGTGTTCCACAGCTGATAGTGATTGCCTTGAATAAA | 125 |
| Target 3_mut-PAM_TS | TTTATTCAAGGCAATCACTATCAGCTGTGGAACACCCAGGTGCTCTAACACAACT | 126 |
| FQ substrates | | |
| ssDNA-FQ reporter | /56-FAM/TTATT/3IABkFQ/ | |
| ssRNA-FQ reporter | /56-FAM/rUrUrArUrU/3IABkFQ/ | |
| Dnase-Alert substrate (IDT) | proprietary | |
| RPA primers | | |
| Plasmid 1_F | GCAAACCACCTATAGGGGAACAC | 127 |
| Plasmid 1_R | CAGCCAACTCAGCTTCCTTTC | 128 |
| Plasmid 2_F | CATGCCGCCACGTCTAATGTTTC | 129 |
| Plasmid 2_R | GGTGAAGCACGCATACCTGTG | 130 |
| HPV16-L1_F | TTGTTGGGGTAACCAACTATTTGTTACTGTT | 131 |
| HPV16-L1_R | CCTCCCCATGTCTGAGGTACTCCTTAAAG | 132 |
| HPV18-L1_F | GCATAATCAATTATTTGTTACTGTGGTAGATACCACT | 133 |
| HPV18-L1-R | GCTATACTGCTTAAATTTGGTAGCATCATATTGC | 134 |

Materials and Methods

Protein expression and purification. DNA sequences encoding SpCas9 and Cas12 proteins and mutants were cloned into a custom pET-based expression vector containing an N-terminal 10×His-tag, maltose-binding protein (MBP) and TEV protease cleavage site. Point mutations were introduced by around-the-horn PCR and verified by DNA sequencing. Proteins were purified as described, with the following modifications: *E. coli* BL21(DE3) containing SpCas9 or Cas12 expression plasmids were grown in Terrific Broth at 16° C. for 14 hr. Cells were harvested and resuspended in Lysis Buffer (50 mM Tris-HCl, pH 7.5, 500 mM NaCl, 5% (v/v) glycerol, 1 mM TCEP, 0.5 mM PMSF and 0.25 mg/ml lysozyme), disrupted by sonication, and purified using Ni-NTA resin. After overnight TEV cleavage at 4° C., proteins were purified over an MBPTrap HP column connected to a HiTrap Heparin HP column for cation exchange chromatography. The final gel filtration step (Superdex 200) was carried out in elution buffer containing 20 mM Tris-HCl, pH 7.5, 200 mM NaCl (or 250 mM NaCl for AaCas12b), 5% (v/v) glycerol and 1 mM TCEP. All proteins tested in this study are shown in FIG. 30.

Nucleic acid preparation. DNA substrates were synthesized commercially (IDT). For FQ-reporter assays, activator DNA duplexes were prepared by annealing 5-fold molar excess of the NTS to TS in 1× hybridization buffer (20 nM Tris-Cl, pH 7.5, 100 mM KCl, 5 mM $MgCl_2$), heating at 95° C. and slow-cooling on the benchtop. HPV16 and HPV18 fragments were synthesized as gBlocks (IDT) and cloned into a custom pET-based vector via Gibson assembly. Plasmid DNA for titration experiments was quantified using a Qubit fluorometer (Invitrogen). For radiolabeled cleavage assays, PAGE-purified DNA oligos were prepared as described.

sgRNA templates were PCR amplified from a pUC19 vector or overlapping primers containing a T7 promoter, 20 nucleotide target sequence and an sgRNA scaffold. The amplified PCR product served as the DNA template for in vitro transcription reactions, which were performed as described. crRNAs were transcribed in vitro using a single-stranded DNA template containing a T7 promoter, repeat and spacer in the reverse complement orientation, which was annealed to T7 forward primer in 1× hybridization buffer.

DNA cleavage assays. Generally, Cas12a-mediated cleavage assays were carried out in cleavage buffer consisting of 20 mM HEPES (pH 7.5), 150 mM KCl, 10 mM $MgCl_2$, 1% glycerol and 0.5 mM DTT. For M13-targeting assays, 30 nM Cas12a was pre-assembled with either 36 nM of M13-targeting crRNA (cis) or with 36 nM of crRNA and 40 nM complementary ssDNA (activator) with no sequence homology to M13 (trans) at 37° C. for 10 min. The reaction was initiated by adding 10 nM M13mp18 ssDNA (New England Biolabs) and incubated at 37° C. for indicated timepoints. Reactions were quenched with DNA loading buffer (30% (v/v) glycerol, 0.25% (w/v) bromophenol blue, 0.25% (w/v) xylene cyanol) containing 15 mM EDTA and separated by 1.5% agarose gel pre-stained with SYBER Gold (Invitrogen).

For radiolabeled cleavage assays, the substrates used were 5'-end-labeled with T4 PNK (NEB) in the presence of gamma $^{32}$P-ATP. For dsDNA substrates, the non-target strand was first 5'-end-labeled and then annealed with excess corresponding target strand. The concentrations of Cas12a (or SpCas9), guide RNA and $^{32}$P-labeled substrates used in the reaction were 30 nM, 36 nM and 1-3 nM (unless otherwise stated), respectively. Reactions were incubated for 30 min (unless otherwise stated) at 37° C. (or 47.5° C. for the thermophilic AaCas12b) and quenched with formamide loading buffer (final concentration 45% formamide and 15 mM EDTA, with trace amount of xylene cyanol and bromophenol blue) for 2-3 min at 90° C. The substrates and products were resolved by 12% urea-denaturing PAGE gel and quantified with Amersham Typhoon (GE Healthcare).

For substrate turnover studies, the pre-assembled Cas12a-crRNA or Cas12a-crRNA-activator (target ssDNA or dsDNA) were incubated at 37° C. for 10 min, and 30 nM of the pre-assembled RNP were used for each reaction with various substrate concentrations at 15, 30, 45, and 60 nM, respectively.

Fluorophore quencher (FQ)-labeled reporter assays. LbCas12a-crRNA complexes were pre-assembled by incubating 200 nM LbCpf1 with 250 nM crRNA and 4 nM activator (ssDNA, dsDNA or ssRNA) at 37° C. for 30 min. The reaction was initiated by diluting LbCas12a complexes to a final concentration of 50 nM LbCas12a: 62.5 nM crRNA: 1 nM activator in a solution containing 1× Binding Buffer (20 mM Tris-HCl, pH 7.5, 100 mM KCl, 5 mM $MgCl_2$, 1 mM DTT, 5% glycerol, 50 μg $ml^{-1}$ heparin) and 50 nM DNaseAlert Substrate™ (IDT) or custom ssDNA/ssRNA FQ reporter substrates in a 20 μl reaction. HPV detection assays were performed as above, with the following modifications: LbCas12a was pre-assembled with an HPV16 or HPV18-targeting crRNA and diluted in a solution containing 1× Binding Buffer, custom ssDNA-FQ reporter and 1, 10, 100, or 1000 nM of HPV16- or HPV18-containing plasmids. Reactions (20 l, 384-well microplate format) were incubated in a fluorescence plate reader (Tecan Infinite Pro F200) for up to 120 minutes at 37° C. with fluorescence measurements taken every 30 seconds (DNaseAlert substrate=$\lambda_{ex}$: 535 nm; $\lambda_{em}$: 595 nm, custom ssDNA/ssRNA FQ substrates=$\lambda_{ex}$: 485 nm; $\lambda_{em}$: 535 nm).

For trans-cleavage rate determination, background-corrected fluorescence values were calculated by subtracting fluorescence values obtained from reactions carried out in the absence of target plasmid. The resulting data were fit to a single exponential decay curve (GraphPad Software), according to the following equation: Fraction cleaved=A× (1−exp(−k×t)), where A is the amplitude of the curve, k is the first-order rate constant, and t is time.

For Michaelis-Menten analysis, LbCas12a-crRNA-activator (target ssDNA or dsDNA) complexes were prepared as described above, and reaction was initiated by diluting LbCas12a complexes to a final concentration of 5 nM LbCas12a:6.25 nM crRNA:0.1 nM activator (effective complex=0.1 nM) in a solution containing 1× Binding Buffer and 0.001, 0.01, 0.1, 0.2, 0.5, 1 or 2 uM of DNaseAlert™ substrate (IDT). Reactions were incubated in a fluorescence plate reader for up to 30 minutes at 37° C. with fluorescence measurements taken every 30 seconds ($\lambda_{ex}$: 535 nm; $\lambda_{em}$: 595 nm). The initial velocity ($V_0$) was calculated by fitting to a linear regression and plotted against the substrate concentration to determine the Michaelis-Menten constants (GraphPad Software), according to the following equation: Y=($V_{max}$×X)/($K_m$+X), where X is the substrate concentration and Y is the enzyme velocity. The turnover number ($k_{cat}$) was determined by the following equation: $k_{cat}$=$V_{max}$/$E_t$, where $E_t$=0.1 nM.

Human clinical sample collection and DNA preparation. Anal sample donors were recruited from the UCSF Anal Neoplasia Clinic, Research and Education Center (ANCRE). The study was approved by the UCSF Committee on Human Research. After informed consent was obtained, participants had an anal swab inserted into a Thinprep™ vial for anal cytology and HPV testing. Cell suspension left over from the first swab after monolayer cytology slides were made was used for HPV DNA PCR.

A crude DNA preparation was made by pelleting 1.5 ml of the cell suspension. After the pellet was allowed to dry, it was suspended in 100 μl Tris-EDTA with proteinase K (Life Technologies) at a concentration of 200 μg/ml and incubated at 56° C. for 1 hour, then the proteinase K was heat inactivated. Five μl of this was used in the HPV consensus PCR. DNA preparation from human cell lines (SiHa, HeLa, BJAB) was performed as above, with the following modifications: $10^6$-$10^7$ cells were harvested, resuspended in 100 μl Tris-EDTA with proteinase K, incubated at 56° C. for 1 hour, then the proteinase K was heat inactivated. One μl of this sample was used for DETECTR experiments.

DETECTR assays. DETECTR combined Recombinase Polymerase Amplification (RPA) using TwistAmp Basic (Twist Biosciences) followed by Cas12a detection in the same reaction. Briefly, 50 µl reactions containing 1 µl sample, 0.48 µM forward and reverse primer, 1× rehydration buffer, 14 mM magnesium acetate and RPA mix were incubated at 37° C. for 10 minutes. The RPA reaction (18 µl) was transferred to a 384-well microplate and 50 nM LbCas12a:62.5 nM crRNA:50 nM custom ssDNA-FQ reporter was added directly to the reaction (20 µl final volume). Reactions were incubated in a fluorescence plate reader (Tecan Infinite Pro F200) for 1-2 h at 37° C. with fluorescence measurements taken every minute ($\lambda_{ex}$: 485 nm; $\lambda_{em}$: 535 nm).

For HPV identification by DETECTR, detection values of HPV types 16 or 18 in human samples were normalized to the maximum mean fluorescence signal obtained using the HPV16- or HPV18-targeting crRNA, respectively. A one-way ANOVA with Dunnett's post test was used to determine the positive cutoff (set at p≤0.05) for identification of HPV16 or HPV18 in patient samples. Based on this cutoff, 100% of samples were accurately identified for HPV16 infection (25/25 agreement with PCR-based results), while 92% of samples were accurately identified for HPV18 infection (23/25 agreement with PCR-based results).

HPV genotyping and validation. PCR was performed as described previously using a modified pool of MY09/MY11 consensus HPV L1 primers as well as primers for amplification of the human beta-globin as an indicator of specimen adequacy as described previously. After 40 amplification cycles, specimens were probed with a biotin-labeled HPV L1 consensus probe mixture. A separate membrane was probed with a biotin-labeled probe to the human beta-globin gene. Specimens were typed by hybridizing to 38 different HPV types, 6/11, 16, 18, 26/69, 30, 31, 32/42, 33, 34, 35, 39, 45, 51, 52, 53, 54, 56, 57/2/27, 58, 59, 61, 62, 66, 67, 68, 70, 71, 72, 73, 81, 82, 83, 84, 85, 86/87, 90/106, 97, 102/89, as well as two separate mixtures. Mix1 contains 7, 13, 40, 43, 44, 55, 74, and 91, and Mix 2 contains 3, 10, 28, 29, 77, 78, and 94. Specimens negative for beta-globin gene amplification were excluded from analysis. The results of PCR were recorded on a scale from 0 to 5 based on the intensity of the signal on the dot-blots, as described previously. Samples with results recorded as 1 or more were considered to be positive.

Figure 43B:
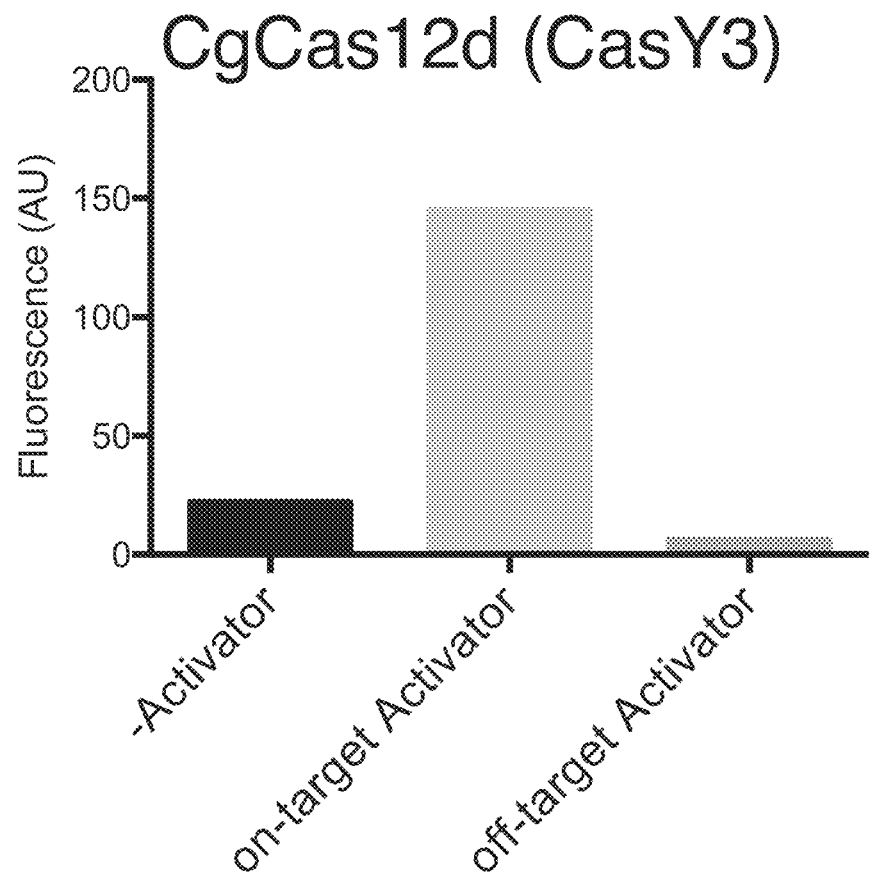

Example 4: Trans-Cleavage Activity of Cas12d and Cas12e trans-cleavage activity was demonstrated for two additional type V CRISPR/Cas effector proteins, CasX (Cas12e) and CasY (Cas12d) using a DETECTR assay (FIGS. 43A-43B).

Figure 44:
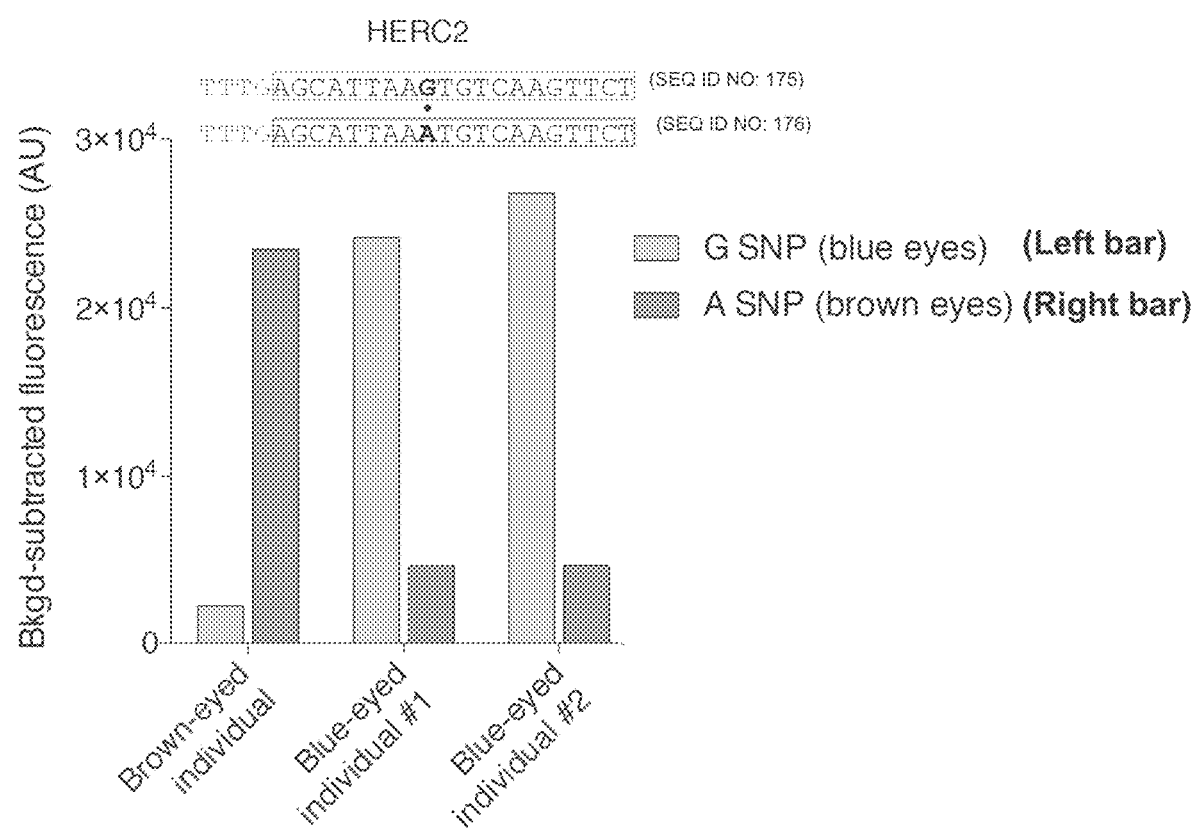
FIG. 44 presents data showing identification of a single nucleotide polymorphism (SNP) within the HERC2 gene responsible for brown or blue eyes using DETECTR.

Example 5: Identification of a Single Nucleotide Polymorphism (SNP) within the HERC2 Gene Responsible for Brown or Blue Eyes DETECTR was used to detect eye color SNPs from saliva samples using Cas12a (FIG. 44). Sample preparation: 500 µL of phosphate buffered saline was added to ~500 µL of volunteer saliva and centrifuged for 5 min at 1800 g. The supernatant was decanted and the pellet was resuspended in 100 µL phosphate buffered saline with 0.2% Triton X-100 before incubation at 95° C. for 5 min. 1 µL of sample was used as direct input into RPA reactions. The following nucleic acids were used for these experiments:

```
RPA primers:
F primer:
                                       (SEQ ID NO: 153)
CAAAGAGAAGCCTCGGCC R primer:
                                       (SEQ ID NO: 154)
GTGTTAATACAAAGGTACAGGAACAAAGAATTTG HERC2 G-SNP crRNA:
                                       (SEQ ID NO: 155)
GTAATTTCTACTAAGTGTAGATAGCATTAAGTGTCAAGTTCT HERC2 A-SNP crRNA:
                                       (SEQ ID NO: 156)
GTAATTTCTACTAAGTGTAGATAGCATTAAATGTCAAGTTCT
```

Figure 45:
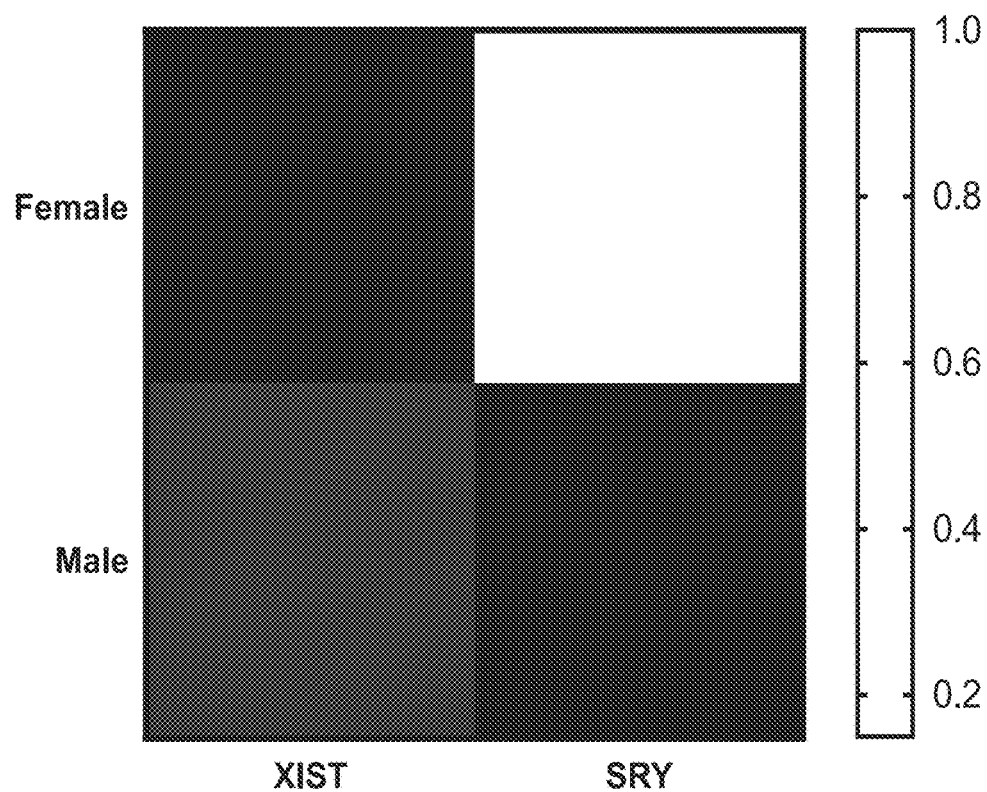
FIG. 45 presents data showing identification of the X or Y chromosomes through detection of the XIST (within X chromosome) or SRY (within Y chromosome) genes from human saliva (using the DETECTR assay).

Example 6: Identification of the X or Y Chromosomes Through Detection of the XIST (within X Chromosome) or SRY (within Y Chromosome) Genes from Human Saliva FIG. 45 provides data demonstrating the identification of the X or Y chromosomes through detection of the XIST (within X chromosome) or SRY (within Y chromosome) genes from human saliva. The following nucleic acids were used for these experiments:

```
XIST crRNA:
                                       (SEQ ID NO: 157)
GTAATTTCTACTAAGTGTAGATACTAGTCCCTTGTACTGATA

SRY crRNA:
                                       (SEQ ID NO: 158)
GTAATTTCTACTAAGTGTAGATGCATTCTGGGATTCTCTAGA

XIST RPA primers:
F primer:
                                       (SEQ ID NO: 159)
CTATCTGAATGAATTGATTTGGGGCTTG R primer:
                                       (SEQ ID NO: 160)
GCAATGTCAAAATCGCCATTTTAAGC SRY RPA primers:
F primer:
                                       (SEQ ID NO: 161)
AGGCAACGTCCAGGATAGAGTG R primer:
                                       (SEQ ID NO: 162)
CAGTAAGCATTTTCCACTGGTATCCCAG
```

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of assaying for a target nucleic acid in a sample, the method comprising:
   a) contacting the sample to a single volume comprising:
      i) reagents for amplification;
      ii) a type V CRISPR/Cas effector protein;
      iii) a guide nucleic acid comprising a nucleotide sequence that hybridizes to a nucleic acid segment of an amplification product of the target nucleic acid; and
      iv) a detector DNA molecule;
   b) amplifying the target nucleic acid in the single volume; and
   c) assaying for a signal produced by cleavage of the detector DNA molecule by the type V CRISPR/Cas effector protein upon hybridization of the guide nucleic acid to the segment of the amplification product of the target nucleic acid in the single volume.

2. The method of claim 1, wherein the reagents for amplification comprise a primer, a polymerase, or a combination thereof.

3. The method of claim 1, wherein the amplifying comprises isothermal amplification.

4. The method of claim 1, wherein the amplifying comprises one or more of: loop-mediated isothermal amplification (LAMP), helicase-dependent amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), ramification (RAM), circular helicase-dependent amplification (cHDA), single primer isothermal amplification (SPIA), self-sustained sequence replication (3SR), genome exponential amplification reaction (GEAR), isothermal multiple displacement amplification (IMDA), RNA amplification via T7 promoter, or polymerase chain reaction (PCR).

5. The method of claim 1, wherein the single volume is incubated at a single temperature.

6. The method of claim 1, wherein the single volume is incubated from about 37° C. to about 95° C.

7. The method of claim 1, comprising contacting the sample to reagents for reverse transcription and reverse transcribing the target nucleic acid.

8. The method of claim 1, wherein the reagents for reverse transcription comprise a reverse transcriptase and Rnase H.

9. The method of claim 1, wherein the single volume comprises reagents for reverse transcription and the method comprises reverse transcribing the target nucleic acid comprising RNA, amplifying the reverse transcribed target nucleic acid by LAMP, and assaying for the signal upon cleavage of the detector DNA molecule by the type V CRISPR/Cas effector protein.

10. The method of claim 9, wherein the reagents for reverse transcription are in the single volume.

11. The method of claim 1, wherein the target nucleic acid is single stranded or double stranded.

12. The method of claim 1, wherein the target nucleic acid is DNA or RNA.

13. The method of claim 1, wherein the target nucleic acid is a viral nucleic acid or a bacterial nucleic acid.

14. The method of claim 1, wherein the target nucleic acid is a papovavirus, a human papillomavirus (HPV), a hepadnavirus, a Hepatitis B Virus (HBV), a herpesvirus, a varicella zoster virus (VZV), an Epstein Barr virus (EBV), a Kaposi's sarcoma-associated herpesvirus, an adenovirus, a poxvirus, a parvovirus, an influenza virus, or a respiratory syncytial virus nucleic acid.

15. The method of claim 1, wherein the target nucleic acid is from a human cell.

16. The method of claim 1, wherein the target nucleic acid is a human fetal nucleic acid or a cancer cell nucleic acid.

17. The method of claim 1, wherein the type V CRISPR/Cas effector protein is a Cas12 protein comprising a Cas12a polypeptide, a Cas12b polypeptide, a Cas12c polypeptide, a Cas12d polypeptide, a Cas12e polypeptide, a C2c4 polypeptide, a C2c8 polypeptide, a C2c5 polypeptide, a C2c10 polypeptide, or a C2c9 polypeptide.

18. The method of claim 1, wherein the sample comprises a cell or a cell lysate.

19. The method of claim 1, wherein the sample is blood, saliva, biopsy, plasma, serum, bronchoalveolar lavage, sputum, a fecal sample, cerebrospinal fluid, a fine needle aspirate, a buccal swab, a cervical swab, a nasal swab, interstitial fluid, synovial fluid, nasal discharge, tears, buffy coat, or a mucous membrane sample.

20. The method of claim 1, comprising determining an amount of the target nucleic acid.

21. The method of claim 1, wherein the assaying for the signal produced by cleavage of the detector DNA molecule comprises one or more of: visual based detection, sensor based detection, color detection, gold nanoparticle based detection, fluorescence polarization, colloid phase transition/dispersion, electrochemical detection, and semiconductor-based sensing.

22. The method of claim 1, wherein the detector DNA molecule produces the signal prior to cleavage of the detector DNA molecule, and the signal is reduced after cleavage of the detector DNA molecule.

23. The method of claim 1, wherein the signal increases after cleavage of the detector DNA molecule.

24. The method of claim 1, wherein the detector DNA molecule comprises one or more fluorescence-emitting dye pairs.

25. The method of claim 24, wherein the one or more fluorescence-emitting dye pairs includes a fluorescence resonance energy transfer (FRET) pair, a quencher and fluorophore pair, or a combination thereof.

26. The method of claim 1, wherein the detector DNA molecule comprises a modified nucleobase, a modified sugar moiety, a modified nucleic acid linkage, or a combination thereof.

27. The method of claim 1, wherein the guide nucleic acid comprises a constant region comprising the nucleotide sequence set forth in SEQ ID NO:11.

* * * * *

SEQUENCE LISTING

<160> NUMBER OF SEQ ID NOS: 179

<210> SEQ ID NO 1
<211> LENGTH: 1228
<212> TYPE: PRT
<213> ORGANISM: Unknown
<220> FEATURE:
<223> OTHER INFORMATION: Lachnospiraceae bacterium

<400> SEQUENCE: 1

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
```

```
             355                 360                 365
Ile His Leu Lys Lys Ala Val Val Thr Glu Lys Tyr Glu Asp Asp
        370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
Ile Ile Ile Gln Lys Val Asp Glu Ile Tyr Lys Val Tyr Gly Ser Ser
                420                 425                 430
Glu Lys Leu Phe Asp Ala Asp Phe Val Leu Glu Lys Ser Leu Lys Lys
            435                 440                 445
Asn Asp Ala Val Val Ala Ile Met Lys Asp Leu Leu Asp Ser Val Lys
        450                 455                 460
Ser Phe Glu Asn Tyr Ile Lys Ala Phe Phe Gly Glu Gly Lys Glu Thr
465                 470                 475                 480
Asn Arg Asp Glu Ser Phe Tyr Gly Asp Phe Val Leu Ala Tyr Asp Ile
                485                 490                 495
Leu Leu Lys Val Asp His Ile Tyr Asp Ala Ile Arg Asn Tyr Val Thr
                500                 505                 510
Gln Lys Pro Tyr Ser Lys Asp Lys Phe Lys Leu Tyr Phe Gln Asn Pro
            515                 520                 525
Gln Phe Met Gly Gly Trp Asp Lys Asp Lys Glu Thr Asp Tyr Arg Ala
        530                 535                 540
Thr Ile Leu Arg Tyr Gly Ser Lys Tyr Tyr Leu Ala Ile Met Asp Lys
545                 550                 555                 560
Lys Tyr Ala Lys Cys Leu Gln Lys Ile Asp Lys Asp Val Asn Gly
                565                 570                 575
Asn Tyr Glu Lys Ile Asn Tyr Lys Leu Leu Pro Gly Pro Asn Lys Met
                580                 585                 590
Leu Pro Lys Val Phe Phe Ser Lys Lys Trp Met Ala Tyr Tyr Asn Pro
            595                 600                 605
Ser Glu Asp Ile Gln Lys Ile Tyr Lys Asn Gly Thr Phe Lys Lys Gly
        610                 615                 620
Asp Met Phe Asn Leu Asn Asp Cys His Lys Leu Ile Asp Phe Phe Lys
625                 630                 635                 640
Asp Ser Ile Ser Arg Tyr Pro Lys Trp Ser Asn Ala Tyr Asp Phe Asn
                645                 650                 655
Phe Ser Glu Thr Glu Lys Tyr Lys Asp Ile Ala Gly Phe Tyr Arg Glu
                660                 665                 670
Val Glu Glu Gln Gly Tyr Lys Val Ser Phe Glu Ser Ala Ser Lys Lys
            675                 680                 685
Glu Val Asp Lys Leu Val Glu Gly Lys Leu Tyr Met Phe Gln Ile
        690                 695                 700
Tyr Asn Lys Asp Phe Ser Asp Lys Ser His Gly Thr Pro Asn Leu His
705                 710                 715                 720
Thr Met Tyr Phe Lys Leu Leu Phe Asp Glu Asn Asn His Gly Gln Ile
                725                 730                 735
Arg Leu Ser Gly Gly Ala Glu Leu Phe Met Arg Arg Ala Ser Leu Lys
                740                 745                 750
Lys Glu Glu Leu Val Val His Pro Ala Asn Ser Pro Ile Ala Asn Lys
            755                 760                 765
Asn Pro Asp Asn Pro Lys Lys Thr Thr Thr Leu Ser Tyr Asp Val Tyr
        770                 775                 780
```

```
Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Asp Gly Lys Gly
        835                 840                 845

Asn Ile Val Glu Gln Tyr Ser Leu Asn Glu Ile Ile Asn Asn Phe Asn
850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Lys Gln Val Tyr Gln
930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu Thr Ser Lys Ile Asp Pro Ser Thr
        995                 1000                1005

Gly Phe Val Asn Leu Leu Lys Thr Lys Tyr Thr Ser Ile Ala Asp
1010                1015                1020

Ser Lys Lys Phe Ile Ser Ser Phe Asp Arg Ile Met Tyr Val Pro
1025                1030                1035

Glu Glu Asp Leu Phe Glu Phe Ala Leu Asp Tyr Lys Asn Phe Ser
1040                1045                1050

Arg Thr Asp Ala Asp Tyr Ile Lys Lys Trp Lys Leu Tyr Ser Tyr
1055                1060                1065

Gly Asn Arg Ile Arg Ile Phe Arg Asn Pro Lys Lys Asn Asn Val
1070                1075                1080

Phe Asp Trp Glu Glu Val Cys Leu Thr Ser Ala Tyr Lys Glu Leu
1085                1090                1095

Phe Asn Lys Tyr Gly Ile Asn Tyr Gln Gln Gly Asp Ile Arg Ala
1100                1105                1110

Leu Leu Cys Glu Gln Ser Asp Lys Ala Phe Tyr Ser Ser Phe Met
1115                1120                1125

Ala Leu Met Ser Leu Met Leu Gln Met Arg Asn Ser Ile Thr Gly
1130                1135                1140

Arg Thr Asp Val Asp Phe Leu Ile Ser Pro Val Lys Asn Ser Asp
1145                1150                1155

Gly Ile Phe Tyr Asp Ser Arg Asn Tyr Glu Ala Gln Glu Asn Ala
1160                1165                1170

Ile Leu Pro Lys Asn Ala Asp Ala Asn Gly Ala Tyr Asn Ile Ala
1175                1180                1185
```

-continued

```
Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His
    1220                1225

<210> SEQ ID NO 2
<211> LENGTH: 1307
<212> TYPE: PRT
<213> ORGANISM: Acidaminococcus sp.BV3L6

<400> SEQUENCE: 2

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335
```

```
Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
            450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
            530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
            595                 600                 605

Ser Thr Gln Leu Lys Ala Val Thr Ala His Phe Gln Thr His Thr Thr
            610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
            675                 680                 685

Lys Thr Thr Ser Ile Asp Leu Ser Ser Leu Arg Pro Ser Ser Gln Tyr
            690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750
```

```
Gly His His Gly Lys Pro Asn Leu His Thr Leu Tyr Trp Thr Gly Leu
            755                 760                 765

Phe Ser Pro Glu Asn Leu Ala Lys Thr Ser Ile Lys Leu Asn Gly Gln
        770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
        995                 1000                1005

Lys Ala Val Tyr Gln Gln Phe Glu Lys Met Leu Ile Asp Lys Leu
    1010                1015                1020

Asn Cys Leu Val Leu Lys Asp Tyr Pro Ala Glu Lys Val Gly Gly
    1025                1030                1035

Val Leu Asn Pro Tyr Gln Leu Thr Asp Gln Phe Thr Ser Phe Ala
    1040                1045                1050

Lys Met Gly Thr Gln Ser Gly Phe Leu Phe Tyr Val Pro Ala Pro
    1055                1060                1065

Tyr Thr Ser Lys Ile Asp Pro Leu Thr Gly Phe Val Asp Pro Phe
    1070                1075                1080

Val Trp Lys Thr Ile Lys Asn His Glu Ser Arg Lys His Phe Leu
    1085                1090                1095

Glu Gly Phe Asp Phe Leu His Tyr Asp Val Lys Thr Gly Asp Phe
    1100                1105                1110

Ile Leu His Phe Lys Met Asn Arg Asn Leu Ser Phe Gln Arg Gly
    1115                1120                1125

Leu Pro Gly Phe Met Pro Ala Trp Asp Ile Val Phe Glu Lys Asn
    1130                1135                1140

Glu Thr Gln Phe Asp Ala Lys Gly Thr Pro Phe Ile Ala Gly Lys
    1145                1150                1155

Arg Ile Val Pro Val Ile Glu Asn His Arg Phe Thr Gly Arg Tyr
```

```
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290

Ser Asn  Gln Asp Trp Leu Ala  Tyr Ile Gln Glu Leu  Arg Asn
    1295                1300                1305

<210> SEQ ID NO 3
<211> LENGTH: 1300
<212> TYPE: PRT
<213> ORGANISM: Francisella novicida

<400> SEQUENCE: 3

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220
```

```
Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
            245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
            325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
            405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
            485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
            565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
```

-continued

```
                645                 650                 655
Ile Val Tyr Lys Leu Leu Pro Gly Ala Asn Lys Met Leu Pro Lys Val
                660                 665                 670

Phe Phe Ser Ala Lys Ser Ile Lys Phe Tyr Asn Pro Ser Glu Asp Ile
                675                 680                 685

Leu Arg Ile Arg Asn His Ser Thr His Thr Lys Asn Gly Ser Pro Gln
        690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
                740                 745                 750

Phe Tyr Arg Glu Val Glu Asn Gln Gly Tyr Lys Leu Thr Phe Glu Asn
                755                 760                 765

Ile Ser Glu Ser Tyr Ile Asp Ser Val Val Asn Gln Gly Lys Leu Tyr
        770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
                820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
        900                 905                 910

Ile Leu Ser Ile Asp Arg Gly Glu Arg His Leu Ala Tyr Tyr Thr Leu
        915                 920                 925

Val Asp Gly Lys Gly Asn Ile Ile Lys Gln Asp Thr Phe Asn Ile Ile
        930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
        980                 985                 990

Ala Lys Leu Val Ile Glu Tyr Asn Ala Ile Val Val Phe Glu Asp Leu
        995                 1000                1005

Asn Phe Gly Phe Lys Arg Gly Arg Phe Lys Val Glu Lys Gln Val
        1010                1015                1020

Tyr Gln Lys Leu Glu Lys Met Leu Ile Glu Lys Leu Asn Tyr Leu
        1025                1030                1035

Val Phe Lys Asp Asn Glu Phe Asp Lys Thr Gly Gly Val Leu Arg
        1040                1045                1050

Ala Tyr Gln Leu Thr Ala Pro Phe Glu Thr Phe Lys Lys Met Gly
        1055                1060                1065
```

-continued

```
Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn
    1295                1300

<210> SEQ ID NO 4
<211> LENGTH: 1246
<212> TYPE: PRT
<213> ORGANISM: Porphyromonas macacae

<400> SEQUENCE: 4

Met Lys Thr Gln His Phe Phe Glu Asp Phe Thr Ser Leu Tyr Ser Leu
1                 5                   10                  15

Ser Lys Thr Ile Arg Phe Glu Leu Lys Pro Ile Gly Lys Thr Leu Glu
                20                  25                  30

Asn Ile Lys Lys Asn Gly Leu Ile Arg Arg Asp Glu Gln Arg Leu Asp
        35                  40                  45

Asp Tyr Glu Lys Leu Lys Lys Val Ile Asp Glu Tyr His Glu Asp Phe
    50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Glu Ser Glu Ala Arg Ala Lys Ile Glu
                85                  90                  95

Lys Thr Met Arg Asp Thr Leu Ala Lys Ala Phe Ser Glu Asp Glu Arg
                100                 105                 110

Tyr Lys Ser Ile Phe Lys Lys Glu Leu Val Lys Lys Asp Ile Pro Val
```

```
                115             120             125
Trp Cys Pro Ala Tyr Lys Ser Leu Cys Lys Lys Phe Asp Asn Phe Thr
    130             135             140
Thr Ser Leu Val Pro Phe His Glu Asn Arg Lys Asn Leu Tyr Thr Ser
145             150             155             160
Asn Glu Ile Thr Ala Ser Ile Pro Tyr Arg Ile Val His Val Asn Leu
                165             170             175
Pro Lys Phe Ile Gln Asn Ile Glu Ala Leu Cys Glu Leu Gln Lys Lys
                180             185             190
Met Gly Ala Asp Leu Tyr Leu Glu Met Met Glu Asn Leu Arg Asn Val
            195             200             205
Trp Pro Ser Phe Val Lys Thr Pro Asp Asp Leu Cys Asn Leu Lys Thr
            210             215             220
Tyr Asn His Leu Met Val Gln Ser Ser Ile Ser Glu Tyr Asn Arg Phe
225             230             235             240
Val Gly Gly Tyr Ser Thr Glu Asp Gly Thr Lys His Gln Gly Ile Asn
                245             250             255
Glu Trp Ile Asn Ile Tyr Arg Gln Arg Asn Lys Glu Met Arg Leu Pro
            260             265             270
Gly Leu Val Phe Leu His Lys Gln Ile Leu Ala Lys Val Asp Ser Ser
                275             280             285
Ser Phe Ile Ser Asp Thr Leu Glu Asn Asp Asp Gln Val Phe Cys Val
    290             295             300
Leu Arg Gln Phe Arg Lys Leu Phe Trp Asn Thr Val Ser Ser Lys Glu
305             310             315             320
Asp Asp Ala Ala Ser Leu Lys Asp Leu Phe Cys Gly Leu Ser Gly Tyr
                325             330             335
Asp Pro Glu Ala Ile Tyr Val Ser Asp Ala His Leu Ala Thr Ile Ser
                340             345             350
Lys Asn Ile Phe Asp Arg Trp Asn Tyr Ile Ser Asp Ala Ile Arg Arg
                355             360             365
Lys Thr Glu Val Leu Met Pro Arg Lys Lys Glu Ser Val Glu Arg Tyr
            370             375             380
Ala Glu Lys Ile Ser Lys Gln Ile Lys Lys Arg Gln Ser Tyr Ser Leu
385             390             395             400
Ala Glu Leu Asp Asp Leu Leu Ala His Tyr Ser Glu Glu Ser Leu Pro
                405             410             415
Ala Gly Phe Ser Leu Leu Ser Tyr Phe Thr Ser Leu Gly Gly Gln Lys
                420             425             430
Tyr Leu Val Ser Asp Gly Glu Val Ile Leu Tyr Glu Glu Gly Ser Asn
            435             440             445
Ile Trp Asp Glu Val Leu Ile Ala Phe Arg Asp Leu Gln Val Ile Leu
            450             455             460
Asp Lys Asp Phe Thr Glu Lys Lys Leu Gly Lys Asp Glu Glu Ala Val
465             470             475             480
Ser Val Ile Lys Lys Ala Leu Asp Ser Ala Leu Arg Leu Arg Lys Phe
                485             490             495
Phe Asp Leu Leu Ser Gly Thr Gly Ala Glu Ile Arg Arg Asp Ser Ser
            500             505             510
Phe Tyr Ala Leu Tyr Thr Asp Arg Met Asp Lys Leu Lys Gly Leu Leu
            515             520             525
Lys Met Tyr Asp Lys Val Arg Asn Tyr Leu Thr Lys Lys Pro Tyr Ser
            530             535             540
```

```
Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
            565                 570                 575

Asn Gly Tyr Tyr Tyr Leu Gly Ile Met Thr Pro Lys Gly Lys Asn Leu
                580                 585                 590

Phe Lys Thr Leu Pro Lys Leu Gly Ala Glu Met Phe Tyr Glu Lys
        595                 600                 605

Met Glu Tyr Lys Gln Ile Ala Glu Pro Met Leu Met Leu Pro Lys Val
    610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
                660                 665                 670

Thr Val His Glu Trp Lys Leu Phe Asn Phe Ser Phe Ser Pro Thr Glu
        675                 680                 685

Gln Tyr Arg Asn Ile Gly Glu Phe Phe Asp Glu Val Arg Glu Gln Ala
    690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
                740                 745                 750

Ala Leu Phe Ser Glu Gln Asn Gln Ser Arg Val Tyr Lys Leu Cys Gly
        755                 760                 765

Gly Gly Glu Leu Phe Tyr Arg Lys Ala Ser Leu His Met Gln Asp Thr
    770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe Phe His Val Pro Ile Ser Ile Asn Tyr
                820                 825                 830

Lys Asn Lys Lys Ile Thr Asn Val Asn Gln Met Val Arg Asp Tyr Ile
        835                 840                 845

Ala Gln Asn Asp Asp Leu Gln Ile Ile Gly Ile Asp Arg Gly Glu Arg
    850                 855                 860

Asn Leu Leu Tyr Ile Ser Arg Ile Asp Thr Arg Gly Asn Leu Leu Glu
865                 870                 875                 880

Gln Phe Ser Leu Asn Val Ile Glu Ser Asp Lys Gly Asp Leu Arg Thr
                885                 890                 895

Asp Tyr Gln Lys Ile Leu Gly Asp Arg Glu Gln Glu Arg Leu Arg Arg
                900                 905                 910

Arg Gln Glu Trp Lys Ser Ile Glu Ser Ile Lys Asp Leu Lys Asp Gly
        915                 920                 925

Tyr Met Ser Gln Val Val His Lys Ile Cys Asn Met Val Val Glu His
    930                 935                 940

Lys Ala Ile Val Val Leu Glu Asn Leu Asn Leu Ser Phe Met Lys Gly
945                 950                 955                 960
```

```
Arg Lys Lys Val Glu Lys Ser Val Tyr Glu Lys Phe Glu Arg Met Leu
                965                 970                 975

Val Asp Lys Leu Asn Tyr Leu Val Asp Lys Lys Asn Leu Ser Asn
            980                 985                 990

Glu Pro Gly Gly Leu Tyr Ala Ala Tyr Gln Leu Thr Asn Pro Leu Phe
            995                1000                1005

Ser Phe Glu Glu Leu His Arg Tyr Pro Gln Ser Gly Ile Leu Phe
    1010                1015                1020

Phe Val Asp Pro Trp Asn Thr Ser Leu Thr Asp Pro Ser Thr Gly
    1025                1030                1035

Phe Val Asn Leu Leu Gly Arg Ile Asn Tyr Thr Asn Val Gly Asp
    1040                1045                1050

Ala Arg Lys Phe Phe Asp Arg Phe Asn Ala Ile Arg Tyr Asp Gly
    1055                1060                1065

Lys Gly Asn Ile Leu Phe Asp Leu Asp Leu Ser Arg Phe Asp Val
    1070                1075                1080

Arg Val Glu Thr Gln Arg Lys Leu Trp Thr Leu Thr Thr Phe Gly
    1085                1090                1095

Ser Arg Ile Ala Lys Ser Lys Ser Gly Lys Trp Met Val Glu
    1100                1105                1110

Arg Ile Glu Asn Leu Ser Leu Cys Phe Leu Glu Leu Phe Glu Gln
    1115                1120                1125

Phe Asn Ile Gly Tyr Arg Val Glu Lys Asp Leu Lys Lys Ala Ile
    1130                1135                1140

Leu Ser Gln Asp Arg Lys Glu Phe Tyr Val Arg Leu Ile Tyr Leu
    1145                1150                1155

Phe Asn Leu Met Met Gln Ile Arg Asn Ser Asp Gly Glu Glu Asp
    1160                1165                1170

Tyr Ile Leu Ser Pro Ala Leu Asn Glu Lys Asn Leu Gln Phe Asp
    1175                1180                1185

Ser Arg Leu Ile Glu Ala Lys Asp Leu Pro Val Asp Ala Asp Ala
    1190                1195                1200

Asn Gly Ala Tyr Asn Val Ala Arg Lys Gly Leu Met Val Val Gln
    1205                1210                1215

Arg Ile Lys Arg Gly Asp His Glu Ser Ile His Arg Ile Gly Arg
    1220                1225                1230

Ala Gln Trp Leu Arg Tyr Val Gln Glu Gly Ile Val Glu
    1235                1240                1245

<210> SEQ ID NO 5
<211> LENGTH: 1373
<212> TYPE: PRT
<213> ORGANISM: Moraxella bovoculi

<400> SEQUENCE: 5

Met Leu Phe Gln Asp Phe Thr His Leu Tyr Pro Leu Ser Lys Thr Val
1               5                   10                  15

Arg Phe Glu Leu Lys Pro Ile Asp Arg Thr Leu Glu His Ile His Ala
            20                  25                  30

Lys Asn Phe Leu Ser Gln Asp Glu Thr Met Ala Asp Met His Gln Lys
        35                  40                  45

Val Lys Val Ile Leu Asp Asp Tyr His Arg Asp Phe Ile Ala Asp Met
    50                  55                  60

Met Gly Glu Val Lys Leu Thr Lys Leu Ala Glu Phe Tyr Asp Val Tyr
65                  70                  75                  80
```

```
Leu Lys Phe Arg Lys Asn Pro Lys Asp Asp Glu Leu Gln Lys Gln Leu
                85                  90                  95

Lys Asp Leu Gln Ala Val Leu Arg Lys Glu Ile Val Lys Pro Ile Gly
                100                 105                 110

Asn Gly Gly Lys Tyr Lys Ala Gly Tyr Asp Arg Leu Phe Gly Ala Lys
                115                 120                 125

Leu Phe Lys Asp Gly Lys Glu Leu Gly Asp Leu Ala Lys Phe Val Ile
130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
                180                 185                 190

His Glu Asn Leu Pro Arg Phe Ile Asp Asn Leu Gln Ile Leu Thr Thr
                195                 200                 205

Ile Lys Gln Lys His Ser Ala Leu Tyr Asp Gln Ile Ile Asn Glu Leu
                210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
                260                 265                 270

Glu Leu Ile Asn Ser His His Asn Gln His Cys His Lys Ser Glu Arg
                275                 280                 285

Ile Ala Lys Leu Arg Pro Leu His Lys Gln Ile Leu Ser Asp Gly Met
290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
                340                 345                 350

Tyr Val Glu His Lys Asn Leu Asn Glu Leu Ser Lys Gln Ala Phe Gly
                355                 360                 365

Asp Phe Ala Leu Leu Gly Arg Val Leu Asp Gly Tyr Tyr Val Asp Val
370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
                420                 425                 430

His Asp Asp Glu Ser Val Gln Ala Gly Lys Leu Gly Gln Tyr Phe Lys
                435                 440                 445

His Gly Leu Ala Gly Val Asp Asn Pro Ile Gln Lys Ile His Asn Asn
450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495
```

-continued

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
            515                 520                 525

Asn Phe Tyr Gly Glu Phe Gly Val Leu Tyr Asp Glu Leu Ala Lys Ile
            530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
            565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
            595                 600                 605

Val Phe Asp Asn Ala Pro Asn Thr Gly Lys Ser Ile Tyr Gln Lys Met
            610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
            645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
            675                 680                 685

Lys Lys Phe Glu Gly Ala Ile Gly Asp Ile Gln Leu Phe Lys Lys Asp
            690                 695                 700

Lys Lys Gly Arg Glu Val Pro Ile Ser Glu Lys Asp Leu Phe Asp Lys
705                 710                 715                 720

Ile Asn Gly Ile Phe Ser Ser Lys Pro Lys Leu Glu Met Glu Asp Phe
            725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
            755                 760                 765

Glu Asn Phe Tyr Asn Asn His Pro Lys Phe Lys Lys Asp Leu Val Arg
            770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
            805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
            835                 840                 845

Gln Leu Tyr Leu Phe Gln Ile Tyr Asn Lys Asp Phe Ser Pro Lys Ala
            850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
            885                 890                 895

Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys

-continued

```
                915                 920                 925
Arg Gln Phe Val Tyr Asp Ile Ile Lys Asp Lys Arg Tyr Thr Gln Asp
    930                 935                 940
Lys Phe Met Leu His Val Pro Ile Thr Met Asn Phe Gly Val Gln Gly
945                 950                 955                 960
Met Thr Ile Lys Glu Phe Asn Lys Val Asn Gln Ser Ile Gln Gln
                965                 970                 975
Tyr Asp Glu Val Asn Val Ile Gly Ile Asp Arg Gly Glu Arg His Leu
            980                 985                 990
Leu Tyr Leu Thr Val Ile Asn Ser Lys Gly Glu Ile Leu Glu Gln Cys
            995                 1000                1005
Ser Leu Asn Asp Ile Thr Thr Ala Ser Ala Asn Gly Thr Gln Met
    1010                1015                1020
Thr Thr Pro Tyr His Lys Ile Leu Asp Lys Arg Glu Ile Glu Arg
    1025                1030                1035
Leu Asn Ala Arg Val Gly Trp Gly Glu Ile Glu Thr Ile Lys Glu
    1040                1045                1050
Leu Lys Ser Gly Tyr Leu Ser His Val Val His Gln Ile Ser Gln
    1055                1060                1065
Leu Met Leu Lys Tyr Asn Ala Ile Val Val Leu Glu Asp Leu Asn
    1070                1075                1080
Phe Gly Phe Lys Arg Gly Arg Phe Lys Val Glu Lys Gln Ile Tyr
    1085                1090                1095
Gln Asn Phe Glu Asn Ala Leu Ile Lys Lys Leu Asn His Leu Val
    1100                1105                1110
Leu Lys Asp Lys Ala Asp Asp Glu Ile Gly Ser Tyr Lys Asn Ala
    1115                1120                1125
Leu Gln Leu Thr Asn Asn Phe Thr Asp Leu Lys Ser Ile Gly Lys
    1130                1135                1140
Gln Thr Gly Phe Leu Phe Tyr Val Pro Ala Trp Asn Thr Ser Lys
    1145                1150                1155
Ile Asp Pro Glu Thr Gly Phe Val Asp Leu Leu Lys Pro Arg Tyr
    1160                1165                1170
Glu Asn Ile Ala Gln Ser Gln Ala Phe Phe Gly Lys Phe Asp Lys
    1175                1180                1185
Ile Cys Tyr Asn Ala Asp Lys Asp Tyr Phe Glu Phe His Ile Asp
    1190                1195                1200
Tyr Ala Lys Phe Thr Asp Lys Ala Lys Asn Ser Arg Gln Ile Trp
    1205                1210                1215
Thr Ile Cys Ser His Gly Asp Lys Arg Tyr Val Tyr Asp Lys Thr
    1220                1225                1230
Ala Asn Gln Asn Lys Gly Ala Ala Lys Gly Ile Asn Val Asn Asp
    1235                1240                1245
Glu Leu Lys Ser Leu Phe Ala Arg His His Ile Asn Glu Lys Gln
    1250                1255                1260
Pro Asn Leu Val Met Asp Ile Cys Gln Asn Asn Asp Lys Glu Phe
    1265                1270                1275
His Lys Ser Leu Met Tyr Leu Leu Lys Thr Leu Leu Ala Leu Arg
    1280                1285                1290
Tyr Ser Asn Ala Ser Ser Asp Glu Asp Phe Ile Leu Ser Pro Val
    1295                1300                1305
Ala Asn Asp Glu Gly Val Phe Phe Asn Ser Ala Leu Ala Asp Asp
    1310                1315                1320
```

```
Thr Gln Pro Gln Asn Ala Asp Ala Asn Gly Ala Tyr His Ile Ala
    1325                1330                1335

Leu Lys Gly Leu Trp Leu Leu Asn Glu Leu Lys Asn Ser Asp Asp
    1340                1345                1350

Leu Asn Lys Val Lys Leu Ala Ile Asp Asn Gln Thr Trp Leu Asn
    1355                1360                1365

Phe Ala Gln Asn Arg
    1370

<210> SEQ ID NO 6
<211> LENGTH: 1259
<212> TYPE: PRT
<213> ORGANISM: Moraxella bovoculi

<400> SEQUENCE: 6

Met Gly Ile His Gly Val Pro Ala Ala Leu Phe Gln Asp Phe Thr His
1               5                   10                  15

Leu Tyr Pro Leu Ser Lys Thr Val Arg Phe Glu Leu Lys Pro Ile Gly
                20                  25                  30

Arg Thr Leu Glu His Ile His Ala Lys Asn Phe Leu Ser Gln Asp Glu
            35                  40                  45

Thr Met Ala Asp Met Tyr Gln Lys Val Lys Val Ile Leu Asp Asp Tyr
    50                  55                  60

His Arg Asp Phe Ile Ala Asp Met Met Gly Glu Val Lys Leu Thr Lys
65                  70                  75                  80

Leu Ala Glu Phe Tyr Asp Val Tyr Leu Lys Phe Arg Lys Asn Pro Lys
                85                  90                  95

Asp Asp Gly Leu Gln Lys Gln Leu Lys Asp Leu Gln Ala Val Leu Arg
            100                 105                 110

Lys Glu Ser Val Lys Pro Ile Gly Ser Gly Gly Lys Tyr Lys Thr Gly
        115                 120                 125

Tyr Asp Arg Leu Phe Gly Ala Lys Leu Phe Lys Asp Gly Lys Glu Leu
    130                 135                 140

Gly Asp Leu Ala Lys Phe Val Ile Ala Gln Glu Gly Glu Ser Ser Pro
145                 150                 155                 160

Lys Leu Ala His Leu Ala His Phe Glu Lys Phe Ser Thr Tyr Phe Thr
                165                 170                 175

Gly Phe His Asp Asn Arg Lys Asn Met Tyr Ser Asp Glu Asp Lys His
            180                 185                 190

Thr Ala Ile Ala Tyr Arg Leu Ile His Glu Asn Leu Pro Arg Phe Ile
        195                 200                 205

Asp Asn Leu Gln Ile Leu Thr Thr Ile Lys Gln Lys His Ser Ala Leu
    210                 215                 220

Tyr Asp Gln Ile Ile Asn Glu Leu Thr Ala Ser Gly Leu Asp Val Ser
225                 230                 235                 240

Leu Ala Ser His Leu Asp Gly Tyr His Lys Leu Leu Thr Gln Glu Gly
                245                 250                 255

Ile Thr Ala Tyr Asn Arg Ile Ile Gly Glu Val Asn Gly Tyr Thr Asn
            260                 265                 270

Lys His Asn Gln Ile Cys His Lys Ser Glu Arg Ile Ala Lys Leu Arg
        275                 280                 285

Pro Leu His Lys Gln Ile Leu Ser Asp Gly Met Gly Val Ser Phe Leu
    290                 295                 300

Pro Ser Lys Phe Ala Asp Asp Ser Glu Met Cys Gln Ala Val Asn Glu
```

```
                305                 310                 315                 320
            Phe Tyr Arg His Tyr Thr Asp Val Phe Ala Lys Val Gln Ser Leu Phe
                            325                 330                 335

Asp Gly Phe Asp Asp His Gln Lys Asp Gly Ile Tyr Val Glu His Lys
                            340                 345                 350

Asn Leu Asn Glu Leu Ser Lys Gln Ala Phe Gly Asp Phe Ala Leu Leu
                            355                 360                 365

Gly Arg Val Leu Asp Gly Tyr Tyr Val Asp Val Val Asn Pro Glu Phe
                370                 375                 380

Asn Glu Arg Phe Ala Lys Ala Lys Thr Asp Asn Ala Lys Ala Lys Leu
            385                 390                 395                 400

Thr Lys Glu Lys Asp Lys Phe Ile Lys Gly Val His Ser Leu Ala Ser
                            405                 410                 415

Leu Glu Gln Ala Ile Glu His His Thr Ala Arg His Asp Asp Glu Ser
                            420                 425                 430

Val Gln Ala Gly Lys Leu Gly Gln Tyr Phe Lys His Gly Leu Ala Gly
                            435                 440                 445

Val Asp Asn Pro Ile Gln Lys Ile His Asn Asn His Ser Thr Ile Lys
                450                 455                 460

Gly Phe Leu Glu Arg Glu Arg Pro Ala Gly Glu Arg Ala Leu Pro Lys
            465                 470                 475                 480

Ile Lys Ser Gly Lys Asn Pro Glu Met Thr Gln Leu Arg Gln Leu Lys
                            485                 490                 495

Glu Leu Leu Asp Asn Ala Leu Asn Val Ala His Phe Ala Lys Leu Leu
                            500                 505                 510

Thr Thr Lys Thr Thr Leu Asp Asn Gln Asp Gly Asn Phe Tyr Gly Glu
                            515                 520                 525

Phe Gly Val Leu Tyr Asp Glu Leu Ala Lys Ile Pro Thr Leu Tyr Asn
                            530                 535                 540

Lys Val Arg Asp Tyr Leu Ser Gln Lys Pro Phe Ser Thr Glu Lys Tyr
            545                 550                 555                 560

Lys Leu Asn Phe Gly Asn Pro Thr Leu Leu Asn Gly Trp Asp Leu Asn
                            565                 570                 575

Lys Glu Lys Asp Asn Phe Gly Val Ile Leu Gln Lys Asp Gly Cys Tyr
                            580                 585                 590

Tyr Leu Ala Leu Leu Asp Lys Ala His Lys Lys Val Phe Asp Asn Ala
                            595                 600                 605

Pro Asn Thr Gly Lys Asn Val Tyr Gln Lys Met Val Tyr Lys Leu Leu
                            610                 615                 620

Pro Gly Pro Asn Lys Met Leu Pro Lys Val Phe Phe Ala Lys Ser Asn
            625                 630                 635                 640

Leu Asp Tyr Tyr Asn Pro Ser Ala Glu Leu Leu Asp Lys Tyr Ala Lys
                            645                 650                 655

Gly Thr His Lys Lys Gly Asp Asn Phe Asn Leu Lys Asp Cys His Ala
                            660                 665                 670

Leu Ile Asp Phe Phe Lys Ala Gly Ile Asn Lys His Pro Glu Trp Gln
                            675                 680                 685

His Phe Gly Phe Lys Phe Ser Pro Thr Ser Tyr Arg Asp Leu Ser
                            690                 695                 700

Asp Phe Tyr Arg Glu Val Glu Pro Gln Gly Tyr Gln Val Lys Phe Val
            705                 710                 715                 720

Asp Ile Asn Ala Asp Tyr Ile Asp Glu Leu Val Glu Gln Gly Lys Leu
                            725                 730                 735
```

```
Tyr Leu Phe Gln Ile Tyr Asn Lys Asp Phe Ser Pro Lys Ala His Gly
            740                 745                 750

Lys Pro Asn Leu His Thr Leu Tyr Phe Lys Ala Leu Phe Ser Glu Asp
            755                 760                 765

Asn Leu Ala Asp Pro Ile Tyr Lys Leu Asn Gly Glu Ala Gln Ile Phe
            770                 775                 780

Tyr Arg Lys Ala Ser Leu Asp Met Asn Glu Thr Thr Ile His Arg Ala
785                 790                 795                 800

Gly Glu Val Leu Glu Asn Lys Asn Pro Asp Asn Pro Lys Lys Arg Gln
                805                 810                 815

Phe Val Tyr Asp Ile Ile Lys Asp Lys Arg Tyr Thr Gln Asp Lys Phe
            820                 825                 830

Met Leu His Val Pro Ile Thr Met Asn Phe Gly Val Gln Gly Met Thr
            835                 840                 845

Ile Lys Glu Phe Asn Lys Lys Val Asn Gln Ser Ile Gln Gln Tyr Asp
            850                 855                 860

Glu Val Asn Val Ile Gly Ile Asp Arg Gly Glu Arg His Leu Leu Tyr
865                 870                 875                 880

Leu Thr Val Ile Asn Ser Lys Gly Glu Ile Leu Glu Gln Arg Ser Leu
                885                 890                 895

Asn Asp Ile Thr Thr Ala Ser Ala Asn Gly Thr Gln Val Thr Thr Pro
            900                 905                 910

Tyr His Lys Ile Leu Asp Lys Arg Glu Ile Glu Arg Leu Asn Ala Arg
            915                 920                 925

Val Gly Trp Gly Glu Ile Glu Thr Ile Lys Glu Leu Lys Ser Gly Tyr
            930                 935                 940

Leu Ser His Val Val His Gln Ile Asn Gln Leu Met Leu Lys Tyr Asn
945                 950                 955                 960

Ala Ile Val Val Leu Glu Asp Leu Asn Phe Gly Phe Lys Arg Gly Arg
                965                 970                 975

Phe Lys Val Glu Lys Gln Ile Tyr Gln Asn Phe Glu Asn Ala Leu Ile
            980                 985                 990

Lys Lys Leu Asn His Leu Val Leu Lys Asp Lys Ala Asp Asp Glu Ile
            995                1000                1005

Gly Ser Tyr Lys Asn Ala Leu Gln Leu Thr Asn Asn Phe Thr Asp
           1010                1015                1020

Leu Lys Ser Ile Gly Lys Gln Thr Gly Phe Leu Phe Tyr Val Pro
           1025                1030                1035

Ala Trp Asn Thr Ser Lys Ile Asp Pro Glu Thr Gly Phe Val Asp
           1040                1045                1050

Leu Leu Lys Pro Arg Tyr Glu Asn Ile Ala Gln Ser Gln Ala Phe
           1055                1060                1065

Phe Gly Lys Phe Asp Lys Ile Cys Tyr Asn Thr Asp Lys Gly Tyr
           1070                1075                1080

Phe Glu Phe His Ile Asp Tyr Ala Lys Phe Thr Asp Lys Ala Lys
           1085                1090                1095

Asn Ser Arg Gln Lys Trp Ala Ile Cys Ser His Gly Asp Lys Arg
           1100                1105                1110

Tyr Val Tyr Asp Lys Thr Ala Asn Gln Asn Lys Gly Ala Ala Lys
           1115                1120                1125

Gly Ile Asn Val Asn Asp Glu Leu Lys Ser Leu Phe Ala Arg Tyr
           1130                1135                1140
```

-continued

```
His Ile Asn Asp Lys Gln Pro Asn Leu Val Met Asp Ile Cys Gln
    1145                1150                1155

Asn Asn Asp Lys Glu Phe His Lys Ser Leu Met Cys Leu Leu Lys
    1160                1165                1170

Thr Leu Leu Ala Leu Arg Tyr Ser Asn Ala Ser Ser Asp Glu Asp
    1175                1180                1185

Phe Ile Leu Ser Pro Val Ala Asn Asp Glu Gly Val Phe Phe Asn
    1190                1195                1200

Ser Ala Leu Ala Asp Asp Thr Gln Pro Gln Asn Ala Asp Ala Asn
    1205                1210                1215

Gly Ala Tyr His Ile Ala Leu Lys Gly Leu Trp Leu Leu Asn Glu
    1220                1225                1230

Leu Lys Asn Ser Asp Asp Leu Asn Lys Val Lys Leu Ala Ile Asp
    1235                1240                1245

Asn Gln Thr Trp Leu Asn Phe Ala Gln Asn Arg
    1250                1255
```

<210> SEQ ID NO 7
<211> LENGTH: 1269
<212> TYPE: PRT
<213> ORGANISM: Moraxella bovoculi

<400> SEQUENCE: 7

```
Met Gly Ile His Gly Val Pro Ala Ala Leu Phe Gln Asp Phe Thr His
1               5                   10                  15

Leu Tyr Pro Leu Ser Lys Thr Val Arg Phe Glu Leu Lys Pro Ile Gly
                20                  25                  30

Lys Thr Leu Glu His Ile His Ala Lys Asn Phe Leu Asn Gln Asp Glu
            35                  40                  45

Thr Met Ala Asp Met Tyr Gln Lys Val Lys Ala Ile Leu Asp Asp Tyr
        50                  55                  60

His Arg Asp Phe Ile Ala Asp Met Met Gly Glu Val Lys Leu Thr Lys
65                  70                  75                  80

Leu Ala Glu Phe Tyr Asp Val Tyr Leu Lys Phe Arg Lys Asn Pro Lys
                85                  90                  95

Asp Asp Gly Leu Gln Lys Gln Leu Lys Asp Leu Gln Ala Val Leu Arg
            100                 105                 110

Lys Glu Ile Val Lys Pro Ile Gly Asn Gly Gly Lys Tyr Lys Ala Gly
        115                 120                 125

Tyr Asp Arg Leu Phe Gly Ala Lys Leu Phe Lys Asp Gly Lys Glu Leu
    130                 135                 140

Gly Asp Leu Ala Lys Phe Val Ile Ala Gln Glu Gly Glu Ser Ser Pro
145                 150                 155                 160

Lys Leu Ala His Leu Ala His Phe Glu Lys Phe Ser Thr Tyr Phe Thr
                165                 170                 175

Gly Phe His Asp Asn Arg Lys Asn Met Tyr Ser Asp Glu Asp Lys His
            180                 185                 190

Thr Ala Ile Ala Tyr Arg Leu Ile His Glu Asn Leu Pro Arg Phe Ile
        195                 200                 205

Asp Asn Leu Gln Ile Leu Ala Thr Ile Lys Gln Lys His Ser Ala Leu
    210                 215                 220

Tyr Asp Gln Ile Ile Asn Glu Leu Thr Ala Ser Gly Leu Asp Val Ser
225                 230                 235                 240

Leu Ala Ser His Leu Asp Gly Tyr His Lys Leu Leu Thr Gln Glu Gly
                245                 250                 255
```

```
Ile Thr Ala Tyr Asn Thr Leu Leu Gly Gly Ile Ser Gly Glu Ala Gly
            260                 265                 270

Ser Arg Lys Ile Gln Gly Ile Asn Glu Leu Ile Asn Ser His His Asn
        275                 280                 285

Gln His Cys His Lys Ser Glu Arg Ile Ala Lys Leu Arg Pro Leu His
    290                 295                 300

Lys Gln Ile Leu Ser Asp Gly Met Gly Val Ser Phe Leu Pro Ser Lys
305                 310                 315                 320

Phe Ala Asp Asp Ser Glu Val Cys Gln Ala Val Asn Glu Phe Tyr Arg
                325                 330                 335

His Tyr Ala Asp Val Phe Ala Lys Val Gln Ser Leu Phe Asp Gly Phe
            340                 345                 350

Asp Asp Tyr Gln Lys Asp Gly Ile Tyr Val Glu Tyr Lys Asn Leu Asn
        355                 360                 365

Glu Leu Ser Lys Gln Ala Phe Gly Asp Phe Ala Leu Leu Gly Arg Val
    370                 375                 380

Leu Asp Gly Tyr Tyr Val Asp Val Val Asn Pro Glu Phe Asn Glu Arg
385                 390                 395                 400

Phe Ala Lys Ala Lys Thr Asp Asn Ala Lys Ala Lys Leu Thr Lys Glu
                405                 410                 415

Lys Asp Lys Phe Ile Lys Gly Val His Ser Leu Ala Ser Leu Glu Gln
            420                 425                 430

Ala Ile Glu His Tyr Thr Ala Arg His Asp Asp Glu Ser Val Gln Ala
        435                 440                 445

Gly Lys Leu Gly Gln Tyr Phe Lys His Gly Leu Ala Gly Val Asp Asn
    450                 455                 460

Pro Ile Gln Lys Ile His Asn Asn His Ser Thr Ile Lys Gly Phe Leu
465                 470                 475                 480

Glu Arg Glu Arg Pro Ala Gly Glu Arg Ala Leu Pro Lys Ile Lys Ser
                485                 490                 495

Asp Lys Ser Pro Glu Ile Arg Gln Leu Lys Glu Leu Leu Asp Asn Ala
            500                 505                 510

Leu Asn Val Ala His Phe Ala Lys Leu Leu Thr Thr Lys Thr Thr Leu
        515                 520                 525

His Asn Gln Asp Gly Asn Phe Tyr Gly Glu Phe Gly Ala Leu Tyr Asp
    530                 535                 540

Glu Leu Ala Lys Ile Ala Thr Leu Tyr Asn Lys Val Arg Asp Tyr Leu
545                 550                 555                 560

Ser Gln Lys Pro Phe Ser Thr Glu Lys Tyr Lys Leu Asn Phe Gly Asn
                565                 570                 575

Pro Thr Leu Leu Asn Gly Trp Asp Leu Asn Lys Glu Lys Asp Asn Phe
            580                 585                 590

Gly Val Ile Leu Gln Lys Asp Gly Cys Tyr Tyr Leu Ala Leu Leu Asp
        595                 600                 605

Lys Ala His Lys Lys Val Phe Asp Asn Ala Pro Asn Thr Gly Lys Ser
    610                 615                 620

Val Tyr Gln Lys Met Ile Tyr Lys Leu Leu Pro Gly Pro Asn Lys Met
625                 630                 635                 640

Leu Pro Lys Val Phe Phe Ala Lys Ser Asn Leu Asp Tyr Tyr Asn Pro
                645                 650                 655

Ser Ala Glu Leu Leu Asp Lys Tyr Ala Gln Gly Thr His Lys Lys Gly
            660                 665                 670
```

```
Asp Asn Phe Asn Leu Lys Asp Cys His Ala Leu Ile Asp Phe Phe Lys
            675                 680                 685
Ala Gly Ile Asn Lys His Pro Glu Trp Gln His Phe Gly Phe Lys Phe
    690                 695                 700
Ser Pro Thr Ser Ser Tyr Gln Asp Leu Ser Asp Phe Tyr Arg Glu Val
705                 710                 715                 720
Glu Pro Gln Gly Tyr Gln Val Lys Phe Val Asp Ile Asn Ala Asp Tyr
                725                 730                 735
Ile Asn Glu Leu Val Glu Gly Gln Leu Tyr Leu Phe Gln Ile Tyr
            740                 745                 750
Asn Lys Asp Phe Ser Pro Lys Ala His Gly Lys Pro Asn Leu His Thr
        755                 760                 765
Leu Tyr Phe Lys Ala Leu Phe Ser Glu Asp Asn Leu Val Asn Pro Ile
    770                 775                 780
Tyr Lys Leu Asn Gly Glu Ala Glu Ile Phe Tyr Arg Lys Ala Ser Leu
785                 790                 795                 800
Asp Met Asn Glu Thr Thr Ile His Arg Ala Gly Glu Val Leu Glu Asn
                805                 810                 815
Lys Asn Pro Asp Asn Pro Lys Lys Arg Gln Phe Val Tyr Asp Ile Ile
            820                 825                 830
Lys Asp Lys Arg Tyr Thr Gln Asp Lys Phe Met Leu His Val Pro Ile
        835                 840                 845
Thr Met Asn Phe Gly Val Gln Gly Met Thr Ile Lys Glu Phe Asn Lys
    850                 855                 860
Lys Val Asn Gln Ser Ile Gln Gln Tyr Asp Glu Val Asn Val Ile Gly
865                 870                 875                 880
Ile Asp Arg Gly Glu Arg His Leu Leu Tyr Leu Thr Val Ile Asn Ser
                885                 890                 895
Lys Gly Glu Ile Leu Glu Gln Arg Ser Leu Asn Asp Ile Thr Thr Ala
            900                 905                 910
Ser Ala Asn Gly Thr Gln Met Thr Thr Pro Tyr His Lys Ile Leu Asp
        915                 920                 925
Lys Arg Glu Ile Glu Arg Leu Asn Ala Arg Val Gly Trp Gly Glu Ile
    930                 935                 940
Glu Thr Ile Lys Glu Leu Lys Ser Gly Tyr Leu Ser His Val Val His
945                 950                 955                 960
Gln Ile Ser Gln Leu Met Leu Lys Tyr Asn Ala Ile Val Val Leu Glu
                965                 970                 975
Asp Leu Asn Phe Gly Phe Lys Arg Gly Arg Phe Lys Val Glu Lys Gln
            980                 985                 990
Ile Tyr Gln Asn Phe Glu Asn Ala Leu Ile Lys Lys Leu Asn His Leu
        995                 1000                1005
Val Leu Lys Asp Lys Ala Asp Asp Glu Ile Gly Ser Tyr Lys Asn
    1010                1015                1020
Ala Leu Gln Leu Thr Asn Asn Phe Thr Asp Leu Lys Ser Ile Gly
    1025                1030                1035
Lys Gln Thr Gly Phe Leu Phe Tyr Val Pro Ala Trp Asn Thr Ser
    1040                1045                1050
Lys Ile Asp Pro Glu Thr Gly Phe Val Asp Leu Leu Lys Pro Arg
    1055                1060                1065
Tyr Glu Asn Ile Ala Gln Ser Gln Ala Phe Phe Gly Lys Phe Asp
    1070                1075                1080
Lys Ile Cys Tyr Asn Ala Asp Arg Gly Tyr Phe Glu Phe His Ile
```

```
            1085                1090                1095
Asp Tyr Ala Lys Phe Asn Asp Lys Ala Lys Asn Ser Arg Gln Ile
    1100                1105                1110

Trp Lys Ile Cys Ser His Gly Asp Lys Arg Tyr Val Tyr Asp Lys
    1115                1120                1125

Thr Ala Asn Gln Asn Lys Gly Ala Thr Ile Gly Val Asn Val Asn
    1130                1135                1140

Asp Glu Leu Lys Ser Leu Phe Thr Arg Tyr His Ile Asn Asp Lys
    1145                1150                1155

Gln Pro Asn Leu Val Met Asp Ile Cys Gln Asn Asp Lys Glu
    1160                1165                1170

Phe His Lys Ser Leu Met Tyr Leu Leu Lys Thr Leu Leu Ala Leu
    1175                1180                1185

Arg Tyr Ser Asn Ala Ser Ser Asp Glu Asp Phe Ile Leu Ser Pro
    1190                1195                1200

Val Ala Asn Asp Glu Gly Val Phe Phe Asn Ser Ala Leu Ala Asp
    1205                1210                1215

Asp Thr Gln Pro Gln Asn Ala Asp Ala Asn Gly Ala Tyr His Ile
    1220                1225                1230

Ala Leu Lys Gly Leu Trp Leu Leu Asn Glu Leu Lys Asn Ser Asp
    1235                1240                1245

Asp Leu Asn Lys Val Lys Leu Ala Ile Asp Asn Gln Thr Trp Leu
    1250                1255                1260

Asn Phe Ala Gln Asn Arg
    1265

<210> SEQ ID NO 8
<211> LENGTH: 1306
<212> TYPE: PRT
<213> ORGANISM: Thiomicrospira sp.XS5

<400> SEQUENCE: 8

Met Gly Ile His Gly Val Pro Ala Ala Thr Lys Thr Phe Asp Ser Glu
1               5                   10                  15

Phe Phe Asn Leu Tyr Ser Leu Gln Lys Thr Val Arg Phe Glu Leu Lys
                20                  25                  30

Pro Val Gly Glu Thr Ala Ser Phe Val Glu Asp Phe Lys Asn Glu Gly
            35                  40                  45

Leu Lys Arg Val Val Ser Glu Asp Glu Arg Ala Val Asp Tyr Gln
    50                  55                  60

Lys Val Lys Glu Ile Ile Asp Asp Tyr His Arg Asp Phe Ile Glu Glu
65                  70                  75                  80

Ser Leu Asn Tyr Phe Pro Glu Gln Val Ser Lys Asp Ala Leu Glu Gln
                85                  90                  95

Ala Phe His Leu Tyr Gln Lys Leu Lys Ala Ala Lys Val Glu Glu Arg
            100                 105                 110

Glu Lys Ala Leu Lys Glu Trp Glu Ala Leu Gln Lys Lys Leu Arg Glu
        115                 120                 125

Lys Val Val Lys Cys Phe Ser Asp Ser Asn Lys Ala Arg Phe Ser Arg
    130                 135                 140

Ile Asp Lys Lys Glu Leu Ile Lys Glu Asp Leu Ile Asn Trp Leu Val
145                 150                 155                 160

Ala Gln Asn Arg Glu Asp Asp Ile Pro Thr Val Glu Thr Phe Asn Asn
                165                 170                 175
```

-continued

```
Phe Thr Thr Tyr Phe Thr Gly Phe His Glu Asn Arg Lys Asn Ile Tyr
            180                 185                 190
Ser Lys Asp Asp His Ala Thr Ala Ile Ser Phe Arg Leu Ile His Glu
        195                 200                 205
Asn Leu Pro Lys Phe Phe Asp Asn Val Ile Ser Phe Asn Lys Leu Lys
    210                 215                 220
Glu Gly Phe Pro Glu Leu Lys Phe Asp Lys Val Lys Glu Asp Leu Glu
225                 230                 235                 240
Val Asp Tyr Asp Leu Lys His Ala Phe Glu Ile Glu Tyr Phe Val Asn
            245                 250                 255
Phe Val Thr Gln Ala Gly Ile Asp Gln Tyr Asn Tyr Leu Leu Gly Gly
            260                 265                 270
Lys Thr Leu Glu Asp Gly Thr Lys Lys Gln Gly Met Asn Glu Gln Ile
        275                 280                 285
Asn Leu Phe Lys Gln Gln Thr Arg Asp Lys Ala Arg Gln Ile Pro
    290                 295                 300
Lys Leu Ile Pro Leu Phe Lys Gln Ile Leu Ser Glu Arg Thr Glu Ser
305                 310                 315                 320
Gln Ser Phe Ile Pro Lys Gln Phe Glu Ser Asp Gln Glu Leu Phe Asp
            325                 330                 335
Ser Leu Gln Lys Leu His Asn Asn Cys Gln Asp Lys Phe Thr Val Leu
            340                 345                 350
Gln Gln Ala Ile Leu Gly Leu Ala Glu Ala Asp Leu Lys Lys Val Phe
        355                 360                 365
Ile Lys Thr Ser Asp Leu Asn Ala Leu Ser Asn Thr Ile Phe Gly Asn
    370                 375                 380
Tyr Ser Val Phe Ser Asp Ala Leu Asn Leu Tyr Lys Glu Ser Leu Lys
385                 390                 395                 400
Thr Lys Lys Ala Gln Glu Ala Phe Glu Lys Leu Pro Ala His Ser Ile
            405                 410                 415
His Asp Leu Ile Gln Tyr Leu Glu Gln Phe Asn Ser Ser Leu Asp Ala
            420                 425                 430
Glu Lys Gln Gln Ser Thr Asp Thr Val Leu Asn Tyr Phe Ile Lys Thr
        435                 440                 445
Asp Glu Leu Tyr Ser Arg Phe Ile Lys Ser Thr Ser Glu Ala Phe Thr
    450                 455                 460
Gln Val Gln Pro Leu Phe Glu Leu Glu Ala Leu Ser Ser Lys Arg Arg
465                 470                 475                 480
Pro Pro Glu Ser Glu Asp Glu Gly Ala Lys Gly Gln Glu Gly Phe Glu
            485                 490                 495
Gln Ile Lys Arg Ile Lys Ala Tyr Leu Asp Thr Leu Met Glu Ala Val
            500                 505                 510
His Phe Ala Lys Pro Leu Tyr Leu Val Lys Gly Arg Lys Met Ile Glu
        515                 520                 525
Gly Leu Asp Lys Asp Gln Ser Phe Tyr Glu Ala Phe Glu Met Ala Tyr
    530                 535                 540
Gln Glu Leu Glu Ser Leu Ile Ile Pro Ile Tyr Asn Lys Ala Arg Ser
545                 550                 555                 560
Tyr Leu Ser Arg Lys Pro Phe Lys Ala Asp Lys Phe Lys Ile Asn Phe
            565                 570                 575
Asp Asn Asn Thr Leu Leu Ser Gly Trp Asp Ala Asn Lys Glu Thr Ala
            580                 585                 590
Asn Ala Ser Ile Leu Phe Lys Lys Asp Gly Leu Tyr Tyr Leu Gly Ile
```

```
                595                 600                 605
Met Pro Lys Gly Lys Thr Phe Leu Phe Asp Tyr Phe Val Ser Ser Glu
        610                 615                 620

Asp Ser Glu Lys Leu Lys Gln Arg Arg Gln Lys Thr Ala Glu Glu Ala
625                 630                 635                 640

Leu Ala Gln Asp Gly Glu Ser Tyr Phe Glu Lys Ile Arg Tyr Lys Leu
                645                 650                 655

Leu Pro Gly Ala Ser Lys Met Leu Pro Lys Val Phe Phe Ser Asn Lys
            660                 665                 670

Asn Ile Gly Phe Tyr Asn Pro Ser Asp Ile Leu Arg Ile Arg Asn
            675                 680                 685

Thr Ala Ser His Thr Lys Asn Gly Thr Pro Gln Lys Gly His Ser Lys
690                 695                 700

Val Glu Phe Asn Leu Asn Asp Cys His Lys Met Ile Asp Phe Lys
705                 710                 715                 720

Ser Ser Ile Gln Lys His Pro Glu Trp Gly Ser Phe Gly Phe Thr Phe
                725                 730                 735

Ser Asp Thr Ser Asp Phe Glu Asp Met Ser Ala Phe Tyr Arg Glu Val
            740                 745                 750

Glu Asn Gln Gly Tyr Val Ile Ser Phe Asp Lys Ile Lys Glu Thr Tyr
            755                 760                 765

Ile Gln Ser Gln Val Glu Gln Gly Asn Leu Tyr Leu Phe Gln Ile Tyr
770                 775                 780

Asn Lys Asp Phe Ser Pro Tyr Ser Lys Gly Lys Pro Asn Leu His Thr
785                 790                 795                 800

Leu Tyr Trp Lys Ala Leu Phe Glu Glu Ala Asn Leu Asn Asn Val Val
                805                 810                 815

Ala Lys Leu Asn Gly Glu Ala Glu Ile Phe Phe Arg Arg His Ser Ile
            820                 825                 830

Lys Ala Ser Asp Lys Val Val His Pro Ala Asn Gln Ala Ile Asp Asn
            835                 840                 845

Lys Asn Pro His Thr Glu Lys Thr Gln Ser Thr Phe Glu Tyr Asp Leu
850                 855                 860

Val Lys Asp Lys Arg Tyr Thr Gln Asp Lys Phe Phe His Val Pro
865                 870                 875                 880

Ile Ser Leu Asn Phe Lys Ala Gln Gly Val Ser Lys Phe Asn Asp Lys
                885                 890                 895

Val Asn Gly Phe Leu Lys Gly Asn Pro Asp Val Asn Ile Ile Gly Ile
            900                 905                 910

Asp Arg Gly Glu Arg His Leu Leu Tyr Phe Thr Val Val Asn Gln Lys
            915                 920                 925

Gly Glu Ile Leu Val Gln Glu Ser Leu Asn Thr Leu Met Ser Asp Lys
930                 935                 940

Gly His Val Asn Asp Tyr Gln Gln Lys Leu Asp Lys Lys Glu Gln Glu
945                 950                 955                 960

Arg Asp Ala Ala Arg Lys Ser Trp Thr Thr Val Glu Asn Ile Lys Glu
                965                 970                 975

Leu Lys Glu Gly Tyr Leu Ser His Val Val His Lys Leu Ala His Leu
            980                 985                 990

Ile Ile Lys Tyr Asn Ala Ile Val Cys Leu Glu Asp Leu Asn Phe Gly
            995                 1000                1005

Phe Lys Arg Gly Arg Phe Lys Val Glu Lys Gln Val Tyr Gln Lys
        1010                1015                1020
```

```
Phe Glu Lys Ala Leu Ile Asp Lys Leu Asn Tyr Leu Val Phe Lys
    1025                1030                1035

Glu Lys Glu Leu Gly Glu Val Gly His Tyr Leu Thr Ala Tyr Gln
    1040                1045                1050

Leu Thr Ala Pro Phe Glu Ser Phe Lys Lys Leu Gly Lys Gln Ser
    1055                1060                1065

Gly Ile Leu Phe Tyr Val Pro Ala Asp Tyr Thr Ser Lys Ile Asp
    1070                1075                1080

Pro Thr Thr Gly Phe Val Asn Phe Leu Asp Leu Arg Tyr Gln Ser
    1085                1090                1095

Val Glu Lys Ala Lys Gln Leu Leu Ser Asp Phe Asn Ala Ile Arg
    1100                1105                1110

Phe Asn Ser Val Gln Asn Tyr Phe Glu Phe Glu Ile Asp Tyr Lys
    1115                1120                1125

Lys Leu Thr Pro Lys Arg Lys Val Gly Thr Gln Ser Lys Trp Val
    1130                1135                1140

Ile Cys Thr Tyr Gly Asp Val Arg Tyr Gln Asn Arg Arg Asn Gln
    1145                1150                1155

Lys Gly His Trp Glu Thr Glu Glu Val Asn Val Thr Glu Lys Leu
    1160                1165                1170

Lys Ala Leu Phe Ala Ser Asp Ser Lys Thr Thr Val Ile Asp
    1175                1180                1185

Tyr Ala Asn Asp Asp Asn Leu Ile Asp Val Ile Leu Glu Gln Asp
    1190                1195                1200

Lys Ala Ser Phe Phe Lys Glu Leu Leu Trp Leu Leu Lys Leu Thr
    1205                1210                1215

Met Thr Leu Arg His Ser Lys Ile Lys Ser Glu Asp Asp Phe Ile
    1220                1225                1230

Leu Ser Pro Val Lys Asn Glu Gln Gly Glu Phe Tyr Asp Ser Arg
    1235                1240                1245

Lys Ala Gly Glu Val Trp Pro Lys Asp Ala Asp Ala Asn Gly Ala
    1250                1255                1260

Tyr His Ile Ala Leu Lys Gly Leu Trp Asn Leu Gln Gln Ile Asn
    1265                1270                1275

Gln Trp Glu Lys Gly Lys Thr Leu Asn Leu Ala Ile Lys Asn Gln
    1280                1285                1290

Asp Trp Phe Ser Phe Ile Gln Glu Lys Pro Tyr Gln Glu
    1295                1300                1305

<210> SEQ ID NO 9
<211> LENGTH: 1214
<212> TYPE: PRT
<213> ORGANISM: Butyrivibrio sp.NC3005

<400> SEQUENCE: 9

Met Gly Ile His Gly Val Pro Ala Ala Tyr Tyr Gln Asn Leu Thr Lys
1               5                   10                  15

Lys Tyr Pro Val Ser Lys Thr Ile Arg Asn Glu Leu Ile Pro Ile Gly
            20                  25                  30

Lys Thr Leu Glu Asn Ile Arg Lys Asn Ile Leu Glu Ser Asp Val
            35                  40                  45

Lys Arg Lys Gln Asp Tyr Glu His Val Lys Gly Ile Met Asp Glu Tyr
        50                  55                  60

His Lys Gln Leu Ile Asn Glu Ala Leu Asp Asn Tyr Met Leu Pro Ser
```

```
            65                  70                  75                  80
Leu Asn Gln Ala Ala Glu Ile Tyr Leu Lys Lys His Val Asp Val Glu
                    85                  90                  95

Asp Arg Glu Glu Phe Lys Lys Thr Gln Asp Leu Leu Arg Arg Glu Val
                100                 105                 110

Thr Gly Arg Leu Lys Glu His Glu Asn Tyr Thr Lys Ile Gly Lys Lys
                115                 120                 125

Asp Ile Leu Asp Leu Leu Glu Lys Leu Pro Ser Ile Ser Glu Glu Asp
    130                 135                 140

Tyr Asn Ala Leu Glu Ser Phe Arg Asn Phe Tyr Thr Tyr Phe Thr Ser
145                 150                 155                 160

Tyr Asn Lys Val Arg Glu Asn Leu Tyr Ser Asp Glu Glu Lys Ser Ser
                165                 170                 175

Thr Val Ala Tyr Arg Leu Ile Asn Glu Asn Leu Pro Lys Phe Leu Asp
                180                 185                 190

Asn Ile Lys Ser Tyr Ala Phe Val Lys Ala Ala Gly Val Leu Ala Asp
            195                 200                 205

Cys Ile Glu Glu Glu Gln Asp Ala Leu Phe Met Val Glu Thr Phe
    210                 215                 220

Asn Met Thr Leu Thr Gln Gly Ile Asp Met Tyr Asn Tyr Gln Ile
225                 230                 235                 240

Gly Lys Val Asn Ser Ala Ile Asn Leu Tyr Asn Gln Lys Asn His Lys
                245                 250                 255

Val Glu Glu Phe Lys Lys Ile Pro Lys Met Lys Val Leu Tyr Lys Gln
                260                 265                 270

Ile Leu Ser Asp Arg Glu Glu Val Phe Ile Gly Glu Phe Lys Asp Asp
            275                 280                 285

Glu Thr Leu Leu Ser Ser Ile Gly Ala Tyr Gly Asn Val Leu Met Thr
    290                 295                 300

Tyr Leu Lys Ser Glu Lys Ile Asn Ile Phe Phe Asp Ala Leu Arg Glu
305                 310                 315                 320

Ser Glu Gly Lys Asn Val Tyr Val Lys Asn Asp Leu Ser Lys Thr Thr
                325                 330                 335

Met Ser Asn Ile Val Phe Gly Ser Trp Ser Ala Phe Asp Glu Leu Leu
            340                 345                 350

Asn Gln Glu Tyr Asp Leu Ala Asn Glu Asn Lys Lys Lys Asp Asp Lys
    355                 360                 365

Tyr Phe Glu Lys Arg Gln Lys Glu Leu Lys Lys Asn Lys Ser Tyr Thr
    370                 375                 380

Leu Glu Gln Met Ser Asn Leu Ser Lys Glu Asp Ile Ser Pro Ile Glu
385                 390                 395                 400

Asn Tyr Ile Glu Arg Ile Ser Glu Asp Ile Glu Lys Ile Cys Ile Tyr
                405                 410                 415

Asn Gly Glu Phe Glu Lys Ile Val Val Asn Glu His Asp Ser Ser Arg
                420                 425                 430

Lys Leu Ser Lys Asn Ile Lys Ala Val Lys Val Ile Lys Asp Tyr Leu
            435                 440                 445

Asp Ser Ile Lys Glu Leu Glu His Asp Ile Lys Leu Ile Asn Gly Ser
    450                 455                 460

Gly Gln Glu Leu Glu Lys Asn Leu Val Val Tyr Val Gly Gln Glu Glu
465                 470                 475                 480

Ala Leu Glu Gln Leu Arg Pro Val Asp Ser Leu Tyr Asn Leu Thr Arg
                485                 490                 495
```

```
Asn Tyr Leu Thr Lys Lys Pro Phe Ser Thr Glu Lys Val Lys Leu Asn
            500                 505                 510
Phe Asn Lys Ser Thr Leu Leu Asn Gly Trp Asp Lys Asn Lys Glu Thr
            515                 520                 525
Asp Asn Leu Gly Ile Leu Phe Phe Lys Asp Gly Lys Tyr Tyr Leu Gly
            530                 535                 540
Ile Met Asn Thr Thr Ala Asn Lys Ala Phe Val Asn Pro Pro Ala Ala
545                 550                 555                 560
Lys Thr Glu Asn Val Phe Lys Val Asp Tyr Lys Leu Leu Pro Gly
                565                 570                 575
Ser Asn Lys Met Leu Pro Lys Val Phe Phe Ala Lys Ser Asn Ile Gly
            580                 585                 590
Tyr Tyr Asn Pro Ser Thr Glu Leu Tyr Ser Asn Tyr Lys Lys Gly Thr
            595                 600                 605
His Lys Lys Gly Pro Ser Phe Ser Ile Asp Asp Cys His Asn Leu Ile
            610                 615                 620
Asp Phe Phe Lys Glu Ser Ile Lys Lys His Glu Asp Trp Ser Lys Phe
625                 630                 635                 640
Gly Phe Glu Phe Ser Asp Thr Ala Asp Tyr Arg Asp Ile Ser Glu Phe
                645                 650                 655
Tyr Arg Glu Val Glu Lys Gln Gly Tyr Lys Leu Thr Phe Thr Asp Ile
                660                 665                 670
Asp Glu Ser Tyr Ile Asn Asp Leu Ile Glu Lys Asn Glu Leu Tyr Leu
            675                 680                 685
Phe Gln Ile Tyr Asn Lys Asp Phe Ser Glu Tyr Ser Lys Gly Lys Leu
            690                 695                 700
Asn Leu His Thr Leu Tyr Phe Met Met Leu Phe Asp Gln Arg Asn Leu
705                 710                 715                 720
Asp Asn Val Val Tyr Lys Leu Asn Gly Glu Ala Glu Val Phe Tyr Arg
                725                 730                 735
Pro Ala Ser Ile Ala Glu Asn Glu Leu Val Ile His Lys Ala Gly Glu
                740                 745                 750
Gly Ile Lys Asn Lys Asn Pro Asn Arg Ala Lys Val Lys Glu Thr Ser
            755                 760                 765
Thr Phe Ser Tyr Asp Ile Val Lys Asp Lys Arg Tyr Ser Lys Tyr Lys
770                 775                 780
Phe Thr Leu His Ile Pro Ile Thr Met Asn Phe Gly Val Asp Glu Val
785                 790                 795                 800
Arg Arg Phe Asn Asp Val Ile Asn Asn Ala Leu Arg Thr Asp Asp Asn
                805                 810                 815
Val Asn Val Ile Gly Ile Asp Arg Gly Glu Arg Asn Leu Leu Tyr Val
            820                 825                 830
Val Val Ile Asn Ser Glu Gly Lys Ile Leu Glu Gln Ile Ser Leu Asn
            835                 840                 845
Ser Ile Ile Asn Lys Glu Tyr Asp Ile Glu Thr Asn Tyr His Ala Leu
            850                 855                 860
Leu Asp Glu Arg Glu Asp Asp Arg Asn Lys Ala Arg Lys Asp Trp Asn
865                 870                 875                 880
Thr Ile Glu Asn Ile Lys Glu Leu Lys Thr Gly Tyr Leu Ser Gln Val
            885                 890                 895
Val Asn Val Val Ala Lys Leu Val Leu Lys Tyr Asn Ala Ile Ile Cys
            900                 905                 910
```

Leu Glu Asp Leu Asn Phe Gly Phe Lys Arg Gly Arg Gln Lys Val Glu
            915                 920                 925

Lys Gln Val Tyr Gln Lys Phe Glu Lys Met Leu Ile Glu Lys Leu Asn
        930                 935                 940

Tyr Leu Val Ile Asp Lys Ser Arg Glu Gln Val Ser Pro Glu Lys Met
945                 950                 955                 960

Gly Gly Ala Leu Asn Ala Leu Gln Leu Thr Ser Lys Phe Lys Ser Phe
                965                 970                 975

Ala Glu Leu Gly Lys Gln Ser Gly Ile Ile Tyr Val Pro Ala Tyr
            980                 985                 990

Leu Thr Ser Lys Ile Asp Pro Thr Thr Gly Phe Val Asn Leu Phe Tyr
            995                1000                1005

Ile Lys Tyr Glu Asn Ile Glu Lys Ala Lys Gln Phe Phe Asp Gly
    1010                1015                1020

Phe Asp Phe Ile Arg Phe Asn Lys Lys Asp Asp Met Phe Glu Phe
    1025                1030                1035

Ser Phe Asp Tyr Lys Ser Phe Thr Gln Lys Ala Cys Gly Ile Arg
    1040                1045                1050

Ser Lys Trp Ile Val Tyr Thr Asn Gly Glu Arg Ile Ile Lys Tyr
    1055                1060                1065

Pro Asn Pro Glu Lys Asn Asn Leu Phe Asp Glu Lys Val Ile Asn
    1070                1075                1080

Val Thr Asp Glu Ile Lys Gly Leu Phe Lys Gln Tyr Arg Ile Pro
    1085                1090                1095

Tyr Glu Asn Gly Glu Asp Ile Lys Glu Ile Ile Ser Lys Ala
    1100                1105                1110

Glu Ala Asp Phe Tyr Lys Arg Leu Phe Arg Leu Leu His Gln Thr
    1115                1120                1125

Leu Gln Met Arg Asn Ser Thr Ser Asp Gly Thr Arg Asp Tyr Ile
    1130                1135                1140

Ile Ser Pro Val Lys Asn Asp Arg Gly Glu Phe Phe Cys Ser Glu
    1145                1150                1155

Phe Ser Glu Gly Thr Met Pro Lys Asp Ala Asp Ala Asn Gly Ala
    1160                1165                1170

Tyr Asn Ile Ala Arg Lys Gly Leu Trp Val Leu Glu Gln Ile Arg
    1175                1180                1185

Gln Lys Asp Glu Gly Glu Lys Val Asn Leu Ser Met Thr Asn Ala
    1190                1195                1200

Glu Trp Leu Lys Tyr Ala Gln Leu His Leu Leu
    1205                1210

<210> SEQ ID NO 10
<211> LENGTH: 1129
<212> TYPE: PRT
<213> ORGANISM: Unknown
<220> FEATURE:
<223> OTHER INFORMATION: Synthetic sequence

<400> SEQUENCE: 10

Met Ala Val Lys Ser Ile Lys Val Lys Leu Arg Leu Asp Asp Met Pro
1               5                   10                  15

Glu Ile Arg Ala Gly Leu Trp Lys Leu His Lys Glu Val Asn Ala Gly
            20                  25                  30

Val Arg Tyr Tyr Thr Glu Trp Leu Ser Leu Leu Arg Gln Glu Asn Leu
        35                  40                  45

```
Tyr Arg Arg Ser Pro Asn Gly Asp Gly Glu Gln Glu Cys Asp Lys Thr
    50              55                  60

Ala Glu Glu Cys Lys Ala Glu Leu Leu Glu Arg Leu Arg Ala Arg Gln
65                  70                  75                  80

Val Glu Asn Gly His Arg Gly Pro Ala Gly Ser Asp Asp Glu Leu Leu
                85                  90                  95

Gln Leu Ala Arg Gln Leu Tyr Glu Leu Leu Val Pro Gln Ala Ile Gly
            100                 105                 110

Ala Lys Gly Asp Ala Gln Gln Ile Ala Arg Lys Phe Leu Ser Pro Leu
            115                 120                 125

Ala Asp Lys Asp Ala Val Gly Gly Leu Gly Ile Ala Lys Ala Gly Asn
130                 135                 140

Lys Pro Arg Trp Val Arg Met Arg Glu Ala Gly Glu Pro Gly Trp Glu
145                 150                 155                 160

Glu Glu Lys Glu Lys Ala Glu Thr Arg Lys Ser Ala Asp Arg Thr Ala
                165                 170                 175

Asp Val Leu Arg Ala Leu Ala Asp Phe Gly Leu Lys Pro Leu Met Arg
            180                 185                 190

Val Tyr Thr Asp Ser Glu Met Ser Ser Val Glu Trp Lys Pro Leu Arg
            195                 200                 205

Lys Gly Gln Ala Val Arg Thr Trp Asp Arg Asp Met Phe Gln Gln Ala
210                 215                 220

Ile Glu Arg Met Met Ser Trp Glu Ser Trp Asn Gln Arg Val Gly Gln
225                 230                 235                 240

Glu Tyr Ala Lys Leu Val Glu Gln Lys Asn Arg Phe Glu Gln Lys Asn
                245                 250                 255

Phe Val Gly Gln Glu His Leu Val His Leu Val Asn Gln Leu Gln Gln
            260                 265                 270

Asp Met Lys Glu Ala Ser Pro Gly Leu Glu Ser Lys Glu Gln Thr Ala
            275                 280                 285

His Tyr Val Thr Gly Arg Ala Leu Arg Gly Ser Asp Lys Val Phe Glu
            290                 295                 300

Lys Trp Gly Lys Leu Ala Pro Asp Ala Pro Phe Asp Leu Tyr Asp Ala
305                 310                 315                 320

Glu Ile Lys Asn Val Gln Arg Arg Asn Thr Arg Arg Phe Gly Ser His
                325                 330                 335

Asp Leu Phe Ala Lys Leu Ala Glu Pro Glu Tyr Gln Ala Leu Trp Arg
            340                 345                 350

Glu Asp Ala Ser Phe Leu Thr Arg Tyr Ala Val Tyr Asn Ser Ile Leu
            355                 360                 365

Arg Lys Leu Asn His Ala Lys Met Phe Ala Thr Phe Thr Leu Pro Asp
370                 375                 380

Ala Thr Ala His Pro Ile Trp Thr Arg Phe Asp Lys Leu Gly Gly Asn
385                 390                 395                 400

Leu His Gln Tyr Thr Phe Leu Phe Asn Glu Phe Gly Glu Arg Arg His
                405                 410                 415

Ala Ile Arg Phe His Lys Leu Leu Lys Val Glu Asn Gly Val Ala Arg
            420                 425                 430

Glu Val Asp Asp Val Thr Val Pro Ile Ser Met Ser Glu Gln Leu Asp
            435                 440                 445

Asn Leu Leu Pro Arg Asp Pro Asn Glu Pro Ile Ala Leu Tyr Phe Arg
450                 455                 460

Asp Tyr Gly Ala Glu Gln His Phe Thr Gly Glu Phe Gly Gly Ala Lys
```

```
                465                 470                 475                 480
Ile Gln Cys Arg Arg Asp Gln Leu Ala His Met His Arg Arg Arg Gly
                    485                 490                 495
Ala Arg Asp Val Tyr Leu Asn Val Ser Val Arg Val Gln Ser Gln Ser
                    500                 505                 510
Glu Ala Arg Gly Glu Arg Arg Pro Pro Tyr Ala Ala Val Phe Arg Leu
                    515                 520                 525
Val Gly Asp Asn His Arg Ala Phe Val His Phe Asp Lys Leu Ser Asp
                    530                 535                 540
Tyr Leu Ala Glu His Pro Asp Asp Gly Lys Leu Gly Ser Glu Gly Leu
545                 550                 555                 560
Leu Ser Gly Leu Arg Val Met Ser Val Asp Leu Gly Leu Arg Thr Ser
                    565                 570                 575
Ala Ser Ile Ser Val Phe Arg Val Ala Arg Lys Asp Glu Leu Lys Pro
                    580                 585                 590
Asn Ser Lys Gly Arg Val Pro Phe Phe Phe Pro Ile Lys Gly Asn Asp
                    595                 600                 605
Asn Leu Val Ala Val His Glu Arg Ser Gln Leu Leu Lys Leu Pro Gly
                    610                 615                 620
Glu Thr Glu Ser Lys Asp Leu Arg Ala Ile Arg Glu Arg Gln Arg
625                 630                 635                 640
Thr Leu Arg Gln Leu Arg Thr Gln Leu Ala Tyr Leu Arg Leu Leu Val
                    645                 650                 655
Arg Cys Gly Ser Glu Asp Val Gly Arg Arg Glu Arg Ser Trp Ala Lys
                    660                 665                 670
Leu Ile Glu Gln Pro Val Asp Ala Ala Asn His Met Thr Pro Asp Trp
                    675                 680                 685
Arg Glu Ala Phe Glu Asn Glu Leu Gln Lys Leu Lys Ser Leu His Gly
                    690                 695                 700
Ile Cys Ser Asp Lys Glu Trp Met Asp Ala Val Tyr Glu Ser Val Arg
705                 710                 715                 720
Arg Val Trp Arg His Met Gly Lys Gln Val Arg Asp Trp Arg Lys Asp
                    725                 730                 735
Val Arg Ser Gly Glu Arg Pro Lys Ile Arg Gly Tyr Ala Lys Asp Val
                    740                 745                 750
Val Gly Gly Asn Ser Ile Glu Gln Ile Glu Tyr Leu Glu Arg Gln Tyr
                    755                 760                 765
Lys Phe Leu Lys Ser Trp Ser Phe Phe Gly Lys Val Ser Gly Gln Val
770                 775                 780
Ile Arg Ala Glu Lys Gly Ser Arg Phe Ala Ile Thr Leu Arg Glu His
785                 790                 795                 800
Ile Asp His Ala Lys Glu Asp Arg Leu Lys Lys Leu Ala Asp Arg Ile
                    805                 810                 815
Ile Met Glu Ala Leu Gly Tyr Val Tyr Ala Leu Asp Glu Arg Gly Lys
                    820                 825                 830
Gly Lys Trp Val Ala Lys Tyr Pro Pro Cys Gln Leu Ile Leu Leu Glu
                    835                 840                 845
Glu Leu Ser Glu Tyr Gln Phe Asn Asn Asp Arg Pro Pro Ser Glu Asn
850                 855                 860
Asn Gln Leu Met Gln Trp Ser His Arg Gly Val Phe Gln Glu Leu Ile
865                 870                 875                 880
Asn Gln Ala Gln Val His Asp Leu Leu Val Gly Thr Met Tyr Ala Ala
                    885                 890                 895
```

```
Phe Ser Ser Arg Phe Asp Ala Arg Thr Gly Ala Pro Gly Ile Arg Cys
            900                 905                 910

Arg Arg Val Pro Ala Arg Cys Thr Gln Glu His Asn Pro Glu Pro Phe
            915                 920                 925

Pro Trp Trp Leu Asn Lys Phe Val Val Glu His Thr Leu Asp Ala Cys
            930                 935                 940

Pro Leu Arg Ala Asp Asp Leu Ile Pro Thr Gly Glu Gly Ile Phe
945                 950                 955                 960

Val Ser Pro Phe Ser Ala Glu Glu Gly Asp Phe His Gln Ile His Ala
            965                 970                 975

Asp Leu Asn Ala Ala Gln Asn Leu Gln Gln Arg Leu Trp Ser Asp Phe
            980                 985                 990

Asp Ile Ser Gln Ile Arg Leu Arg Cys Asp Trp Gly Glu Val Asp Gly
            995                 1000                1005

Glu Leu Val Leu Ile Pro Arg Leu Thr Gly Lys Arg Thr Ala Asp
    1010                1015                1020

Ser Tyr Ser Asn Lys Val Phe Tyr Thr Asn Thr Gly Val Thr Tyr
    1025                1030                1035

Tyr Glu Arg Glu Arg Gly Lys Lys Arg Arg Lys Val Phe Ala Gln
    1040                1045                1050

Glu Lys Leu Ser Glu Glu Ala Glu Leu Leu Val Glu Ala Asp
    1055                1060                1065

Glu Ala Arg Glu Lys Ser Val Val Leu Met Arg Asp Pro Ser Gly
    1070                1075                1080

Ile Ile Asn Arg Gly Asn Trp Thr Arg Gln Lys Glu Phe Trp Ser
    1085                1090                1095

Met Val Asn Gln Arg Ile Glu Gly Tyr Leu Val Lys Gln Ile Arg
    1100                1105                1110

Ser Arg Val Pro Leu Gln Asp Ser Ala Cys Glu Asn Thr Gly Asp
    1115                1120                1125

Ile

<210> SEQ ID NO 11
<211> LENGTH: 20
<212> TYPE: RNA
<213> ORGANISM: Unknown
<220> FEATURE:
<223> OTHER INFORMATION: Lachnospiraceae bacterium

<400> SEQUENCE: 11
aauuucuacu aaguguagau                                                 20

<210> SEQ ID NO 12
<211> LENGTH: 19
<212> TYPE: RNA
<213> ORGANISM: Acidaminococcus sp.BV3L6

<400> SEQUENCE: 12
aauuucuacu cuuguagau                                                  19

<210> SEQ ID NO 13
<211> LENGTH: 19
<212> TYPE: RNA
<213> ORGANISM: Francisella novicida

<400> SEQUENCE: 13
aauuucuacu guuguagau                                                  19
```

```
<210> SEQ ID NO 14
<211> LENGTH: 19
<212> TYPE: RNA
<213> ORGANISM: Porphyromonas macacae

<400> SEQUENCE: 14
aauuucuacu auuguagau                                                  19

<210> SEQ ID NO 15
<211> LENGTH: 20
<212> TYPE: RNA
<213> ORGANISM: Moraxella bovoculi

<400> SEQUENCE: 15
aauuucuacu guuuguagau                                                 20

<210> SEQ ID NO 16
<211> LENGTH: 19
<212> TYPE: RNA
<213> ORGANISM: Thiomicrospira sp.XS5

<400> SEQUENCE: 16
aauuucuacu guuguagau                                                  19

<210> SEQ ID NO 17
<211> LENGTH: 19
<212> TYPE: RNA
<213> ORGANISM: Btyrivibrio sp.NC3005

<400> SEQUENCE: 17
aauuucuacu auuguagau                                                  19

<210> SEQ ID NO 18
<211> LENGTH: 10
<212> TYPE: RNA
<213> ORGANISM: Artificial sequence
<220> FEATURE:
<223> OTHER INFORMATION: Synthetic sequence

<400> SEQUENCE: 18
aaaaaaaaaa                                                            10

<210> SEQ ID NO 19
<211> LENGTH: 91
<212> TYPE: RNA
<213> ORGANISM: Unknown
<220> FEATURE:
<223> OTHER INFORMATION: Synthetic sequence

<400> SEQUENCE: 19
gucuagagga cagaauuuuu caacggguguu gccaauggcc acuuccagg uggcaaagcc    60 cguugagcuu cucaaaucug agaaguggca c                                    91

<210> SEQ ID NO 20
<211> LENGTH: 41
<212> TYPE: RNA
<213> ORGANISM: Artificial sequence
<220> FEATURE:
<223> OTHER INFORMATION: Synthetic sequence

<400> SEQUENCE: 20
uaauuucuac uaaguguaga ucgucgccgu ccagcucgac c                         41
```

```
<210> SEQ ID NO 21
<211> LENGTH: 45
<212> TYPE: RNA
<213> ORGANISM: Artificial sequence
<220> FEATURE:
<223> OTHER INFORMATION: Synthetic sequence

<400> SEQUENCE: 21
uaauuucuac uaaguguaga ucaacgucgu gacugggaaa acccu            45

<210> SEQ ID NO 22
<211> LENGTH: 41
<212> TYPE: RNA
<213> ORGANISM: Artificial sequence
<220> FEATURE:
<223> OTHER INFORMATION: Synthetic sequence

<400> SEQUENCE: 22
uaauuucuac uaaguguaga uaacgaacca ccagcagaag a                41

<210> SEQ ID NO 23
<211> LENGTH: 41
<212> TYPE: RNA
<213> ORGANISM: Artificial sequence
<220> FEATURE:
<223> OTHER INFORMATION: Synthetic sequence

<400> SEQUENCE: 23
uaauuucuac uaaguguaga ugaucguuac gcuaacuaug a                41

<210> SEQ ID NO 24
<211> LENGTH: 41
<212> TYPE: RNA
<213> ORGANISM: Artificial sequence
<220> FEATURE:
<223> OTHER INFORMATION: Synthetic sequence

<400> SEQUENCE: 24
uaauuucuac uaaguguaga uccugggugu uccacagcug a                41

<210> SEQ ID NO 25
<211> LENGTH: 41
<212> TYPE: RNA
<213> ORGANISM: Artificial sequence
<220> FEATURE:
<223> OTHER INFORMATION: Synthetic sequence

<400> SEQUENCE: 25
uaauuucuac uaaguguaga ucuacauuac aggcuaacaa a                41

<210> SEQ ID NO 26
<211> LENGTH: 41
<212> TYPE: RNA
<213> ORGANISM: Artificial sequence
<220> FEATURE:
<223> OTHER INFORMATION: Synthetic sequence

<400> SEQUENCE: 26
uaauuucuac uaaguguaga uguacauugc aagauacuaa a                41

<210> SEQ ID NO 27
<211> LENGTH: 41
<212> TYPE: RNA
<213> ORGANISM: Artificial sequence
<220> FEATURE:
<223> OTHER INFORMATION: Synthetic sequence
```

<400> SEQUENCE: 27
uaauuucuac uaaguguaga uugaaguaga uauggcagca c                41

<210> SEQ ID NO 28
<211> LENGTH: 41
<212> TYPE: RNA
<213> ORGANISM: Artificial sequence
<220> FEATURE:
<223> OTHER INFORMATION: Synthetic sequence

<400> SEQUENCE: 28
uaauuucuac uaaguguaga uacaauaugu gcuucuacac a                41

<210> SEQ ID NO 29
<211> LENGTH: 40
<212> TYPE: RNA
<213> ORGANISM: Artificial sequence
<220> FEATURE:
<223> OTHER INFORMATION: Synthetic sequence

<400> SEQUENCE: 29
uaauuucuac ucuuguagau gaucguuacg cuaacuauga                  40

<210> SEQ ID NO 30
<211> LENGTH: 40
<212> TYPE: RNA
<213> ORGANISM: Artificial sequence
<220> FEATURE:
<223> OTHER INFORMATION: Synthetic sequence

<400> SEQUENCE: 30
uaauuucuac uguuguagau gaucguuacg cuaacuauga                  40

<210> SEQ ID NO 31
<211> LENGTH: 111
<212> TYPE: RNA
<213> ORGANISM: Artificial sequence
<220> FEATURE:
<223> OTHER INFORMATION: Synthetic sequence

<400> SEQUENCE: 31
gucuagagga cagaauuuuu caacggugu gccaauggcc acuuccagg uggcaaagcc      60 cguugagcuu ucaaaucug agaaguggca cgaucguuac gcuaacuaug a            111

<210> SEQ ID NO 32
<211> LENGTH: 116
<212> TYPE: RNA
<213> ORGANISM: Artificial sequence
<220> FEATURE:
<223> OTHER INFORMATION: Synthetic sequence

<400> SEQUENCE: 32
cgucgccguc cagcucgacc guuuuagagc uaugcuguuu uggaaacaaa acagcauagc    60
aaguuaaaau aaggcuaguc cguuaucaac uugaaaaagu ggcaccgagu cggugc       116

<210> SEQ ID NO 33
<211> LENGTH: 116
<212> TYPE: RNA
<213> ORGANISM: Artificial sequence
<220> FEATURE:
<223> OTHER INFORMATION: Synthetic sequence

<400> SEQUENCE: 33
aacgaaccac cagcagaaga guuuuagagc uaugcuguuu uggaaacaaa acagcauagc    60
aaguuaaaau aaggcuaguc cguuaucaac uugaaaaagu ggcaccgagu cggugc      116

<210> SEQ ID NO 34
<211> LENGTH: 116
<212> TYPE: RNA
<213> ORGANISM: Artificial sequence
<220> FEATURE:
<223> OTHER INFORMATION: Synthetic sequence

<400> SEQUENCE: 34
gaucguuacg cuaacuauga guuuuagagc uaugcuguuu uggaaacaaa acagcauagc    60
aaguuaaaau aaggcuaguc cguuaucaac uugaaaaagu ggcaccgagu cggugc      116

<210> SEQ ID NO 35
<211> LENGTH: 135
<212> TYPE: RNA
<213> ORGANISM: Artificial sequence
<220> FEATURE:
<223> OTHER INFORMATION: Synthetic sequence

<400> SEQUENCE: 35
gaucguuacg cuaacuauga guuguagcuc ccuuucucau uucgcagugc gaaagcacug    60
cgaaaugaga accguugcua caauaaggcc gucugaaaag augugccgca acgcucugcc   120
ccuuaaagcu ucugc                                                   135

<210> SEQ ID NO 36
<211> LENGTH: 139
<212> TYPE: RNA
<213> ORGANISM: Artificial sequence
<220> FEATURE:
<223> OTHER INFORMATION: Synthetic sequence

<400> SEQUENCE: 36
gaucguuacg cuaacuauga guuuuagucc cuuuuuaaau uucuuuaugg uaaaauuaua    60
aucucauaag aaauuuaaaa agggacuaaa auaaagaguu ugcgggacuc ugcgggguua   120 caaucccua aaaccgcuu                                                139

<210> SEQ ID NO 37
<211> LENGTH: 55
<212> TYPE: RNA
<213> ORGANISM: Artificial sequence
<220> FEATURE:
<223> OTHER INFORMATION: Synthetic sequence

<400> SEQUENCE: 37
gccggggugg ugcccauccu ggucgagcug gacggcgacg uaaacggcca caagc         55

<210> SEQ ID NO 38
<211> LENGTH: 55
<212> TYPE: RNA
<213> ORGANISM: Artificial sequence
<220> FEATURE:
<223> OTHER INFORMATION: Synthetic sequence

<400> SEQUENCE: 38
uagcauucca cagacagccc ucauaguuag cguaacgauc uaaaguuuug ucguc         55

<210> SEQ ID NO 39
<211> LENGTH: 58
<212> TYPE: DNA
<213> ORGANISM: Artificial sequence

```
<220> FEATURE:
<223> OTHER INFORMATION: Synthetic sequence

<400> SEQUENCE: 39
agcttgtctg ccatggacat gcagactata ctgttattgt tgtacagacc gaattccc      58

<210> SEQ ID NO 40
<211> LENGTH: 58
<212> TYPE: DNA
<213> ORGANISM: Artificial sequence
<220> FEATURE:
<223> OTHER INFORMATION: Synthetic sequence

<400> SEQUENCE: 40
gggaattcgg tctgtacaac aataacagta tagtctgcat gtccatggca gacaagct      58

<210> SEQ ID NO 41
<211> LENGTH: 55
<212> TYPE: DNA
<213> ORGANISM: Artificial sequence
<220> FEATURE:
<223> OTHER INFORMATION: Synthetic sequence

<400> SEQUENCE: 41
gcttgtggcc gtttacgtcg ccgtccagct cgaccaggat gggcaccacc ccggc         55

<210> SEQ ID NO 42
<211> LENGTH: 55
<212> TYPE: DNA
<213> ORGANISM: Artificial sequence
<220> FEATURE:
<223> OTHER INFORMATION: Synthetic sequence

<400> SEQUENCE: 42
gccggggtgg tgcccatcct ggtcgagctg gacggcgacg taaacggcca caagc         55

<210> SEQ ID NO 43
<211> LENGTH: 55
<212> TYPE: DNA
<213> ORGANISM: Artificial sequence
<220> FEATURE:
<223> OTHER INFORMATION: Synthetic sequence

<400> SEQUENCE: 43
gcttgtggcc gtttacgtcg ccgtccagct cgaggaggat gggcaccacc ccggc         55

<210> SEQ ID NO 44
<211> LENGTH: 55
<212> TYPE: DNA
<213> ORGANISM: Artificial sequence
<220> FEATURE:
<223> OTHER INFORMATION: Synthetic sequence

<400> SEQUENCE: 44
gccggggtgg tgcccatcct cctcgagctg gacggcgacg taaacggcca caagc         55

<210> SEQ ID NO 45
<211> LENGTH: 55
<212> TYPE: DNA
<213> ORGANISM: Artificial sequence
<220> FEATURE:
<223> OTHER INFORMATION: Synthetic sequence

<400> SEQUENCE: 45
gcttgtggcc gtttacgtcg ccgtccagct cctccaggat gggcaccacc ccggc         55
```

<210> SEQ ID NO 46
<211> LENGTH: 55
<212> TYPE: DNA
<213> ORGANISM: Artificial sequence
<220> FEATURE:
<223> OTHER INFORMATION: Synthetic sequence

<400> SEQUENCE: 46
gccggggtgg tgcccatcct ggaggagctg gacggcgacg taaacggcca caagc    55

<210> SEQ ID NO 47
<211> LENGTH: 55
<212> TYPE: DNA
<213> ORGANISM: Artificial sequence
<220> FEATURE:
<223> OTHER INFORMATION: Synthetic sequence

<400> SEQUENCE: 47
gcttgtggcc gtttacgtcg ccgtccagca ggaccaggat gggcaccacc ccggc    55

<210> SEQ ID NO 48
<211> LENGTH: 55
<212> TYPE: DNA
<213> ORGANISM: Artificial sequence
<220> FEATURE:
<223> OTHER INFORMATION: Synthetic sequence

<400> SEQUENCE: 48
gccggggtgg tgcccatcct ggtcctgctg gacggcgacg taaacggcca caagc    55

<210> SEQ ID NO 49
<211> LENGTH: 55
<212> TYPE: DNA
<213> ORGANISM: Artificial sequence
<220> FEATURE:
<223> OTHER INFORMATION: Synthetic sequence

<400> SEQUENCE: 49
gcttgtggcc gtttacgtcg ccgtccacgt cgaccaggat gggcaccacc ccggc    55

<210> SEQ ID NO 50
<211> LENGTH: 55
<212> TYPE: DNA
<213> ORGANISM: Artificial sequence
<220> FEATURE:
<223> OTHER INFORMATION: Synthetic sequence

<400> SEQUENCE: 50
gccggggtgg tgcccatcct ggtcgacgtg gacggcgacg taaacggcca caagc    55

<210> SEQ ID NO 51
<211> LENGTH: 55
<212> TYPE: DNA
<213> ORGANISM: Artificial sequence
<220> FEATURE:
<223> OTHER INFORMATION: Synthetic sequence

<400> SEQUENCE: 51
gcttgtggcc gtttacgtcg ccgtcgtgct cgaccaggat gggcaccacc ccggc    55

<210> SEQ ID NO 52
<211> LENGTH: 55
<212> TYPE: DNA
<213> ORGANISM: Artificial sequence
<220> FEATURE:
<223> OTHER INFORMATION: Synthetic sequence

<400> SEQUENCE: 52
gccggggtgg tgcccatcct ggtcgagcac gacggcgacg taaacggcca caagc        55

<210> SEQ ID NO 53
<211> LENGTH: 55
<212> TYPE: DNA
<213> ORGANISM: Artificial sequence
<220> FEATURE:
<223> OTHER INFORMATION: Synthetic sequence

<400> SEQUENCE: 53
gcttgtggcc gtttacgtcg ccgagcagct cgaccaggat gggcaccacc ccggc        55

<210> SEQ ID NO 54
<211> LENGTH: 55
<212> TYPE: DNA
<213> ORGANISM: Artificial sequence
<220> FEATURE:
<223> OTHER INFORMATION: Synthetic sequence

<400> SEQUENCE: 54
gccggggtgg tgcccatcct ggtcgagctg ctcggcgacg taaacggcca caagc        55

<210> SEQ ID NO 55
<211> LENGTH: 55
<212> TYPE: DNA
<213> ORGANISM: Artificial sequence
<220> FEATURE:
<223> OTHER INFORMATION: Synthetic sequence

<400> SEQUENCE: 55
gcttgtggcc gtttacgtcg cgctccagct cgaccaggat gggcaccacc ccggc        55

<210> SEQ ID NO 56
<211> LENGTH: 55
<212> TYPE: DNA
<213> ORGANISM: Artificial sequence
<220> FEATURE:
<223> OTHER INFORMATION: Synthetic sequence

<400> SEQUENCE: 56
gccggggtgg tgcccatcct ggtcgagctg gagcgcgacg taaacggcca caagc        55

<210> SEQ ID NO 57
<211> LENGTH: 55
<212> TYPE: DNA
<213> ORGANISM: Artificial sequence
<220> FEATURE:
<223> OTHER INFORMATION: Synthetic sequence

<400> SEQUENCE: 57
gcttgtggcc gtttacgtcc gcgtccagct cgaccaggat gggcaccacc ccggc        55

<210> SEQ ID NO 58
<211> LENGTH: 55
<212> TYPE: DNA
<213> ORGANISM: Artificial sequence
<220> FEATURE:
<223> OTHER INFORMATION: Synthetic sequence

<400> SEQUENCE: 58
gccggggtgg tgcccatcct ggtcgagctg gacgcggacg taaacggcca caagc        55

<210> SEQ ID NO 59

```
<211> LENGTH: 55
<212> TYPE: DNA
<213> ORGANISM: Artificial sequence
<220> FEATURE:
<223> OTHER INFORMATION: Synthetic sequence

<400> SEQUENCE: 59
gcttgtggcc gtttacgagg ccgtccagct cgaccaggat gggcaccacc ccggc      55

<210> SEQ ID NO 60
<211> LENGTH: 55
<212> TYPE: DNA
<213> ORGANISM: Artificial sequence
<220> FEATURE:
<223> OTHER INFORMATION: Synthetic sequence

<400> SEQUENCE: 60
gccggggtgg tgcccatcct ggtcgagctg acggcctcg taaacggcca caagc       55

<210> SEQ ID NO 61
<211> LENGTH: 55
<212> TYPE: DNA
<213> ORGANISM: Artificial sequence
<220> FEATURE:
<223> OTHER INFORMATION: Synthetic sequence

<400> SEQUENCE: 61
gcttgtggcc gtttagctcg ccgtccagct cgaccaggat gggcaccacc ccggc      55

<210> SEQ ID NO 62
<211> LENGTH: 55
<212> TYPE: DNA
<213> ORGANISM: Artificial sequence
<220> FEATURE:
<223> OTHER INFORMATION: Synthetic sequence

<400> SEQUENCE: 62
gccggggtgg tgcccatcct ggtcgagctg acggcgagc taaacggcca caagc       55

<210> SEQ ID NO 63
<211> LENGTH: 55
<212> TYPE: DNA
<213> ORGANISM: Artificial sequence
<220> FEATURE:
<223> OTHER INFORMATION: Synthetic sequence

<400> SEQUENCE: 63
gcttgtggcc gagcacgtcg ccgtccagct cgaccaggat gggcaccacc ccggc      55

<210> SEQ ID NO 64
<211> LENGTH: 55
<212> TYPE: DNA
<213> ORGANISM: Artificial sequence
<220> FEATURE:
<223> OTHER INFORMATION: Synthetic sequence

<400> SEQUENCE: 64
gccggggtgg tgcccatcct ggtcgagctg acggcgacg tgctcggcca caagc       55

<210> SEQ ID NO 65
<211> LENGTH: 20
<212> TYPE: DNA
<213> ORGANISM: Artificial sequence
<220> FEATURE:
<223> OTHER INFORMATION: Synthetic sequence

<400> SEQUENCE: 65
```

```
cgacgtaaac ggccacaagc                                                    20

<210> SEQ ID NO 66
<211> LENGTH: 25
<212> TYPE: DNA
<213> ORGANISM: Artificial sequence
<220> FEATURE:
<223> OTHER INFORMATION: Synthetic sequence

<400> SEQUENCE: 66
gacggcgacg taaacggcca caagc                                              25

<210> SEQ ID NO 67
<211> LENGTH: 30
<212> TYPE: DNA
<213> ORGANISM: Artificial sequence
<220> FEATURE:
<223> OTHER INFORMATION: Synthetic sequence

<400> SEQUENCE: 67
agctggacgg cgacgtaaac ggccacaagc                                         30

<210> SEQ ID NO 68
<211> LENGTH: 35
<212> TYPE: DNA
<213> ORGANISM: Artificial sequence
<220> FEATURE:
<223> OTHER INFORMATION: Synthetic sequence

<400> SEQUENCE: 68
ggtcgagctg gacggcgacg taaacggcca caagc                                   35

<210> SEQ ID NO 69
<211> LENGTH: 40
<212> TYPE: DNA
<213> ORGANISM: Artificial sequence
<220> FEATURE:
<223> OTHER INFORMATION: Synthetic sequence

<400> SEQUENCE: 69
atcctggtcg agctggacgg cgacgtaaac ggccacaagc                              40

<210> SEQ ID NO 70
<211> LENGTH: 20
<212> TYPE: DNA
<213> ORGANISM: Artificial sequence
<220> FEATURE:
<223> OTHER INFORMATION: Synthetic sequence

<400> SEQUENCE: 70
gcttgtggcc gtttacgtcg                                                    20

<210> SEQ ID NO 71
<211> LENGTH: 25
<212> TYPE: DNA
<213> ORGANISM: Artificial sequence
<220> FEATURE:
<223> OTHER INFORMATION: Synthetic sequence

<400> SEQUENCE: 71
gcttgtggcc gtttacgtcg ccgtc                                              25

<210> SEQ ID NO 72
<211> LENGTH: 30
<212> TYPE: DNA
```

<213> ORGANISM: Artificial sequence
<220> FEATURE:
<223> OTHER INFORMATION: Synthetic sequence

<400> SEQUENCE: 72
gcttgtggcc gtttacgtcg ccgtccagct                                              30

<210> SEQ ID NO 73
<211> LENGTH: 35
<212> TYPE: DNA
<213> ORGANISM: Artificial sequence
<220> FEATURE:
<223> OTHER INFORMATION: Synthetic sequence

<400> SEQUENCE: 73
gcttgtggcc gtttacgtcg ccgtccagct cgacc                                        35

<210> SEQ ID NO 74
<211> LENGTH: 40
<212> TYPE: DNA
<213> ORGANISM: Artificial sequence
<220> FEATURE:
<223> OTHER INFORMATION: Synthetic sequence

<400> SEQUENCE: 74
gcttgtggcc gtttacgtcg ccgtccagct cgaccaggat                                   40

<210> SEQ ID NO 75
<211> LENGTH: 55
<212> TYPE: DNA
<213> ORGANISM: Artificial sequence
<220> FEATURE:
<223> OTHER INFORMATION: Synthetic sequence

<400> SEQUENCE: 75
gacgacaaaa ctttagatcg ttacgctaac tatgagggct gtctgtggaa tgcta                  55

<210> SEQ ID NO 76
<211> LENGTH: 55
<212> TYPE: DNA
<213> ORGANISM: Artificial sequence
<220> FEATURE:
<223> OTHER INFORMATION: Synthetic sequence

<400> SEQUENCE: 76
tagcattcca cagacagccc tcatagttag cgtaacgatc taaagttttg tcgtc                  55

<210> SEQ ID NO 77
<211> LENGTH: 55
<212> TYPE: DNA
<213> ORGANISM: Artificial sequence
<220> FEATURE:
<223> OTHER INFORMATION: Synthetic sequence

<400> SEQUENCE: 77
gacgacaaaa ctttagatcg ttacgctaac tatctgggct gtctgtggaa tgcta                  55

<210> SEQ ID NO 78
<211> LENGTH: 55
<212> TYPE: DNA
<213> ORGANISM: Artificial sequence
<220> FEATURE:
<223> OTHER INFORMATION: Synthetic sequence

<400> SEQUENCE: 78
tagcattcca cagacagccc agatagttag cgtaacgatc taaagttttg tcgtc                  55

<210> SEQ ID NO 79
<211> LENGTH: 55
<212> TYPE: DNA
<213> ORGANISM: Artificial sequence
<220> FEATURE:
<223> OTHER INFORMATION: Synthetic sequence

<400> SEQUENCE: 79
gacgacaaaa ctttagatcg ttacgctaac ttagagggct gtctgtggaa tgcta    55

<210> SEQ ID NO 80
<211> LENGTH: 55
<212> TYPE: DNA
<213> ORGANISM: Artificial sequence
<220> FEATURE:
<223> OTHER INFORMATION: Synthetic sequence

<400> SEQUENCE: 80
tagcattcca cagacagccc tctaagttag cgtaacgatc taaagttttg tcgtc    55

<210> SEQ ID NO 81
<211> LENGTH: 55
<212> TYPE: DNA
<213> ORGANISM: Artificial sequence
<220> FEATURE:
<223> OTHER INFORMATION: Synthetic sequence

<400> SEQUENCE: 81
gacgacaaaa ctttagatcg ttacgctaag aatgagggct gtctgtggaa tgcta    55

<210> SEQ ID NO 82
<211> LENGTH: 55
<212> TYPE: DNA
<213> ORGANISM: Artificial sequence
<220> FEATURE:
<223> OTHER INFORMATION: Synthetic sequence

<400> SEQUENCE: 82
tagcattcca cagacagccc tcattcttag cgtaacgatc taaagttttg tcgtc    55

<210> SEQ ID NO 83
<211> LENGTH: 55
<212> TYPE: DNA
<213> ORGANISM: Artificial sequence
<220> FEATURE:
<223> OTHER INFORMATION: Synthetic sequence

<400> SEQUENCE: 83
gacgacaaaa ctttagatcg ttacgctttc tatgagggct gtctgtggaa tgcta    55

<210> SEQ ID NO 84
<211> LENGTH: 55
<212> TYPE: DNA
<213> ORGANISM: Artificial sequence
<220> FEATURE:
<223> OTHER INFORMATION: Synthetic sequence

<400> SEQUENCE: 84
tagcattcca cagacagccc tcatagaaag cgtaacgatc taaagttttg tcgtc    55

<210> SEQ ID NO 85
<211> LENGTH: 55
<212> TYPE: DNA
<213> ORGANISM: Artificial sequence
<220> FEATURE:

<223> OTHER INFORMATION: Synthetic sequence

<400> SEQUENCE: 85
gacgacaaaa ctttagatcg ttacggaaac tatgagggct gtctgtggaa tgcta    55

<210> SEQ ID NO 86
<211> LENGTH: 55
<212> TYPE: DNA
<213> ORGANISM: Artificial sequence
<220> FEATURE:
<223> OTHER INFORMATION: Synthetic sequence

<400> SEQUENCE: 86
tagcattcca cagacagccc tcatagtttc cgtaacgatc taaagttttg tcgtc    55

<210> SEQ ID NO 87
<211> LENGTH: 55
<212> TYPE: DNA
<213> ORGANISM: Artificial sequence
<220> FEATURE:
<223> OTHER INFORMATION: Synthetic sequence

<400> SEQUENCE: 87
gacgacaaaa ctttagatcg ttagcctaac tatgagggct gtctgtggaa tgcta    55

<210> SEQ ID NO 88
<211> LENGTH: 55
<212> TYPE: DNA
<213> ORGANISM: Artificial sequence
<220> FEATURE:
<223> OTHER INFORMATION: Synthetic sequence

<400> SEQUENCE: 88
tagcattcca cagacagccc tcatagttag gctaacgatc taaagttttg tcgtc    55

<210> SEQ ID NO 89
<211> LENGTH: 55
<212> TYPE: DNA
<213> ORGANISM: Artificial sequence
<220> FEATURE:
<223> OTHER INFORMATION: Synthetic sequence

<400> SEQUENCE: 89
gacgacaaaa ctttagatcg tatcgctaac tatgagggct gtctgtggaa tgcta    55

<210> SEQ ID NO 90
<211> LENGTH: 55
<212> TYPE: DNA
<213> ORGANISM: Artificial sequence
<220> FEATURE:
<223> OTHER INFORMATION: Synthetic sequence

<400> SEQUENCE: 90
tagcattcca cagacagccc tcatagttag cgatacgatc taaagttttg tcgtc    55

<210> SEQ ID NO 91
<211> LENGTH: 55
<212> TYPE: DNA
<213> ORGANISM: Artificial sequence
<220> FEATURE:
<223> OTHER INFORMATION: Synthetic sequence

<400> SEQUENCE: 91
gacgacaaaa ctttagatcc atacgctaac tatgagggct gtctgtggaa tgcta    55

```
<210> SEQ ID NO 92
<211> LENGTH: 55
<212> TYPE: DNA
<213> ORGANISM: Artificial sequence
<220> FEATURE:
<223> OTHER INFORMATION: Synthetic sequence

<400> SEQUENCE: 92
tagcattcca cagacagccc tcatagttag cgtatggatc taaagttttg tcgtc       55

<210> SEQ ID NO 93
<211> LENGTH: 55
<212> TYPE: DNA
<213> ORGANISM: Artificial sequence
<220> FEATURE:
<223> OTHER INFORMATION: Synthetic sequence

<400> SEQUENCE: 93
gacgacaaaa ctttagaagg ttacgctaac tatgagggct gtctgtggaa tgcta       55

<210> SEQ ID NO 94
<211> LENGTH: 55
<212> TYPE: DNA
<213> ORGANISM: Artificial sequence
<220> FEATURE:
<223> OTHER INFORMATION: Synthetic sequence

<400> SEQUENCE: 94
tagcattcca cagacagccc tcatagttag cgtaaccttc taaagttttg tcgtc       55

<210> SEQ ID NO 95
<211> LENGTH: 55
<212> TYPE: DNA
<213> ORGANISM: Artificial sequence
<220> FEATURE:
<223> OTHER INFORMATION: Synthetic sequence

<400> SEQUENCE: 95
gacgacaaaa ctttacttcg ttacgctaac tatgagggct gtctgtggaa tgcta       55

<210> SEQ ID NO 96
<211> LENGTH: 55
<212> TYPE: DNA
<213> ORGANISM: Artificial sequence
<220> FEATURE:
<223> OTHER INFORMATION: Synthetic sequence

<400> SEQUENCE: 96
tagcattcca cagacagccc tcatagttag cgtaacgaag taaagttttg tcgtc       55

<210> SEQ ID NO 97
<211> LENGTH: 55
<212> TYPE: DNA
<213> ORGANISM: Artificial sequence
<220> FEATURE:
<223> OTHER INFORMATION: Synthetic sequence

<400> SEQUENCE: 97
gacgacaaaa cagcagatcg ttacgctaac tatgagggct gtctgtggaa tgcta       55

<210> SEQ ID NO 98
<211> LENGTH: 55
<212> TYPE: DNA
<213> ORGANISM: Artificial sequence
<220> FEATURE:
<223> OTHER INFORMATION: Synthetic sequence
```

<400> SEQUENCE: 98
tagcattcca cagacagccc tcatagttag cgtaacgatc tgctgttttg tcgtc    55

<210> SEQ ID NO 99
<211> LENGTH: 55
<212> TYPE: DNA
<213> ORGANISM: Artificial sequence
<220> FEATURE:
<223> OTHER INFORMATION: Synthetic sequence

<400> SEQUENCE: 99
gacgacaaaa ctttagatcg ttacgctaac tatgagggcg agttgtggaa tgcta    55

<210> SEQ ID NO 100
<211> LENGTH: 55
<212> TYPE: DNA
<213> ORGANISM: Artificial sequence
<220> FEATURE:
<223> OTHER INFORMATION: Synthetic sequence

<400> SEQUENCE: 100
tagcattcca caactcgccc tcatagttag cgtaacgatc taaagttttg tcgtc    55

<210> SEQ ID NO 101
<211> LENGTH: 55
<212> TYPE: DNA
<213> ORGANISM: Artificial sequence
<220> FEATURE:
<223> OTHER INFORMATION: Synthetic sequence

<400> SEQUENCE: 101
gacgacaaaa ctttagatcg ttacgctaac tatgagggcc aaatgtggaa tgcta    55

<210> SEQ ID NO 102
<211> LENGTH: 55
<212> TYPE: DNA
<213> ORGANISM: Artificial sequence
<220> FEATURE:
<223> OTHER INFORMATION: Synthetic sequence

<400> SEQUENCE: 102
tagcattcca catttggccc tcatagttag cgtaacgatc taaagttttg tcgtc    55

<210> SEQ ID NO 103
<211> LENGTH: 55
<212> TYPE: DNA
<213> ORGANISM: Artificial sequence
<220> FEATURE:
<223> OTHER INFORMATION: Synthetic sequence

<400> SEQUENCE: 103
agttgtgtta gtttacctgg gtgttccaca gctgatagtg attgccttga ataaa    55

<210> SEQ ID NO 104
<211> LENGTH: 55
<212> TYPE: DNA
<213> ORGANISM: Artificial sequence
<220> FEATURE:
<223> OTHER INFORMATION: Synthetic sequence

<400> SEQUENCE: 104
tttattcaag gcaatcacta tcagctgtgg aacacccagg taaactaaca caact    55

<210> SEQ ID NO 105
<211> LENGTH: 55

<212> TYPE: DNA
<213> ORGANISM: Artificial sequence
<220> FEATURE:
<223> OTHER INFORMATION: Synthetic sequence

<400> SEQUENCE: 105
agttgtgtta gtttacctgg gtgttccaca gctcttagtg attgccttga ataaa    55

<210> SEQ ID NO 106
<211> LENGTH: 55
<212> TYPE: DNA
<213> ORGANISM: Artificial sequence
<220> FEATURE:
<223> OTHER INFORMATION: Synthetic sequence

<400> SEQUENCE: 106
tttattcaag gcaatcacta agagctgtgg aacacccagg taaactaaca caact    55

<210> SEQ ID NO 107
<211> LENGTH: 55
<212> TYPE: DNA
<213> ORGANISM: Artificial sequence
<220> FEATURE:
<223> OTHER INFORMATION: Synthetic sequence

<400> SEQUENCE: 107
agttgtgtta gtttacctgg gtgttccaca ggagatagtg attgccttga ataaa    55

<210> SEQ ID NO 108
<211> LENGTH: 55
<212> TYPE: DNA
<213> ORGANISM: Artificial sequence
<220> FEATURE:
<223> OTHER INFORMATION: Synthetic sequence

<400> SEQUENCE: 108
tttattcaag gcaatcacta tctcctgtgg aacacccagg taaactaaca caact    55

<210> SEQ ID NO 109
<211> LENGTH: 55
<212> TYPE: DNA
<213> ORGANISM: Artificial sequence
<220> FEATURE:
<223> OTHER INFORMATION: Synthetic sequence

<400> SEQUENCE: 109
agttgtgtta gtttacctgg gtgttccact cctgatagtg attgccttga ataaa    55

<210> SEQ ID NO 110
<211> LENGTH: 55
<212> TYPE: DNA
<213> ORGANISM: Artificial sequence
<220> FEATURE:
<223> OTHER INFORMATION: Synthetic sequence

<400> SEQUENCE: 110
tttattcaag gcaatcacta tcaggagtgg aacacccagg taaactaaca caact    55

<210> SEQ ID NO 111
<211> LENGTH: 55
<212> TYPE: DNA
<213> ORGANISM: Artificial sequence
<220> FEATURE:
<223> OTHER INFORMATION: Synthetic sequence

<400> SEQUENCE: 111
agttgtgtta gtttacctgg gtgttcctga gctgatagtg attgccttga ataaa    55

<210> SEQ ID NO 112
<211> LENGTH: 55
<212> TYPE: DNA
<213> ORGANISM: Artificial sequence
<220> FEATURE:
<223> OTHER INFORMATION: Synthetic sequence

<400> SEQUENCE: 112
tttattcaag gcaatcacta tcagctcagg aacacccagg taaactaaca caact    55

<210> SEQ ID NO 113
<211> LENGTH: 55
<212> TYPE: DNA
<213> ORGANISM: Artificial sequence
<220> FEATURE:
<223> OTHER INFORMATION: Synthetic sequence

<400> SEQUENCE: 113
agttgtgtta gtttacctgg gtgttggaca gctgatagtg attgccttga ataaa    55

<210> SEQ ID NO 114
<211> LENGTH: 55
<212> TYPE: DNA
<213> ORGANISM: Artificial sequence
<220> FEATURE:
<223> OTHER INFORMATION: Synthetic sequence

<400> SEQUENCE: 114
tttattcaag gcaatcacta tcagctgtcc aacacccagg taaactaaca caact    55

<210> SEQ ID NO 115
<211> LENGTH: 55
<212> TYPE: DNA
<213> ORGANISM: Artificial sequence
<220> FEATURE:
<223> OTHER INFORMATION: Synthetic sequence

<400> SEQUENCE: 115
agttgtgtta gtttacctgg gtgaaccaca gctgatagtg attgccttga ataaa    55

<210> SEQ ID NO 116
<211> LENGTH: 55
<212> TYPE: DNA
<213> ORGANISM: Artificial sequence
<220> FEATURE:
<223> OTHER INFORMATION: Synthetic sequence

<400> SEQUENCE: 116
tttattcaag gcaatcacta tcagctgtgg ttcacccagg taaactaaca caact    55

<210> SEQ ID NO 117
<211> LENGTH: 55
<212> TYPE: DNA
<213> ORGANISM: Artificial sequence
<220> FEATURE:
<223> OTHER INFORMATION: Synthetic sequence

<400> SEQUENCE: 117
agttgtgtta gtttacctgg gacttccaca gctgatagtg attgccttga ataaa    55

<210> SEQ ID NO 118
<211> LENGTH: 55
<212> TYPE: DNA
<213> ORGANISM: Artificial sequence

```
<220> FEATURE:
<223> OTHER INFORMATION: Synthetic sequence

<400> SEQUENCE: 118
tttattcaag gcaatcacta tcagctgtgg aagtcccagg taaactaaca caact         55

<210> SEQ ID NO 119
<211> LENGTH: 55
<212> TYPE: DNA
<213> ORGANISM: Artificial sequence
<220> FEATURE:
<223> OTHER INFORMATION: Synthetic sequence

<400> SEQUENCE: 119
agttgtgtta gtttacctgc ctgttccaca gctgatagtg attgccttga ataaa         55

<210> SEQ ID NO 120
<211> LENGTH: 55
<212> TYPE: DNA
<213> ORGANISM: Artificial sequence
<220> FEATURE:
<223> OTHER INFORMATION: Synthetic sequence

<400> SEQUENCE: 120
tttattcaag gcaatcacta tcagctgtgg aacaggcagg taaactaaca caact         55

<210> SEQ ID NO 121
<211> LENGTH: 55
<212> TYPE: DNA
<213> ORGANISM: Artificial sequence
<220> FEATURE:
<223> OTHER INFORMATION: Synthetic sequence

<400> SEQUENCE: 121
agttgtgtta gtttaccacg gtgttccaca gctgatagtg attgccttga ataaa         55

<210> SEQ ID NO 122
<211> LENGTH: 55
<212> TYPE: DNA
<213> ORGANISM: Artificial sequence
<220> FEATURE:
<223> OTHER INFORMATION: Synthetic sequence

<400> SEQUENCE: 122
tttattcaag gcaatcacta tcagctgtgg aacaccgtgg taaactaaca caact         55

<210> SEQ ID NO 123
<211> LENGTH: 55
<212> TYPE: DNA
<213> ORGANISM: Artificial sequence
<220> FEATURE:
<223> OTHER INFORMATION: Synthetic sequence

<400> SEQUENCE: 123
agttgtgtta gtttaggtgg gtgttccaca gctgatagtg attgccttga ataaa         55

<210> SEQ ID NO 124
<211> LENGTH: 55
<212> TYPE: DNA
<213> ORGANISM: Artificial sequence
<220> FEATURE:
<223> OTHER INFORMATION: Synthetic sequence

<400> SEQUENCE: 124
tttattcaag gcaatcacta tcagctgtgg aacacccacc taaactaaca caact         55
```

```
<210> SEQ ID NO 125
<211> LENGTH: 55
<212> TYPE: DNA
<213> ORGANISM: Artificial sequence
<220> FEATURE:
<223> OTHER INFORMATION: Synthetic sequence

<400> SEQUENCE: 125
agttgtgtta gagcacctgg gtgttccaca gctgatagtg attgccttga ataaa         55

<210> SEQ ID NO 126
<211> LENGTH: 55
<212> TYPE: DNA
<213> ORGANISM: Artificial sequence
<220> FEATURE:
<223> OTHER INFORMATION: Synthetic sequence

<400> SEQUENCE: 126
tttattcaag gcaatcacta tcagctgtgg aacacccagg tgctctaaca caact         55

<210> SEQ ID NO 127
<211> LENGTH: 23
<212> TYPE: DNA
<213> ORGANISM: Artificial sequence
<220> FEATURE:
<223> OTHER INFORMATION: Synthetic sequence

<400> SEQUENCE: 127
gcaaaccacc tatagggaa cac                                             23

<210> SEQ ID NO 128
<211> LENGTH: 21
<212> TYPE: DNA
<213> ORGANISM: Artificial sequence
<220> FEATURE:
<223> OTHER INFORMATION: Synthetic sequence

<400> SEQUENCE: 128
cagccaactc agcttccttt c                                              21

<210> SEQ ID NO 129
<211> LENGTH: 23
<212> TYPE: DNA
<213> ORGANISM: Artificial sequence
<220> FEATURE:
<223> OTHER INFORMATION: Synthetic sequence

<400> SEQUENCE: 129
catgccgcca cgtctaatgt ttc                                            23

<210> SEQ ID NO 130
<211> LENGTH: 21
<212> TYPE: DNA
<213> ORGANISM: Artificial sequence
<220> FEATURE:
<223> OTHER INFORMATION: Synthetic sequence

<400> SEQUENCE: 130
ggtgaagcac gcatacctgt g                                              21

<210> SEQ ID NO 131
<211> LENGTH: 31
<212> TYPE: DNA
<213> ORGANISM: Artificial sequence
<220> FEATURE:
<223> OTHER INFORMATION: Synthetic sequence
```

<400> SEQUENCE: 131
ttgttggggt aaccaactat ttgttactgt t                                          31

<210> SEQ ID NO 132
<211> LENGTH: 29
<212> TYPE: DNA
<213> ORGANISM: Artificial sequence
<220> FEATURE:
<223> OTHER INFORMATION: Synthetic sequence

<400> SEQUENCE: 132
cctccccatg tctgaggtac tccttaaag                                             29

<210> SEQ ID NO 133
<211> LENGTH: 37
<212> TYPE: DNA
<213> ORGANISM: Artificial sequence
<220> FEATURE:
<223> OTHER INFORMATION: Synthetic sequence

<400> SEQUENCE: 133
gcataatcaa ttatttgtta ctgtggtaga taccact                                    37

<210> SEQ ID NO 134
<211> LENGTH: 34
<212> TYPE: DNA
<213> ORGANISM: Artificial sequence
<220> FEATURE:
<223> OTHER INFORMATION: Synthetic sequence

<400> SEQUENCE: 134
gctatactgc ttaaatttgg tagcatcata ttgc                                       34

<210> SEQ ID NO 135
<211> LENGTH: 4
<212> TYPE: PRT
<213> ORGANISM: Artificial sequence
<220> FEATURE:
<223> OTHER INFORMATION: Synthetic sequence

<400> SEQUENCE: 135

Ala Ala Ala Ala
1

<210> SEQ ID NO 136
<211> LENGTH: 7
<212> TYPE: PRT
<213> ORGANISM: Artificial sequence
<220> FEATURE:
<223> OTHER INFORMATION: Synthetic sequence

<400> SEQUENCE: 136

Pro Lys Lys Lys Arg Lys Val
1               5

<210> SEQ ID NO 137
<211> LENGTH: 16
<212> TYPE: PRT
<213> ORGANISM: Artificial sequence
<220> FEATURE:
<223> OTHER INFORMATION: Synthetic sequence

<400> SEQUENCE: 137

Lys Arg Pro Ala Ala Thr Lys Lys Ala Gly Gln Ala Lys Lys Lys Lys
1               5                   10                  15

<210> SEQ ID NO 138
<211> LENGTH: 9
<212> TYPE: PRT
<213> ORGANISM: Artificial sequence
<220> FEATURE:
<223> OTHER INFORMATION: Synthetic sequence

<400> SEQUENCE: 138

Pro Ala Ala Lys Arg Val Lys Leu Asp
1               5

<210> SEQ ID NO 139
<211> LENGTH: 11
<212> TYPE: PRT
<213> ORGANISM: Artificial sequence
<220> FEATURE:
<223> OTHER INFORMATION: Synthetic sequence

<400> SEQUENCE: 139

Arg Gln Arg Arg Asn Glu Leu Lys Arg Ser Pro
1               5                   10

<210> SEQ ID NO 140
<211> LENGTH: 38
<212> TYPE: PRT
<213> ORGANISM: Artificial sequence
<220> FEATURE:
<223> OTHER INFORMATION: Synthetic sequence

<400> SEQUENCE: 140

Asn Gln Ser Ser Asn Phe Gly Pro Met Lys Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 141
<211> LENGTH: 42
<212> TYPE: PRT
<213> ORGANISM: Artificial sequence
<220> FEATURE:
<223> OTHER INFORMATION: Synthetic sequence

<400> SEQUENCE: 141

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 142
<211> LENGTH: 8
<212> TYPE: PRT
<213> ORGANISM: Artificial sequence
<220> FEATURE:
<223> OTHER INFORMATION: Synthetic sequence

<400> SEQUENCE: 142

Val Ser Arg Lys Arg Pro Arg Pro
1               5

```
<210> SEQ ID NO 143
<211> LENGTH: 8
<212> TYPE: PRT
<213> ORGANISM: Artificial sequence
<220> FEATURE:
<223> OTHER INFORMATION: Synthetic sequence

<400> SEQUENCE: 143

Pro Pro Lys Lys Ala Arg Glu Asp
1               5

<210> SEQ ID NO 144
<211> LENGTH: 8
<212> TYPE: PRT
<213> ORGANISM: Artificial sequence
<220> FEATURE:
<223> OTHER INFORMATION: Synthetic sequence

<400> SEQUENCE: 144

Pro Gln Pro Lys Lys Lys Pro Leu
1               5

<210> SEQ ID NO 145
<211> LENGTH: 12
<212> TYPE: PRT
<213> ORGANISM: Artificial sequence
<220> FEATURE:
<223> OTHER INFORMATION: Synthetic sequence

<400> SEQUENCE: 145

Ser Ala Leu Ile Lys Lys Lys Lys Lys Met Ala Pro
1               5                   10

<210> SEQ ID NO 146
<211> LENGTH: 5
<212> TYPE: PRT
<213> ORGANISM: Artificial sequence
<220> FEATURE:
<223> OTHER INFORMATION: Synthetic sequence

<400> SEQUENCE: 146

Asp Arg Leu Arg Arg
1               5

<210> SEQ ID NO 147
<211> LENGTH: 7
<212> TYPE: PRT
<213> ORGANISM: Artificial sequence
<220> FEATURE:
<223> OTHER INFORMATION: Synthetic sequence

<400> SEQUENCE: 147

Pro Lys Gln Lys Lys Arg Lys
1               5

<210> SEQ ID NO 148
<211> LENGTH: 10
<212> TYPE: PRT
<213> ORGANISM: Artificial sequence
<220> FEATURE:
<223> OTHER INFORMATION: Synthetic sequence

<400> SEQUENCE: 148

Arg Lys Leu Lys Lys Lys Ile Lys Lys Leu
1               5                   10

<210> SEQ ID NO 149
```

```
<211> LENGTH: 10
<212> TYPE: PRT
<213> ORGANISM: Artificial sequence
<220> FEATURE:
<223> OTHER INFORMATION: Synthetic sequence

<400> SEQUENCE: 149

Arg Glu Lys Lys Lys Phe Leu Lys Arg Arg
1               5                   10

<210> SEQ ID NO 150
<211> LENGTH: 20
<212> TYPE: PRT
<213> ORGANISM: Artificial sequence
<220> FEATURE:
<223> OTHER INFORMATION: Synthetic sequence

<400> SEQUENCE: 150

Lys Arg Lys Gly Asp Glu Val Asp Gly Val Asp Glu Val Ala Lys Lys
1               5                   10                  15

Lys Ser Lys Lys
            20

<210> SEQ ID NO 151
<211> LENGTH: 17
<212> TYPE: PRT
<213> ORGANISM: Artificial sequence
<220> FEATURE:
<223> OTHER INFORMATION: Synthetic sequence

<400> SEQUENCE: 151

Arg Lys Cys Leu Gln Ala Gly Met Asn Leu Glu Ala Arg Lys Thr Lys
1               5                   10                  15

Lys

<210> SEQ ID NO 152
<211> LENGTH: 17
<212> TYPE: PRT
<213> ORGANISM: Artificial sequence
<220> FEATURE:
<223> OTHER INFORMATION: Synthetic sequence

<400> SEQUENCE: 152

Arg Lys Cys Leu Gln Ala Gly Met Asn Leu Glu Ala Arg Lys Thr Lys
1               5                   10                  15

Lys

<210> SEQ ID NO 153
<211> LENGTH: 18
<212> TYPE: DNA
<213> ORGANISM: Artificial sequence
<220> FEATURE:
<223> OTHER INFORMATION: Synthetic sequence

<400> SEQUENCE: 153
caaagagaag cctcggcc                                                 18

<210> SEQ ID NO 154
<211> LENGTH: 34
<212> TYPE: DNA
<213> ORGANISM: Artificial sequence
<220> FEATURE:
<223> OTHER INFORMATION: Synthetic sequence

<400> SEQUENCE: 154
```

```
gtgttaatac aaaggtacag gaacaaagaa tttg                                34
```

<210> SEQ ID NO 155
<211> LENGTH: 42
<212> TYPE: DNA
<213> ORGANISM: Artificial sequence
<220> FEATURE:
<223> OTHER INFORMATION: Synthetic sequence

<400> SEQUENCE: 155

```
gtaatttcta ctaagtgtag atagcattaa gtgtcaagtt ct                       42
```

<210> SEQ ID NO 156
<211> LENGTH: 42
<212> TYPE: DNA
<213> ORGANISM: Artificial sequence
<220> FEATURE:
<223> OTHER INFORMATION: Synthetic sequence

<400> SEQUENCE: 156

```
gtaatttcta ctaagtgtag atagcattaa atgtcaagtt ct                       42
```

<210> SEQ ID NO 157
<211> LENGTH: 42
<212> TYPE: DNA
<213> ORGANISM: Artificial sequence
<220> FEATURE:
<223> OTHER INFORMATION: Synthetic sequence

<400> SEQUENCE: 157

```
gtaatttcta ctaagtgtag atactagtcc cttgtactga ta                       42
```

<210> SEQ ID NO 158
<211> LENGTH: 42
<212> TYPE: DNA
<213> ORGANISM: Artificial sequence
<220> FEATURE:
<223> OTHER INFORMATION: Synthetic sequence

<400> SEQUENCE: 158

```
gtaatttcta ctaagtgtag atgcattctg ggattctcta ga                       42
```

<210> SEQ ID NO 159
<211> LENGTH: 28
<212> TYPE: DNA
<213> ORGANISM: Artificial sequence
<220> FEATURE:
<223> OTHER INFORMATION: Synthetic sequence

<400> SEQUENCE: 159

```
ctatctgaat gaattgattt ggggcttg                                       28
```

<210> SEQ ID NO 160
<211> LENGTH: 26
<212> TYPE: DNA
<213> ORGANISM: Artificial sequence
<220> FEATURE:
<223> OTHER INFORMATION: Synthetic sequence

<400> SEQUENCE: 160

```
gcaatgtcaa aatcgccatt ttaagc                                         26
```

<210> SEQ ID NO 161
<211> LENGTH: 22
<212> TYPE: DNA
<213> ORGANISM: Artificial sequence

```
<220> FEATURE:
<223> OTHER INFORMATION: Synthetic sequence

<400> SEQUENCE: 161
aggcaacgtc caggatagag tg                                              22

<210> SEQ ID NO 162
<211> LENGTH: 28
<212> TYPE: DNA
<213> ORGANISM: Artificial sequence
<220> FEATURE:
<223> OTHER INFORMATION: Synthetic sequence

<400> SEQUENCE: 162
cagtaagcat tttccactgg tatcccag                                        28

<210> SEQ ID NO 163
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 163
actggctttg gtgctatgga ctttactaca ttacaggcta acaaaagtga               50

<210> SEQ ID NO 164
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 164
actggatatg gtgccatgga ctttagtaca ttgcaagata ctaaatgtga               50

<210> SEQ ID NO 165
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 165
tttactacat tacaggctaa caaa                                            24

<210> SEQ ID NO 166
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 166
tttagtacat tgcaagatac taaa                                            24

<210> SEQ ID NO 167
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 167
tttacgtacg ccgtccagct cgacc                                           25
```

<210> SEQ ID NO 168
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 168
aaatgcagcg gcaggtcgag ctgg                                              24

<210> SEQ ID NO 169
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 169
tttagatcgt tacgctaact atga                                              24

<210> SEQ ID NO 170
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 170
aaatctagca atgcgattga tact                                              24

<210> SEQ ID NO 171
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 171
tttatcttct gctggtggtt cgtt                                              24

<210> SEQ ID NO 172
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 172
aaatagaaga cgaccaccaa gcaa                                              24

<210> SEQ ID NO 173
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 173
aatatgtcat tatgtgctgc catatctact tcagaaact                              39

<210> SEQ ID NO 174
<211> LENGTH: 39
<212> TYPE: DNA
<213> ORGANISM: Artificial Sequence
<220> FEATURE:
<223> OTHER INFORMATION: Synthetic Sequence

```
<400> SEQUENCE: 174
aatttaacaa tatgtgcttc tacacagtct cctgtacct                              39

<210> SEQ ID NO 175
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 175
tttgagcatt aagtgtcaag ttct                                              24

<210> SEQ ID NO 176
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 176
tttgagcatt aaatgtcaag ttct                                              24

<210> SEQ ID NO 177
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 177
taaacggcca caagc                                                        15

<210> SEQ ID NO 178
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 178
gcttgtggcc gttta                                                        15

<210> SEQ ID NO 179
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: Misc_feature
<222> LOCATION: (5)..(24)
<223> OTHER INFORMATION: n is A, G, C, or T

<400> SEQUENCE: 179
tttannnnnn nnnnnnnnnn nnnn                                              24
```